(12) United States Patent
Scholten et al.

(10) Patent No.: US 8,883,466 B2
(45) Date of Patent: Nov. 11, 2014

(54) BACTERIAL CELLS EXHIBITING FORMATE DEHYDROGENASE ACTIVITY FOR THE MANUFACTURE OF SUCCINIC ACID

(75) Inventors: Edzard Scholten, Mannheim (DE); Stefan Haefner, Speyer (DE); Hartwig Schröder, Nußloch (DE)

(73) Assignee: BASF SE, Ludwigschafen (DE)

(*) Notice: Subject to any disclaimer, the term of this patent is extended or adjusted under 35 U.S.C. 154(b) by 401 days.

(21) Appl. No.: 12/643,058

(22) Filed: Dec. 21, 2009

(65) Prior Publication Data
US 2010/0159542 A1 Jun. 24, 2010

(30) Foreign Application Priority Data

Dec. 23, 2008 (EP) .................................. 08172795

(51) Int. Cl.
| | | |
|---|---|---|
| C12P 7/46 | (2006.01) | |
| C12N 1/20 | (2006.01) | |
| C12P 21/06 | (2006.01) | |
| C12P 19/34 | (2006.01) | |
| C07H 21/04 | (2006.01) | |
| C07K 1/00 | (2006.01) | |
| C12N 9/02 | (2006.01) | |
| C12N 9/04 | (2006.01) | |
| C12N 9/10 | (2006.01) | |

(52) U.S. Cl.
CPC .............. C12N 9/0006 (2013.01); C12P 7/46 (2013.01); C12N 9/0008 (2013.01); C12Y 101/02003 (2013.01); C12N 9/1029 (2013.01); C12Y 102/01002 (2013.01); C12Y 203/01054 (2013.01)
USPC ............... 435/145; 435/252.3; 435/252.1; 435/69.1; 435/91.1; 536/23.1; 536/23.2; 530/350

(58) Field of Classification Search
USPC ................ 435/145, 252.3, 252.1, 69.1, 91.1; 536/23.1, 23.2; 530/350
See application file for complete search history.

(56) References Cited

U.S. PATENT DOCUMENTS

| | | | |
|---|---|---|---|
| 4,550,185 A | 10/1985 | Mabry et al. | |
| 5,504,004 A | 4/1996 | Guettler et al. | |
| 5,573,931 A | 11/1996 | Guettler et al. | |
| 5,723,322 A | 3/1998 | Guettler et al. | |
| 6,596,521 B1 | 7/2003 | Chang et al. | |
| 7,063,968 B2 | 6/2006 | Lee et al. | |
| 7,192,761 B2 | 3/2007 | Zeikus et al. | |
| 7,241,594 B2* | 7/2007 | Lee et al. | 435/71.2 |
| 7,256,016 B2* | 8/2007 | San et al. | 435/69.1 |
| 7,262,046 B2* | 8/2007 | Ka-Yiu et al. | 435/252.33 |
| 7,470,531 B2 | 12/2008 | Rehberger et al. | |
| 2007/0042481 A1 | 2/2007 | Lee et al. | |
| 2008/0293101 A1 | 11/2008 | Peters et al. | |
| 2009/0137825 A1 | 5/2009 | Bauduin et al. | |
| 2009/0155869 A1* | 6/2009 | Buelter et al. | 435/160 |
| 2010/0044626 A1 | 2/2010 | Fischer et al. | |
| 2010/0159543 A1* | 6/2010 | Scholten et al. | 435/145 |
| 2010/0324258 A1 | 12/2010 | Zelder et al. | |
| 2011/0008851 A1 | 1/2011 | Scholten et al. | |
| 2011/0300589 A1 | 12/2011 | Schroder et al. | |

FOREIGN PATENT DOCUMENTS

| | | |
|---|---|---|
| EP | 0805208 | 5/1997 |
| EP | 1842843 A1 | 10/2007 |
| EP | 2202294 | 6/2010 |
| EP | 2204443 | 7/2010 |
| JP | 2008011714 | 1/2008 |
| WO | WO-02/00846 A1 | 1/2002 |
| WO | WO-03/040690 | 5/2003 |
| WO | WO-2005/052135 A1 | 6/2005 |
| WO | WO-2006/034156 | 3/2006 |
| WO | WO-2006/066839 A2 | 6/2006 |
| WO | WO-2008/013405 A1 | 1/2008 |
| WO | WO-2009/024294 | 2/2009 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kimchi-Sarfaty et al., A "Silent" polymorphism in the MDR1 gene changes substrate specificty. Science, 2007, vol. 315: 525-528.*
Kisselev L., Polypeptide release factors in prokaryotes and eukaryotes: same function, different structure. Structure, 2002, vol. 10: 8-9.*
Nackley et al., Human Caechol-O-Methytransferase haplotypes modulate protein expression by altering mRNA secondary structure. Science, 2006, vol. 314: 1930-1933.*
Sauna et al., Silent polymorhisms speak: How they affect pharmacogenomics and the treatment of cancer. Cancer Res., 2007, vol. 67(20): 9609-9612.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Thomson et al., The complete genome sequence and comaparative genome analysis of high pathogenecity *Yersinia enterocolitica* strain 8081. PLos Genetics, 2006, vol. 2 (12): 2039-2051.*
Whisstock et al., Prediction of protein function from protein sequence. Q. Rev. Biophysics., 2003, vol. 36 (3): 307-340.*

(Continued)

*Primary Examiner* — Ganapathirama Raghu
(74) *Attorney, Agent, or Firm* — Drinker Biddle & Reath LLP

(57) ABSTRACT

The present invention relates to a bacterial cell of the genus *Pasteurella* comprising a heterologous polypeptide having formate dehydrogenase activity. The present invention also relates to a method of manufacturing succinic acid and the use of the bacterial cell for the manufacture of succinic acid.

6 Claims, 35 Drawing Sheets

(56) References Cited

OTHER PUBLICATIONS

Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Guo et al., Protein tolerance to random amino acid change. PNAS., 2004, vol. 101 (25): 9205-9210.*
Database EBI Accession No. UniProt: A1JRX1, Feb. 6, 2007, Isocitrate lyase, XP-002576046.
Database EBI accession No. UniProt: A1JRX8, Feb. 6, 2007, Malate Synthase, XP-002576047.
Berrios-Rivera, S., et al., "The Effect of Increasing NADH Availability on the Redistribution of Metabolic Fluxes in *Escherichia coli* Chemostat Cultures", Metabolic Engineering, vol. 4, No. 3, (2002), pp. 230-237.
Dharmadi, Y, et al., "Anaerobic Fermentation of Glycerol by *Escherichia coli*: A New Platform for Metabolic Engineering", Biotech Bioeng., vol. 94, (2006), pp. 821-829.
Durchschlag, H., et al., "Large-Scale Purification and Some Properties of Malate Synthase from Baker's Yeast", Eur. J. biochem., vol. 114, (1981), pp. 114-255.
Eggerer, H., et al., "Über das Katalyseprinzip der Malat-Synthase", European J. Biochem., vol. 1, (1967), pp. 447-475.
European Search Report EP 09 17 8050 dated Feb. 23, 2010.
Feng, D.-F., et al., "Progressive Sequence Alignment as a Prerequisite to Correct Phylogenetic Trees", J. Mol. Evol., vol. 25, (1987), pp. 351-360.
Ferry, J. G., "Formate Dehydrogenase", FEMS Microbiology Reviews, vol. 87, (1990), pp. 377-382.
Frey, J., "Construction of a Broad Host Range Shuttle Vector for Gene Cloning and Expression in *Actinobacillus pleuropneumoniae* and Other *Pasteurellaceae*", Res. Microbial, vol. 143, (1992), pp. 263-269.
Higgins, D. G., et al., "Fast and Sensitive Multiple Sequence Alignments on a Microcomputer", vol. 5, No. 2, (1989, pp. 151-163.
Hoyt, J. C., et al., "*Escherichia coli* Isocitrate Lyase: Properties and Comparisons", Biochimica et Biophysica Acta, vol. 966, (1988), pp. 30-35.
Kim, J. M., et al., "Development of a Markerless Gene Knock-Out System for *Mannheimia succiniciproducens* Using a Temperature-Sensitive Plasmid", FEMS Microbiol Lett, vol. 278, (2008), pp. 78-85.
Kuhnert and Christensen, "Pasteurellaceae, Biology, Genomics, and Molecular Aspects", (2008), ISBN 978-1-904455-34-9.
Lee, S. Y., et al., "From Genome Sequence to Integrated Bioprocess for Succinic Acid Production by *Mannheimia succiniciproducens*", Applied Microbiology Biotechnology, vol. 79, No. 1, (2008), pp. 11-22.
Lee, P.C., et al., "Isolation and Characterization of a New Succinic Acid-Producing Bacterium, *Mannheimia succiniciproducens* MBEL55E, From Bovine Rumen", Appl. Microbiol Biotechnol., vol. 58, (2002), pp. 663-668.
Lee, et al., "Genome-Based Metabolic Engineering of *Mannheimia succiniciproducens* for Succinic Acid Production," Applied and Environmental Microbiology (Mar. 2006), vol. 72, No. 3, pp. 1939-1948.
Lee, S. Y., "BTEC 18Genome-Scale Metabolic engineering of *Mannheimia succiniciproducens* for Enhanced Succinic Acid Production", Genomic and Systems Approaches to Metabolic Engineering, The 229th ACS National Meeting in San Diego, CA., Mar. 13-17, 2005.
Lee, et al., "Succinic Acid Production with Reduced By-Product Formation in the Fermentation of *Anaerobiospirillum succiniciproducens* Using Glycerol as a Carbon Source," Biotech Bioeng, vol. 72, pp. 41-48, 2001.
Leenhouts, K. J., et al., "Campbell-Like Integration of Heterologous Plasmid DNA into the Chromosome of *Lactococcus lactis* subsp. *lactis*", Applied and Environmental Microbiology, vol. 55, (1989), pp. 394-400.
Mackintosh, C., et al., "Purification and Regulatory Properties of Isocitrate Lyase From *Escherichia coli* ML308", Biochem. J., vol. 250, (1988), pp. 25-31.
Müller, U., et al., "Formate Dehydrogenase from *Pseudomonas oxalaticus*", Eur. J. Biochem, vol. 83, (1978), pp. 485-498.
Needleman, S. B., et al., "A General Method Applicable to the Search for Similarities in the Amino Acid Sequence of Two Proteins", J. Mol. Biol., vol. 48, (1970), pp. 443-453.
Robertson, E. F., et al., "Purification and Characterization of Isocitrate Lyase from *Escherichia coli*", Current Microbiology, vol. 14, (1987), pp. 347-350.
Scholten, E., et al., "Succinic Acid Production by a Newly Isolated Bacterium", Biotechnology Letters, vol. 30, No. 12, (2008), pp. 2143-2146.
Smith, et al., "Identification of Common Molecular Subsequences," J. Mol. Biol. (1981), vol. 147, pp. 195-197.
Sundaram, T. K., et al, Monomeric Malate Synthase from a Thermophilic *Bacillus*, Archives of Biochemistry and Biophysics, vol. 199, No. 2, (1980), pp. 515-525.
Tishkov, V.I, et al., "Catalytic Mechanism and Application of Formate Dehydrogenase", Biochemistry (Moscow), vol. 69, No. 11, (2004), pp. 1252-1267.
Watanabe, S., et al., "Purification and Characterization of a Cold-Adapted Isocitrate Lyase and a Malate Synthase from *Colwellia maris*, a Psychrophilic Bacterium", Biosci. Biotechnol. Biochem., vol. 65, No. 5, (2001), pp. 1095-1103.
European Opinion EP 09 17 8050 dated Feb. 23, 2010.
Scholten, E., et al., "Continuous Cultivation Approach for Fermentative Succinic Acid Production from Crude Glycerol by *Basfia succiniciproducens* DD1", Biotechnol Lett, vol. 31, (2009), pp. 1947-1951.
"*Mannheimia succiniproducens* MBEL55E, complete genome", EMBL database, Accession No. AE016827, Sep. 18, 2004.
"pflD PflD protein [*Mannheimia succiniciproducens* MBEL55E]", Database NCBI, Accession No. 3075405, Dec. 18, 2010.
"IdhA D-lactate dehydrogenase [*Mannheimia succiniciproducens* MBEL55E (strain; MBEL55E", Database NCBI, Accession No. 3075603, May 21, 2011.
"pflA pyruvate formate lyase-activating enzyme 1 [*Shigella boydii* CDC 3083-94]", Database NCBI, Accession No. 6268899, Jan. 14, 2011.
"ybiW predicted pyruvate formate lyase [*Escherichia coli* str. K-12 substr. MG1655]", Database NCBI, Accession No. 945444, Feb. 28, 2011.
"pflB pyruvate formate lyase I [*Escherichia coli* str. K-12 substr. MG1655]", Database NCBI, Accession No. 945514, Feb. 28, 2011.
"IdhA fermentative D-lactate dehydrogenase, NAD-dependent [*Escherichia coli* str. K-12 substr. MG1655]" Database NCBI, Accession No. 946315, May 21, 2011.
"tdcE pyruvate formate-lyase 4/2-ketobutyrate formate-lyase [*Escherichia coli* str. K-12 substr. MG1655]", Database NCBI, Accession No. 947623, Feb. 28, 2011.
"pflD predicted formate acetyltransferase 2 (pyruvate formate lyase II) [*Escherichia coli* str. K-12 substr. MG1655]", Database NCBI, Accession No. 948454, Feb. 28, 2011.
"Pyruvate formate lyase-activating enzyme 1 [*Shigella boydii* CDC 3083-94]", Database NCBI, Accession No. YP_001880903.1, Jan. 5, 2011.
"Formate acetyltransferase 1", Database UniProtKB, Accession No. P09373, Feb. 8, 2011.
"Formate acetyltransferase 2", Database UniProtKB, Accession No. P32674, Feb. 8, 2011.
"Keto-acid formate acetyltransferase", Database UniProtKB, Accession No. P42632, Feb. 8, 2011.
"Putative formate acetyltransferase", Database UniProtKB, Accession No. P75793, Feb. 8, 2011.
"PflD protein", Database UniProtKB, Accession No. Q65VK2, Nov. 30, 2010.
Dharmadi, Y., et al., "Anaerobic Fermentation of Glycerol by *Escherichia coli*: A New Platform for Metabolic Engineering," Biotechnology and Bioengineering, 2006, vol. 94, No. 5, pp. 821-829.

(56) References Cited

OTHER PUBLICATIONS

Dousse, F., et al., "Routine phenotypic identification of bacterial species of the family Pasteurellaceae isolated from animals," J. Vet. Diagn. Invest., 2008, vol. 20, pp. 716-724.

Guettler, M.V. et al., "*Actinobacillus succinogenes* sp. nov., a novel succinic-acid-producing strain from the bovine rumen," Int'l. J. of Systematic Bacteriol., 1999, vol. 49, pp. 207-216.

Hong, S.H., et al., "Metabolic Flux Analysis for Succinic Acid Production by Recombinant *Escherichia coli* with Amplified Malic Enzyme Activity," Biotechnology and Bioengineering, 2001, vol. 74, No. 2, pp. 89-96.

Hong, S.H. et al.: "The genome sequence of the capnophilic rumen bacterium *Mannheimia succiniciproducens*", Nature Biotechnology, Oct. 2004, vol. 22, No. 10, pp. 1275-1281.

Janssen, P.H., "Characterization of a succinate-fermenting anaerobic bacterium isolated from a glycolate-degrading mixed culture", Arch. Microbiol., 1991, vol. 155, pp. 288-293.

Knappe, J., et al., "A radical-chemical route to acetyl-CoA: the anaerobically induced pyruvate formate-lyase system of *Escherichia coli*," FEMS Microbiology Reviews, 1990, vol. 75, pp. 383-398.

Knappe, J., et al., "Pyruvate formate-lyase mechanism involving the protein-based glycyl radical," Biochemical Society Transactions, 1993, vol. 21, pp. 731-734.

Lee, P.C., et al., "Isolation and characterization of new succinic acid-producing bacterium, *Mannheimia succiniciproducens* MBEL55E, from bovine rumen," Appl. Microbiol. Biotechnol. (2002), vol. 58, pp. 663-668.

Lee, P.C., et al., "Succinic Acid Production with Reduced By-Product Formation in the Fermentation of *Anaerobiospirillum succiniciproducens* Using Glycerol as a Carbon Source," Biotechnology and Bioengineering, 2001, vol. 72, No. 1, pp. 41-48.

Lee, S. J., et al., "Genome-Based Metabolic Engineering of *Mannheimia succiniciproducens* for Succinic Acid Production," Applied and Environmental Microbiology, 2006, vol. 72, No. 3, pp. 1939-1948.

Lee, J., "Biological conversion of lignocellulosic biomass to ethanol", 1997, J. Biotech., vol. 56, pp. 1-24.

Lin, H., et al., "Effect of *Sorghum vulgare* phosphoenolpyruvate carboxylase and *Lactococcus lactis* pyruvate carboxylase coexpression on succinate production in mutant strains of *Escherichia coli*," Appl. Microbiol. Biotechnol., 2005, vol. 67, pp. 515-523.

Maidak, B.L. et al., "A new version of the RDP (Ribosomal Database Project)", Nucl. Acids Res., 1999, vol. 27, No. 1, pp. 171-173.

McKinlay, J. et al., "Insights into *Actinobacillus succinogenes* fermentative metabolism in a chemically defined growth medium", Appl. and Environ. Microbiol., 2005, vol. 71, pp. 6651-6656.

Nili, N. et al., "A defined medium for rumen bacteria and identification of strains impaired in de novo biosynthesis of certain amino acids", Lett. Appl. Microbiol., 1995, vol. 21, pp. 69-74.

Pascal, M. C., et al., "Mutants of *Escherichia coli* K 12 with Defects in Anaerobic Pyruvate Metabolism," J. Gen. Microbiol., 1981, vol. 124, pp. 35-42.

Peters-Wendisch, P. G., et al., "C3-Carboxylation as an anaplerotic reaction in phosphoenolpyruvate carboxylase-deficient *Corynebacterium glutamicum*," Arch. Microbiol., 1996, vol. 165, pp. 387-396.

Rainey, F.A. et al., "The genus *Nocardiopsis* represents a phylogenetically coherent taxon and a distinct actinomycete lineage: Proposal of Nocardiopsaceae fam. nov.", 1996, Int. J. Syst. Bacteriol., vol. 46, pp. 1088-1092.

Redfield, R.J., et al., "Evolution of competence and DNA uptake specificity in the Pasteurellaceae", BMC Evolutionary Biology, 2006, vol. 6, No. 82, pp. 1-15.

Saitou, N. et al., "The neighbor-joining method: a new method for reconstructing phylogenetic trees", Mol. Biol. Evol., 1987, vol. 4, pp. 406-425.

Sanchez, A. M., et al., "Novel pathway engineering design of the anaerobic central metabolic pathway in *Escherichia coli* to increase succinate yield and productivity," Metabolic Engineering, 2005, vol. 7, pp. 229-239.

Song, H. et al., "Production of succinic acid by bacterial fermentation", Enzyme and Microbial Technology, 2006, vol. 39, pp. 352-361.

Song, H. et al., "Development of chemically defined medium for *Mannheimia succiniciproducens* based on its genome sequence", Appl. Microbiol. Biotechnol., 2008, vol. 79, pp. 263-272.

Varenne, S., et al., "A Mutant of *Escherichia coli* Deficient in Pyruvate Formate Lyase," Molec. Gen. Genet., 1975, vol. 141, pp. 181-184.

Vlysidis, A., et al., "Experimental and Modelling Studies of the Bioconversion of Glycerol to Succinic Acid by *Actinobacillus succinogenes*", AlChe100 Annual Meeting, Fuels and Petrochemicals Division (202h), Nov. 18, 2008.

White, W. T., et al., "Species and size compositions and reproductive biology of rays (Chondrichthyes, Batoidea) caught in target and non-target fisheries in eastern Indonesia," J. Fish Biol., 2007, vol. 70, pp. 1809-1837.

Zeikus, J.G., et al., "Biotechnology of succinic acid production and markets for derived industrial products", Appl. Microbiol. Biotechnol. 1999, vol. 51, pp. 545-552.

Yazdani, S. S., et al., "Anaerobic fermentation of glycerol: a path to economic viability for the biofuels industry," Current Opinion in Biotechnology, 2007, vol. 18, pp. 213-219.

Zhang, X., et al., "Fermentation of Glycerol to Succinate by Metabolically Engineered Strains of *Escherichia coli*," Applied and Environmental Microbiology, 2010, vol. 76, No. 8, pp. 2397-2401.

Zhu, J., et al., "Effect of a single-gene knockout on the metabolic regulation in *Escherichia coli* for D-lactate production under microaerobic condition," Metab. Engineering, 2005, vol. 7, pp. 104-115.

International Preliminary Report on Patentability, PCT/EP2010/051798, issued May 12, 2011.

International Preliminary Report on Patentability, PCT/EP2008/006714, issued Feb. 24, 2010.

European Search Report EP 09 17 8048, dated Mar. 31, 2010.

Patentability Opinion of EP Searching Authority—EP 09 178 048.6, mailed Apr. 13, 2010.

\* cited by examiner

FIG. 6 pJFF224 PEFTU- Glyox operon Y_molaretii

FIG. 11

| SEQ ID NO | NO | Description | Sequence |
|---|---|---|---|
| 1 | 1 | Isocitrate Lyase DNA (icl) from Y. molaretii | ATGACAACCTCTCGTACTCAACAAATTCAGCAGTTGGAACAGGAATGGAAATCACCGCGCTGGAAGGGCATCACCCGCCCCTATAGCGCCGAAGAAGTGATCAAACTGCGCGGTTCCGTTAACCCAGAATGTACGCTGGCACAGCACGGCGCGAAAAGATTGTGGGAGTTGCTGCACGGCGAATCGCGTAAAGGCTACATCAACTGTCTGGGGGCGCTAACAGGCGGTCAGGCATTGCAACAGGCAAAGGCCGGTGTTGAAGCGATTTATCTGTCGGGTTGGCAGGTCGCCGCCGATGCCAATACCGCCTCCAGCATGTATCCCGATCAATCTCTTTACCCGGTCGACTCTGTTCCGGCCGTGGTTAAGCGTATTAATAACAGCTTCCGCCGTGCAGATCAGATTCAGTGGTCGAATAATATTGAGCCGGGCAGCAAAGGCTATACCGACTATTTCCTGCCGATTGTGGCGGATGCCGAAGCGGGTTTTGGCGGCGTATTGAATGCGTTTGAATTGATGAAAGCCATGATTGAAGCCGGTGCTGCGGGCGTTCACTTTGAAGATCAATTGGCGGCGGTGAAGAAATGCGGCCATATGGGCGGCAAAGTTTTGGTGCCAACACAAGAAGCGATTCAGAAGCTGGTTGCTGCCCGCTTAGCCGCTGACGTTCTTGGCGTGCCAACACTGCTGATTGCGCGCACTGATGCTGATGCTGCGGATTTGCTGACCTCTGATTGCGACCCTTATGACAGCGAATTTATTGCTGGTGATCGTACTGCTGAGGGCTTCTTCCGCACTCACGCGGGCATTGAGCAAGCCATCAGCCGTGGTCTGGCCTATGCCCCTTACGCCGACTTGGTGTGGTGTGAAACCTCGACGCCAGATCTGGCGCTGGCTAAACGCTTTGCAGATGCCGGTTCACGCTAAATTCCCCGGTAAATTATTGGCTTATAACTGTTCGCCATCATTTAACTGGAAAAAGAACCTGACTGACCAGCAGATCGCCAGCTTCCAAGATGACCTCTCCGCGATGGGCTACAAATATCAATTTATTACCTTGGCGGGCATCCACAGTATGTGGTTCAACATGTTCGACTTGGCCCATGCTTACGCGCAAGGCGAGGGCATGAAGCACTATGTTGAGAAAGTGCAGCAGCCAGAATTTGCCTCCGTTGAACGCGGCTACACCTTTGCTTCCCATCAACAAGAAGTGGGCACGGGCTATTTTGATAAAGTCACCAATATCATTCAGGGCGGCGAGTCATCAGTCACTGCACTGACTGGCTCGACGGAAGAGCAGCAGTTCTAA |
| 2 | 2 | Isocitrate Lyase Prot. (Icl) from Y. molaretii | MTTSRTQQIQQLEQEWKSPRWKGITRPYSAEEVIKLRGSVNPECTLAQHGAKRLWELLHGESRKGYINCLGALTGGQALQQAKAGVEAIYLSGWQVAADANTASSMYPDQSLYPVDSVPAVVKRINNSFRRADQIQWSNNIEPGSKGYTDYFLPIVADAEAGFGGVLNAFELMKAMIEAGAAGVHFEDQLAAVKKCGHMGGKVLVPTQEAIQKLVAARLAADVLGVPTLLIARTDADAADLLTSDCDPYDSEFIAGDRTAEGFFRTHAGIEQAISRGLAYAPYADLVWCETSTPDLALAKRFADAVHAKFPGKLLAYNCSPSFNWKKNLTDQQIASFQDDLSAMGYKYQFITLAGIHSMWFNMFDLAHAYAQGEGMKHYVEKVQQPEFASVERGYTFASHQQEVGTGYFDKVTNIIQGGESSVTALTGSTEEQQF |
| 3 | 3 | Malate synthase DNA (ms) from Y. molaretii | ATGATCGTCGAGAGATGGGGAAGGGGAAGGGGAATGACACAACAGATAGTCGGCACGGAGTTAGTTTTCACCCAGCATTTTAATGCTGCTGAGCGGCAGGTTTTGCCCGATGAGGCCATCGAATTTTTGGCAGAATTGGTGGCGAAATTTGCAGAGCCGCGTAGCAAACTCCTTGCTGCACGGGCCGCTTGGCAACAGGCCATTGACCAAGGCGCATTGCCTGATTTCATTTCGGAAACCAATTCCATTCGTAATGGTGACTGGAAAATTCAAAGTATTCCTGCGGATTTACGTGATCGTCGCGTTCGAGATCACCGGGCCGGTTGAGCGCAAAATGGTGATTAATGCCCTCAATGCGAATGTGAAAGTCTTTATGCGTGACTTTGAGGATTCGCTGGCACCCAGTTGGGATAAGGTTATCGAAGGTCAGATTAATTTGCACGATGCGGTCAAAGGCACAATCTCTTACGCGAATGAATCCGGTAAGATTTATCAGCTAAAACCCAATCCAGCGGTGTTGATTGCTCGGGTGCGTGGTCTGCACTTGCCAGAAAAACACGTGAAGTGGCAGGGGGAGGATATCCCCGGTGGCTTATTCGATTTCGCGTTGTATTTCTACCATAACTATAAGTTACTGCTTGCCAATGGCAGCGGCCCCTATTTCTATCTACCCAAGATGCAGTCTTATCAGGAAGCGGCTTGGTGGAGTGATGTTTTCAGCTTTACCGAGCAGCGTTTCGATCTGCCGCAAGGCACCATTAAGGCCACAGTATTAATCGAGACATTGCCTGCGGTATTCCAGATGGATGAGATCCTCTACCATCTGCGCCATCACATTGTTGCCCTGAATTGTGGCCGTTGGGACTACATTTTCAGCTATATCAAAAACGCTGAAAAATCACAGCGATCGCGTGCTGCCCGATCGCCAGTCGGTCACGATGACGAAACCCTTCCTGAGTGCCTACTCTCGTTTACTGATCAAAACCTGCCATAAGCGCGGTGCCTTGGCGATGGGCGGCATGGCGGCCTTTATCCCGAACAAAGATCCAGAAAAAAATGCGCTGGTCTTAGATAAAGTTCGCGCTGACAAAGAGCTGGAAGCCAGCAACGGCCACGATGGTACATGGGTCGCACACCCCGGTCTGGCCGATACCGTGATGGACGTTTTCAACAAAGTACTGGGCGATCGTCCAAACCAATTAGAGGTGAGTCGCGCGCAAGATAAACCAATCACTGCCGCTGAGTTGCTAGAGCCTTGCACGGGTGAGCGCACCGAAGAGGGGATGCGGGCCAATATCCGGGTCGCAGTGCAATACATCGAAGCATGGATATCGGGCAATGCTGTGTACCGATTTATGGCCTGATGGAAGATGCCGCGACGGCTGAGATTTCCCGTACTTCTATCTGGCAATGGATACATCACCAGAAAAGCCTGAGCAATGGTCAGACGGTGACCAAAGAGCTGTTCCGTAACATGTTGAGTGAAGAAATGCAGGTCGTGAAACTTGAACTTGGCGCAGAGCGTTTTGATGGCGGGCGGTTTGAAGAAGCCGCACGTCTGATGGAGCGGATTACAACACAAGACGAGCTTATCGACTTTCTGACGTTGCCGGGCTACGCATTACTCGCCTAG |
| 4 | 4 | Malate synthase Prot. (Ms) from Y. molaretii | MIVERWGRGRGMTQQIVGTELVFTQHFNAAERQVLPDEAIEFLAELVAKFAEPRSKLLAARAAWQQAIDQGALPDFISETNSIRNGDWKIQSIPADLRDRRVEITGPVERKMVINALNANVKVFMADFEDSLAPSWDKVIEGQINLHDAVKGTISYANESGKIYQLKPNPAVLIARVRGLHLPEKHVKWQGEDIPGGLFDFALYFYHNYKLLLANGSGPYFYLPKMQSYQEAAWWSDVFSFTEQRFDLPQGTIKATVLIETLPAVFQMDEILYHLRHHIVALNCGRWDYIFSYIKTLKNHSDRVLPDRQSV |

FIG. 11 (Continued)

| | | | |
|---|---|---|---|
| | | | TMTKPFLSAYSRLLIKTCHKRGALAMGGMAAFIPNKDPEKNALVLDKVRADKELEASNGHD GTWVAHPGLADTVMDVFNKVLGDRPNQLEVSRAQDKPITAAELLEPCTGERTEEGMRANI RVAVQYIEAWISGNGCVPIYGLMEDAATAEISRTSIWQWIHHQKSLSNGQTVTKELFRNMLS EEMQVVKLELGAERFDGGRFEEAARLMERITTQDELIDFLTLPGYALLA |
| 5 | 5 | Formate dehydrogenase DNA (*fdh*) from C. boidinii | ATGAAGATCGTTTTAGTCTTATATGATGCTGGTAAGCACGCTGCTGATGAAGAAAATTA TATGGTTGTACTGAAAATAAATTAGGTATTGCTAATTGGTTAAAAGATCAAGGTCATGAA CTAATTACTACTTCTGATAAAGAAGGTGAAACAAGTGAATTGGATAAACATATCCCAGAT GCTGATATTATCATCACCACTCCTTTCCATCCTGCTTATATCACTAAGGAAAGACTTGAC AAGGCTAAGAACTTAAAATTAGTCGTTGTCGCTGGTGTTGGTTCTGATCACATTGATTTA GATTATATTAATCAAACAGGTAAGAAAATCTCAGTCTTGGAAGTTACAGGTTCTAATGTT GTCTCTGTTGCTGAACACGTTGTCATGACCATGCTTGTCTTGGTTAGAAATTTCGTTCCA GCACATGAACAAATTATTAACCACGATTGGGAGGTTGCTGCTATCGCTAAGGATGCTTA CGATATCGAAGGTAAAACTATTGCTACCATTGGTGCTGGTAGAATTGGTTACAGAGTCTT GGAAAGATTACTCCCTTTTAATCCAAAAGAATTATTATACTACGATTATCAAGCTTTACCA AAAGAAGCTGAAGAAAAAGTTGGTGCTAGAAGAGTTGAAAATATTGAAGAATTAGTTGCT CAAGCTGATATCGTTACAGTTAATGCTCCATTACACGCAGGTACAAAAGGTTTAATTAAT AAGGAATTATTATCTAAATTTAAAAAAGGTGCTTGGTTAGTCAATACCGCAAGAGGTGCT ATTTGTGTTGCTGAAGATGTTGCAGCAGCTTTAGAATCTGGTCAATTAAGAGGTTACGGT GGTGATGTTTGGTTCCCACAACCAGCTCCAAAGGATCACCCATGGAGAGATATGAGAAA TAAATATGGTGCTGGTAATGCCATGACTCCTCACTACTCTGGTACTACTTTAGATGCTCA AACAAGATACGCTGAAGGTACTAAAAATATCTTGGAATCATTCTTTACTGGTAAATTTGAT TACAGACCACAAGATATTATCTTATTAAATGGTGAATACGTTACTAAAGCTTACGGTAAA CACGATAAGAAA |
| 6 | 6 | Formate dehydrogenase Prot. (Fdh) from C. boidinii | MKIVLVLYDAGKHAADEEKLYGCTENKLGIANWLKDQGHELITTSDKEGETSELDKHIPDADI IITTPFHPAYITKERLDKAKNLKLVVVAGVGSDHIDLDYINQTGKKISVLEVTGSNVVSVAEHV VMTMLVLVRNFVPAHEQIINHDWEVAAIAKDAYDIEGKTIATIGAGRIGYRVLERLLPFNPKEL LYYDYQALPKEAEEKVGARRVENIEELVAQADIVTVNAPLHAGTKGLINKELLSKFKKGAWL VNTARGAICVAEDVAAALESGQLRGYGGDVWFPQPAPKDHPWRDMRNKYGAGNAMTPH YSGTTLDAQTRYAEGTKNILESFFTGKFDYRPQDIILLNGEYVTKAYGKHDKK |
| 7 | 7 | 16SrDNA | ATTGAAGAGTTTGATCATGGCTCAGATTGAACGCTGGCGGCAGGCTTAACACATGCAA GTCGAACGGTAGCGGGAGGAAAGCTTGCTTTCTTTGCCGACGAGTGGCGGACGGGTG AGTAATGCTTGGGGATCTGGCTTATGGAGGGGGAATAACGACGGGAAACTGTCGCTAAT ACCGCGTAATATCTTCGGATTAAAGGGTGGGACTTTCGGGCCACCCGCCATAAGATGA GCCCAAGTGGGATTAGGTAGTTGGTGGGGTAAAGGCCTACCAAGCCGACGATCTCTAG CTGGTCTGAGAGGATGACCAGCCACACTGGAACTGAGACACGGTCCAGACTCCTACG GGAGGCAGCAGTGGGGAATATTGCACAATGGGGGGAACCCTGATGCAGCCATGCCGC GTGAATGAAGAAGGCCTTCGGGTTGTAAAGTTCTTTCGGTGACGAGGAAGGTGTTTGTT TTAATAGGACAAGCAATTGACGTTAATCACAGAAGAAGCACCGGCTAACTCCGTGCCAG CAGCCGCGGTAATACGGAGGGTGCGAGCGTTAATCGGAATAACTGGGCGTAAAGGGC ATGCAGGCGGACTTTTAAGTGAGATGTGAAAGCCCCGGGCTTAACCTGGGAATTGCAT TCAGACTGGGAGTCTAGAGTACTTTAGGGAGGGGTAGAATTCCACGTGTAGCGGTGA AATGCGTAGAGATGTGGAGGAATACCGAAGGCGAAGGCAGCCCCTTGGGAAGATACT GACGCTCATATGCGAAAGCGTGGGGAGCAAACAGGATTAGATACCCTGGTAGTCCACG CGGTAAACGCTGTCGATTTGGGGATTGGGCTTTAGGCCTGGTGCTCGTAGCTAACGTG ATAAATCGACCGCCTGGGGAGTACGGCCGCAAGGTTAAAACTCAAATGAATTGACGGG GGCCCGCACAAGCGGTGGAGCATGTGGTTTAATTCGATGCAACGCGAAGAACCTTACC TACTCTTGACATCCAGAGAATCCTGTAGAGATACGGGAGTGCCTTCGGGAGCTCTGAG ACAGGTGCTGCATGGCTGTCGTCAGCTCGTGTTGTGAAATGTTGGGTTAAGTCCCGCA ACGAGCGCAACCCTTATCCTTTGTTGCCAGCATGTAAAGATGGGAACTCAAAGGAGACT GCCGGTGACAAACCGGAGGAAGGTGGGGATGACGTCAAGTCATCATGGCCCTTACGA GTAGGGCTACACACGTGCTACAATGGTGCATACAGAGGGCGGCGATACCGCGAGGTA GAGCGAATCTCAGAAAGTGCATCGTAGTCCGGATTGGAGTCTGCAACTCGACTCCATG AAGTCGGAATCGCTAGTAATCGCAAATCAGAATGTTGCGGTGAATACGTTCCCGGGCC TTGTACACACCGCCCGTCACACCATGGGAGTGGGTTGTACCAGAAGTAGATAGCTTAA CCTTCGGGGGGCGTTTACCACGGTATGATTCATGACTGGGGTGAAGTCGTAACAAGGT AACCGTAGGGGAACCTGCGGTTGGATCACCTCCTTAC |
| 8 | 8 | 23SrDNA | GTTAAGTGACTAAGCGTACAAGGTGGATGCCTTGGCAATCAGAGGCGAAGAAGGACGT GCTAATCTGCGAAAAGCTTGGGTGAGTTGATAAGAAGCGTCTAACCCAAGATATCCGAA TGGGGCAACCCAGTAGATGAAGAATCTACTATCAATAACCGAATCCATAGGTTATTGAG GCAAACCGGGAGAACTGAAACATCTAAGTACCCCGAGGAAAAGAAATCAACCGAGATTA CGTCAGTAGCGGCGAGCGAAAGCGTAAGAGCCGGCAAGTGATAGCATGAGGATTAGA GGAATCGGCTGGGAAGCCGGGCGGCACAGGGTGATAGCCCCGTACTTGAAAATCATT GTGTGGTACTGAGCTTGCGAGAAGTAGGCGCGGACACGAGAAATCCTGTTTGAAGAAG GGGGGACCATCCTCCAAGGCTAAATACTCCTGATTGACCGATAGTGAACAGTACTGTGA AGGAAAGGCGAAAAGAACCCCGGTGAGGGGAGTGAAATAGAACCTGAAACCTTGTACG TACAAGCAGTGGGAGCCCGCGAGGGTGACTGCGTACCTTTTGTATAATGGGTCAGCGA CTTATATTATGTAGCGAGGTTAACCGAATAGGGGAGCCGAAGGGAAACCGAGTCTTAAC TGGGCGTCGAGTTGCATGATATAGACCCGAAACCCGGTGATCTAGCCATGGGCAGGTT GAAGGTTGGGTAACACTAACTGGAGGACCGAACCGACTAATGTTGAAAAATTAGCGGAT GACCTGTGGCTGGGGGTGAAAGGCCAATCAAACCGGGAGATAGCTGGTTCTCCCCGAA |

FIG. 11 (Continued)

| | | | |
|---|---|---|---|
| | | | ATCTATTTAGGTAGAGCCTTATGTGAATACCTTCGGGGGTAGAGCACTGTTTCGGCTAG<br>GGGGCCATCCCGGCTTACCAACCCGATGCAAACTGCGAATACCGAAGAGTAATGCATA<br>GGAGACACACGGCGGGTGCTAACGTTCGTCGTGGAGAGGGAAACAACCCAGACCGCC<br>AGCTAAGGTCCCAAAGTTTATATTAAGTGGGAAACGAAGTGGGAAGGCTTAGACAGCTA<br>GGATGTTGGCTTAGAAGCAGCCATCATTTAAAGAAAGCGTAATAGCTCACTAGTCGAGT<br>CGGCCTGCGCGGAAGATGTAACGGGGCTCAAATATAGCACCGAAGCTGCGGCATCAG<br>GCGTAAGCCTGTTGGGTAGGGGAGCGTCGTGTAAGCGGAAGAAGGTGGTTCGAGAGG<br>GCTGCTGGACGTATCACGAGTGCGAATGCTGACATAAGTAACGATAAAACGGGTGAAA<br>AACCCGTTCGCCGGAAGACCAAGGGTTCCTGTCCAACGTTAATCGGGGCAGGGTGAGT<br>CGGCCCCTAAGGCGAGGCTGAAGAGCGTAGTCGATGGGAAACGGGTTAATATTCCCGT<br>ACTTGTTATAATTGCGATGTGGGGACGGAGTAGGTTAGGTTATCGACCTGTTGGAAAAG<br>GTCGTTTAAGTTGGTAGGTGGAGCGTTTAGGCAAATCCGGACGCTTATCAACACCGAGA<br>GATGATGACGAGGCGCTAAGGTGCCGAAGTAACCGATACCACACTTCCAGGAAAAGCC<br>ACTAAGCGTCAGATTATAATAAACCGTACTATAAACCGACACAGGTGGTCAGGTAGAGA<br>ATACTCAGGCGCTTGAGAGAACTCGGGTGAAGGAACTAGGCAAAATAGCACCGTAACT<br>TCGGGAGAAGGTGCGCCGGCGTAGATTGTAGAGGTATACCCTTGAAGGTTGAACCGGT<br>CGAAGTGACCCGCTGGCTGCAACTGTTTATTAAAAACACAGCACTCTGCAAACACGAAA<br>GTGGACGTATAGGGTGTGATGCCTGCCCGGTGCTGGAAGGTTAATTGATGGCGTTATC<br>GCAAGAGAAGCGCCTGATCGAAGCCCCAGTAAACGGCGGCCGTAACTATAACGGTCCT<br>AAGGTAGCGAAATTCCTTGTCGGGTAAGTTCCGACCTGCACGAATGGCATAATGATGGC<br>CAGGCTGTCTCCACCCGAGACTCAGTGAAATTGAAATCGCCGTGAAGATGCGGTGTAC<br>CCGCGGCTAGACGGAAAGACCCCGTGAACCTTTACTATAGCTTGACACTGAACCTTGAA<br>TTTTGATGTGTAGGATAGGTGGGAGGCTTTGAAGCGGTAACGCCAGTTATCGTGGAGC<br>CATCCTTGAAATACCACCCTTTAACGTTTGATGTTCTAACGAAGTGCCCGGAACGGGTA<br>CTCGGACAGTGTCTGGTGGGTAGTTTGACTGGGGCGGTCTCCTCCCAAAGAGTAACGG<br>AGGAGCACGAAGGTTTGCTAATGACGGTCGGACATCGTCAGGTTAGTGCAATGGTATA<br>AGCAAGCTTAACTGCGAGACGGACAAGTCGAGCAGGTGCGAAAGCAGGTCATAGTGAT<br>CCGGTGGTTCTGAATGGAAGGGCCATCGCTCAACGGATAAAAGGTACTCCGGGGATAA<br>CAGGCTGATACCGCCCAAGAGTTCATATCGACGGCGGTGTTTGGCACCTCGATGTCGG<br>CTCATCACATCCTGGGGCTGAAGTAGGTCCCAAGGGTATGGCTGTTCGCCATTTAAAGT<br>GGTACGCGAGCTGGGTTTAAAACGTCGTGAGACAGTTTGGTCCCTATCTGCCGTGGGC<br>GTTGGAGAATTGAGAGGGGCTGCTCCTAGTACGAGAGGACCGGAGTGGACGCATCACT<br>GGTGTTCCGGTTGTGTCGCCAGACGCATTGCCGGGTAGCTACATGCGGAAGAGATAAG<br>TGCTGAAAGCATCTAAGCACGAAACTTGCCTCGAGATGAGTTCTCCCAGTATTTAATACT<br>GTAAGGGTTGTTGGAGACGACGACGTAGATAGGCCGGGTGTGTAAGCGTTGCGAGAC<br>GTTGAGCTAACCGGTACTAATTGCCCGAGAGGCTTA |
| 9 | 9 | pSacB | TCGAGAGGCCTGACGTCGGGCCCGGTACCACGCGTCATATGACTAGTTCGGACCTAGG<br>GATATCGTCGACATCGATGCTCTTCTGCGTTAATTAACAATTGGGATCCTCTAGACTCCA<br>TAGGCCGCTTTCCTGGCTTTGCTTCCAGATGTATGCTCTTCCTCCGGAGAGTACCGTGAC<br>TTTATTTTCGGCACAAATACAGGGGTCGATGGATAAATACGGCGATAGTTTCCTGACGG<br>ATGATCCGTATGTACCGGCGGAAGACAAGCTGCAAACCTGTCAGATGGAGATTGATTTA<br>ATGGCGGATGTGCTGAGAGCACCGCCCCGTGAATCCGCAGAACTGATCCGCTATGTGT<br>TGCGGATGATTGGCCGGAATAAATAAAGCCGGGCTTAATACAGATTAAGCCCGTATAG<br>GTATTATTACTGAATACCAAACAGCTTACGGAGGACGGAATGTTACCCATTGAGACAA<br>CCAGACTGCCTTCTGATTATTAATATTTTTCACTATTAATCAGAAGGAATAACCATGAATT<br>TACCCGGATTGACCTGAATACCTGGAATCGCAGGGAACACTTTGCCCTTTATCGTCAG<br>CAGATTAAATGCGGATTCAGCCTGACCACCAAACTCGATATTACCGCTTTGCGTACCGC<br>ACTGGCGGAGACAGGTTATAAGTTTTATCCGCTGATGATTTACCTGATCTCCCGGGCTG<br>TTAATCAGTTTCCGGAGTTCCGGATGGCACTGAAAGACAATGAACTTATTTACTGGGAC<br>CAGTCAGACCCGGTCTTTACTGTCTTTCATAAAGAAACCGAAACATTCTCTGCACTGTCC<br>TGCCGTTATTTTCCGGATCTCAGTGAGTTTATGGCAGGTTATAATGCGGTAACGGCAGA<br>ATATCAGCATGATACCAGATTGTTTCCGCAGGGAAATTTACCGGAGAATCACCTGAATAT<br>ATCATCATTACCGTGGGTGAGTTTTGACGGGATTTAACCTGAACATCACCGGAAATGAT<br>GATTATTTTGCCCCGGTTTTTACGATGGCAAAGTTTCAGCAGGAAGGTGACCGCGTATT<br>ATTACCTGTTTCTGTACAGGTTCATCATCGACGTTTCATGCAGCACGGTT<br>TATTAATACACTTCAGCTGATGTGTGATAACATACTGAAATAAATTAATTAATTCTGTATTT<br>AAGCCACCGTATCCGGCAGGAATGGTGGCTTTTTTTTTATATTTTAACCGTAATCTGTAA<br>TTTCGTTTCAGACTGGTTCAGGATGAGCTCGCTTGGACTCCTGTTGATAGATCCAGTAA<br>TGACCTCAGAACTCCATCTGGATTTGTTCAGAACCGCTCGGTTGCCGCCGGCGTTTTTT<br>ATTGGTGAGAATCCAAGCACTAGCGGCGCGCCGGCCGGCCCGGTGTGAAATACCGCA<br>CAGATGCGTAAGGAGAAAATACCGCATCAGGCGCTCTTCCGCTTCCTCGCTCACTGACT<br>CGCTGCGCTCGGTCGTTCGGCTGCGGCGAGCGGTATCAGCTCACTCAAAGGCGGTAA<br>TACGGTTATCCACAGAATCAGGGGATAACGCAGGAAAGAACATGTGAGCAAAAGGCCA<br>GCAAAAGGCCAGGAACCGTAAAAAGGCCGCGTTGCTGGCGTTTTTCCATAGGCTCCGC<br>CCCCCTGACGAGCATCACAAAAATCGACGCTCAAGTCAGAGGTGGCGAAACCCGACAG<br>GACTATAAAGATACCAGGCGTTTCCCCCTGGAAGCTCCCTCGTGCGCTCTCCTGTTCCG<br>ACCCTGCCGCTTACCGGATACCTGTCCGCCTTTCTCCCTTCGGGAAGCGTGGCGCTTT<br>CTCATAGCTCACGCTGTAGGTATCTCAGTTCGGTGTAGGTCGTTCGCTCCAAGCTGGG<br>CTGTGTGCACGAACCCCCCGTTCAGCCCGACCGCTGCGCCTTATCCGGTAACTATCGT<br>CTTGAGTCCAACCCGGTAAGACACGACTTATCGCCACTGGCAGCAGCCACTGGTAACA<br>GGATTAGCAGAGCGAGGTATGTAGGCGGTGCTACAGAGTTCTTGAAGTGGTGGCCTAA<br>CTACGGCTACACTAGAAGGACAGTATTTGGTATCTGCGCTCTGCTGAAGCCAGTTACCT<br>TCGGAAAAAGAGTTGGTAGCTCTTGATCCGGCAAACAAACCACCGCTGGTAGCGGTGG<br>TTTTTTTGTTTGCAAGCAGCAGATTACGCGCAGAAAAAAAGGATCTCAAGAAGATCCTTT |

FIG. 11 (Continued)

| | | | |
|---|---|---|---|
| | | | GATCTTTTCTACGGGGTCTGACGCTCAGTGGAACGAAAACTCACGTTAAGGGATTTTGG<br>TCATGAGATTATCAAAAAGGATCTTCACCTAGATCCTTTTAAAGGCCGGCCGCGGCCGC<br>CATCGGCATTTTCTTTTGCGTTTTTATTTGTTAACTGTTAATTGTCCTTGTTCAAGGATGC<br>TGTCTTTGACAACAGATGTTTTCTTGCCTTTGATGTTCAGCAGGAAGCTCGGCGCAAAC<br>GTTGATTGTTTGTCTGCGTAGAATCCTCTGTTTGTCATATAGCTTGTAATCACGACATTG<br>TTTCCTTTCGCTTGAGGTACAGCGAAGTGTGAGTAAGTAAAGGTTACATCGTTAGGATC<br>AAGATCCATTTTTAACACAAGGCCAGTTTTGTTCAGCGGCTTGTATGGGCCAGTTAAAG<br>AATTAGAAACATAACCAAGCATGTAAATATCGTTAGACGTAATGCCGTCAATCGTCATTT<br>TTGATCCGCGGGAGTCAGTGAACAGGTACCATTTGCCGTTCATTTTAAAGACGTTCGCG<br>CGTTCAATTTCATCTGTTACTGTGTTAGATGCAATCAGCGGTTTCATCACTTTTTTCAGTG<br>TGTAATCATCGTTTAGCTCAATCATACCGAGAGCGCCGTTTGCTAACTCAGCCGTGCGT<br>TTTTTATCGCTTTGCAGAAGTTTTTGACTTTCTTGACGGAAGAATGATGTGCTTTTGCCAT<br>AGTATGCTTTGTTAAATAAAGATTCTTCGCCTTGGTAGCCATCTTCAGTTCCAGTGTTTG<br>CTTCAAATACTAAGTATTTGTGGCCTTTATCTTCTACGTAGTGAGGATCTCTCAGCGTAT<br>GGTTGTCGCCTGAGCTGTAGTTGCCTTCATCGATGAACTGCTGTACATTTTGATACGTTT<br>TTCCGTCACCGTCAAAGATTGATTTATAATCCTCTACACCGTTGATGTTCAAAGAGCTGT<br>CTGATGCTGATACGTTAACTTGTGCAGTTGTCAGTGTTTGTTGCCGTAATGTTTACCGG<br>AGAAATCAGTGTAGAATAAACGGATTTTTCCGTCAGATGTAAATGTGGCTGAACCTGAC<br>CATTCTTGTGTTTGGTCTTTAGGATAGAATCATTTGCATCGAATTTGTCGCTGTCTTTAA<br>AGACGCGGCCAGCGTTTTTCCAGCTGTCAATAGAAGTTTCGCCGACTTTTTGATAGAAC<br>ATGTAAATCGATGTGTCATCCGCATTTTTAGGATCTCCGGCTAATGCAAAGACGATGTG<br>GTAGCCGTGATAGTTTGCGACAGTGCCGTCAGCGTTTTGTAATGGCCAGCTGTCCCAAA<br>CGTCCAGGCCTTTTGCAGAAGAGATATTTTAATTGTGGACGAATCAAATTCAGAAACTT<br>GATATTTTTCATTTTTTTGCTGTTCAGGGATTTGCAGCATATCATGGCGTGTAATATGGG<br>AAATGCCGTATGTTTCCTTATATGGCTTTTGGTTCGTTTCTTTCGCAAACGCTTGAGTTG<br>CGCCTCCTGCCAGCAGTGCGGTAGTAAAGGTTAATACTGTTGCTTGTTTTGCAAACTTTT<br>TGATGTTCATCGTTCATGTCTCCTTTTTTATGTACTGTGTTAGCGGTCTGCTTCTTCCAG<br>CCCTCCTGTTTGAAGATGGCAAGTTAGTTACGCACAATAAAAAAAGACCTAAAATATGTA<br>AGGGGTGACGCCAAGTATACACTTTGCCCTTTACACATTTTAGGTCTTGCCTGCTTTAT<br>CAGTAACAAACCCGCGCGATTTACTTTTCGACCTCATTCTATTAGACTCTCGTTTGGATT<br>GCAACTGGTCTATTTTCCTCTTTTGTTTGATAGAAAATCATAAAAGGATTTGCAGACTAC<br>GGGCCTAAAGAACTAAAAAATCTATCTGTTTCTTTTCATTCTCTGTATTTTTATAGTTTCT<br>GTTGCATGGGCATAAGTTGCCTTTTTAATCACAATTCAGAAAATATCATAATATCTCATT<br>TCACTAAATAATAGTGAACGGCAGGTATATGTGATGGGTTAAAAAGGATCGGCGGCCGC<br>TCGATTTAAATC |
| 10 | 10 | pSacB<br>(delta *ldh*) | TCGAGAGGCCTGACGTCGGGCCCGGTACCACGCGTCATATGACTAGTTCGGACCTAGG<br>GATATCGTCGACATCGATGCTCTTCTGCGTTAATTAACAATTGGGATCCTCTAGACCCG<br>GGGATTCCAACCTGAAGACTGGCTCGGTATGACCGAACCCGTCAATATTCCGGGAACC<br>AGCACTCAATATGCTAACTGGCGGCGCCGTTTAACCGCAAATATAGAGGATATTTTTGC<br>CGATACGGATATTCAACATCTGTTAAAAGAGGTGAATGCTATTCGTAAGGAATAATTTTG<br>TTGCGAACGCAATGTGATTTTAACGGGTGCCGGATATGGCACCCTTATCAAAACGACGA<br>ATATTATAGACCTCTTACGATGACGCATCTTTCCCCAGATACGCAGGATTAGACGGATG<br>ATGTTACGGAATATCCCGTCCCTGTGCGGCAACATAAACCTTAATCCATTCTTCCTCAGT<br>GAAGGAAATTCGTAACGCATCCGCCGCGCTTTTTACCCGTTCAATTTTACCGGACCCCA<br>TAACCGGCATAATTTTTGCCGGATGCGCCAATAACCAGGCATAAGCCAATGTATCTAAA<br>CGGGTTTCTCCTTTCGTTTCACCGATTTCGAGTAATGTTTTTTGCACCGCCCGACTGTTC<br>TCATCCTGATTGAATAAACGACCGCCGGCAAGTGGCGACCATGCCATCGGTTGAATAC<br>GTTTTTTCCAGTAAAAAATCCAGGGTACCGTCATCAAAAGCCTGACGATGAAGAGGCGAA<br>ATCTCAATTTGATTAGTGATTAACGGCTGATTCACATAAGATTGCAACATGGCGAACTTA<br>GCCGGCGTATAGTTAGATACCCCGAAATAACGTACTTTYCCGGTTTGATAAAGTTCATCA<br>AAAGCCCGCGCGATTTGTTCGGGATCCGCACAGGGAGAAAGWCGGTGAATCAGCAAT<br>ACATCTAAATAGTCGCATTGCAGTTTTTCAATGGAACGTTGCGCCGACCACATAATATGG<br>CGGTAGCTGTTGTCATAGTGATGGGATTTTATATCGGGTAATTCTTCATTAGGATACAAA<br>ATCCCGCATTTGGTCACCAAAGTAAGCTGTGCGCGCAAGGATTTATCCAGCGCCAGCG<br>CCCGTCCGAATTCCGCCTCGGAAGTAAAAGCCCCGTAACAAGCGGCATGATCCAGCGT<br>ATCAACGCCTAATTCTAATCCTTGCTTAACGAATGTAAGCAATTCCTGCGGCGATTTCCG<br>CCAGCTTTTTAACCGCCAGAATCCTTGAATTAAGCGACTGAATGTTAAATCGGGAGCCA<br>GTTGAATGTGTTGCATAAAACCTCCAAATAAATTGAATCAAACAGACTTAAGTATAAATCT<br>TTAAAGAAAAAGTGCGGTAGAAAAAATATGGATTTTCCGCATAAAAAAAGCGTACCCGATT<br>AGGTACGCTATTAAAAATATAAGCGGCGCTATTCTACTCTCTTATGGATCTCAGTCAAGA<br>AAGGATCCGGCAACCRCCCGAACAAATGGAGRCGAARAAATTGAAAAGACGAGGAAATC<br>AGCGCGTTAAAAATTCCCGAAAACCCACCGCACTTTTTATTGGAATTTGCTAACCTTAAA<br>AGTGCGGTCAAAAAGTTAAAAATTTTAAGATTGCAATTCCAACGGATTCTTACCCGCTTT<br>ACGCAAAGCCTGATGTTCTTTAATAATCGCCATAAAAGGCTGTCCGAAGCGCTGCCATT<br>TGATGGCGCCGACACCGTTGATTTGCAGCATTTCCACTTTGCTGGTCGGCTGATACAAC<br>GACATTTCCTGCAAGGTCGCGTCACTGAACACAATATAAGGCGGAATGTTTCTTTGTC<br>GGCAATCTGTTTGCGCAGGAAACGCAGGCGGGCAAATAAATCTTTGTCGTAGTTGGTTA<br>CCGCATTGCGTTGCGGAGCCTGTACCATGGTAATGGAAGATAATCTCGGCATGGCCAG<br>TTCCAAAGACACTTCGCCGCGCAGCACGGGACGCGCGCTTTCGGTGAGCTGTAATCTG<br>GTCCCCATGCCGAAATCGCTGATGATTTGTTGCACAAAGCCCAAATGAATCAGCTGACG<br>AATTACCGATTGCCAGTATTCTTTGCTTTTATCTTTGCCAATTCCGTAGACTTTCAACTCA<br>TCATGTTGATTTTCTTTTATTTTCTGATTCTGCAAACCGCGCATTACGCCGATTACGTATT<br>GCGTGCCGAAACGTTGCCCGGTGCGATAAATGGTCGAAAGGATTTTCTGCGCGTCTAA<br>TAATCCGTCATATTTTTTCGGCGGATCGAGGCAGATATCACAGTTATTACATGGCGTTTG |

FIG. 11 (Continued)

```
GCGGTTTTCGCCGAAATAATTTAACAGCACTAAACGACGGCAGGTCTGGCTTTCGGCAA
ATTCGCCGATGGCTTCCAGCTTATGCCGTTTAATATCCCGTTGCGGGCTTTCCGGCTCT
TCCAATAAAATTTTATGCAACCAGGCATAATCCGCCGGCTCGTAAAACAGTACCGCTTC
CGCCGGCAGGTCGTCCCGCCCCGCGCGCCCGGTTTCCTGATAATACGCCTCAATGCT
GCGAGATAAATCAAAATGCGCCACAAAACGCACATTAGATTTGTTGATCCCCATACCAA
AAGCAATGGTCGCCACCACCACTTGAATATTATCCCGTTGAAACGCCTGTTGCACCGCT
TCCCGCTGCGACGGCTCCATGCCCGCATGATAAGCGGCTGCGGAAATGCCTCTTTTCT
TCAGGGCTTCCGCAATGCGCTCCACTTTGCTACGGCTGTTGCAATAGACGATACCGCTT
TTACCTTTTTGCGCCGCCACAAAATTGTATAATTGCTCCATCGGTTTGAATTTTTCCACC
AAGGTATAACGAATATTCGGGCGGTCAAAACTACCTACATACAAGTGCGGTTCGTTCAG
GCTGACCCGGGATTTAAATCGCTAGCGGGCTGCTAAAGGAAGCGGAACACGTAGAAAG
CCAGTCCGCAGAAACGGTGCTGACCCCGGATGAATGTCAGCTACTGGGCTATCTGGAC
AAGGGAAAACGCAAGCGCAAAGAGAAAGCAGGTAGCTTGCAGTGGGCTTACATGGCGA
TAGCTAGACTGGGCGGTTTTATGGACAGCAAGCGAACCGGAATTGCCAGCTGGGGCGC
CCTCTGGTAAGGTTGGGAAGCCCTGCAAAGTAAACTGGATGGCTTTCTTGCCGCCAAG
GATCTGATGGCGCAGGGGATCAAGATCTGATCAAGAGACAGGATGAGGATCGTTTCGC
ATGATTGAACAAGATGGATTGCACGCAGGTTCTCCGGCCGCTTGGGTGGAGAGGCTAT
TCGGCTATGACTGGGCACAACAGACAATCGGCTGCTCTGATGCCGCCGTGTTCCGGCT
GTCAGCGCAGGGGCGCCCGGTTCTTTTTGTCAAGACCGACCTGTCCGGTGCCCTGAAT
GAACTGCAGGACGAGGCAGCGCGGCTATCGTGGCTGGCCACGACGGGCGTTCCTTGC
GCAGCTGTGCTCGACGTTGTCACTGAAGCGGGAAGGGACTGGCTGCTATTGGGCGAA
GTGCCGGGGCAGGATCTCCTGTCATCTCACCTTGCTCCTGCCGAGAAAGTATCCATCAT
GGCTGATGCAATGCGGCGGCTGCATACGCTTGATCCGGCTACCTGCCCATTCGACCAC
CAAGCGAAACATCGCATCGAGCGAGCACGTACTCGGATGGAAGCCGGTCTTGTCGATC
AGGATGATCTGGACGAAGAGCATCAGGGGCTCGCGCCAGCCGAACTGTTCGCCAGGC
TCAAGGCGCGCATGCCCGACGGCGAGGATCTCGTCGTGACCCATGGCGATGCCTGCT
TGCCGAATATCATGGTGGAAAATGGCCGCTTTTCTGGATTCATCGACTGTGGCCGGCTG
GGTGTGGCGGACCGCTATCAGGACATAGCGTTGGCTACCCGTGATATTGCTGAAGAGC
TTGGCGGCGAATGGGCTGACCGCTTCCTCGTGCTTTACGGTATCGCCGCTCCCGATTC
GCAGCGCATCGCCTTCTATCGCCTTCTTGACGAGTTCTTCTGAGCGGGACTCTGGGGT
TCGAAATGACCGACCAAGCGACGCCCAACCTGCCATCACGAGATTTCGATTCCACCGC
CGCCTTCTATGAAAGGTTGGGCTTCGGAATCGTTTTCCGGGACGCCGGCTGGATGATC
CTCCAGCGCGGGGATCTCATGCTGGAGTTCTTCGCCCACGCTAGCGGCGCGCCGGCC
GGCCCGGTGTGAAATACCGCACAGATGCGTAAGGAGAAAATACCGCATCAGGCGCTCT
TCCGCTTCCTCGCTCACTGACTCGCTGCGCTCGGTCGTTCGGCTGCGGCGAGCGGTAT
CAGCTCACTCAAAGGCGGTAATACGGTTATCCACAGAATCAGGGGATAACGCAGGAAA
GAACATGTGAGCAAAAGGCCAGCAAAAGGCCAGGAACCGTAAAAAGGCCGCGTTGCTG
GCGTTTTTCCATAGGCTCCGCCCCCCTGACGAGCATCACAAAAATCGACGCTCAAGTCA
GAGGTGGCGAAACCCGACAGGACTATAAAGATACCAGGCGTTTCCCCCTGGAAGCTCC
CTCGTGCGCTCTCCTGTTCCGACCCTGCCGCTTACCGGATACCTGTCCGCCTTTCTCCC
TTCGGGAAGCGTGGCGCTTTCTCATAGCTCACGCTGTAGGTATCTCAGTTCGGTGTAG
GTCGTTCGCTCCAAGCTGGGCTGTGTGCACGAACCCCCCGTTCAGCCCGACCGCTGC
GCCTTATCCGGTAACTATCGTCTTGAGTCCAACCCGGTAAGACACGACTTATCGCCACT
GGCAGCAGCCACTGGTAACAGGATTAGCAGAGCGAGGTATGTAGGCGGTGCTACAGA
GTTCTTGAAGTGGTGGCCTAACTACGGCTACACTAGAAGGACAGTATTTGGTATCTGCG
CTCTGCTGAAGCCAGTTACCTTCGGAAAAAGAGTTGGTAGCTCTTGATCCGGCAAACAA
ACCACCGCTGGTAGCGGTGGTTTTTTTGTTTGCAAGCAGCAGATTACGCGCAGAAAAAA
AGGATCTCAAGAAGATCCTTTGATCTTTTCTACGGGGTCTGACGCTCAGTGGAACGAAA
ACTCACGTTAAGGGATTTTGGTCATGAGATTATCAAAAAGGATCTTCACCTAGATCCTTT
TAAAGGCCGGCCGCGGCCGCCATCGGCATTTTCTTTTGCGTTTTTATTTGTTAACTGTTA
ATTGTCCTTGTTCAAGGATGCTGTCTTTGACAACAGATGTTTTCTTGCCTTTGATGTTCA
GCAGGAAGCTCGGCGCAAACGTTGATTGTTTGTCTGCGTAGAATCCTCTGTTTGTCATA
TAGCTTGTAATCACGACATTGTTTCCTTTCGCTTGAGGTACAGCGAAGTGTGAGTAAGTA
AAGGTTACATCGTTAGGATCAAGATCCATTTTTAACACAAGGCCAGTTTTGTTCAGCGGC
TTGTATGGGCCAGTTAAAGAATTAGAAACATAACCAAGCATGTAAATATCGTTAGACGTA
ATGCCGTCAATCGTCATTTTTGATCCGCGGGAGTCAGTGAACAGGTACCATTTGCCGTT
CATTTTAAAGACGTTCGCGCGTTCAATTTCATCTGTTACTGTGTTAGATGCAATCAGCGG
TTTCATCACTTTTTTTCAGTGTGTAATCATCGTTTAGCTCAATCATACCGAGAGCGCCGTT
TGCTAACTCAGCCGTGCGTTTTTTATCGCTTTGCAGAAGTTTTTGACTTTCTTGACGGAA
GAATGATGTGCTTTTGCCATAGTATGCTTTGTTAAATAAAGATTCTTCGCCTTGGTAGCC
ATCTTCAGTTCCAGTGTTTGCTTCAAATACTAAGTATTTGTGGCCTTTATCTTCTACGTAG
TGAGGATCTCTCAGCGTATGGTTGTCGCCTGAGCTGTAGTTGCCTTCATCGATGAACTG
CTGTACATTTTGATACGTTTTCCGTCACCGTCAAAGATTGATTTATAATCCTCTACACCG
TTGATGTTCAAAGAGCTGTCTGATGCTGATACGTTAACTTGTGCAGTTGTCAGTGTTTGT
TTGCCGTAATGTTTACCGGAGAAATCAGTGTAGAATAAACGGATTTTTCCGTCAGATGTA
AATGTGGCTGAACCTGACCATTCTTGTGTTTGGTCTTTTAGGATAGAATCATTTGCATCG
AATTTGTCGCTGTCTTTAAAGACGCGGCCAGCGTTTTTCCAGCTGTCAATAGAAGTTTC
GCCGACTTTTTGATAGAACATGTAAATCGATGTGTCATCGCATTTTTAGGATCTCCGGC
TAATGCAAAGACGATGTGGTAGCCGTGATAGTTTGCGACAGTGCCGTCAGCGTTTTGTA
ATGGCCAGCTGTCCCAAACGTCCAGGCCTTTTGCAGAAGAGATATTTTAATTGTGGAC
GAATCAAATTCAGAAACTTGATATTTTTCATTTTTTTGCTGTTCAGGGATTTGCAGCATAT
CATGGCGTGTAATATGGGAAATGCCGTATGTTTCCTTATATGGCTTTTGGTTCGTTTCTT
TCGCAAACGCTTGAGTTGCGCCTCCTGCCAGCAGTGCGGTAGTAAAGGTTAATACTGTT
GCTTGTTTTGCAAACTTTTTTGATGTTCATCGTTCATGTCTCCTTTTTTATGTACTGTGTTA
```

FIG. 11 (Continued)

| | | | |
|---|---|---|---|
| | | | GCGGTCTGCTTCTTCCAGCCCTCCTGTTTGAAGATGGCAAGTTAGTTACGCACAATAAA
AAAAGACCTAAAATATGTAAGGGGTGACGCCAAAGTATACACTTTGCCCTTTACACATTT
TAGGTCTTGCCTGCTTTATCAGTAACAAACCCGCGCGATTTACTTTTCGACCTCATTCTA
TTAGACTCTCGTTTGGATTGCAACTGGTCTATTTTCCTCTTTTGTTTGATAGAAAATCATA
AAAGGATTTGCAGACTACGGGCCTAAAGAACTAAAAAATCTATCTGTTTCTTTTCATTCT
CTGTATTTTTTATAGTTTCTGTTGCATGGGCATAAAGTTGCCTTTTTAATCACAATTCAGA
AAATATCATAATATCTCATTTCACTAAATAATAGTGAACGGCAGGTATATGTGATGGGTT
AAAAAGGATCGGCGGCCGCTCGATTTAAATC |
| 11 | 11 | pSacB (delta *pflD*) | TCGAGAGGCCTGACGTCGGGCCCGGTACCACGCGTCATATGACTAGTTCGGACCTAGG
GATGGGATCGAGCTCTTTTCCTTGCCGACAAGGCGGAAGCTTAGGGGAAATTCCCGT
AGGTGCCGTATTGGTGGATGAACGGGGCAATATCATTGGTGAAGGCTGGAACCTCTCT
ATTGTGAACTCGGATCCCACCGCCCATGCCGAAATTATTGCGTTGCGTAACGCCGCGC
AGAAAATCCAAAATTACCGCCTGCTCAATACCACTTTATACGTGACTTTAGAACCCTGCA
CCATGTGCGCCGGCGCGATTTTACACAGCCGAATCAAACGCTTGGTATTCGGGCGTC
CGATTACAAAACCGGTGCGGTGGGTTCCAGATTTCATTTTTTTGAGGATTATAAAATGAA
TCATGGGGTTGAGATCACAAGCGGTGTCTTATAGGATCAATGCAGTCAGAAGTTAAGCC
GCTTTTTCCAAAAGCGCAGGGAACAGAAAAAACAACAAAAAGCTACCGCACTTTTACAA
CACCCCCGGCTTAACTCCTCTGAAAAATAGTGACAAAAAAACCGTCATAATGTTTACGAC
GGTTTTTTTATTTCTTCTAATATGTCACATTAAGCCCGTAGCCTGCAAGCAACCCCTTAA
CATGCTCCATTAATTCTTTTGTCGGCGGTTTTACATCTTCAAGCTCGTATTTATCGCCGA
GTACTTCCCATTTATGGGCGCCTAGACGGTGATAAGGTAATAATTCCACTTTTTCGATAT
TCTTCATATCTTTAATGAAATTCCCCAGCATGTGCAAATCTTCGTCACTATCTGTATAACC
CGGCACTACAACATGGCGGATCCAGGTACGCTGATTTCGATCCGCTAAATATTTTGCGA
ATTCGAGCACTCTTTTATTCGGCACGCCAATCAGGCTTTCGTGAACCCGTTCATTCATTT
CTTTCAGGTCAAGCAACACAAGATCCGTGTCATCAATCAATTCATCAATAATATGATCAT
GATGACGGACGAAACCGTTGGTATCCAAGCAAGTATTAATTCCTTCTTTATGGCAGGCT
CTGAACCAGTCCCGTACAAATTCCGCCTGTAAATAGCTTCACCGCCGGAAGCGGTAAC
TCCGCCGCCCGAGGCGTTCATAAAATGGCGATAGGTCACCACTTCTTTCATTAATTCTT
CAACGGAAATTTCTTTACCGCCGTGCAAATCCCAGGTGTCTCTGTTATGGCAATATTTAC
AACGCATTAAGCAGCCTTGTAAAAATAAAATAAAGCGGATTCCCGGCCCGTCAACTGTC
CCGCAGGTTTCAAATGAATGAATTCGTCCTAAAACCGACATAATATGCCCTTAATAATC
AACAAAATATAGCAAGAAGATTATAGCAAAGAATTTCGTTTTTTTCAGAGAATAGTCAAAT
CTTCGCAAAAAACTACCGCACTTTTATCCGCTTTAATCAGGGGAATTAAAACAAAAAAAT
TCCGCCTATTGAGGCGGAATTTATTAAGCAATAAGACAAACTCTCAATTTTAATACTTCC
TTCTTTTCTAGTATTGATAAGATTGAAACCTTGCAAGGATGACGGCGGATTTGCCGTCAC
TCTCACCCAACTAATGTGGACGACTGGTAAACCATTGCATTAGACCAATGCAAACACCA
CCACCGACGATGTTACCTAAAGTAACAGGAATTAAATTTTTAATTACTAAATGGTACATAT
CTAAATTTGCAAACTGCTCGGCATTTAAACCCGTTGCCTGCCAGAATTCCGGCGATGCG
AAATTTGCAATTACCATGCCCATAGGGATCATAAACATATTTGCTACGCAGTGTTCAAAG
CCTGAAGCGACAAAYAACCCGATCGGCAGGATCATAATAAAAGCTTTATCCGTTAGAGT
YTTGCCGGCATAGGCCATCCAAACGGCAATACATACCATAATGTTGCAAAGAATACCTA
AACAGAAGGCTTCAAYCCAGGTATGTTCTATTTTATGTTGTGCCGTATTTAAAATGGTTA
ATCCCCACTGACCGTTTGCCGCCATGATCTGACCGGAAAACCAAATTAATGCAACAATA
AATAAACCGCCGACAAAATTACCGAARTAAACCACAATCCAGTTACGTAACATCTGAATT
GTTGTAATTTTACTCTCAAAGCGGGCAATAGTCGATAAAGTTGATGAAGTAAATAGTTCA
CAGCCGCAAACCGCCACCATAATTACCCCGAGAGAGAACACCAAACCGCCGACCAGTT
TAGTTAATCCCCAAGGCGCTCCCGCAGAGGCTGTTTGAGTTGTTGTATAAAAAACGAAT
GCAAGAGCAATAAACATACCGGCAGAGATCGCCGATAAAAATGAATAGGCTTGTTTTTT
CGTAGCTTTATAAACGCCGACGTCTAACCCGGTTTGAGCCATCTCGGTTGGCGAAGCC
ATCCAAGCCAATTTAAAATCTTCCGATTTCATTGAGCTTTCCTTAGTAATAAAACTACTCG
GAAATGAGTAGAACTGCCTTAAAGCATAAATGATAGATTAAAAAATCCAAAATTGTTGAA
TATTATTTAACGGGGGGATTATAAAAGATTCATAAATTAGATAATAGCTAATTTGAGTGAT
CCATATCACCTTTTACAGATTTTTTGACCTAAATCAAAATTACCCAAATAGAGTAATAATA
CCATTATAAAGGGTGTGGATTTATTCCTTTGGTTTACGAGATAAATTGCTATTTAAGCTG
ATTTCTGATAAAAAGTGCGGTAGATTTTTCCCAAAAATAAGGAAACACAAAATGGCAGAA
GAAACAATTTTCAGTAAAATTATTCGTAAAGAAATTCCCGCCGACATTATATATCAAGAC
GATCTTGTCACCGCATTTCGCGATATTGCGCCGCAGGCAAAAACTCATATTTTAATTATT
CCGAATAAATTGATTCCGACAGTAAACGACGTAACCGCCCATCGTCGACATCGATGCTC
TTCTGCGTTAATTAACAATTGGGATCCTCTAGACTTTGCTTCCAGATGTATGCTCTCCTC
CGGAGAGTACCGTGACTTTATTTTCGGCACAAATACAGGGGTCGATGGATAAATACGGC
GATAGTTTCCTGACGGATGATCCGTATGTACCGGCGGAAGACAAGCTGCAAACCTGTC
AGATGGAGATTGATTTAATGGCGGATGTGCTGAGAGCACCGCCCCGTGAATCCGCAGA
ACTGATCCGCTATGTGTTTGCGGATGATTGGCCGGAATAAATAAAGCCGGGCTTAATAC
AGATTAAGCCCGTATAGGGTATTATTACTGAATACCAAACAGCTTACGGAGGACGGAAT
GTTACCCATTGAGACAACCAGACTGCCTTCTGATTATTAATATTTTCACTATTAATCAGA
AGGAATAACCATGAATTTTACCCGGATTGACCTGAATACCTGGAATCGCAGGGAACACT
TTGCCCTTTATCGTCAGCAGATTAAATGCGGATTCAGCCTGACCACCAAACTCGATATTA
CCGCTTTGCGTACCGCACTGGCGGAGACAGGTTTATAAGTTTTATCCGCTGATGATTTAC
CTGATCTCCCGGGCTGTTAATCAGTTTCCGGAGTTCCGGATGGCACTGAAAGACAATGA
ACTTATTTACTGGGACCAGTCAGACCCGGTCTTTACTGTCTTTCATAAAGAAACCGAAAC
ATTCTCTGCACTGTCCTGCCGTTATTTTCCGGATCTCAGTGAGTTTATGGCAGGTTATAA
TGCGGTAACGGCCAGAATATCAGCATGATACCAGATTGTTTCCGCAGGGAAATTTACCGG
AGAATCACCTGAATATATCATCATTACCGTGGGTGAGTTTTGACGGGATTTAACCTGAAC
ATCACCGGAAATGATGATTATTTTGCCCCGGTTTTTACGATGGCAAAGTTTCAGCAGGA |

FIG. 11 (Continued)

| | | | |
|---|---|---|---|
| | | | AGGTGACCGCGTATTATTACCTGTTTCTGTACAGGTTCATCATGCAGTCTGTGATGGCTT<br>TCATGCAGCACGGTTTATTAATACACTTCAGCTGATGTGTGATAACATACTGAAATAAAT<br>TAATTAATTCTGTATTTAAGCCACCGTATCCGGCAGGAATGGTGGCTTTTTTTTTATATTT<br>TAACCGTAATCTGTAATTTCGTTTCAGACTGGTTCAGGATGAGCTCGCTTGGACTCCTGT<br>TGATAGATCCAGTAATGACCTCAGAACTCCATCTGGATTTGTTCAGAACGCTCGGTTGC<br>CGCCGGGCGTTTTTTATTGGTGAGAATCCAAGCACTAGCGGCGCGCCGGCCGGCCCG<br>GTGTGAAATACCGCACAGATGCGTAAGGAGAAAATACCGCATCAGGCGCTCTTCCGCT<br>TCCTCGCTCACTGACTCGCTGCGCTCGGTCGTTCGGCTGCGGCGAGCGGTATCAGCTC<br>ACTCAAAGGCGGTAATACGGTTATCCACAGAATCAGGGGATAACGCAGGAAAGAACAT<br>GTGAGCAAAAGGCCAGCAAAAGGCCAGGAACCGTAAAAAGGCCGCGTTGCTGGCGTTT<br>TTCCATAGGCTCCGCCCCCCTGACGAGCATCACAAAAATCGACGCTCAAGTCAGAGGT<br>GGCGAAACCCGACAGGACTATAAAGATACCAGGCGTTTCCCCCTGGAAGCTCCCTCGT<br>GCGCTCTCCTGTTCCGACCCTGCCGCTTACCGGATACCTGTCCGCCTTTCTCCCTTCG<br>GGAAGCGTGGCGCTTTCTCATAGCTCACGCTGTAGGTATCTCAGTTCGGTGTAGGTCG<br>TTCGCTCCAAGCTGGGCTGTGTGCACGAACCCCCCGTTCAGCCCGACCGCTGCGCCTT<br>ATCCGGTAACTATCGTCTTGAGTCCAACCCGGTAAGACACGACTTATCGCCACTGGCAG<br>CAGCCACTGGTAACAGGATTAGCAGAGCGAGGTATGTAGGCGGTGCTACAGAGTTCTT<br>GAAGTGGTGGCCTAACTACGGCTACACTAGAAGGACAGTATTTGGTATCTGCGCTCTGC<br>TGAAGCCAGTTACCTTCGGAAAAAGAGTTGGTAGCTCTTGATCCGGCAAACAAACCACC<br>GCTGGTAGCGGTGGTTTTTTTGTTTGCAAGCAGCAGATTACGCGCAGAAAAAAAGGATC<br>TCAAGAAGATCCTTTGATCTTTTCTACGGGGTCTGACGCTCAGTGGAACGAAAACTCAC<br>GTTAAGGGATTTTGGTCATGAGATTATCAAAAAGGATCTTCACCCTAGATCCTTTTAAAGG<br>CCGGCCGCGGCCGCCATCGGCATTTTCTTTTGCGTTTTTATTTGTTAACTGTTAATTGTC<br>CTTGTTCAAGGATGCTGTCTTTGACAACAGATGTTTTCTTGCCTTTGATGTTCAGCAGGA<br>AGCTCGGCGCAAACGTTGATTGTTGTCTGCGTAGAATCCTCTGTTTGTCATATAGCTTG<br>TAATCACGACATTGTTTCCTTTCGCTTGAGGTACAGCGAAGTGTGAGTAAGTAAAGGTTA<br>CATCGTTAGGATCAAGATCCATTTTTAACACAAGGCCAGTTTTGTTCAGCGGCTTGTATG<br>GGCCAGTTAAAGAATTAGAAACATAACCAAGCATGTAAATATCGTTAGACGTAATGCCGT<br>CAATCGTCATTTTTGATCCGCGGGAGTCAGTGAACAGGTACCATTTGCCGTTCATTTTAA<br>AGACGTTCGCGCGTTCAATTTCATCTGTTACTGTGTTAGATGCAATCAGCGGTTTCATCA<br>CTTTTTTCAGTGTGTAATCATCGTTTAGCTCAATCATACCGAGAGCGCCGTTTGCTAACT<br>CAGCCGTGCGTTTTTTATCGCTTTGCAGAAGTTTTTGACTTTCTTGACGGAAGAATGATG<br>TGCTTTTGCCATAGTATGCTTTGTTAAATAAAGATTCTTCGCCTTGGTAGCCATCTTCAG<br>TTCCAGTGTTTGCTTCAAATACTAAGTATTTGTGGCCTTTATCTTCTACGTAGTGAGGAT<br>CTCTCAGCGTATGGTTGTCGCCTGAGCTGTAGTTGCCTTCATCGATGAACTGCTGTACA<br>TTTTGATACGTTTTTCCGTCACCGTCAAAGATTGATTTATAATCCTCTACACCGTTGATGT<br>TCAAAGAGCTGTCTGATGCTGATACGTTAACTTGTGCAGTTGTCAGTGTTTGTTTGCCGT<br>AATGTTTACCGGAGAAATCAGTGTAGAATAAACGGATTTTTCCGTCAGATGTAAATGTGG<br>CTGAACCTGACCATTCTTGTGTTTGGTCTTTTAGGATAGAATCATTTGCATCGAATTTGT<br>CGCTGTCTTTAAAGACGCGGCCAGCGTTTTTCCAGCTGTCAATAGAAGTTTCGCCGACT<br>TTTTGATAGAACATGTAAATCGATGTGTCATCCGCATTTTTAGGATCTCCGGCTAATGCA<br>AAGACGATGTGGTAGCCGTGATAGTTTGCGACAGTGCCGTCAGCGTTTTGTAATGGCC<br>AGCTGTCCCAAACGTCCAGGCCTTTTGCAGAAGAGATATTTTTAATTGTGGACGAATCA<br>AATTCAGAAACTTGATATTTTTCATTTTTTTGCTGTTCAGGGATTTGCAGCATATCATGGC<br>GTGTAATATGGGAAATGCCGTATGTTTCCTTATATGGCTTTTGGTTCGTTTCTTTCGCAA<br>ACGCTTGAGTTGCGCCTCCTGCCAGCAGTGCGGTAGTAAAGGTTAATACTGTTGCTTGT<br>TTTGCAAACTTTTTGATGTTCATCGTTCATGTCTCCTTTTTATGTACTGTGTTAGCGGTC<br>TGCTTCTTCCAGCCCTCCTGTTTGAAGATGGCAAGTTAGTTACGCACAATAAAAAAGAC<br>CTAAAATATGTAAGGGGTGACGCCAAAGTATACACTTTGCCCTTTACACATTTTAGGTCT<br>TGCCTGCTTTATCAGTAACAAACCCGCGCGATTTACTTTTCGACCTCATTCTATTAGACT<br>CTCGTTTGGATTGCAACTGGTCTATTTTCCTCTTTTGTTTGATAGAAAATCATAAAGGAT<br>TTGCAGACTACGGGCCTAAAGAACTAAAAAATCTATCTGTTTCTTTTCATTCTCTGTATTT<br>TTTATAGTTTCTGTTGCATGGGCATAAAGTTGCCTTTTTAATCACAATTCAGAAAATATCA<br>TAATATCTCATTTCACTAAATAATAGTGAACGGCAGGTATATGTGATGGGTTAAAAAGGA<br>TCGGCGGCCGCTCGATTTAAATC |
| 12 | 12 | pJFF224 (icl ms Y.m.) | GATCCCCAGTAGATTTACGTTTAAACATTTTTATTTCCTTTTTAATTTAATTTAATTAACAG<br>TTGGTGCTATGACACTTTACCTCATAGCTGGCATAATTCGCAATACTCTGGGTCTTCGAG<br>AGGTATCCAACCTGAGTTGAAATACTTTACCATCGATTTAGCAGTTGTATCAGTTATATTT<br>ATATTACCTTTAACTCTTCGCCATCCAGGAGTTTTACCGTACAGATTAGAGGATAATAAT<br>AACACATAATTCTCGTAAGCAATATGAGATAATTTCCAAGACTCTATATTAGCTCGTGAT<br>GTTTTCCAAGGTCTAAAATCGTCACGGTTCATATAATTAGCCAATCTCATATGCTCTCTA<br>ACTTCCGATGATAAGCTGTCAAACATGAGAATTAACGATCTGATAGAGAAGGGTTTGCT<br>CGGGTCGGTGGCTCTGGTAACGACCAGTATCCCGATCCCGGCTGGCCGTCCTGGCCG<br>CCACATGAGGCATGTTCCGCGTCCTTGCAATACTGTGTTTACATACAGTCTATCGCTTA<br>GCGGAAAGTTCTTTTACCCTCAGCCGAAATGCCTGCCGTTGCTAGACATTGCCAGCCAG<br>TGCCCGTCACTCCCGTACTAACTGTCACGAACCCCTGCAATAACTGTCACGCCCCCTG<br>CAATAACTGTCACGAACCCCTGCAATAACTGTCACGCCCCCAAACCTGCAAACCCAGCA<br>GGGGCGGGGCTGGCGGGTGTTGGAAAAATCCATCCATGATTATCTAAGAATAATCC<br>ACTAGGCGCGGTTATCAGCGCCCTTGTGGGGCGCTGCTGCCCTTGCCCAATATGCCG<br>GCCAGAGGCCGGATAGCTGGTCTATTCGCTGCGCTAGGCTACACACCGCCCCACCGCT<br>GCGCGGCAGGGGGAAAGGCGGGCAAAGCCCGCTAAACCCCACACCCAAACCCCGCAGA<br>AATACGCTGGGAGCGCTTTTAGCCGCTTTAGCGGCCTTTCCCCCTACCCGAAGGGTGG<br>GGGCGCGTGTGCAGCCCCGCAGGGCCTGTCTCGGTCGATCATTCAGCCCGGCTCATC<br>CTTCTGGCGTGGCGGCAGACCGAACAAGGCGCGGTCGTGGTCGCGTTCAAGGTACGC |

FIG. 11 (Continued)

```
ATCCATTGCCGCCATGAGCCGATCCTCCGGCCACTCGCTGCTGTTCACCTTGGCCAAA
ATCATGGCCCCCACCAGCACCTTGCGCCTTGTTTCGTTCTTGCGCTATTGCTGCTGTTC
CCTTGCCCGCACCCGCTGAATTTCGGCATTGATTCGCGCTCGTTGTTCTTCGAGCTTGG
CCAGCCGATCCGCCGCCTTGTTGCTCCCCTTAACCATCTTGACACCCCATTGTTAATGT
GCTGTCTCGTAGGCTATCATGGAGGCACAGCGGCGGCAATCCCGACCCTACTTTGTAG
GGGAGGGCCATTGCATGGAGCCGAAAAGCAAAAGCAACAGCGAGGCAGCATGGCGAT
TTATCACCTTACGGCGAAAACCGGCAGCAGGTCGGGCGGCCAATCGGCCAGGGCCAA
GGCCGACTACATCCAGCGCGAAGGCAAGTATGCCCGCGACATGGATGAAGTCTTGCAC
GCCGAATCCGGGCACATGCCGGAGTTCGTCGAGCGGCCCGCCGACTACTGGGATGCT
GCCGACCTGTATGAACGCGCCAATGGGCGGCTGTTCAAGGAGGTCGAATTTGCCCTGC
CGGTCGAGCTGACCCTCGACCAGCAGAAGGCGCTGGCGTCCGAGTTCGCCCAGCACC
TGACCGGTGCCGAGCGCCTGCCGTATACGCTGGCCATCCATGCCGGTGGCGGCGAGA
ACCCGCACTGCCACCTGATGATCTCCGAGCGGATCAATGACGGCATCGAGCGGCCCG
CCGCTCAGTGGTTCAAGCGGTACAACGGCAAGACCCCGGAGAAGGGCGGGGCACAGA
AGACCGAAGCGCTCAAGCCCAAGGCATGGCTTGAGCAGACCCGCGAGGCATGGGCCG
ACCATGCCAACCGGGCATTAGAGCGGGCTGGCCACGACGCCCGCATTGACCACAGAA
CACTTGAGGCGCAGGGCATCGAGCGCCTGCCCGGTGTTCACCTGGGGCCGAACGTGG
TGGAGATGGAAGGCCGGGCATCCGCACCGACCGGGCAGACGTGGCCCTGAACATCG
ACACCGCCAACGCCCAGATCATCGACTTACAGGAATACCGGGAGGCAATAGACCATGA
ACGCAATCGACAGAGTGAAGAAATCCAGAGGCATCAACGAGTTAGCGGAGCAGATCGA
ACCGCTGGCCCAGAGCATGGCGACACTGGCCGACGAAGCCCGGCAGGTCATGAGCCA
GACCCAGCAGGCCAGCGAGGCGCAGGCGGCGGAGTGGCTGAAAGCCCAGCGCCAGA
CAGGGGCGGCATGGGTGGAGCTGGCCAAAGAGTTGCGGGAGGTAGCCGCCGAGGTG
AGCAGCGCCGCGCAGAGCGCCCGGAGCGCGTCGCGGGGGTGGCACTGGAAGCTATG
GCTAACCGTGATGCTGGCTTCCATGATGCCTACGGTGGTGCTGCTGATCGCATCGTTG
CTCTTGCTCGACCTGACGCCACTGACAACCGAGGACGGCTCGATCTGGCTGCGCTTGG
TGGCCCGATGAAGAACGACAGGACTTTGCAGGCCATAGGCCGACAGCTCAAGGCCATG
GGCTGTGAGCGCTTCGATATCGGCGTCAGGGACGCCACCACCGGCCAGATGATGAAC
CGGGAATGGTCAGCCGCCGAAGTGCTCCAGAACACGCCATGGCTCAAGCGGATGAAT
GCCCAGGGCAATGACGTGTATATCAGGCCCGCCGAGCAGGAGCGGCATGGTCTGGTG
CTGGTGGACGACCTCAGCGAGTTTGACCTGGATGACATGAAAGCCGAGGGCCGGGAG
CCTGCCCTGGTAGTGGAAACCAGCCCGAAGAACTATCAGGCATGGGTCAAGGTGGCC
GACGCCGCAGGCGGTGAACTTCGGGGGCAGATTGCCCGGACGCTGGCCAGCGAGTAC
GACGCCGACCCGGCCAGCGCCGACAGCCGCCACTATGGCCGCTTGGCGGGCTTCACC
AACCGCAAGGACAAGCACACCACCCGCGCCGGTTATCAGCCGTGGGTGCTGCTGCGT
GAATCCAAGGGCAAGACCGCCACCGCTGGCCCGGCGCTGGTGCAGCAGGCTGGCCA
GCAGATCGAGCAGGCCCAGCGGCAGCAGGAGAAGGCCCGCAGGCTGGCCAGCCTCG
AACTGCCCGAGCGGCAGCTTAGCCGCCACCGGCGCACGGCGCTGGACGAGTACCGCA
GCGAGATGGCCGGGCTGGTCAAGCGCTTCGGTGATGACCTCAGCAAGTGCGACTTTAT
CGCCGCGCAGAAGCTGGCCAGCCGGGGCCGCAGTGCCGAGGAAATCGGCAAGGCCA
TGGCCGAGGCCAGCCCAGCGCTGGCAGAGCGCAAGCCCGGCCACGAAGCGGATTACA
TCGAGCGCACCGTCAGCAAGGTCATGGGTCTGCCCAGCGTCCAGCTTGCGCGGGCCG
AGCTGGCACGGGCACCGGCACCCCGCCAGCGAGGCATGGACAGGGGCGGGCCAGAT
TTCAGCATGTAGTGCTTGCGTTGGTACTCACGCCTGTTATACTATGAGTACTCACGCAC
AGAAGGGGGTTTTATGGAATACGAAAAAAGCGCTTCAGGGTCGGTCTACCTGATCAAAA
GTGACAAGGGCTATTGGTTGCCCGGTGGCTTTGGTTATACGTCAAACAAGGCCGAGGC
TGGCCGCTTTTCAGTCGCTGATATGGCCAGCCTTAACCTTGACGGCTGCACCTTGTCCT
TGTTCCGCGAAGACAAGCCTTTCGGCCCCGGCAAGTTTCTCGGTGACTGATATGAAAG
ACCAAAAGGACAAGCAGACCGGCGACCTGCTGGCCAGCCCTGACGCTGTACGCCAAG
CGCGATATGCCGAGCGCATGAAGGCCAAAGGGATGCGTCAGCGCAAGTTCTGGCTGA
CCGACGACGAATACGAGGCGCTGCGCGAGTGCCTGGAAGAACTCAGAGCGGCGCAGG
GCGGGGGTAGTGACCCCGCCAGCGCCTAACCACCAACTGCCTGCAAAGGAGGCAATC
AATGGCTACCCATAAGCCTATCAATATTCTGGAGGCGTTCGCAGCAGCGCCGCCACCG
CTGGACTACGTTTTGCCCAACATGGTGGCCGGTACGGTCGGGGCGCTGGTGTCGCCC
GGTGGTGCCGGTAAATCCATGCTGGCCCTGCAACTGGCCGCCACAGATTGCAGGCGGG
CCGGATCTGCTGGAGGTGGGCGAACTGCCCACCGGCCCGGTGATCTACCTGCCCGCC
GAAGACCCGCCCACCGCCATTCATCACCGCCTGCACGCCCTTGGGGCGCACCTCAGC
GCCGAGGAACGGCAAGCCGTGGCTGACGGCCTGCTGATCCAGCCGCTGATCGGCAGC
CTGCCCAACATCATGGCCCCGGAGTGGTTCGACGGCCTCAAGCGCGCCGCCGAGGGC
CGCCGCCTGATGGTGCTGGACACGCTGCGCCGGTTCCACATCGAGGAAGAAAACGCC
AGCGGCCCCATGGCCCAGGTCATCGGTCGCATGGAGGCCATCGCCGCCGATACCGGG
TGCTCTATCGTGTTCCTGCACCATGCCAGCAAGGGCGCGGCCATGATGGGCGCAGGC
GACCAGCAGCAGGCCAGCCGGGGCAGCTCGGTACTGGTCGATAACATCCGCTGGCAG
TCCTACCTGTCGAGCATGACCAGCGCCGAGGCCGAGGAATGGGGTGTGGACGACGAC
CAGCGCCGGTTCTTCGTCCGCTTCGGTGTGAGCAAGGCCAACTATGGCGCACCGTTCG
CTGATCGGTGGTTCAGGCGGCATGACGGCGGGGTGCTCAAGCCCGCCGTGCTGGAGA
GGCAGCGCAAGAGCAAGGGGCGTGCCCCGTGGTGAAGCCTAAGAACAAGCACAGCCTC
AGCCACGTCCGGCACGACCCGGCGCACTGTCTGGCCCCCGGCCTGTTCCGTGCCCTC
AAGCGGGGCGAGCGCAAGCGCAGCAAGCTGGACGTGACGTATGACTACGGCGACGGC
AAGCGGATCGAGTTCAGCGGCCCGGAGCCGCTGGGCGCTGATGATCTGCGCATCCTG
CAAGGGCTGGTGGCCATGGCTGGGCCTAATGGCCTAGTGCTTGGCCCGGAACCCAAG
ACCGAAGGCGGACGGCAGCTCCGGCTGTTCCTGGAACCCAAGTGGGAGGCCGTCACC
GCTGATGCCATGGTGGTCAAAGGTAGCTATCGGGCGCTGGCAAAGGAAATCGGGGCA
GAGGTCGATAGTGGTGGGGCGCTCAAGCACATACAGGACTGCATCGAGCGCCTTTGGA
```

FIG. 11 (Continued)

```
AGGTATCCATCATCGCCCAGAATGGCCGCAAGCGGCAGGGGTTTCGGCTGCTGTCGG
AGTACGCCAGCGACGAGGCGGACGGGCGCCTGTACGTGGCCCTGAACCCCTTGATCG
CGCAGGCCGTCATGGGTGGCGGCCAGCATGTGCGCATCAGCATGGACGAGGTGCGG
GCGCTGGACAGCGAAACCGCCCGCCTGCTGCACCAGCGGCTGTGTGGCTGGATCGAC
CCCGGCAAAACCGGCAAGGCTTCCATAGATACCTTGTGCGGCTATGTCTGGCCGTCAG
AGGCCAGTGGTTCGACCATGCGCAAGCGCCGCCAGCGGGTGCGCGAGGCGTTGCCG
GAGCTGGTCGCGCTGGGCTGGACGGTAACCGAGTTCGCGGCGGGCAAGTACGACATC
ACCCCGGCCCAAGGCGGCAGGCTGACCCCCCCCACTCTATTGTAAACAAGACATTTTTTA
TCTTTTATATTCAATGGCTTATTTTCCTGCTAATTGGTAATACCATGAAAAATACCATGCT
CAGAAAAGGCTTAACAATATTTTGAAAAATTGCCTACTGAGCGCTGCCGCACAGCTCCA
TAGGCCGCTTTCCTGGCTTTGCTTCCAGATGTATGCTCTCCTCCGGAGAGTACCGTGAC
TTTATTTTCGGCACAAATACAGGGGTCGATGGATAAATACGGCGATAGTTTCCTGACGG
ATGATCCGTATGTACCGGCGGAAGACAAGCTGCAAACCTGTCAGATGGAGATTGATTTA
ATGGCGGATGTGCTGAGAGCACCGCCCCGTGAATCCGCAGAACTGATCCGCTATGTGT
TGCGGATGATTGGCCGGAATAAATAAAGCCGGCTTAATACAGATTAAGCCCGTATAG
GGTATTATTACTGAATACCAAACAGCTTACGGAGGACGGAATGTTACCCATTGAGACAA
CCAGACTGCCTTCTGATTATTAATATTTTTCACTATTAATCAGAAGGAATAACCATGAATT
TTACCCGGATTGACCTGAATACCTGGAATCGCAGGGAACACTTTGCCCTTTATCGTCAG
CAGATTAAATGCGGATTCAGCCTGACCACCAAACTGATATTACCGCTTTGCGTACCGC
ACTGGCGGAGACAGGTTATAAGTTTTATCCGCTGATGATTTACCTGATCTCCCGGGCTG
TTAATCAGTTTCCGGAGTTCCGGATGGCACTGAAAGACAATGAACTTATTTACTGGGAC
CAGTCAGACCCCGGTCTTTACTGTCTTTCATAAAGAAACCGAAACATTCTCTGCACTGTCC
TGCCGTTATTTTCCGGATCTCAGTGAGTTTATGGCAGGTTATAATGCGGTAACGGCAGA
ATATCAGCATGATACCAGATTGTTTCCGCAGGGAAATTTACCGGAGAATCACCTGAATAT
ATCATCATTACCGTGGGTGAGTTTTGACGGGATTTAACCTGAACATCACCGGAAATGAT
GATTATTTTGCCCCGGTTTTTACGATGGCAAAGTTTCAGCAGGAAGGTGACCGCGTATT
ATTACCTGTTTCTGTACAGGTTCATCATGCAGTCTGTGATGGCTTTCATGCAGCACGGTT
TATTAATACACTTCAGCTGATGTGTGATAACATACTGAAATAAATTAATTAATTCTGTATTT
AAGCCACCGTATCCGGCAGGAATGGTGGCTTTTTTTTTATATTTTAACCGTAATCTGTAA
TTTCGTTTCAGACTGGTTCAGGATCACTGTACGATAATGCCCCCGCAGTTTGGTAATAC
CCTTAATAAAAAAGAAACAGCAAAGACTGACAGCAATAATAATAAAGTAAGCAGTAACAA
TAATATTAACAACACCAGATGCAGTTATAATAATAGTATTTAAGACACCAGAAAGACTGC
TGCGACAGTCATTTTGAACAACACCAAAATGCCGTAAAGGCAGTAGTAACAACACCAGT
GAAAACATCACGATAGCATAGTGATATGCCTGAGTGTGTGTAATTAAACAATAAATAAAC
CGCCATATATAACAGAAGATAGTATTCTGAATGGCATGCTTTTCTGTTCAGTATAAACAT
ATCATCCCGGTTGGTATAAGGATGATATATAATAAGTTAAGCTGAACACATATTTATTTTG
GTTTTATTTTACAAATAAAGTAAGACGATCCGTTAAGTCAAAGCGGGGTATATTTATTATA
CCCTGCTTTTTTATTTGTCCGCCGGGCGCGGATAATGGATCAGATTATGCAGTGTCACA
ATGGCCTTACCGGGATTGGCGTAAGCGTGCGGGATATCCGCATGGAAGCGCAGGGATT
CCCCGGCAGAAACGGTGTGCCACTCATCCCCCAGCCGCAGTTGTAATGCGCCTTCCAG
TACAATGACATGTTCTCTGGTTCTGAAATCCATCCCTGTCGGTGTTGCTTATGCAGTCTG
GTCGGGACTCGGCGTCGTCATAATTACAGCCATTGCCTGGTTGCTTCATGGGCAAAAG
CTTTATGCTTGTAAACCGTTTTGTGAAAAAATTTTTAAAATAAAAAGGGGACCTCTAGG
GTCCCCAATTAATTAGTAATATAATCTATTAAAGGTCATTCAAAAGGTCATCCACCGGAT
CCGGGCCCCCCCTCGAGGTCGACGGTATCGATAAGCTTGATATCGAATTCCCATATTGT
GCATCGAATCCCTGCAAAATTGTCTGAGCGATTAATTGTTCTAATTTTACCGCCATGCTC
ACCCCCCGCCATACGGAACAGAGCCTGCATCAGCAGGCTCCAGATAAAACATAAACTC
ATTAATCAGTGGCTTAGAACTGCTGCTCTTCCGTCGAGCCAGTCAGTGCAGTGACTGAT
GACTCGCCGCCCTGAATGATATTGGTGACTTTATCAAAATAGCCCGTGCCCACTTCTTG
TTGATGGGAAGCAAAGGTGTAGCCGCGTTCAACGGAGGCAAATTCTGGCTGCTGCACT
TTCTCAACATAGTGCTTCATGCCCTCGCCTTGCGCGTAAGCATGGGCCAAGTCGAACAT
GTTGAACCACATACTGTGGATGCCCGCCAAGGTAATAAATTGATATTTGTAGCCCATCG
CGGAGAGGTCATCTTGGAAGCTGGCGATCTGCTGGTCAGTCAGGTTCTTTTTCCAGTTA
AATGATGGCGAACAGTTATAAGCCAATAATTTACCGGGGAATTTAGCGTGAACCGCATC
TGCAAAGCGTTTAGCCAGCGCCAGATCTGGCGTCGAGGTTTCACACCACACCAAGTCG
GCGTAAGGGGCATAGGCCAGACCACGGCTGATGGCTTGCTCAATGCCCGCGTGAGTG
CGGAAGAAGCCCTCAGCAGTACGATCACCAGCAATAAATTCGCTGTCATAAGGGTCGC
AATCAGAGGTCAGCAAATCCGCAGCATCAGCATCAGTGCGCGCAATCAGCAGTGTTGG
CACGCCAAGAACGTCAGCGGCTAAGCGGGCAGCAACCAGCTTCTGAATCGCTTCTTGT
GTTGGCACCCAAAACTTTGCCGCCCCATATGGCCGCATTTCTTCACCGCCGCCAATTGATC
TTCAAAGTGAACGCCCGCAGCACCGGCTTCAATCATGGCTTTCATCAATTCAAACGCAT
TCAATACGCCGCCAAAACCCGCTTCGGCATCCGCCACAATCGGCAGGAAATAGTCGGT
ATAGCCTTTGCTGCCCGGCTCAATATTATTCGACCACTGAATCTGATCTGCACGGCGGA
AGCTGTTATTAATACGCTTAACCACGGCCGGAACAGAGTCGACCGGGTAAAGAGATTGA
TCGGGATACATGCTGGAGGCGGTATTGGCATCGGCGGCGACCTGCCAACCCGACAGA
TAAATCGCTTCAACACCGGCCTTTGCCTGTTGCAATGCCTGACCGCCTGTTAGCGCCCC
CAGACAGTTGATGTAGCCTTTACGCGATTCGCCGTGCAGCAACTCCCACAATCTTTTCG
CGCCGTGCTGTGCCAGCGTACATTCTGGGTTAACGGAACCGCGCAGTTTGATCACTTC
TTCGGCGCTATAGGGGCGGGTGATGCCCTTCCAGCGCGGTGATTTCCATTCCTGTTCC
AACTGCTGAATTTGTTGAGTACGAGAGGTTGTCATGGCGATATTCCTTATTACTTATTTTT
GTAGGGTTAAATAACTGGCCTAGGCGAGTAATGCGTAGCCCGGCAACGTCAGAAAGTC
GATAAGCTCGTCTTGTGTTGTAATCCGCTCCATCAGACGTGCGGCTTCTTCAAACCGCC
CGCCATCAAAACGCTCTGCGCCAAGTTCAAGTTTCACGACCTGCATTTCTTCACTCAAC
ATGTTACGGAACAGCTCTTTGGTCACCGTCTGACCATTGCTCAGGCTTTTCTGGTGATG
```

FIG. 11 (Continued)

| | | | |
|---|---|---|---|
| | | | TATCCATTGCCAGATAGAAGTACGGGAAATCTCAGCCGTCGCGGCATCTTCCATCAGGC CATAAATCGGTACACAGCCATTGCCCGATATCCATGCTTCGATGTATTGCACTGCGACC CGGATATTGGCCCGCATCCCCTCTTCGGTGCGCTCACCCGTGCAAGGCTCTAGCAACT CAGCGGCAGTGATTGGTTTATCTTGCGCGCGACTCACCTCTAATTGGTTTGGACGATCG CCCAGTACTTTGTTGAAAACGTCCATCACGGTATCGGCCAGACCGGGGTGTGCGACCC ATGTACCATCGTGGCCGTTGCTGGCTTCCAGCTCTTTGTCAGCGCGAACTTTATCTAAG ACCAGCGCATTTTTTTCTGGATCTTTGTTCGGGATAAAGGCCGCCATGCCGCCCATCGC CAAGGCACCGCGCTTATGGCAGGTTTTGATCAGTAAACGAGAGTAGGCACTCAGGAAG GGTTTCGTCATCGTGACCGACTGGCGATCGGGCAGCACGCGATCGCTGTGATTTTTCA GCGTTTTGATATAGCTGAAAATGTAGTCCCAACGGCCACAATTCAGGGCAACAATGTGA TGGCGCAGATGGTAGAGGATCTCATCCATCTGGAATACCGCAGGCAATGTCTCGATTAA TACTGTGGCCTTAATGGTGCCTTGCGGCAGATCGAAACGCTGCTCGGTAAAGCTGAAA ACATCACTCCACCAAGCCGCTTCCTGATAAGACTGCATCTTGGGTAGATAGAAATAGGG GCCGCTGCCATTGGCAAGCAGTAACTTATAGTTATGGTAGAAATACAACGCGAAATCGA ATAAGCCACCGGGGATATCCTCCCCCTGCCACTTCACGTGTTTTTCTGGCAAGTGCAGA CCACGCACCCGAGCAATCAACACCGCTGGATTGGGTTTTAGCTGATAAATCTTACCGGA TTCATTCGCGTAAGAGATTGTGCCTTTGACCGCATCGTGCAAATTAATCTGACCTTCGAT AACCTTATCCCAACTGGGTGCCAGCGAATCCTCAAAGTCAGCCATAAAGACTTTCACAT TCGCATTGAGGGCATTAATCACCATTTTGCGCTCAACCGGCCCGGTGATCTCGACGCG ACGATCACGTAAATCCGCAGGAATACTTTGAATTTTCCAGTCACCATTACGAATGGAATT GGTTTCCGAAATGAAATCAGGCAATGCGCCTTGGTCAATGGCCTGTTGCCAAGCGGCC CGTGCAGCAAGGAGTTTGCTACGCGGCTCTGCAAATTTCGCCACCAATTCTGCCAAAAA TTCGATGGCCTCATCGGGCAAAACCTGCCGCTCAGCAGCATTAAAATGCTGGGTGAAA ACTAACTCCGTGCCGACTATCTGTTGTGTCATTCCCCTTCCCCTTCCCCATCTCTCGAC GATCATTTTTCAGTTTCCTTTTGTTATTCCCCAAAAGTGCGGTGCAAATTTGGGGAGTTT TAGTTAATTAAAAAAATTATTTTTTACGAGCTTCGATTACTGCAGCAGCAACACTTGTTGG CGCTTCAGCATATTTTAACGGTTCCATTGAGTATGATGCTCTAGAGCGGCCGCCACCGC GGTGG |
| 13 | 13 | pJFF224 (icl ms S.t.) | GATCCCACCGCGGTGGCGGCCGCTCTAGAGGGTTCCCTCATCCGGCACCACGTCATG CCGGATGGCGCGTTCGCTTATCCGGCCTACGCTATCTGTAGGCCCGGTAAGCGCAGC GCCACCGGGCATCAATCAAAACTGCGCTTCTTCGGTGGAACCCGTTAACGCGGTAACG GATGACGCGCCGCCCTGAATAATGGTGGTGACTTTGTCGAAGTAACCAGTACCCACTTC CTGCTGGTGGGAAACAAAGGTGTAGCCATCTTCGCCGCGGCGAACTCGGGTTGTTGA ACCTTCTCAACATAGTGCTTCATGCCCTCGCCCTGCGCGTATGCATGCGCCAGGTCGA ACATGTTGAACCACATCGTGTGGATGCCCGCCAGGGTAATAAACTGGTATTTGTAACCC ATGTCCGACAACTGCTGCTGGAAGCTGGCAATGGTCTTGTCGTCCAGATTCTTCTGCCA GTTGAAGGATGGTGAACAGTTATAGGCCAGCAGTTTGCCCGGATACTTCGCGTGGATA GCATCGGCAAAACGACGCGCCAGTTCGAGATCCGGCGTAGAGGTTTCGCACCATACCA GATCGGCATACGGGGCATACGCCAGACCGCGGCTGATCGCCTGCTCAATGCCCGCAT GGGTGCGGTAGAAACCTTCGCTGGTGCGTTCGCCGGTAATAAAACCGCTGTCATAGGG ATCGCAGTCGGAGGTGATCAGATCTGCCGCATCCGCATCGGTACGCGCAATCACCAGC GTCGGGACGCCCATCACATCAGCGGCCAGACGCGCAGCAACCAGTTTCTGAATCGCCT CCTGCGTGGGGACCAGCACCTTGCGCCCATATGGCCGCATTCTTCACCGACGCCAG CTGATCTTCGAAGTGAACGGCCGCTGCACCGGCTTCAATCATCGATTTCATCAGTTCGA AGGCATTCAGAACGCCGCCAAAACCGGCTTCCGCATCAGCAACGATCGGCAGGAAGTA ATCCACATAGCGCGGATCGTTGGGTTCAATACCGGATGCCCACTGGATCTGATCTGCA CGACGAAAAGTGTTGTTGATCCGATCCACTACCGCCGGAACAGAGTTTGCCGGGTACA ACGATTGATCCGGATACATGCTGGATGCCAGGTTGGCATCTGCCGCCACCTGCCAGCC TGAAAGATAAATCGCCTCAATACCGGCTTTCGCCTGCTGCAACGCCTGACCGCCGGTC AGCGCGCCAAGGCTGTTGATATAGCCTTTTTTCGCTTCACCGTGCAACAGCCGCCACAT TTTCGCGGCGCCGAGCTGCGCCAGCGTGCATTCCGGGTTAACCGAGCCGCGTAATTTC ACCACCTCCTCCGCGCTGTACGGGCGGGTGATGCCTTCCCAGCGCGGTTGTGTCCACT CTTTCTGTAATTCTTCGATTTGTTGAGTACGGGTTTTCATGTGCAGATGCTCCATATTGTT ATGTGGTGAATTAAGCCAGTAAGCGATAGCCCGGCAGGGTGAGGAAGTCGATTAAGTC ATCTGAGGTGGTGATTTGCTCCATCAGACGTGCGGCATCGTCGAAGCGCCCGCTGCTG TAGCGGTGCTCGCCCAGTTCGTCCTGGATTACCCGCATCTCTTCCGCCAACATTTCGCG GAAAAGCGTTTTCGTTACGGGTTTTCCATTGCTCAGTGTTTTCTCATGGTGAATCCACTG CCAGATAGAGGTTCGTGAGATTTCCGCCGTCGCGGCATCCTCCATCAGACCGTAAATC GGTACACAGCCATTGCCGGAGATCGCACGCTTCAATGTACTGCACTGCCACGCGAATATT GGCGCGCATTCCCGCTTCTGTGCGTTCGCCTTCACATGGCTCCAGTAACTGTTCAGCG GTAATCGGCGCATCTTCATCACGGGTAATGAACAGCTGATTTTTGTGCTCGCCCAGTAC CTCGTTAAAGACGGCCATTGCGGTATCCGCCAACCCAGGATGCGCAATCCACGTGCCG TCGTGGCCGTTGTTCGCTTCCAGCGCTTTATCCGCTTTCACTTTGGCAAGGACCTGATT GTTGCGTTCAACGTCTTTGCTCGGGATAAACGCCGCCATACCGCCCATCGCGAACGCG CCGCGCTTGTGGCAGGTTTTGATCAGCAGGCGCGAGTAGGCGCTCAGAAACGGTTTGT CCATCGTTACCACCTGCCTGTCCGGCAAAACGCGATCCGGGTGATTTTCAACGTTTTG ATATAGCTGAAAATATAATCCCAGCGACCACAGTTGAGACCGACGATATGATCACGCAG CGCATGAAGAATCTCATCCATCTGGAAAACAGCCGGCAGCGTTTCAATCAACAGGGTC GCTTTGATCGTACCGCGCGGCAGGTTAAAGCGGTCTTCGGCGTAGCTGAACACTTCGC TCCACCAGGCTGCCTCCTGCCAGGCTTGCGTTTTCGGCAGGTAAAAATACGGGCCGCT ACCTTTAGCGAGCAGCGCTTTATAGTTGTGGAAAAAGTACAGAGCAAAATCAAACAGGC TGCCGGGAATGGCTTCCCCCCGCCAGGTAACATGTTTTTCTGGCAGATGTAGACCACG TACACGACAAATCAATACGGCCGGATCGGGCTTGAGCTGATAGATTTTTCCGGCTTCGT TGGTATAGCTAATGGTGCCGTTCACCGCATCACGCAGGTTGATTTGACCATCAATAACT |

FIG. 11 (Continued)

```
TTATTCCAGTCCGGCGCCAGCGAGTCTTCAAAATCCGCCCATAAACACTTTCACATTTGC
GTTCAGGGCATTAATCACCATTTTACGTTCAACCGGCCCGGTAATTTCTACTCGGCGAT
CCTGTAAATCCGCCGGAATACCACGAATCTGCCAATTACTTTCTCTAATGGAAGTGGTTT
CCGAAATAAAATCAGGCAACTTACCGTTATCAATATCCTGCTGTTGCTGGATACGGGCA
GCCAGGAGTTTATTGCGTTTTGGCGTAAAACGGGTGACTAACTCCGTCAAAAACTCGAC
TGCTTCAGCGGTCAGGACTTGCTTTTCCAGCTCGCCTTGCGGCCTGGTAAAGGTTAATT
CATCAGTTGTGGTTGCCTGTGGATTCATCATGCAGCTCCTCGTTGTTGATCCAGATACA
TCCCCAATGCGAACGAAGGATCACTGTGCACTTTTCGTTCAACACAACTAAGACTACTC
AATTAAATTTCAAAATCAAAAACAATTTCCATTTTTAATTTAATTATGCATTAACCTATTGA
TAACAATATAAATTAAATTTAATTACATGATGAGGTGCGTTTCGGAAAGACGTCAGGCCT
CTCGAGGGGGGGCCCGGATCCCCAGTAGATTTACGTTTAAACATTTTTATTTCCTTTTTA
ATTTAATTTAATTAACAGTTGGTGCTATGACACTTTACCTCATAGCTGGCATAATTCGCAA
TACTCTGGGTCTTCGAGAGGTATCCAACCTGAGTTGAAATACTTTACCATCGATTTAGCA
GTTGTATCAGTTATATTTATATTACCTTTAACTCTTCGCCATCCAGGAGTTTTACCGTACA
GATTAGAGGATAATAATAACACATAATTCTCGTAAGCAATATGAGATAATTTCCAAGACT
CTATATTAGCTCGTGATGTTTTCCAAGGTCTAAAATCGTCACGGTTCATATAATTAGCCA
ATCTCATATGCTCTCTAACTTCCGATGATAAGCTGTCAAACATGAGAATTAACGATCTGA
TAGAGAAGGGTTTGCTCGGGTCGGTGGCTCTGGTAACGACCAGTATCCCGATCCCGGC
TGGCCGTCCTGGCCGCCACATGAGGCATGTTCCGCGTCCTTGCAATACTGTGTTTACAT
ACAGTCTATCGCTTAGCGGAAAGTTCTTTTACCCTCAGCCGAAATGCCTGCCGTTGCTA
GACATTGCCAGCCAGTGCCCGTCACTCCCGTACTAACTGTCACGAACCCCTGCAATAAC
TGTCACGCCCCCCTGCAATAACTGTCACGAACCCCTGCAATAACTGTCACGCCCCCAAA
CCTGCAAACCCAGCAGGGGCGGGGGCTGGCGGGGTGTTGGAAAAATCCATCCATGAT
TATCTAAGAATAATCCACTAGGCGCGGTTATCAGCGCCCTTGTGGGGCGCTGCTGCCC
TTGCCCAATATGCCCGGCCAGAGGCCGGATAGCTGGTCTATTCGCTGCGCTAGGCTAC
ACACCGCCCCACCGCTGCGCGGCAGGGGGAAAGGCGGGCAAAGCCCGCTAAACCCC
ACACCAAACCCCGCAGAAATACGCTGGGAGCGCTTTTAGCCGCTTTAGCGGCCTTTCC
CCCTACCCGAAGGGTGGGGGCGCGTGTGCAGCCCCGCAGGGCCTGTCTCGGTCGATC
ATTCAGCCCGGCTCATCCTTCTGGCGTGGCGGCAGACCGAACAAGGCGCGGTCGTGG
TCGCGTTCAAGGTACGCATCCATTGCCGCCATGAGCCGATCCTCCGGCCACTCGCTGC
TGTTCACCTTGGCCAAAATCATGGCCCCCACCAGCACCTTGCGCCTTGTTTCGTTCTTG
CGCTATTGCTGCTGTTCCCTTGCCCGGCACCCGCTGAATTTCGGCATTGATTCGCGCTCG
TTGTTCTTCGAGCTTGGCCAGCCGATCCGCCGCCTTGTTGCTCCCCTTAACCATCTTGA
CACCCCATTGTTAATGTGCTGTCTCGTAGGCTATCATGGAGGCACAGCGGCGGCAATC
CCGACCCTACTTTGTAGGGGAGGGCCATTGCATGGAGCCGAAAAGCAAAAGCAACAGC
GAGGCAGCATGGCGATTTATCACCTTACGGCGAAAACCGGCAGCAGGTCGGGCGGCC
AATCGGCCAGGGCCAAGGCCGACTACATCCAGCGCGAAGGCAAGTATGCCCGCGACA
TGGATGAAGTCTTGCACGCCGAATCCGGGCACATGCCGGAGTTCGTCGAGCGGCCCG
CCGACTACTGGGATGCTGCCGACCTGTATGAACGCGCCAATGGGCGGCGTGTTCAAGGA
GGTCGAATTTGCCCTGCCGGTCGAGCTGACCCTCGACCAGCAGAAGGCGCTGGCGTC
CGAGTTCGCCCAGCACCTGACCGGTGCCGAGCGCCTGCCGTATACGCTGGCCATCCA
TGCCGGTGGCGGCGAGAACCCGCACTGCCACCTGATGATCTCCGAGCGGATCAATGA
CGGCATCGAGCGGCCCGCCGCTCAGTGGTTCAAGCGGTACAACGGCAAGACCCCGGA
GAAGGGCGGGGCACAGAAGACCGAAGCGCTCAAGCCCAAGGCATGGCTTGAGCAGAC
CCGCGAGGCATGGGCCGACCATGCCAACCGGGCATTAGAGCGGGCTGGCCACGACG
CCCGCATTGACCACAGAACACTTGAGGCGCAGGGCATCGAGCGCCTGCCCGGTGTTC
ACCTGGGGCCGAACGTGGTGGAGATGGAAGGCCGGGGCATCCGCACCGACCGGGCA
GACGTGGCCCTGAACATCGACACCGCCAACGCCCAGATCATCGACTTACAGGAATACC
GGGAGGCAATAGACCATGAACGCAATCGACAGAGTGAAGAAATCCAGAGGCATCAACG
AGTTAGCGGAGCAGATCGAACCGCTGGCCCAGAGCATGGCGACACTGGCCGACGAAG
CCCGGCAGGTCATGAGCCAGACCCAGCAGGCCCAGCGAGGCGCAGGCGGCGGAGTGG
CTGAAAGCCCAGCGCCAGACAGGGGCGGCATGGGTGGAGCTGGCCAAAGAGTTGCGG
GAGGTAGCCGCCGAGGTGAGCAGCGCCGCGCAGAGCGCCCGGAGCGCGTCGCGGG
GGTGGCACTGGAAGCTATGGCTAACCGTGATGCTGGCTTCCATGATGCCTACGGTGGT
GCTGCTGATCGCATCGTTGCTCTTGCTCGACCTGACGCCACTGACAACCGAGGACGGC
TCGATCTGGCTGCGCTTGGTGGCCCGATGAAGAACGACAGGACTTTGCAGGCCATAGG
CCGACAGCTCAAGGCCATGGGCTGTGAGCGCTTCGATATCGGCGTCAGGGACGCCAC
CACCGGCCAGATGATGAACCGGGAATGGTCAGCCGCCGAAGTGCTCCAGAACACGCC
ATGGCTCAAGCGGATGAATGCCCAGGGCAATGACGTGTATATCAGGCCCGCCGAGCAG
GAGCGGCATGGTCTGGTGCTGGTGGACGACCTCAGCGAGTTTGACCTGGATGACATGA
AAGCCGAGGGCCGGGAGCCTGCCCTGGTAGTGGAAACCAGCCCGAAGAACTATCAGG
CATGGGTCAAGGTGGCCGACGCCGCAGGCGGTGAACTTCGGGGGCAGATTGCCCGGA
CGCTGGCCAGCGAGTACGACGCCGACCCGGCCAGCGCCGACAGCCGCCACTATGGC
CGCTTGGCGGGCTTCACCAACCGCAAGGACAAGCACACCACCCGCGCCGGTTATCAG
CCGTGGGTGCTGCTGCGTGAATCCAAGGGCAAGACCGCCACCGCTGGCCCGGCGCTG
GTGCAGCAGGCTGGCCAGCAGATCGAGCAGGCCCAGCGGCAGCAGGAGAAGGCCCG
CAGGCTGGCCAGCCTCGAACTGCCCGAGCGGCAGCTTAGCCGCCACCGGCCACGG
CGCTGGACGAGTACCGCAGCGAGATGGCCGGGCTGGTCAAGCGCTTCGGTGATGACC
TCAGCAAGTGCGACTTTATCGCCCGCGCAGAAGCTGGCCAGCCGGGGCCGCAGTGCCG
AGGAAATCGGCAAGGCCATGGCCGAGGCCAGCCCAGCGCTGGCAGAGCGCAAGCCC
GGCCACGAAGCGGATTACATCGAGCGCACCGTCAGCAAGGTCATGGGTCTGCCCAGC
GTCCAGCTTGCGCGGGCCGAGCTGGCACGGGCACCGGCACCCCGCCAGCGAGGCAT
GGACAGGGGCGGGCCAGATTTCAGCATGTAGTGCTTGCGTTGGTACTCACGCCTGTTA
TACTATGAGTACTCACGCACAGAAGGGGGTTTTATGGAATACGAAAAAAGCGCTTCAGG
```

FIG. 11 (Continued)

```
GTCGGTCTACCTGATCAAAAGTGACAAGGGCTATTGGTTGCCCGGTGGCTTTGGTTATA
CGTCAAACAAGGCCGAGGCTGGCCGCTTTTCAGTCGCTGATATGGCCAGCCTTAACCT
TGACGGCTGCACCTTGTCCTTGTTCCGCGAAGACAAGCCTTTCGGCCCCGGCAAGTTT
CTCGGTGACTGATATGAAAGACCAAAAGGACAAGCAGACCGGCGACCTGCTGGCCAGC
CCTGACGCTGTACGCCAAGCGCGATATGCCGAGCGCATGAAGGCCAAGGGGATGCGT
CAGCGCAAGTTCTGGCTGACCGACGACGAATACGAGGCGCTGCGCGAGTGCCTGGAA
GAACTCAGAGCGGCGCAGGGCGGGGGTAGTGACCCCGCCAGCGCCTAACCACCAACT
GCCTGCAAAGGAGGCAATCAATGGCTACCCATAAGCCTATCAATATTCTGGAGGCGTTC
GCAGCAGCGCCGCCACCGCTGGACTACGTTTTGCCCAACATGGTGGCCGGTACGGTC
GGGGCGCTGGTGTCGCCCGGTGGTGCCGGTAAATCCATGCTGGCCCTGCAACTGGCC
GCACAGATTGCAGGCGGGCCGGATCTGCTGGAGGTGGGCGAACTGCCCACCGGCCC
GGTGATCTACCTGCCCGCCGAAGACCCGCCCACCGCCATTCATCACCGCCTGCACGCC
CTTGGGGCGCACCTCAGCGCCGAGGAACGGCAAGCCGTGGCTGACGGCCTGCTGATC
CAGCCGCTGATCGGCAGCCTGCCCAACATCATGGCCCCGGAGTGGTTCGACGGCCTC
AAGCGCGCCGCCGAGGGCCGCCGCCTGATGGTGCTGGACACGCTGCGCCGGTTCCA
CATCGAGGAAGAAAACGCCAGCGGCCCCATGGCCCAGGTCATCGGTCGCATGGAGGC
CATCGCCGCCGATACCGGGTGCTCTATCGTGTTCCTGCACCATGCCAGCAAGGGCGCG
GCCATGATGGGCGCAGGCGACCAGCAGCAGGCCAGCCGGGGCAGCTCGGTACTGGT
CGATAACATCCGCTGGCAGTCCTACCTGTCGAGCATGACCAGCGCCGAGGCCGAGGA
ATGGGGTGTGGACGACGACCAGCGCCGGTTCTTCGTCCGCTTCGGTGTGAGCAAGGC
CAACTATGGCGCACCGTTCGCTGATCGGTGGTTCAGGCGGCATGACGGCGGGGTGCT
CAAGCCCGCCGTGCTGGAGAGGCAGCGCAAGAGCAAGGGGGTGCCCCGTGGTGAAG
CCTAAGAACAAGCACAGCCTCAGCCACGTCCGGCACGACCCGGCCGCACTGTCTGGCC
CCCGGCCTGTTCCGTGCCCTCAAGCGGGGCGAGCGCAAGCGCAGCAAGCTGGACGTG
ACGTATGACTACGGCGACGGCAAGCGGATCGAGTTCAGCGGCCCCGGAGCCGCTGGGC
GCTGATGATCTGCGCATCCTGCAAGGGCTGGTGGCCATGGCTGGGCCTAATGGCCTAG
TGCTTGGCCCCGGAACCCAAGACCGAAGGCGGACGGCAGCTCCGGCTGTTCCTGGAAC
CCAAGTGGGAGGCCGTCACCGCTGATGCCATGGTGGTCAAAGGTAGCTATCGGGCGC
TGGCAAAGGAAATCGGGGCAGAGGTCGATAGTGGTGGGGCGCTCAAGCACATACAGG
ACTGCATCGAGCGCCTTTGGAAGGTATCCATCATCGCCCAGAATGGCCGCAAGCGGCA
GGGGTTTCGGCTGCTGTCGGAGTACGCCAGCGACGAGGCCGGACGGGCGCCTGTACGT
GGCCCTGAACCCCTTGATCGCGCAGGCCGTCATGGGTGGCGGCCAGCATGTGCGCAT
CAGCATGGACGAGGTGCGGGCGCTGGACAGCGAAACCGCCCGCCTGCTGCACCAGC
GGCTGTGTGGCTGGATCGACCCCGGCAAAACCGGCAAGGCTTCCATAGATACCTTGTG
CGGCTATGTCTGGCCGTCAGAGGCCAGTGGTTCGACCATGCGCAAGCGCCGCCAGCG
GGTGCGCGAGGCGTTGCCGGAGCTGGTCGCGCTGGGCTGGACGGTAACCGAGTTCG
CGGCGGGCAAGTACGACATCACCCGGCCCAAGGCGGCAGGCTGACCCCCCCCACTCT
ATTGTAAACAAGACATTTTTTATCTTTTATATTCAATGGCTTATTTTCCTGCTAATTGGTAA
TACCATGAAAAATACCATGCTCAGAAAAGGCTTAACAATATTTTGAAAAATTGCCTACTG
AGCGCTGCCGCACAGCTCCATAGGCCGCTTTCCTGGCTTTGCTTCCAGATGTATGCTCT
CCTCCGGAGAGTACCGTGACTTTATTTTCGGCACAAATACAGGGGTCGATGGATAAATA
CGGCGATAGTTTCCTGACGGATGATCCGTATGTACCGGCGGAAGACAAGCTGCAAACC
TGTCAGATGGAGATTGATTTAATGGCGGATGTGCTGAGAGCACCGCCCCGTGAATCCG
CAGAACTGATCCGCTATGTGTTTGCGGATGATTGGCCGGAATAAATAAAGCCGGGCTTA
ATACAGATTAAGCCCGTATAGGGTATTATTACTGAATACCAAACAGCTTACGGAGGACG
GAATGTTACCCATTGAGACAACCAGACTGCCTTCTGATTATTAATATTTTTCACTATTAAT
CAGAAGGAATAACCATGAATTTTACCCGGATTGACCTGAATACCTGGAATCGCAGGGAA
CACTTTGCCCTTTATCGTCAGCAGATTAAATGCGGATTCAGCCTGACCACCAAACTCGA
TATTACCGCTTTGCGTACCGCACTGGCGGAGACAGGTTATAAGTTTTATCCGCTGATGA
TTTACCTGATCTCCCGGGCTGTTAATCAGTTTCCGGAGTTCCGGATGGCACTGAAAGAC
AATGAACTTATTTACTGGGACCAGTCAGACCCGGTCTTTACTGTCTTTCATAAAGAAACC
GAAACATTCTCTGCACTGTCCTGCCGTTATTTTCCGGATCTCAGTGAGTTTATGGCAGG
TTATAATGCGGTAACGGCAGAATATCAGCATGATACCAGATTGTTTCCGCAGGGAAATT
TACCGGAGAATCACCTGAATATATCATCATTACCGTGGGTGAGTTTTGACGGGATTTAA
CCTGAACATCACCGGAAATGATGATTATTTTGCCCCGGTTTTTACGATGGCAAAGTTTCA
GCAGGAAGGTGACCGCGTATTATTACCTGTTTCTGTACAGGTTCATCATGCAGTCTGTG
ATGGCTTTCATGCAGCACGGTTATTAATACACTTCAGCTGATGTGTGATAACATACTGA
AATAAATTAATTAATTCTGTATTTAAGCCACCGTATCCGGCAGGAAGTGGTGGCTTTTTTTT
TATATTTTAACCGTAATCTGTAATTTCGTTTCAGACTGGTTCAGGATCACTGTACGATAAT
GCCCCCGCAGTTTGGTAATACCCTTAATAAAAAAGAAACAGCAAAGACTGACAGCAATA
ATAATAAAGTAAGCAGTAACAATAATATTAACAACACCAGATGCAGTTATAATAATAGTAT
TTAAGACACCAGAAAGACTGCTGCGACAGTCATTTTGAACAACACCAAAATGCCGTAAA
GGCAGTAGTAACAACACCAGTGAAAACATCACGATAGCATAGTGATATGCCTGAGTGTG
TGTAATTAAACAATAAATAAACCGCCATATATAACAGAAGATAGTATTCTGAATGGCATG
CTTTTCTGTTCAGTATAAACATATCATCCCGGTTGGTATAAGGATGATATATAATAAGTTA
AGCTGAACACATATTTATTTTGGTTTTATTTTACAAATAAAGTAAGACGATCCGTTAAGTC
AAAGCGGGGTATATTTATTATACCCTGCTTTTTTATTTGTCCGCCGGGCGCGGATAATG
GATCAGATTATGCAGTGTCACAATGGCCTTACCGGGATTGGCGTAAGCGTGCGGGATA
TCCGCATGGAAGCGCAGGGATTCCCCGGCAGAAACGGTGTGCCACTCATCCCCCAGC
CGCAGTTGTAATGCGCCTTCCAGTACAATGACATGTTCTCTGGTTCTGAAATCCATCCCT
GTCGGTGTTGCTTATGCAGTCTGGTCGGGACTCGGCGTCGTCATAATTACAGCCATTGC
CTGGTTGCTTCATGGGCAAAAGCTTTATGCTTGTAAACCGTTTTGTGAAAAAATTTTTAA
AATAAAAAAGGGGACCTCTAGGGTCCCCAATTAATTAGTAATATAATCTATTAAAGGTCA
TTCAAAAGGTCATCCACCG
```

FIG. 11 (Continued)

| 14 | 14 | pJFF224 (PpckA fdh C.b.) | CTAGTTCTAGAGCGGCCGCCACCGCGGTGGATCCCCAGTAGATTTACGTTTAAACATTT<br>TTATTTCCTTTTTAATTTAATTTAATTAACAGTTGGTGCTATGACACTTTACCTCATAGCTG<br>GCATAATTCGCAATACTCTGGGTCTTCGAGAGGTATCCAACCTGAGTTGAAATACTTTAC<br>CATCGATTTAGCAGTTGTATCAGTTATATTTATATTACCTTTAACTCTTCGCCATCCAGGA<br>GTTTTACCGTACAGATTAGAGGATAATAATAACACATAATTCTCGTAAGCAATATGAGAT<br>AATTTCCAAGACTCTATATTAGCTCGTGATGTTTTCCAAGGTCTAAAATCGTCACGGTTC<br>ATATAATTAGCCAATCTCATATGCTCTCTAACTTCCGATGATAAGCTGTCAAACATGAGA<br>ATTAACGATCTGATAGAGAAGGGTTTGCTCGGGTCGGTGGCTCTGGTAACGACCAGTAT<br>CCCGATCCCGGCTGGCCGTCCTGGCCGCCACATGAGGCATGTTCCGCGTCCTTGCAAT<br>ACTGTGTTTACATACAGTCTATCGCTTAGCGGAAAGTTCTTTTACCCTCAGCCGAAATGC<br>CTGCCGTTGCTAGACATTGCCAGCCAGTGCCCGTCACTCCCGTACTAACTGTCACGAA<br>CCCCTGCAATAACTGTCACGCCCCCTGCAATAACTGTCACGAACCCCTGCAATAACTG<br>TCACGCCCCCAAACCTGCAAACCCAGCAGGGGCGGGGGCTGGCGGGGTGTTGGAAAA<br>ATCCATCCATGATTATCTAAGAATAATCCACTAGGCGCGGTTATCAGCGCCCTTGTGGG<br>GCGCTGCTGCCCTTGCCCAATATGCCCGGCCAGAGGCCGGATAGCTGGTCTATTCGCT<br>GCGCTAGGCTACACACCGCCCCACCGCTGCGCGGCAGGGGGAAAGGCGGGCAAAGC<br>CCGCTAAACCCCACACCAAACCCCGCAGAAATACGCTGGGAGCGCTTTTAGCCGCTTT<br>AGCGGCCTTTCCCCCTACCCGAAGGGTGGGGGCGCGTGTGCAGCCCCGCAGGGCCT<br>GTCTCGGTCGATCATTCAGCCCGGCTCATCCTTCTGGCGTGGCGGCAGACCGAACAAG<br>GCGCGGTCGTGGTCGCGTTCAAGGTACGCATCCATTGCCGCCATGAGCCGATCCTCCG<br>GCCACTCGCTGCTGTTCACCTTGGCCAAAATCATGGCCCCCACCAGCACCTTGCGCCT<br>TGTTTCGTTCTTGCGCTATTGCTGCTGTTCCCTTGCCCGCACCCGCTGAATTTCGGCAT<br>TGATTCGCGCTCGTTGTTCTTCGAGCTTGGCCAGCCGATCCGCCGCCTTGTTGCTCCC<br>CTTAACCATCTTGACACCCCATTGTTAATGTGCTGTCTCGTAGGCTATCATGGAGGCAC<br>AGCGGCGGCAATCCCGACCCTACTTTGTAGGGGAGGGCCATTGCATGGAGCCGAAAA<br>GCAAAAGCAACAGCGAGGCAGCATGGCGATTTATCACCTTACGGCGAAAACCGGCAGC<br>AGGTCGGGCGGCCAATCGGCCAGGGCCAAGGCCGACTACATCCAGCGCGAAGGCAAG<br>TATGCCCGCGACATGGATGAAGTCTTGCACGCCGAATCCGGGCACATGCCGGAGTTCG<br>TCGAGCGGCCCGCCGACTACTGGGATGCTGCCGACCTGTATGAACGCGCCAATGGGC<br>GGCTGTTCAAGGAGGTCGAATTTGCCCTGCCGGTCGAGCTGACCCTCGACCAGCAGAA<br>GGCGCTGGCGTCCGAGTTCGCCCAGCACCTGACCGGTGCCGAGCGCCTGCCGTATAC<br>GCTGGCCATCCATGCCGGTGGCGGCGAGAACCCGCACTGCCACCTGATGATCTCCGA<br>GCGGATCAATGACGGCATCGAGCGGCCCGCCGCTCAGTGGTTCAAGCGGTACAACGG<br>CAAGACCCCGGAGAAGGGCGGGGCACAGAAGACCGAAGCGCTCAAGCCCAAGGCATG<br>GCTTGAGCAGACCCGCGAGGCATGGGCCGACCATGCCAACCGGGCATTAGAGCGGGC<br>TGGCCACGACGCCCGCATTGACCACAGAACACTTGAGGCGCAGGGCATCGAGCGCCT<br>GCCCGGTGTTCACCTGGGGCCGAACGTGGTGGAGATGGAAGGCCGGGGCATCCGCAC<br>CGACCGGGCAGACGTGGCCCTGAACATCGACACCGCCAACGCCCAGATCATCGACTTA<br>CAGGAATACCGGGAGGCAATAGACCATGAACGCAATCGACAGAGTGAAGAAATCCAGA<br>GGCATCAACGAGTTAGCGGAGCAGATCGAACCGCTGGCCCAGAGCATGGCGACACTG<br>GCCGACGAAGCCCGGCAGGTCATGAGCCAGACCCAGCAGGCCAGCGAGGCGCAGGC<br>GGCGGAGTGGCTGAAAGCCCAGCGCCAGACAGGGGCGGCATGGGTGGAGCTGGCCA<br>AAGAGTTGCGGGAGGTAGCCGCCGAGGTGAGCAGCGCCGCGCAGAGCGCCCGGAGC<br>GCGTCGCGGGGGTGGCACTGGAAGCTATGGCTAACCGTGATGCTGGCTTCCATGATG<br>CCTACGGTGGTGCTGCTGATCGCATCGTTGCTCTTGCTCGACCTGACGCCACTGACAA<br>CCGAGGACGGCTCGATCTGGCTGCGCTTGGTGGCCCGATGAAGAACGACAGGACTTT<br>GCAGGCCATAGGCCGACAGCTCAAGGCCATGGGCTGTGAGCGCTTCGATATCGGCGT<br>CAGGGACGCCACCACCGGCCAGATGATGAACCGGGAATGGTCAGCCGCCGAAGTGCT<br>CCAGAACACGCCATGGCTCAAGCGGATGAATGCCCAGGGCAATGACGTGTATATCAGG<br>CCCGCCGAGCAGGAGCGGCATGGTCTGGTGCTGGTGGACGACCTCAGCGAGTTTGAC<br>CTGGATGACATGAAAGCCGAGGGCCGGGAGCCTGCCCTGGTAGTGGAAACCAGCCCG<br>AAGAACTATCAGGCATGGGTCAAGGTGGCCGACGCCGCAGGCGGTGAACTTCGGGGG<br>CAGATTGCCCGGACGCTGGCCAGCGAGTACGACCCGACCCGGCCAGCGCCGACAG<br>CCGCCACTATGGCCGCTTGGCGGGCTTCACCAACCGCAAGCTGGCACGGACAAGCACACCACCCG<br>CGCCGGTTATCAGCCGTGGGTGCTGCTGCGTGAATCCAAGGGCAAGACCGCCACCGC<br>TGGCCCGGCGCTGGTGCAGCAGGCTGGCCAGCAGATCGAGCAGGCCCAGCGGCAGC<br>AGGAGAAGGCCCGCAGGCTGGCCAGCCTCGAACTGCCCGAGCGGCAGCTTAGCCGCC<br>ACCGGCGCACGGCGCTGGACGAGTACCGCAGCGAGATGGCCGGGCTGGTCAAGCGC<br>TTCGGTGATGACCTCAGCAAGTGCGACTTTATCGCCGCGCAGAAGCTGGCCAGCCGGG<br>GCCGCAGTGCCGAGGAAATCGGCAAGGCCATGGCCGAGGCCAGCCCAGCGCTGGCA<br>GAGCGCAAGCCCGGCCACGAAGCGGATTACATCGAGCGCACCGTCAGCAAGGTCATG<br>GGTCTGCCCAGCGTCCAGCTTGCGCGGGCCGAGCTGGCACGGGCACCGGCACCCCG<br>CCAGCGAGGCATGGACAGGGGCGGGCCAGATTTCAGCATGTAGTGCTTGCGTTGGTA<br>CTCACGCCTGTTATACTATGAGTACTCACGCACAGAAGGGGGTTTTATGGAATACGAAA<br>AAAGCGCTTCAGGGTCGGTCTACCTGATCAAAAGTGACAAGGGCTATTGGTTGCCCGG<br>TGGCTTTGGTTATACGTCAAACAAGGCCGAGGCTGGCCGCTTTTCAGTCGCTGATATGG<br>CCAGCCTTAACCTTGACGGCTGCACCTTGTCCTTGTTCCGCGAAGACAAGCCTTTCGGC<br>CCCGGCAAGTTTCTCGGTGACTGATATGAAGACCAAAAGGACAAGCAGACCGGCGAC<br>CTGCTGGCCAGCCCTGACGCTGTACGCCAAGCGCGATATGCCGAGCGCATGAAGGCC<br>AAAGGGGATGCGTCAGCGCAAGTTCTGGCTGACCGACGACGAATACGAGGCGCTGCGC<br>GAGTGCCTGGAAGAACTCAGAGCGGCGCAGGGCGGGGGTAGTGACCCCGCCAGCGC<br>CTAACCACCAACTGCCTGCAAAGGAGGCAATCAATGGCTACCCATAAGCCTATCAATAT<br>TCTGGAGGCGTTCGCAGCAGCGCCGCCACCGCTGGACTACGTTTTGCCCAACATGGTG<br>GCCGGTACGGTCGGGGCGCTGGTGTCGCCCGGTGGTGCCGGTAAATCCATGCTGGCC |

FIG. 11 (Continued)

```
CTGCAACTGGCCGCACAGATTGCAGGCGGGCCGGATCTGCTGGAGGTGGGCGAACTG
CCCACCGGCCCGGTGATCTACCTGCCCGCCGAAGACCCGCCCACCGCCATTCATCAC
CGCCTGCACGCCCTTGGGGCGCACCTCAGCGCCGAGGAACGGCAAGCCGTGGCTGAC
GGCCTGCTGATCCAGCCGCTGATCGGCAGCCTGCCCAACATCATGGCCCCGGAGTGG
TTCGACGGCCTCAAGCGCGCCGCCGAGGGCCGCCGCCTGATGGTGCTGGACACGCTG
CGCCGGTTCCACATCGAGGAAGAAACGCCAGCGGCCCCATGGCCCAGGTCATCGGT
CGCATGGAGGCCATCGCCGCCGATACCGGGTGCTCTATCGTGTTCCTGCACCATGCCA
GCAAGGGCGCGGCCATGATGGGCGCAGGCGACCAGCAGCAGGCCAGCCGGGGCAGC
TCGGTACTGGTCGATAACATCCGCTGGCAGTCCTACCTGTCGAGCATGACCAGCGCCG
AGGCCGAGGAATGGGGTGTGGACGACGACCAGCGCCGGTTCTTCGTCCGCTTCGGTG
TGAGCAAGGCCAACTATGGCGCACCGTTCGCTGATCGGTGGTTCAGGCGGCATGACG
GCGGGGTGCTCAAGCCCGCCGTGCTGGAGAGGCAGCGCAAGAGCAAGGGGGTGCCC
CGTGGTGAAGCCTAAGAACAAGCACAGCCTCAGCCACGTCCGGCACGACCCGGCGCA
CTGTCTGGCCCCCGGCCTGTTCCGTGCCCTCAAGCGGGGCGAGCGCAAGCGCAGCAA
GCTGGACGTGACGTATGACTACGGCGACGGCAAGCGGATCGAGTTCAGCGGCCCGGA
GCCGCTGGGCGCTGATGATCTGCGCATCCTGCAAGGGCTGGTGGCCATGGCTGGGCC
TAATGGCCTAGTGCTTGGCCCGGAACCCAAGACCGAAGGCGGACGGCAGCTCCGGCT
GTTCCTGGAACCCAAGTGGGAGGCCGTCACCGCTGATGCCATGGTGGTCAAAGGTAGC
TATCGGGCGCTGGCAAAGGAAATCGGGGCAGAGGTCGATAGTGGTGGGGCGCTCAAG
CACATACAGGACTGCATCGAGCGCCTTTGGAAGGTATCCATCATCGCCCAGAATGGCC
GCAAGCGGCAGGGGTTTCGGCTGCTGTCGGAGTACGCCAGCGACGAGGCGGACGGG
CGCCTGTACGTGGCCCTGAACCCCTTGATCGCGCAGGCCGTCATGGGTGGCGGCCAG
CATGTGCGCATCAGCATGGACGAGGTGCGGGCGCTGGACAGCGAAACCGCCCGCCTG
CTGCACCAGCGGCTGTGTGGCTGGATCGACCCCGGCAAAACCGGCAAGGCTTCCATA
GATACCTTGTGCGGCTATGTCTGGCCGTCAGAGGCCAGTGGTTCGACCATGCGCAAGC
GCCGCCAGCGGGTGCGCGAGGCGTTGCCGGAGCTGGTCGCGCGCTGGGCTGGACGGTA
ACCGAGTTCGCGGCGGGCAAGTACGACATCACCCGGCCCAAGGCGGCAGGCTGACCC
CCCCCACTCTATTGTAAACAAGACATTTTTTATCTTTTATATTCAATGGCTTATTTTCCTG
CTAATTGGTAATACCATGAAAAATACCATGCTCAGAAAAGGCTTAACAATATTTTGAAAA
ATTGCCTACTGAGCGCTGCCGCACAGCTCCATAGGCCGCTTTCCTGGCTTTGCTTCCA
GATGTATGCTCTCCTCCGGAGAGTACCGTGACTTTATTTTCGGCACAAATACAGGGGTC
GATGGATAAATACGGCGATAGTTTCCTGACGGATGATCCGTATGTACCGGCGGAAGAC
AAGCTGCAAACCTGTCAGATGGAGATTGATTTAATGGCGGATGTGCTGAGAGCACCGC
CCCGTGAATCCGCAGAACTGATCCGCTATGTGTTTGCGGATGATTGGCCGGAATAAATA
AAGCCGGGCTTAATACAGATTAAGCCCGTATAGGGTATTATTACTGAATACCAAACAGC
TTACGGAGGACGGAATGTTACCCATTGAGACAACCAGACTGCCTTCTGATTATTAATATT
TTTCACTATTAATCAGAAGGAATAACCATGAATTTTACCCGGATTGACCTGAATACCTGG
AATCGCAGGGAACACTTTGCCCTTTATCGTCAGCAGATTAAATGCGGATTCAGCCTGAC
CACCAAACTCGATATTACCGCTTTGCGTACCGCACTGGCGGAGACAGGTTATAAGTTTT
ATCCGCTGATGATTTACCTGATCTCCCGGGCTGTTAATCAGTTTCCGGAGTTCCGGATG
GCACTGAAAGACAATGAACTTATTTACTGGGACCAGTCAGACCCGGTCTTTACTGTCTTT
CATAAAGAAACCGAAACATTCTCTGCACTGTCCTGCCGTTATTTTCCGGATCTCAGTGA
GTTTATGGCAGGTTATAATGCGGTAACGGCAGAATATCAGCATGATACCAGATTGTTTC
CGCAGGGAAATTTACCGGAGAATCACCTGAATATATCATCATTACCGTGGGTGAGTTTT
GACGGGATTTAACCTGAACATCACCGGAAATGATGATTTTTGCCCCGGTTTTTACGAT
GGCAAAGTTTCAGCAGGAAGGTGACCGCGTATTATTACCTGTTTCTGTACAGGTTCATC
ATGCAGTCTGTGATGGCTTTCATGCAGCACGGTTTATTAATACACTTCAGCTGATGTGTG
ATAACATACTGAAATAAATTAATTAATTCTGTATTTAAGCCACCGTATCCGGCAGGAATG
GTGGCTTTTTTTTTATATTTTAACCGTAATCTGTAATTTCGTTTCAGACTGGTTCAGGATC
ACTGTACGATAATGCCCCCGCAGTTTGGTAATACCCTTAATAAAAAAGAAACAGCAAAG
ACTGACAGCAATAATAATAAAGTAAGCAGTAACAATAATATTAACAACACCAGATGCAGT
TATAATAATAGTATTTAAGACACCAGAAAGACTGCTGCGACAGTCATTTTGAACAACACC
AAAATGCCGTAAAGGCAGTAGTAACAACACCAGTGAAAACATCACGATAGCATAGTGAT
ATGCCTGAGTGTGTGTAATTAAACAATAAATAAACCGCCATATATAACAGAAGATAGTAT
TCTGAATGGCATGCTTTTCTGTTCAGTATAAACATATCATCCCGGTTGGTATAAGGATGA
TATATAATAAGTTAAGCTGAACACATATTTATTTTGGTTTTATTTTACAAATAAAGTAAGAC
GATCCGTTAAGTCAAAGCGGGGTATATTTATTTATACCCTGCTTTTTTATTTGTCCGCCGG
GCGCGGATAATGGATCAGATTATGCAGTGTCACAATGGCCTTACCGGGATTGGCGTAA
GCGTGCGGGATATCCGCATGGAAGCGCAGGGATTCCCCGGCAGAAACGGTGTGCCAC
TCATCCCCCAGCCGCAGTTGTAATGCGCCTTCCAGTACAATGACATGTTCTCTGGTTCT
GAAATCCATCCCTGTCGGTGTTGCTTATGCAGTCTGGTCGGGACTCGGCGTCGTCATAA
TTACAGCCATTGCCTGGTTGCTTCATGGGCAAAAGCTTTATGCTTGTAAACCGTTTTGTG
AAAAAATTTTTAAAATAAAAAAGGGGACCTCTAGGGTCCCCAATTAATTAGTAATATAATC
TATTAAAGGTCATTCAAAAGGTCATCCACCGGGGGCCCCCCCTCGAGAGGCCTGACGT
CGGGCCCGGTACCACGCGTTTATTTCTTATCGTGTTTACCGTAAGCTTTAGTAACGTATT
CACCATTTAATAAGATAATATCTTGTGGTCTGTAATCAAATTTACCAGTAAAGAATGATTC
CAAGATATTTTTAGTACCTTCAGCGTATCTTGTTGAGCATCTAAAGTAGTACCAGAGTA
GTGAGGAGTCATGGCATTACCAGCACCATATTTATTTCTCATATCTCTCCATGGGTGATC
CTTTGGAGCTGGTTGTGGGAACCAAACATCACCACCGTAACCTCTTAATTGACCAGATT
CTAAAGCTGCTGCAACATCTTCAGCAACACAAATAGCACCTCTTGCGGTATTGACTAAC
CAAGCACCTTTTTTAAATTTAGATAATAATTCCTTATTAATTAAACCTTTTGTACCTGCGT
GTAATGGAGCATTAACTGTAACGATATCAGCTTGAGCAACTAATTCTTCAATATTTTCAA
CTCTTCTAGCACCAACTTTTTCTTCAGCTTCTTTTGGTAAAGCTTGATAATCGTAGTATAA
TAATTCTTTTGGATTAAAAGGGAGTAATCTTTCCAAGACTCTGTAACCAATTCTACCAGC
```

FIG. 11 (Continued)

| | | | |
|---|---|---|---|
| | | | ACCAATGGTAGCAATAGTTTTACCTTCGATATCGTAAGCATCCTTAGCGATAGCAGCAAC CTCCCAATCGTGGTTAATAATTTGTTCATGTGCTGGAACGAAATTTCTAACCAAGACAAG CATGGTCATGACAACGTGTTCAGCAACAGAGACAACATTAGAACCTGTAACTTCCAAGA CTGAGATTTTCTTACCTGTTTGATTAATATAATCTAAATCAATGTGATCAGAACCAACACC AGCGACAACGACTAATTTTAAGTTCTTAGCCTTGTCAAGTCTTTCCTTAGTGATATAAGC AGGATGGAAAGGAGTGGTGATGATAATATCAGCATCTGGGATATGTTTATCCAATTCAC TTGTTTCACCTTCTTTATCAGAAGTAGTAATTAGTTCATGACCTTGATCTTTTAACCAATT AGCAATACCTAATTTATTTTCAGTACAACCATATAATTTTTCTTCATCAGCAGCGTGCTTA CCAGCATCATATAAGACTAAAACGATCTTCATACATCACCTCATAAAATAAATTAAAAAAT AATAAAAACTAATGTTTCGCATTATAGGACAAAAGATACCTAAAAAATGTTATCTAGATCA AATTATTGGAAAATATATGAAAATAATTTTTGTTTAAAAAAGCGAACGACATTAGTATTTTTC ATAAAAATACGTACATTGTTATCCGTCGCTATTTAA |
| 15 | 14a | pJFF224 PEFTU Glyoxylate operon Yersinia molaretii | GATCCCCAGTAGATTTACGTTTAAACATTTTTATTTCCTTTTTAATTTAATTTAATTAACAG TTGGTGCTATGACACTTTACCTCATAGCTGGCATAATTCGCAATACTCTGGGTCTTCGAG AGGTATCCAACCTGAGTTGAAATACTTTACCATCGATTTAGCAGTTGTATCAGTTATATTT ATATTACCTTTAACTCTTCGCCATCCAGGAGTTTTACCGTACAGATTAGAGGATAATAAT AACACATAATTCTCGTAAGCAATATGAGATAATTTCCAAGACTCTATATTAGCTCGTGAT GTTTTCCAAGGTCTAAAATCGTCACGGTTCATATAATTAGCCAATCTCATATGCTCTCTA ACTTCCGATGATAAGCTGTCAAACATGAGAATTAACGATCTGATAGAGAAGGGTTTGCT CGGGTCGGTGGCTCTGGTAACGACCAGTATCCCGATCCCGGCTGGCCGTCCTGGCCG CCACATGAGGCATGTTCCGCGTCCTTGCAATACTGTGTTTACATACAGTCTATCGCTTA GCGGAAAGTTCTTTTACCCTCAGCCGAAATGCCTGCCGTTGCTAGACATTGCCAGCCAG TGCCCGTCACTCCCGTACTAACTGTCACGAACCCCTGCAATAACTGTCACGCCCCCTG CAATAACTGTCACGAACCCCTGCAATAACTGTCACGCCCCCAAACCTGCAAACCCAGCA GGGGCGGGGGCTGGCGGGGTGTTGGAAAAATCCATCCATGATTATCTAAGAATAATCC ACTAGGCGCGGTTATCAGCGCCCTTGTGGGCGCTGCTGCCCTTGCCCAATATGCCCG GCCAGAGGCCGGATAGCTGGTCTATTCGCTGCGCTAGGCTACACACCGCCCCACCGCT GCGCGGCAGGGGGAAAGGCGGGCAAAGCCCGCTAAACCCCACACCAAACCCCGCAGA AATACGCTGGGAGCGCTTTTAGCCGCTTTAGCGGCCTTTCCCCCTACCCGAAGGGTGG GGGCGCGTGTGCAGCCCCGCAGGGCCTGTCTCGGTCGATCATTCAGCCCGGCTCATC CTTCTGGCGTGGCGGCAGACCGAACAAGGCGCGGTCGTGGTCGCGTTCAAGGTACGC ATCCATTGCCGCCATGAGCCGATCCTCCGGCCACTCGCTGCTGTTCACCTTGGCCAAA ATCATGGCCCCCACCAGCACCTTGCGCCTTGTTTCGTTCTTGCGCTATTGCTGCTGTTC CCTTGCCCGCACCCGCTGAATTTCGGCATTGATTCGCGCTCGTTGTTCTTCGAGCTTGG CCAGCCGATCCGCCGCCTTGTTGCTCCCCTTAACCATCTTGACACCCCATTGTTAATGT GCTGTCTCGTAGGCTATCATGGAGGCACAGCGGCGGCAATCCCGACCCTACTTTGTAG GGGAGGGCCATTGCATGGAGCCGAAAAGCAAAGCAACAGCGAGGCAGCATGGCGAT TTATCACCTTACGGCGAAAACCGGCAGCAGGTCGGGCGGCCAATCGGCCAGGGCCAA GGCCGACTACATCCAGCGCGAAGGCAAGTATGCCCGCGACATGGATGAAGTCTTGCAC GCCGAATCCGGGCACATGCCGGAGTTCGTCGAGCGGCCCGCCGACTACTGGGATGCT GCCGACCTGTATGAACGCGCCAATGGCGGCTGTCAAGGAGGTCGAATTTGCCCTGC CGGTCGAGCTGACCCTCGACCAGCAGAAGGCGCTGGCGTCCGAGTTCGCCCAGCACC TGACCGGTGCCGAGCGCCTGCCGTATACGCTGGCCATCCATGCCGGTGGCGGCGAGA ACCCGCACTGCCACCTGATGATCTCCGAGCGGATCAATGACGGGCATCGAGCGGCCCG CCGCTCAGTGGTTCAAGCGGTACAACGGCCAAGACCCCGGAGAAGGGCGGGGCACAGA AGACCGAAGCGCTCAAGCCCAAGGCATGGCTTGAGCAGACCCGCGGAGGCATGGGCCG ACCATGCCAACCGGGCATTAGAGCGGGCTGGCCACGACGCCCGCATTGACCACAGAA CACTTGAGGCGCAGGGCATCGAGCGCCTGCCCGGTGTTCACCTGGGGCCGAACGTGG TGGAGATGGAAGGCCGGGCGCATCCGCACCGACCGGGCAGACGTGGCCCTGAACATCG ACACCGCCAACGCCCAGATCATCGACTTACAGGAATACCGGGAGGCAATAGACCATGA ACGCAATCGACAGAGTGAAGAAATCCAGAGGCATCAACGAGTTAGCGGAGCAGATCGA ACCGCTGGCCCAGAGCATGGCGACACTGGCCGACGAAGCCCGGCAGGTCATGAGCCA GACCCAGCAGGCCAGCGAGGCGCAGGCGGCGGAGTGGCTGAAAGCCCAGCGCGCAGA CAGGGGCGGCATGGGTGGAGCTGGCCAAAGAGTTGCGGGAGGTAGCCGCCGAGGTG AGCAGCGCCGCGCAGAGCGCCCGGAGCGCGTCGCGGGGGTGGCACTGGAAGCTATG GCTAACCGTGATGCTGGCTTCCATGATGCCTACGGTGGTGCTGCTGATCGCATCGTTG CTCTTGCTCGACCTGACGCCACTGACAACCGAGGACGGCTCGATCTGGCTGCGCTTGG TGGCCCGATGAAGAATCGACAGGACTTTGCAGGCCATAGGCCGACAGCTCAAGGCCATG GGCTGTGAGCGCTTCGATATCGGCGTCAGGGACGCCACCACCGGCCAGATGATGAAC CGGGAATGGTCAGCCGCCGAAGTGCTCCAGAACACGCCATGGCTCAAGCGGATGAAT GCCCAGGGCAATGACGTGTATATCAGGCCCGCCGAGCAGGAGCGGCATGGTCTGGTG CTGGTGGACGACCTCAGCGAGTTTGACCTGGATGACATGAAAGCCGAGGGCCGGGAG CCTGCCCTGGTAGTGGAAACCAGCCCGAAGAACTATCAGGCATGGGTCAAGGTGGCC GACGCCGCAGGCGGTGAACTTCGGGGCAGATTGCCCGGACGCTGGCCAGCGAGTAC GACGCCGACCCGGCCAGCGCCGACAGCCGCCACTATGGCCGCTTGGCGGGCTTCACC AACCGCAAGGACAAGCACACCACCCGCGCCGGTTATCGACCCTGGGTGCTGCTGCGT GAATCCAAGGGCAAGACCGCCACCGCTGGCCCGGCGCTGGTGCAGCAGGCTGGCCA GCAGATCGAGCAGGCCCAGCGGCAGCAGGAGAAGGCCCGCAGGCTGGCCAGCCTCG AACTGCCCGAGCGGCAGCTTAGCCGCCACCGGCGCACGGCGCTGGACGAGTACCGCA GCGAGATGGCCGGGCTGGTCAAGCGCTTCGGTGATGACCTCAGCAAGTGCGACTTTAT CGCCGCGCAGAAGCTGGCCAGCCGGGCCGCAGTGCCGAGGAAATCGGCAAGGCCA TGGCCGAGGCCAGCCCAGCGCTGGCAGAGCGCAAGCCCGGCCACGAAGCGGATTACA TCGAGCGCACCGTCAGCAAGGTCATGGGTCTGCCCAGCGTCCAGCTTGCGCGGGCCG AGCTGGCACGGGCACCGGCACCCCGCCAGCGAGGCATGGACAGGGGCGGGCCAGAT |

FIG. 11 (Continued)

```
TTCAGCATGTAGTGCTTGCGTTGGTACTCACGCCTGTTATACTATGAGTACTCACGCAC
AGAAGGGGGTTTTATGGAATACGAAAAAAGCGCTTCAGGGTCGGTCTACCTGATCAAAA
GTGACAAGGGCTATTGGTTGCCCGGTGGCTTTGGTTATACGTCAAACAAGGCCGAGGC
TGGCCGCTTTTCAGTCGCTGATATGGCCAGCCTTAACCTTGACGGCTGCACCTTGTCCT
TGTTCCGCGAAGACAAGCCTTTCGGCCCCGGCAAGTTTCTCGGTGACTGATATGAAAG
ACCAAAAGGACAAGCAGACCGGCGACCTGCTGGCCAGCCCTGACGCTGTACGCCAAG
CGCGATATGCCGAGCGCATGAAGGCCAAAGGGATGCGTCAGCGCAAGTTCTGGCTGA
CCGACGACGAATACGAGGCGCTGCGCGAGTGCCTGGAAGAACTCAGAGCGGCGCAGG
GCGGGGGTAGTGACCCCGCCAGCGCCTAACCACCAACTGCCTGCAAAGGAGGCAATC
AATGGCTACCCATAAGCCTATCAATATTCTGGAGGCGTTCGCAGCAGCGCCGCCACCG
CTGGACTACGTTTTGCCCAACATGGTGGCCGGTACGGTCGGGGCGCTGGTGTCGCCC
GGTGGTGCCGGTAAATCCATGCTGGCCCTGCAACTGGCCGCACAGATTGCAGGCGGG
CCGGATCTGCTGGAGGTGGGCGAACTGCCCACCGGCCCGGTGATCTACCTGCCCGCC
GAAGACCCGCCCACCGCCATTCATCACCGCCTGCACGCCCTTGGGGCGCACCTCAGC
GCCGAGGAACGGCAAGCCGTGGCTGACGGCCTGCTGATCCAGCCGCTGATCGGCAGC
CTGCCCAACATCATGGCCCCGGAGTGGTTCGACGGCCTCAAGCGCGCCGCCGAGGGC
CGCCGCCTGATGGTGCTGGACACGCTGCGCCGGTTCCACATCGAGGAAGAAAACGCC
AGCGGCCCCATGGCCCAGGTCATCGGTCGCATGGAGGCCATCGCCGCCGATACCGGG
TGCTCTATCGTGTTCCTGCACCATGCCAGCAAGGGCGCGGCCATGATGGGCGCAGGC
GACCAGCAGCAGGCCAGCCGGGGCAGCTCGGTACTGGTCGATAACATCCGCTGGCAG
TCCTACCTGTCGAGCATGACCAGCGCCGAGGCCGAGGAATGGGGTGTGGACGACGAC
CAGCGCCGGTTCTTCGTCCGCTTCGGTGTGAGCAAGGCCAACTATGGCGCACCGTTCG
CTGATCGGTGGTTCAGGCGGCATGACGGCGGGGTGCTCAAGCCCGCCGTGCTGGAGA
GGCAGCGCAAGAGCAAGGGGGTGCCCCGTGGTGAAGCCTAAGAACAAGCACAGCCTC
AGCCACGTCCGGCACGACCCGGCGCACTGTCTGGCCCCCGGCCTGTTCCGTGCCCTC
AAGCGGGGCGAGCGCAAGCGCAGCAAGCTGGACGTGACGTATGACTACGGCGACGGC
AAGCGGATCGAGTTCAGCGGCCCGGAGCCGCTGGGCGCTGATGATCTGCGCATCCTG
CAAGGGCTGGTGGCCATGGCTGGGCCTAATGGCCTAGTGCTTGGCCCGGAACCCAAG
ACCGAAGGCGGACGGCAGCTCCGGCTGTTCCTGGAACCCAAGTGGGAGGCCGTCACC
GCTGATGCCATGGTGGTCAAAGGTAGCTATCGGGCGCTGGCAAAGGAAATCGGGGCA
GAGGTCGATAGTGGTGGGGCGCTCAAGCACATACAGGACTGCATCGAGCGCCTTTGGA
AGGTATCCATCATCGCCCAGAATGGCCGCAAGCGGCAGGGGTTTCGGCTGCTGTCGG
AGTACGCCAGCGACGAGGCGGACGGGCCGCCTGTACGTGGCCCTGAACCCCTTGATCG
CGCAGGCCGTCATGGGTGGCGGCCAGCATGTGCGCATCAGCATGGACGAGGTGCGG
GCGCTGGACAGCGAAACCGCCCGCCTGCTGCACCAGCGGCTGTGTGGCTGGATCGAC
CCCGGCAAAACCGGCAAGGCTTCCATAGATACCTTGTGCGGCTATGTCTGGCCGTCAG
AGGCCAGTGGTTCGACCATGCGCAAGCGCCGCCAGCGGGTGCGCGAGGCGTTGCCG
GAGCTGGTCGCGCTGGGCTGGACGGTAACCGAGTTCGCGGCGGGCAAGTACGACATC
ACCCGGCCCAAGGCGGCAGGCTGACCCCCCCCACTCTATTGTAAACAAGACATTTTTTA
TCTTTTATATTCAATGGCTTATTTTCCTGCTAATTGGTAATACCATGAAAAATACCATGCT
CAGAAAAGGCTTAACAATATTTTGAAAAATTGCCTACTGAGCGCTGCCGCACAGCTCCA
TAGGCCGCTTCCTGGCTTTGCTTCCAGATGTATGCTCTCCTCCGGAGAGTACCGTGAC
TTTATTTTCGGCACAAATACAGGGGTCGATGGATAAATACGGCGATAGTTTCCTGACGG
ATGATCCGTATGTACCGGCGGAAGACAAGCTGCAAACCTGTCAGATGGAGATTGATTTA
ATGGCGGATGTGCTGAGAGCACCGCCCCGTGAATCCGCAGAACTGATCCGCTATGTGT
TTGCGGATGATTGGCCGGAATAAATAAAGCCGGGCTTAATACAGATTAAGCCCGTATAG
GGTATTATTACTGAATACCAAACAGCTTACGGAGGACGGAATGTTACCCATTGAGACAA
CCAGACTGCCTTCTGATTATTAATATTTTTCACTATTAATCAGAAGGAATAACCATGAATT
TTACCCGGATTGACCTGAATACCTGGAATCGCAGGGAACACTTTGCCCTTTATCGTCAG
CAGATTAAATGCGGATTCAGCCTGACCACCAAACTCGATATTACCGCTTTGCGTACCGC
ACTGGCGGAGACAGGTTATAAGTTTTATCCGCTGATGATTTACCTGATCTCCCGGGCTG
TTAATCAGTTTCCGGAGTTCCGGATGGCACTGAAAGACAATGAACTTATTTACTGGGAC
CAGTCAGACCCGGTCTTTACTGTCTTTCATAAAGAAACCGAAACATTCTCTGCACTGTCC
TGCCGTTATTTTCCGGATCTCAGTGAGTTTATGGCAGGTTATAATGCGGTAACGGCAGA
ATATCAGCATGATACCAGATTGTTTCCGCAGGGAAATTTACCGGAGAATCACCTGAATAT
ATCATCATTACCGTGGGTGAGTTTTGACGGGATTTAACCTGAACATCACCGGAAATGAT
GATTATTTTGCCCCGGTTTTTACGATGGCAAAGTTTCAGCAGGAAGGTGACCGCGTATT
ATTACCTGTTTCTGTACAGGTTCATCATGCAGTCTGTGATGGCTTTCATGCAGCACGGTT
TATTAATACACTTCAGCTGATGTGTGATAACATACTGAAATAAATTAATTAATTCTGTATTT
AAGCCACCGTATCCGGCAGGAATGGTGGCTTTTTTTTTATATTTTAACCGTAATCTGTAA
TTTCGTTTCAGACTGGTTCAGGATCACTGTACGATAATGCCCCCGCAGTTTGGTAATAC
CCTTAATAAAAAAGAAACAGCAAAGACTGACAGCAATAATAATAAAGTAAGCAGTAACAA
TAATATTAACAACACCAGATGCAGTTATAATAATAGTATTTAAGCACCAGAAAGACTGC
TGCGACAGTCATTTTGAACAACACCAAAATGCCGTAAAGGCAGTAGTAACAACACCAGT
GAAAACATCACGATAGCATAGTGATATGCCTGAGTGTGTGTAATTAAACAATAAATAAAC
CGCCATATATAACAGAAGATAGTATTCTGAATGGCATGCTTTTCTGTTCAGTATAAACAT
ATCATCCCGGTTGGTATAAGGATGATATATAATAAGTTAAGCTGAACACATATTTATTTTG
GTTTTATTTTACAAATAAAGTAAGACGATCCGTTAAGTCAAAGCGGGGTATATTTATTATA
CCCTGCTTTTTTATTTGTCCGCCGGGCGCGGATAATGGATCAGATTATGCAGTGTCACA
ATGGCCTTACCGGGATTGGCGTAAGCGTGCGGGATATCCGCATGGAAGCGCAGGGATT
CCCCGGCAGAAACGGTGTGCCACTCATCCCCCAGCCGCAGTTGTAATGCGCCTTCCAG
TACAATGACATGTTCTCTGGTTCTGAAATCCATCCCTGTCGGTGTTGCTTATGCAGTCTG
GTCGGGACTCGGCGTCGTCATAATTACAGCCATTGCCTGGTTGCTTCATGGGCAAAAG
CTTTATGCTTGTAAACCGTTTTGTGAAAAAATTTTTAAAATAAAAAAGGGGACCTCTAGG
```

FIG. 11 (Continued)

| | | | |
|---|---|---|---|
| | | | GTCCCCAATTAATTAGTAATATAATCTATTAAAGGTCATTCAAAAGGTCATCCACCGGAT<br>CCGGGCCCCCCCTCGAGGTCGACGGTATCGATAAGCTTGATATCGAATTCCCATATTGT<br>GCATCGAATCCCTGCAAAATTGTCTGAGCGATTAATTGTTCTAATTTTACCGCCATGCTC<br>ACCCCCCGCCATACGGAACAGAGCCTGCATCAGCAGGCTCCAGATAAAACATAAACTC<br>ATTAATCAGTGGCTTAGAACTGCTGCTCTTCCGTCGAGCCCAGTCAGTGCAGTGACTGAT<br>GACTCGCCGCCCTGAATGATATTGGTGACTTTATCAAAATAGCCCGTGCCCACTTCTTG<br>TTGATGGGAAGCAAAGGTGTAGCCGCGTTCAACGGAGGCAAATTCTGGCTGCTGCACT<br>TTCTCAACATAGTGCTTCATGCCCTCGCCTTGCGCGTAAGCATGGGCCAAGTCGAACAT<br>GTTGAACCACATACTGTGGATGCCCGCCAAGGTAATAAATTGATATTTGTAGCCCATCG<br>CGGAGAGGTCATCTTGGAAGCTGGCGATCTGCTGGTCAGTCAGGTTCTTTTTCCAGTTA<br>AATGATGGCGAACAGTTATAAGCCAATAATTTACCGGGGAATTTAGCGTGAACCGCATC<br>TGCAAAGCGTTTAGCCAGCGCCAGATCTGGCGTCGAGGTTTCACACCACACCAAGTCG<br>GCGTAAGGGGCATAGGCCAGACCACGGCTGATGGCTTGCTCAATGCCCGCGTGAGTG<br>CGGAAGAAGCCCTCAGCAGTACGATCACCAGCAATAAATTCGCTGTCATAAGGGTCGC<br>AATCAGAGGTCAGCAAATCCGCAGCATCAGCATCAGTGCGCGCAATCAGCAGTGTTGG<br>CACGCCAAGAACGTCAGCGGCTAAGCGGGCAGCAACCAGCTTCTGAATCGCTTCTTGT<br>GTTGGCACCCAAAACTTTGCCGCCCATATGGCCGCATTTCTTCACCGCCGCCAATTGATC<br>TTCAAAGTGAACGCCCGCAGCACCGGCTTCAATCATGGCTTTCATCAATTCAAACGCAT<br>TCAATACGCCGCCAAAACCCGCTTCGGCATCCGCCACAATCGGCAGGAAATAGTCGGT<br>ATAGCCTTTGCTGCCCGGCTCAATATTATTCGACCACTGAATCTGATCTGCACGGCGGA<br>AGCTGTTATTAATACGCTTAACCACGGCCGGAACAGAGTCGACCGGGTAAAGAGATTGA<br>TCGGGATACATGCTGGAGGCGGTATTGGCATCGGCGGCGACCTGCCAACCCGACAGA<br>TAAATCGCTTCAACACCGGCCTTTGCCTGTTGCAATGCCTGACCGCCTGTTAGCGCCCC<br>CAGACAGTTGATGTAGCCTTTACGCGATTCGCCGTGCAGCAACTCCCACAATCTTTTCG<br>CGCCGTGCTGTGCCAGCGTACATTCTGGGTTAACGGAACCGCGCAGTTTGATCACTTC<br>TTCGGCGCTATAGGGGCGGGTGATGCCCTTCCAGCGCGGTGATTTCCATTCCTGTTCC<br>AACTGCTGAATTTGTTGAGTACGAGAGGTTGTCATGGCGATATTCCTTATTACTTATTTTT<br>GTAGGGTTAAATAACTGGCCTAGGCGAGTAATGCGTAGCCCGGCAACGTCAGAAAGTC<br>GATAAGCTCGTCTTGTGTTGTAATCCGCTCCATCAGACGTGCGGCTTCTTCAAACCGCC<br>CGCCATCAAAACGCTCTGCGCCAAGTTCAAGTTTCACGACCTGCATTTCTTCACTCAAC<br>ATGTTACGGAACAGCTCTTTGGTCACCGTCTGACCATTGCTCAGGCTTTTCTGGTGATG<br>TATCCATTGCCAGATAGAAGTACGGGAAATCTCAGCCGTCGCGGCATCTTCCATCAGGC<br>CATAAATCGGTACACAGCCATTGCCCGATATCCATGCTTCGATGTATTGCACTGCGACC<br>CGGATATTGGCCCGCATCCCCTCTTCGGTGCGCTCACCCGTGCAAGGCTCTAGCAACT<br>CAGCGGCAGTGATTGGTTTATCTTGCGCGCGACTCACCTCTAATTGGTTTGGACGATCG<br>CCCAGTACTTTGTTGAAAACGTCCATCACGGTATCGGCCAGACCGGGGTGTGCGACCC<br>ATGTACCATCGTGGCCGTTGCTGGCTTCCAGCTCTTTGTCAGCGCGAACTTTATCTAAG<br>ACCAGCGCATTTTTTTCTGGATCTTTGTTCGGGATAAAGGCCGCCATGCCGCCCATCGC<br>CAAGGCACCGCGCTTATGGCAGGTTTTGATCAGTAAACGAGAGTAGGCACTCAGGAAG<br>GGTTTCGTCATCGTGACCGACTGGCGATCGGGCAGCACGCGATCGCTGTGATTTTTCA<br>GCGTTTTGATATAGCTGAAAATGTAGTCCCAACGGCCACAATTCAGGGCAACAATGTGA<br>TGGCGCAGATGGTAGAGGATCTCATCCATCTGGAATACCGCAGGCAATGTCTCGATTAA<br>TACTGTGGCCTTAATGGTGCCTTGCGGCAGATCGAAACGCTGCTCGGTAAAGCTGAAA<br>ACATCACTCCACCAAGCCGCTTCCTGATAAGACTGCATCTTGGGTAGATAGAAATAGGG<br>GCCGCTGCCATTGGCAAGCAGTAACTTATAGTTATGGTAGAAATACAACGCGAAATCGA<br>ATAAGCCACCGGGGATATCCTCCCCCTGCCACTTCACGTGTTTTTCTGGCAAGTGCAGA<br>CCACGCACCCGAGCAATCAACACCGCTGGATTGGGTTTTAGCTGATAAATCTTACCGGA<br>TTCATTCGCGTAAGAGATTGTGCCTTTGACCGCATCGTGCAAATTAATCTGACCTTCGAT<br>AACCTTATCCCAACTGGGTGCCAGCGAATCCTCAAAGTCAGCCATAAAGACTTTCACAT<br>TCGCATTGAGGGCATTAATCACCATTTTGCGCTCAACCGGCCCGGTGATCTCGACGCG<br>ACGATCACGTAAATCCGCAGGAATACTTTGAATTTTCCAGTCACCATTACGAATGGAATT<br>GGTTTCCGAAATGAAATCAGGCAATGCGCCTTGGTCAATGGCCTGTTGCCAAGCGGCC<br>CGTGCAGCAAGGAGTTTGCTACGCGGCTCTGCAAATTTCGCCACCAATTCTGCCAAAAA<br>TTCGATGGCCTCATCGGGCAAAACCTGCCGCTCAGCAGCATTAAAATGCTGGGTGAAA<br>ACTAACTCCGTGCCGACTATCTGTTGTGTCATTCCCCTTCCCCTTCCCCATCTCTCGAC<br>GATCATTTTTCAGTTTCCTTTTGTTATTCCCCAAAAGTGCGGTGCAAATTTGGGGAGTTT<br>TAGTTAATTAAAAAAATTATTTTTTACGAGCTTCGATTACTGCAGCAGCAACACTTGTTGG<br>CGCTTCAGCATATTTTAACGGTTCCATTGAGTATGATGCTCTAGAGCGGCCGCCACCGC<br>GGTGG |
| 16 | 15 | Alcohol dehydrogenase DNA (adhE) from DD1 | ATGATTATGAGTAACGCTGTTGAAAACACAGTAAGCCCCGCTCAAGCGGAGGTGAACTC<br>ACTGGTTGAGAAAGGTTTAGTGGCACTGGAGCAATTCCGCCAACTAAATCAGGAACAG<br>GTGGACTACATTGTAGCGAAAGCTTCTGTTGCCGCTTTAGACCAACATGGAGCATTGGC<br>GCTACATGCGTTAGAGGAAACCGGGCGCGGCGTGTTCGAGGACAAAGCCACTAAAAAC<br>CTGTTTGCCTGCGAACATGTAGTGAACAAAATGCGACATTGGAAAACCGCCGGGATTAT<br>CAGTGACGACGATGTCACAGGTATCACCGAAATTGCCGATCCGGTGGGAGTGGTCTGC<br>GGCATTACACCTACCACTAATCCTACTTCCACGGCTATCTTCAAATCACTGATCGCTTTA<br>AAAACCCGCAATCCTATTGTTTTCGCTTTCCACCCTTCCGCCCAACAGTCTTCCGCTCAT<br>GCCGCACAAATTGTGCGCGATGCCGCGGTAGCCGCCGGTGCGCCGGAAAACTGTATT<br>CAATGGATTGCACAACCCTCTATGGAAGGAACTAATGCGTTAATGAACCATCCGGGTAT<br>TGCCACCATTCTGGCTACCGGCGGTAACGCTATGGTGCAGGCCGCTTATTCATGCGGC<br>AAGCCGGCGTTGGGAGTCGGTGCCGGAAATGTACCCGCTTATGTGGAAAAATCCGCCG<br>ATATTAAACAGGCAACTCACGATATCGTGATGTCGAAATCCTTTGATAACGGTATGGTAT<br>GCGCTTCAGAGCAAGCCGCTATTGCCGATGCGGAAATTTATGACGAATTCGTCAACGAA<br>TTAAAATCCTACGGTGTGTATTTCGTCAATAAAAAAGAAAAAACTTTATTGGAAGAATTTA |

FIG. 11 (Continued)

| | | | |
|---|---|---|---|
| | | | TGTTCGGTGTAAAAGCTAACGGTGCAAATTGCGCCGGTGCGAAACTAAACGCCGACGT<br>GGTAGGTAAATCCGCATACTGGATTGCTCAACAAGCGGGCTTTGAAGTGCCGAAAAAAA<br>CCAATATTCTTGCCGCAGAATGTAAAGAAGTCAGCCCGAAAGAACCTTTAACCCGGGAA<br>AAATTATCACCGGTGCTTGCCGTTTTAAAATCCCGTTCTACCGAAGAGGGATTAACGCTT<br>GCCGAAGCCATGGTGGAATTTAACGGTTTAGGACACTCCGCGGCAATTCACACCAAAG<br>ATGCGGCGCTTGCCAAACGCTTCGGCGAGCGCGTTAAAGCCATTCGCGTTATCTGGAA<br>TTCGCCTTCTACCTTCGGCGGTATCGGCGACGTTTATAACGCTTTCCTGCCTTCATTAAC<br>CCTGGGTTGCGGTTCTTACGGCAAAAATTCCGTCAGCAACAATGTCAGCGCCATGAACT<br>TAGTAAATATCAAACGTGTGGGAAGACGGAGAAATAATATGCAATGGTTTAAAGTACCTT<br>CAAAAATCTATTTTGAACGGGATTCAATTCAATATTTACAATCCGTACCGGATATGCGAC<br>GAGTAGTTATCGTAACCGACCGCACTATGGTGGATCTTGGGTTTGTACAAAAAATCGCC<br>CATCAGTTGGAATCCCGTCGCGATCCGGTTTCTTACCAGTTATTTGCCGATGTAGAACC<br>GGATCCGAGTATTCAAACCGTGCGCCGCGGTGTGGATTTAATCCGTAATTTCAAACCGG<br>ACACTATTATCGCGCTTGGCGGCGGTTCCGCCATGGATGCGGCAAAAGTGATGTGGTT<br>ATTCTATGAACAACCGGAAATTGACTTCCGTGATTTGGTTCAAAAATTCATGGATATTCG<br>TAAACGTGCCTTTAAATTTCCATCATTGGGAAAAAAAGCCCGCTATATCGGCATTCCGAC<br>CACATCCGGTACGGGTTCGGAAGTGACCCCGTTTGCGGTGATTACCGAAGGTAACAAA<br>AAATATCCGATTGCGGACTATTCGCTAACGCCGACTATCGCTTTAGTGGATCCGGCATT<br>AGTTATGACGGTACCCGCCCATGTAGCGGCGGATACGGGATTAGACGTATTAACTCAT<br>GCCACCGAAGCTTATGTTTCCGTACTGGCCAACGATTATACCGACGGTCTTGCTTTACA<br>GGCGATTAAACTGGTATTCCGGTATTTGGAAAAATCCGTAAAAGAAAATGATCCGGAGG<br>CAAGAGAAAAGATGCATAATGCGTCCACCATTGCGGGTATGGCGTTTGCCAATGCATTC<br>TTAGGTATGAATCATTCCCTTGCGCATAAACTTGGCGGCCATTTCCATACGCCTCACGG<br>GCGCACTAATGCGATCTTAATGCCGCACGTGATCCGTTATAACGGTACTAAACCGACGA<br>AAACCGCCACATGGCCGAAATACAACTATTACAAAGCGGACGAAAAATATCAGGATATC<br>GCCCGTTTATTAGGCTTACCTGCGGCGACCCCGGAAGAGGGCGTGAAATCTTATGCCA<br>AAGCGGTTTACGATTTAGCGGTACGTTGCGGTATTAAAATGTCCTTCAAAGAACAGGGA<br>CTGGAAGAACAGGCCTGGATGGACGCCCGCCATGAAATTGCATTGCTTGCCTATGAAG<br>ACCAATGTTCGCCGGCAAATCCGCGATTACCGATTGTGGCGGACATGGAAGAAATTCTC<br>ACTAACGCCTACTATGGTTATGACGAAAGCAAATAC |
| 17 | 16 | Alcohol dehydrogenase DNA (adhE) from DD1 | M I M S N A V E N T V S P A Q A E V N S L V E K G L V A L E Q F R Q L N Q E Q V D Y I<br>V A K A S V A A L D Q H G A L A L H A L E E T G R G V F E D K A T K N L F A C E H V V<br>N K M R H W K T A G I I S D D D V T G I T E I A D P V G V V C G I T P T T N P T S T A I F<br>K S L I A L K T R N P I V F A F H P S A Q Q S S A H A A Q I V R D A A V A A G A P E N C<br>I Q W I A Q P S M E G T N A L M N H P G I A T I L A T G G N A M V Q A A Y S C G K P A<br>L G V G A G N V P A Y V E K S A D I K Q A T H D I V M S K S F D N G M V C A S E Q A A<br>I A D A E I Y D E F V N E L K S Y G V Y F V N K K E K T L L E E F M F G V K A N G A N C<br>A G A K L N A D V V G K S A Y W I A Q Q A G F E V P K K T N I L A A E C K E V S P K E<br>P L T R E K L S P V L A V L K S R S T E E G L T L A E A M V E F N G L G H S A A I H T K<br>D A A L A K R F G E R V K A I R V I W N S P S T F G G I G D V Y N A F L P S L T L G C G<br>S Y G K N S V S N N V S A M N L V N I K R V G R R R N N M Q W F K V P S K I Y F E R D<br>S I Q Y L Q S V P D M R R V V I V T D R T M V D L G F V Q K I A H Q L E S R R D P V S Y<br>Q L F A D V E P D P S I Q T V R R G V D L I R N F K P D T I I A L G G G S A M D A A K V<br>M W L F Y E Q P E I D F R D L V Q K F M D I R K R A F K F P S L G K K A R Y I G I P T T<br>S G T G S E V T P F A V I T E G N K K Y P I A D Y S L T P T I A L V D P A L V M T P A H<br>V A A D T G L D V L T H A T E A Y V S V L A N D Y T D G L A L Q A I K L V F R Y L E K S<br>V K E N D P E A R E K M H N A S T I A G M A F A N A F L G M N H S L A H K L G G H F H<br>T P H G R T N A I L M P H V I R Y N G T K P T K T A T W P K Y N Y Y K A D E K Y Q D I A<br>R L L G L P A A T P E E G V K S Y A K A V Y D L A V R C G I K M S F K E Q G L E E Q A<br>W M D A R H E I A L L A Y E D Q C S P A N P R L P I V A D M E E I L T N A Y Y G Y D E S<br>K Y |
| 18 | 17 | pSacB (delta adhE) | TCGAGATAAATTCGCGGAACCGGCGCAGGCTCACCTGGCTGTTGCGATCGATAGGTAC<br>GTTGATTATGGTGTTGATTACATCTCTTGTACCTGGCACATTTGCCGTTTTATCAATTTCA<br>CTGCTCACCTCGTTTTGTGCGTTCACGTTGATTACAATGATGTTTTTTAATTGATTCTTTA<br>CCGCTTCCTGATACATACCTTCCTGACCCGCAACATCATAAATATCAATTAAGCCGGACA<br>GTCCTAAATTATCCGTTAAACCGCCGTCCACCAAATGAATAAAAGGGCGTTCTTTGCTGT<br>TTTGATATAAAGACAAGGTATTTTTTAATTCTTCCAGATTTTTTGATTTTTGCGCATCATTG<br>CTGATATTTTGGCTGATTTGAATTAATTCCGGTATATCGAAATGGCAGTTGCCGCCGTTG<br>TTGTTTAAAGTCAACGGGCTGAACAGCAACGGTACCGAACTTGATGCGGCGACGGCAC<br>GGGAAATTTCCATTTTACTTAAGTCAATACAAAGACCGTCGAAAAATTCTTGCGTAAAGG<br>TTATTTTTTGTCCTAAATTCATATCCGTCGCACTCACTACGACAAACGGTCCTTTACGTTT<br>TCGCTCAAGATCACCGAAGGTAGCGCCTTTGTATAATGTTTGATCCAGCTGTTCCTGTA<br>ATAAGTCGCCGCGACCGAATTGAGGGGAGGTTATTCGCGGTAAATTGGAAAGGGATAA<br>AACCTGACTGATAATTTCCCGCTGGAAATTTTTTTAGGAAGTTTTCTTCAAATTTAGGC<br>ACCGCATCCCGCCCGTATAGGGAATAATAAGTGGCTAAAACGGATCCGCCGGATACGC<br>CGTATACCAAATCCACATTATCAATTAGGGTTGTACCTTTTGCCGTCGGGCGCACGGCG<br>GCGTTTTAAATTCCTCTAACACGCCGTAGCCCAAACTTGCCGCCCGGCTGCCGCCGC<br>CCGAAAACATTAAAATAATCAAATTGCCGTCGGGTTGCTGAATGGCATTTCTCATTCGAT<br>ACCCTTGCTTAGCGTTCACATGGCTGATGGTATCAACGGGCTGATAAGTCACTAAGGTA<br>CAAGCTGACAACAACAAAACAGTCAAACCGGCGAAAATATTTTTTAGCATCATAGTTGTA<br>ACGGATAAATCTAAATTTTTATTTATAGAAAAAGAAAATAATATGCTACATCGTACTATATT<br>AATTTTATCCTGCGTTCATATCTTATCAGAAGGCAAACCGCTTTTTCTATGCAAGGAAAA<br>TTTTATAAATGACTAATGTACTCAAATAATGAAGAAAGATAAACAAACATTTTTTCATGAG<br>AAAATTCTTATGAATTCTAAGCCTCGGTAATTCCTATTGGTATTTTATTTTGAAACCGATT |

FIG. 11 (Continued)

```
ACCTTTTAAATTAAAATTTTTTATTTGATTTAAATCAATTTAATCGCATTATTAATCCCATTT
CATAACTCCAAAGTAGTAAAATTCGCACCAGTAACCAAATTTAAATATTAAACAACTTTAG
GAGAATAATTTGTAAAATTCTTAAAAATCGTACCGCACTTTTTCTAAAAGTGCGGTATTTT
TTTGATTGTTTTTATCCGTCTAAAGGGTAAAATCAACGGGATTTATTGATATTAAAGGAAA
CAATTATGGCAACAACTATTCATACAGAAAACGCGCCCGCAGCAATCGGTCCTTATGTT
CAAGCGGTAGATTTAGGCAATTTAGTGCTGACTTCGGGGCAAATTCCGGTGAATCCGG
CAACCGGCGAAGTGCCGGCGGATATTAGCGCACAAGCCCGCCAATCTTTAGAAAACGT
TAAAGCGATTATCGAACAGGCAGGGTTAACCGTGGCGGATATTGTAAAAACTACGGTTT
TTGTTAAGGATTTAAACGATTTTGCCACCGTAAATGCGGAATACGAACGTTTTTTCAAAG
AGAATGACCATCCGAATTTCCCTGCTCGCTCATGCGTTGAAGTGGCGCGTTTACCGAAA
GACGTCGGCTTGGAAATTGAAGCTATTGCGGTGCGCAAATAAGGCTGGGTTAAGCGCT
TATTTATACAAAAGTGCGGTCAAAAAATCCGTTTTTTGTAAAAGAAAAGGCATAGTTTTAT
TGACCGTGCCTTTTTGCTATTTGATGATTTATTTGCGCAACTTCACTTCTTGTACCGCAT
GGTCGGCACCTTTGCGTAAAATTAAATTTGCCCGTTCACGGGTCGGCAAAATATTTTGC
CGTAAATTTAAGCCGTTAATAGTATTCCAAATATTAGCGGCGGTTTCAACCGCTTCTTCT
TTAGAGAGTTTTGCATAATCTTTAAAATAGGAATTCGGATCGGTAAACGCGCTTTCACGG
AATTTCAAAAAGCGGCGAATATACCATTCCTTTAATAAGGCTTCATCGGCGTCCACATAA
ACGGAAAAATCAACAAAATCGGAGACAAAAGTCTGTTCCGCTTTGCGCGAACCGGTTTG
TAATACGTTTAAACCTTCCAATATAAGAATATCCGGGCGATCTACCTTGTTAAATTTATCG
GGGATAATATCATAGGTCAAATGCGAATAAATCGGCGCCGACACGTTCGGTTTGCCGG
ATTTTACGTCCGCCAGAAATTTGATTAATTTGGGCGTATCGTAAGAGACGGGGAAGCCT
TTTTTATGCAATAAATTTTCTTTTTTTAATTTTTCTAAAGGATAGAGAAAACCGTCGGTGG
TAATCAAATCCACTTTGCGATTTTCAGGCCAGTTAGACAGTAAAGACTGCAAAATACGCG
CGGAAGTGCTTTTCCCGACCGAAACGCTGCCGGCAATACTGATAATATAAGGTACATTG
GCGTTGGTATTGCCGAGAAAACGGTTCATTACGGTCTGGCGACGTAAATTTTCTTCAAT
ATAATAATTAATTAAACGCGCAAGAGGCAGGTAAATGGTGCTGACTTCTTCCAACGATAA
TTCTTCGTTAAAACCGAGTAAAGGCTTTAAATCTTGTTCTGTCAGTTTTAAAGGCACGGA
TTTCCGCAATTCCGCCCATTGTTTACGGGTAAATGTCAAAAACGGGCTGAATTTCTCTGA
AACTGACGATTGGCTTTCTATGTTCACGGCTCATTCTAATGTTAAGAAAGTAAAAATCTA
GACTCCATAGGCCGCTTTCCTGGCTTTGCTTCCAGATGTATGCTCTCCTCCGGAGAGTA
CCGTGACTTTATTTTCGGCACAAATACAGGGGTCGATGGATAAATACGGCGATAGTTTC
CTGACGGATGATCCGTATGTACCGGCGGAAGACAAGCTGCAAACCTGTCAGATGGAGA
TTGATTTAATGGCGGATGTGCTGAGAGCACCGCCCCGTGAATCCGCAGAACTGATCCG
CTATGTGTTTGCGGATGATTGGCCGGAATAAATAAAGCCGGGCTTAATACAGATTAAGC
CCGTATAGGGTATTATTACTGAATACCAAACAGCTTACGGAGGACGGAATGTTACCCAT
TGAGACAACCAGACTGCCTTCTGATTATTAATATTTTTCACTATTAATCAGAAGGAATAAC
CATGAATTTTACCCGGATTGACCTGAATACCTGGAATCGCAGGGAACACTTTGCCCTTT
ATCGTCAGCAGATTAAATGCGGATTCAGCCTGACCACCAAACTCGATATTACCGCTTTG
CGTACCGCACTGGCGGAGACAGGTTATAAGTTTTATCCGCTGATGATTTACCTGATCTC
CCGGGCTGTTAATCAGTTTCCGGAGTTCCGGATGGCACTGAAAGACAATGAACTTATTT
ACTGGGACCAGTCAGACCCGGTCTTTACTGTCTTTCATAAAGAAACCGAAACATTCTCT
GCACTGTCCTGCCGTTATTTTCCGGATCTCAGTGAGTTTATGGCAGGTTATAATGCGGT
AACGGCAGAATATCAGCATGATACCAGATTGTTTCCGCAGGGAAATTTACCGGAGAATC
ACCTGAATATATCATCATTACCGTGGGTGAGTTTTGACGGGATTTAACCTGAACATCACC
GGAAATGATGATTATTTTGCCCCGGTTTTTACGATGGAGCAAAGTTTCAGCAGGAAGGTGA
CCGCGTATTATTACCTGTTTCTGTACAGGTTCATCATGCAGTCTGTGATGGCTTTCATGC
AGCACGGTTTATTAATACACTTCAGCTGATGTGTGATAACATACTGAAATAAATTAATTAA
TTCTGTATTTAAGCCACCGTATCCGGCAGGAATGGTGGCTTTTTTTTTATATTTTAACCG
TAATCTGTAATTTCGTTTCAGACTGGTTCAGGATGAGCTCGCTTGGACTCCTGTTGATAG
ATCCAGTAATGACCTCAGAACTCCATCTGGATTTGTTCAGAACGCTCGGTTGCCGCCGG
GCGTTTTTTATTGGTGAGAATCCAAGCACTAGCGGCGCGCCGGCCGGCCCGGTGTGAA
ATACCGCACAGATGCGTAAGGAGAAAATACCGCATCAGGCGCTCTTCCGCTTCCTCGC
TCACTGACTCGCTGCGCTCGGTCGTTCGGCTGCGGCGAGCGGTATCAGCTCACTCAAA
GGCGGTAATACGGTTATCCACAGAATCAGGGGATAACGCAGGAAAGAACATGTGAGCA
AAAGGCCAGCAAAAGGCCAGGAACCGTAAAAAGGCCGCGTTGCTGGCGTTTTTCCATA
GGCTCCGCCCCCCTGACGAGCATCACAAAAATCGACGCTCAAGTCAGAGGTGGCGAAA
CCCGACAGGACTATAAAGATACCAGGCGTTTCCCCCTGGAAGCTCCCTCGTGCGCTCT
CCTGTTCCGACCCTGCCGCTTACCGGATACCTGTCCGCCTTTCTCCCTTCGGGAAGCG
TGGCGCTTTCTCATAGCTCACGCTGTAGGTATCTCAGTTCGGTGTAGGTCGTTCGCTCC
AAGCTGGGCTGTGTGCACGAACCCCCCGTTCAGCCCGACCGCTGCGCCTTATCCGGTA
ACTATCGTCTTGAGTCCAACCCGGTAAGACACGACTTATCGCCACTGGCAGCAGCCACT
GGTAACAGGATTAGCAGAGCGAGGTATGTAGGCGGTGCTACAGAGTTCTTGAAGTGGT
GGCCTAACTACGGCTACACTAGAAGGACAGTATTTGGTATCTGCGCTCTGCTGAAGCCA
GTTACCTTCGGAAAAAGAGTTGGTAGCTCTTGATCCGGCAAACAAACCACCGCTGGTAG
CGGTGGTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAGGG
ATTTTGGTCATGAGATTATCAAAAAGGATCTTCACCTAGATCCTTTTAAAGGCCGGCCGC
GGCCGCCATCGGCATTTTCTTTTGCGTTTTATTTGTTAACTGTTAATTGTCCTTGTTCAA
GGATGCTGTCTTTGACAACAGATGTTTTCTTGCCTTTGATGTTCAGCAGGAAGCTCGGC
GCAAACGTTGATTGTTTGTCTGCGTAGAATCCTCTGTTTGTCATATAGCTTGTAATCACG
ACATTGTTTCCTTTCGCTTGAGGTACAGCGAAGTGTGAGTAAGTAAAGGTTACATCGTTA
GGATCAAGATCCATTTTTAACACAAGGCCAGTTTTGTTCAGCGGCTTGTATGGGCCAGT
TAAAGAATTAGAAACATAACCAAGCATGTAAATATCGTTAGACGTAATGCCGTCAATCGT
CATTTTTGATCCGCGGGAGTCAGTGAACAGGTACCATTTGCCGTTCATTTTAAAGACGTT
```

FIG. 11 (Continued)

| | | | |
|---|---|---|---|
| | | | CGCGCGTTCAATTTCATCTGTTACTGTGTTAGATGCAATCAGCGGTTTCATCACTTTTTT<br>CAGTGTGTAATCATCGTTTAGCTCAATCATACCGAGAGCGCCGTTTGCTAACTCAGCCG<br>TGCGTTTTTTATCGCTTTGCAGAAGTTTTTGACTTTCTTGACGGAAGAATGATGTGCTTTT<br>GCCATAGTATGCTTTGTTAAATAAAGATTCTTCGCCTTGCGTAGCCATCTTCAGTTCCAGT<br>GTTTGCTTCAAATACTAAGTATTTGTGGCCTTTATCTTCTACGTAGTGAGGATCTCTCAG<br>CGTATGGTTGTCGCCTGAGCTGTAGTTGCCTTCATCGATGAACTGCTGTACATTTTGATA<br>CGTTTTTCCGTCACCGTCAAAGATTGATTTATAATCCTCTACACCGTTGATGTTCAAAGA<br>GCTGTCTGATGCTGATACGTTAACTTGTGCAGTTGTCAGTGTTTGTTTGCCGTAATGTTT<br>ACCGGAGAAATCAGTGTAGAATAAACGGATTTTTCCGTCAGATGTAAATGTGGCTGAAC<br>CTGACCATTCTTGTGTTTGGTCTTTTAGGATAGAATCATTTGCATCGAATTTGTCGCTGT<br>CTTTAAAGACGCGGCCAGCGTTTTTCCAGCTGTCAATAGAAGTTTCGCCGACTTTTTGAT<br>AGAACATGTAAATCGATGTGTCATCCGCATTTTTAGGATCTCCGGCTAATGCAAAGACG<br>ATGTGGTAGCCGTGATAGTTTGCGACAGTGCCGTCAGCGTTTTGTAATGGCCAGCTGTC<br>CCAAACGTCCAGGCCTTTTGCAGAAGAGATATTTTTAATTGTGGACGAATCAAATTCAGA<br>AACTTGATATTTTTCATTTTTTTGCTGTTCAGGGATTTGCAGCATATCATGGCGTGTAATA<br>TGGGAAATGCCGTATGTTTCCTTATATGGCTTTTGGTTCGTTTCTTTCGCAAACGCTTGA<br>GTTGCGCCTCCTGCCAGCAGTGCGGTAGTAAAGGTTAATACTGTTGCTTGTTTTGCAAA<br>CTTTTTTGATGTTCATCGTTCATGTCTCCTTTTTTATGTACTGTGTTAGCGGTCTGCTTCTT<br>CCAGCCCTCCTGTTTGAAGATGGCAAGTTAGTTACGCACAATAAAAAAAGACCTAAAATA<br>TGTAAGGGGTGACGCCAAAGTATACACTTTGCCCTTTACACATTTTAGGTCTTGCCTGCT<br>TTATCAGTAACAAACCCGCGCGATTTACTTTTCGACCTCATTCTATTAGACTCTCGTTTG<br>GATTGCAACTGGTCTATTTTCCTCTTTTGTTTGATAGAAAATCATAAAAGGATTTGCAGAC<br>TACGGGCCTAAAGAACTAAAAAATCTATCTGTTTCTTTTCATTCTCTGTATTTTTTATAGTT<br>TCTGTTGCATGGGCATAAAGTTGCCTTTTTAATCACAATTCAGAAAATATCATAATATCTC<br>ATTTCACTAAATAATAGTGAACGGCAGGTATATGTGATGGGTTAAAAAGGATCGGCGGC<br>CGCTCGATTTAAATC |
| 19 | 18 | Formate dehydrogenase DNA (fdh) from Wolinella succinogenes | ATGAGTGAAGCGTTAAGCGGACGCGGGAACGATCGAAGAAAGTTCCTAAAGATGTCGG<br>CTTTAGCAGGAGTCGCAGGCGTGAGTCAAGCGGTTGGCTCCGACCAAAGCAAAGTGCT<br>TAGACCTGCAACAAAACAAGAGTTAATCGAAAAATACCCAGTGTCCAAAAAGGTAAAAA<br>CGATTTGCACCTATTGCTCGGTCGGATGTGGAATTATAGCGGAAGTGGTCGATGGTGTA<br>TGGGTACGCCAAGAGGTCGCTCAAGATCACCCCATTAGTCAAGGGGGTCACTGCTGCA<br>AGGGCGCCGATATGATTGATAAGGCTCGAAGCGAAACAAGACTTCGATACCCCATTGA<br>GAAAGTTGGCGGAAAATGGCGTAAAACTTCATGGGATAGCGCCATGGATAAGATTGCC<br>AAGCAGCTTCAGGATCTCACCCAAAAATGGCCCTGATAGCGTCATGTTCATTGGCGG<br>CTCCAAGTGTTCGATTGAACAATCCTATTATTTTAGAAAGTTTGCCGCCTTTTTTGGCAC<br>CAACAATCTCGATACCATCGCACGAATCTGCCATGCCCCAACAGTTGCTGGAGTCTCCA<br>ATACCCTTGGATATGGCGGTATGACCAATCACTTGGCAGACATGATGCACTCCAAGGCG<br>ATTTTTATCATTGGTGGAAATCCCGCAGTGAATCACCCTGTAGGCATGGTGCATATCTTG<br>CGCGCTAAAGAGGCAGGAGCAAAAATCATCGTTGTGGATCCCCACTTCAGTCGAACAG<br>CAACTAAAGCCGATCACTATGTGAGATTGCGCAATGGCACGGATGTCGCCTTCATGTAT<br>GGGATGATTCGCCATATTGTAAAAAATGGACTAGAAGATAAAGAATTTATTCGACAACGC<br>CTATTTGGCTACGAAGAGATTCTTAAAGAGTGCGAACAGTACACCCCGTCAAGTGGTCGA<br>AGAGGTCACAGGCGTGCCCGCCCAACAACTTATTGAGATCACGGAGATCTTCGCTAAA<br>GCCAAGCCTGCTTCACTGATCTGGGGGATGGGTCTCACCCAGCACACCACAGGTACAA<br>GCAACACTCGTTTGGCCCCTATTTTACAGATGATTCTTGGAAACATTGGCAAACGAGGT<br>GGAGGCACTAACGTTTTACGAGGTCATGACAATGTCCAAGGCGCGACGGACATGGGCA<br>ACCTAGCCGACAGTCTTCCTGGCTATTATGGGTTAGACAAAAATGCATGGAATCACTTC<br>TGTGGAATCTGGAAAGTGGATTTCGAAGCAATGCAAAAACGCTTTAAGACCCCTGATAT<br>GATGCATAAAAAAGGTTTCAGTGTATCCACATGGAGATATGGGGTGACTGAAGAGGAGA<br>ACATCCCCCACAATGCAGGCACTAAACTTCGATCCTTGATTGTCGTGGGAAGCGGAATC<br>TCTACGATCGCACGCGTGGATACCACCAAAGACGCTCTAGACAAGATGGATTTAGTCGT<br>CTTTTTTGATCCCTATTTCAATGATGCAGCCGCCCTCACCAACCGAAAAGATAATCTCTA<br>TATCCTTCCTGCCGCCACACAGATGGAGACCAGCGGAAGAGTCGCAGCGACGAATCGA<br>AGCTATCAGTGGCGATCCATGGTTATGAAGCCACTCTTTGAGTGTCGACCTGACGAAGA<br>GATTCTCTTTGATTTAGCTAAGCGACTTGGATTCTATGAGGAGTACACTCGCTCTTTGGG<br>GGATGGCAAAGGAAACTTTGTATGGCCCGATGATGCGACTAGAGAGGTGGCCAAGGCT<br>ATACGAACTGTCGGCTTCCAAGGCAGAACTCCAGAACGACTCAAGGCTCATGCAGAAA<br>ACTGGCATATGTTTGATAAGTTCACCCTCAGAGGAAAGGGCGGCCCCGTCAAAGGCGA<br>ATACTATGGTCTTCCTTGGCCTTGCTGGAGCGAAAAGCATCCTGGAACACCAAATCTAT<br>GGGATGACAGCATCCCTGTAATGGATGGAGGTCTTGGCTTTAGGGTTCGATGGGGTGA<br>TGTGTCACCCACAGGAGAAAGTTTGTTGGCCAGCCAGGACAGCTCTTTGCCCGGCTCA<br>AAATTCAAGGGCGGTCATAGCATGATCACCGATAAAAATGTCGAAGCTATCACTGGAAT<br>CGCCCTCACCGAAGAGGAAAAAGCCAAAGTGGCAGGCAAGACATGGGCGACTGACAC<br>CACCAATATCTTGGTTGAAAAAGCACTCGCCGCAGGTCTCTCCCCTATGGGTAATGGTA<br>GAGCTAGAGCGATTGTTTGGGAGTGGACGGATCAGATTCCTAAACACCGTGAACCCAT<br>CTACACAATTCGACACGATCTCATTAGCCAATATCCAACCTTCAAAGACAAGCCCAACCA<br>CTTTAGGGCAAATATTCGCTATGAGAGCCGCCAAAAAGAGAAAGATTGGACCAAAGAGT<br>TCCCGCTTAATATGCTTTCTGGACGACTAGTAGCACAGTTTGGCACAGGCACAGAGACA<br>AGATCAGCTCATTACCTCGCCGAGGTTCAGCCTGAGATGTTTGTGGAGATTCATCCCGA<br>AACAGCCACGGATTTAGGCGTGAAGCATGGTGACATGGTTTGGGTGCACGGCACCAAT<br>GGGGCAAAGATTCTCGTGAAAGCGAGACATAGCTACAAGGTCAACAAAACAAGTGTTTT<br>CCTCCCCCAGAATTTCGGAGGAATGTATCAAGGAGAGTCACTGGTTCCGTATCATATTG<br>CAGGCACAGAGCCTTATGTTATTGGTGAATCATGCAATACCATCACAAGTGATGCATAC<br>GACATCAACACCAGTACTCCTGAAACCAAGTGCGGCCTCTGCCGCATCGAAAAAGCGT |

FIG. 11 (Continued)

| | | | |
|---|---|---|---|
| | | | AGGGGGTGAAGCATGGAAAGTCAAGCTAGAGTCAAGTTCTATTGTGATGAGGCTAGAT
GTATTGATTGTCATGGATGTGATGTGGCTTGTAAAGAGGCCCATCACCTTCCTGTGGGA
GTCAACCGAAGAAGAGTGGTGACCCTCAATGAAGGTCTTGTAGGCAAAGAGAAATCCC
TCTCTATTGCCTGCATGCACTGCTCTGATGCCCCTTGTGCTCAGGTCTGCCCAGTGGAC
TGCTTCTATGTTCGAGCCGATGGGATTGTATTGCATGACAAAGAGAAGTGCATTGGATG
CGGTTACTGCCTCTATGCCTGCCCCTTTGGTGCTCCTCAATTCCCCAAGAGTGGAATCT
TTGGTTCAAGAGGACCTATGGATAAGTGCACCTTCTGTGCTGGAGGTCCTGAAGAGACT
CACAGCGAGAAGGAGTATAAGCTCTATGGACAGAATCGTATCGCTGAGGGCAAAGTCC
CTGTATGTGCAGCGATGTGCTCCACCAAGGCACTCCTAGCAGGAGATTCTGATAGCATC
TCGCTCATCATTCGTGAGAGAGTGCTCAAGCGAGGCAGTGGAACAGCCAGTGTTCCTT
ACACCTGGTCACAAGCCTACAAGGATTAAGAATGAAAAAGCCTCTATTGCCCCTCCTCT
CCCTTCTGGGAGCCTTGGGGGCACAAGCTTCTGAGAATCTCAAGGAGCCCTTGGATTT
CAGCTACAACACCCAAATCTATGGAAAGCCCATGATTGAGGCAATCCCCACTTGGGGAA
GTGGAGGGATTCTAGGTCTTGGAGAGATTGGAGGAATAGGAGGATTAGGAGAGCTCTT
CACCTTCTTGCAAAGTGGTTACTTTGCTCTTATCTTCCTAGCGATCATCATCGCTATCCC
TTTGGTCTTCCTAGGTCACTATATGGTGATTGGACCCAAGCGATTCTCTCATGAGGGGA
AGAAGATCAAGGTCTTTAACACCTTCAACATCATGGTGCACTGGATTGCAGGGATTCCC
TTTGTGCTTCTTTGCATCACAGGACTTCTGATGGTCTTTGGAGATGCCCTAGGGGGTGG
AGCTTTTATTCGATTCGCTAGAGATGTGCATGGATTAGCCACGATCATCTTTGCGATCTT
TGGTCCCCTCATGTTCATCATGTGGGTGAAGCACGCTCTCTTTAAGATGTATGACATCG
ACTGGATGCTCATTCTTGGAGGGTATCTAAGCAAGGTGAAGAGACCTATTCCTGCAGGC
AAATTCAATGCGGGTCAGAAGATGTGGTTCTGGGTCTGCACGATGGGAGGATTCTTCAT
GGTCTATAGTGGCTATGTGATGTTCTTCCAAGAGGGCAATATTGAGACCCTAAGACTCA
TGGCGATCTTGCACAATGTAGTGGGGTTTGCTGTGGTGGCTCTCCTTATGACTCACATC
TATATGGCAGCCTTTGCGATTGAGGGTGCATTGCACTCCATCCTAGATGGTCATATGGG
TGAAGAGGAGGTAGCGATTCTTCATAGTTTCTACTATAAAGAGTTGCAGGCGGAGGGGA
AAGTATGAGACACACCGATAGATTTGTTAAAAAGGTGGTGATTGAACGAATCGGCGATC
AGAGAGTGCTCGCCGAGGAGGAAGATGTGGTGATCAAAGAGGAGAGAATCTCTCTCTA
TCTTAATGGCACCAAGCTTATGTCCATGATGTCTCTTCCTTCCGATCAAGATGCTCATGC
GGTGGGCTTCTTGATGAGTGAGGGGGTGATTGAGAAGATCGAAGACTTAAAGAGTGTT
CAAATCTCTTCTGATGGGAGCTCTGTCTATGTAGAGGCTCTCATCAACCATGAGAACAT
CACCAATCTCTTCAAAGAGAAGACACTCACTTCAGGTTGTTGTGTCGGAGTGACGGGGA
ATCTTGAAGGCAATGTCCTAAGAAAGTTCATCGCTACTCCCATGCAGATTTCTTTGGAGA
GAATCTGGGAAGGGATGGAAGAGTTTGAGATGAGCAGCCATCTCTTTCATGAGACAGG
CTGCGTTCATAAAGCCTCCCTTCTCTTAGAAGATGGAAGCAAGATCACGGCTGAGGATA
TTGGTCGTCATAATGCAATTGATAAGGTGATGGGTAAAGCCAGGCTAGGGAGAATAGAT
ACAGAGAAGGCTGTGCTAGTGGTGAGCGGAAGACTCTCCATGGAGATGGTGGTTAAAG
CTGTCATGCACAACATTCCCATGATTGTCTCTAGGGCAGCAGCAACCTTTCTTGGAATC
AAGACAGCCCAAGAGCTAGGGGTGACTCTAGTGGGCTTTGCTAGAGGGGAGAAGATGA
ATATCTACACCCATTCTGGTCGAGTGGACTTGAGGGCTTGCAAGAGGAAAAGAGGGGT
GACTCTTCACGCTCCAAATCAATCTAGCTCTCTTCTTCGT |
| 20 | 19 | pJFF224<br>(fdh W.s.) | TCGAGGGGGGGCCCGGATCCCCAGTAGATTTACGTTTAAACATTTTTATTTCCTTTTTAA
TTTAATTTAATTAACAGTTGGTGCTATGACACTTTACCTCATAGCTGGCATAATTCGCAAT
ACTCTGGGTCTTCGAGAGGTATCCAACCTGAGTTGAAATACTTTACCATCGATTTAGCA
GTTGTATCAGTTATATTTATATTACCTTTAACTCTTCGCCATCCAGGAGTTTTACCGTACA
GATTAGAGGATAATAATAACACATAATTCTCGTAAGCAATATGAGATAATTTCCAAGACT
CTATATTAGCTCGTGATGTTTTCCAAGGTCTAAAATCGTCACGGTTCATATAATTAGCCA
ATCTCATATGCTCTCTAACTTCCGATGATAAGCTGTCAAACATGAGAATTAACGATCTGA
TAGAGAAGGGTTTGCTCGGGTCGGTGGCTCTGGTAACGACCAGTATCCCGATCCCGGC
TGGCCGTCCTGGCCGGCCACATGAGGCATGTTCCGCGTCCTTGCAATACTGTGTTTACAT
ACAGTCTATCGCTTAGCGGAAAGTTCTTTTACCCTCAGCCGAAATGCCTGCCGTTGCTA
GACATTGCCAGCCAGTGCCCGTCACTCCCGTACTAACTGTCACGAACCCCTGCAATAAC
TGTCACGCCCCCCTGCAATAACTGTCACGAACCCCTGCAATAACTGTCACGCCCCCAAA
CCTGCAAACCCAGCAGGGGCGGGGGCTGGCGGGGTGTTGGAAAAATCCATCCATGAT
TATCTAAGAATAATCCACTAGGCGCGGTTATCAGCGCCCTTGTGGGGCGCTGCTGCCC
TTGCCCAATATGCCCGGCCAGAGGCCGGATAGCTGGTCTATTCGCTGCGCTAGGCTAC
ACACCGCCCCACCGCTGCGCGGCAGGGGGAAAGGCGGGCAAAGCCCGCTAAACCCC
ACACCAAACCCCGCAGAAATACGCTGGGAGCGCTTTTAGCCGCTTTAGCGGCCTTTCC
CCCTACCCGAAGGGTGGGGGCGCGTGTGCAGCCCCGCAGGGCCTGTCTCGGTCGATC
ATTCAGCCCGGCTCATCCTTCTGGCGTGGCGGCAGACCGAACAAGGCGCGGTCGTGG
TCGCGTTCAAGGTACGCATCCATTGCCGCCATGAGCCGATCCTCCGGCCACTCGCTGC
TGTTCACCTTGGCCAAAATCATGGCCCCCACCAGCACCTTGCGCCTTGTTTCGTTCTTG
CGCTATTGCTGCTGTTCCCTTGCCCGCACCCGCTGAATTTCGGCATTGATTCGCGCTCG
TTGTTCTTCGAGCTTGGCCAGCCGATCCGCCGCCTTGTTGCTCCCCTTAACCATCTTGA
CACCCCATTGTTAATGTGCTGTCTCGTAGGCTATCATGGAGGCACAGCGGCGGCAATC
CCGACCCTACTTTGTAGGGGAGGGCGCATTGCATGGAGCCAAAAAGCAAAAGCAACAGC
GAGGCAGCATGGCGATTTATCACCTTACGGCGAAAACCGGCAGCAGGTCGGGCGGCC
AATCGGCCAGGGCCAAGGCCGACTACATCCAGCGCGAAGGCAAGTATGCCCGCGACA
TGGATGAAGTCTTGCACGCCGAATCCGGGCACATGCCGGAGTTCGTCGAGCGGCCCG
CCGACTACTGGGATGCTGCCGACCTGTATGAACGCGCAATGGCGGCGTTCAAGGA
GGTCGAATTTGCCCTGCCGGTCGAGCTGACCCTCGACCAGCAGAAGGCGCTGGCGTC
CGAGTTCGCCCAGCACCTGACCGGTGCCGAGCGCCTGCCGTATACGCTGGCCATCCA
TGCCGGTGGCGGCGAGAACCCGCACTGCCACCTGATGATCTCCGAGCGGATCAATGA
CGGCATCGAGCGGCCCGCCGCTCAGTGGTTCAAGCGGTACAACGGCAAGACCCCGGA |

FIG. 11 (Continued)

```
GAAGGGCGGGGCACAGAAGACCGAAGCGCTCAAGCCCAAGGCATGGCTTGAGCAGAC
CCGCGAGGCATGGGCCGACCATGCCAACCGGGCATTAGAGCGGGCTGGCCACGACG
CCCGCATTGACCACAGAACACTTGAGGCGCAGGGCATCGAGCGCCTGCCCGGTGTTC
ACCTGGGGCCGAACGTGGTGGAGATGGAAGGCCGGGGCATCCGCACCGACCGGGCA
GACGTGGCCCTGAACATCGACACCGCCAACGCCCAGATCATCGACTTACAGGAATACC
GGGAGGCAATAGACCATGAACGCAATCGACAGAGTGAAGAAATCCAGAGGCATCAACG
AGTTAGCGGAGCAGATCGAACCGCTGGCCCAGAGCATGGCGACACTGGCCGACGAAG
CCCGGCAGGTCATGAGCCAGACCCAGCAGGCCAGCGAGGCGCAGGCGGCGGAGTGG
CTGAAAGCCCAGCGCCAGACAGGGGCGGCATGGGTGGAGCTGGCCAAAGAGTTGCGG
GAGGTAGCCGCCGAGGTGAGCAGCGCCGCGCAGAGCGCCCGGAGCGCGTCGCGGG
GGTGGCACTGGAAGCTATGGCTAACCGTGATGCTGGCTTCCATGATGCCTACGGTGGT
GCTGCTGATCGCATCGTTGCTCTTGCTCGACCTGACGCCACTGACAACCGAGGACGGC
TCGATCTGGCTGCGCTTGGTGGCCCGATGAAGAACGACAGGACTTTGCAGGCCATAGG
CCGACAGCTCAAGGCCATGGGCTGTGAGCGCTTCGATATCGGCGTCAGGGACGCCAC
CACCGGCCAGATGATGAACCGGGAATGGTCAGCCGCCGAAGTGCTCCAGAACACGCC
ATGGCTCAAGCGGATGAATGCCCAGGGCAATGACGTGTATATCAGGCCCGCCGAGCAG
GAGCGGCATGGTCTGGTGCTGGTGGACGACCTCAGCGAGTTTGACCTGGATGACATGA
AAGCCGAGGGCCGGGAGCCTGCCCTGGTAGTGGAAACCAGCCCGAAGAACTATCAGG
CATGGGTCAAGGTGGCCGACGCCGCAGGCGGTGAACTTCGGGGGCAGATTGCCCGGA
CGCTGGCCAGCGAGTACGACGCCGACCCGGCCAGCGCCGACAGCCGCCACTATGGC
CGCTTGGCGGGCTTCACCAACCGCAAGGACAAGCACACCACCCGCGCCGGTTATCAG
CCGTGGGTGCTGCTGCGTGAATCCAAGGGCAAGACCGCCACCGCTGGCCCGGCGCTG
GTGCAGCAGGCTGGCCAGCAGATCGAGCAGGCCCAGCGGCAGCAGGAGAAGGCCCG
CAGGCTGGCCAGCCTCGAACTGCCCGAGCGGCAGCTTAGCCGCGCCACCGGCGCACGG
CGCTGGACGAGTACCGCAGCGAGATGGCCGGGCTGGTCAAGCGCTTCGGTGATGACC
TCAGCAAGTGCGACTTTATCGCCGCGCAGAAGCTGGCCAGCCGGGGCCGCAGTGCCG
AGGAAATCGGCAAGGCCATGGCCGAGGCCAGCCCAGCGCTGGCAGAGCGCAAGCCC
GGCCACGAAGCGGATTACATCGAGCGCACCGTCAGCAAGGTCATGGGTCTGCCCAGC
GTCCAGCTTGCGCGGGCCGAGCTGGCACGGGCACCGGCACCCCGCCAGCGAGGCAT
GGACAGGGGCGGGCCAGATTTCAGCATGTAGTGCTTGCGTTGGTACTCACGCCTGTTA
TACTATGAGTACTCACGCACAGAAGGGGTTTTATGGAATACGAAAAAAGCGCTTCAGG
GTCGGTCTACCTGATCAAAAGTGACAAGGGCTATTGGTTGCCCGGTGGCTTTGGTTATA
CGTCAAACAAGGCCGAGGCTGGCCGCTTTTCAGTCGCTGATATGGCCAGCCTTAACCT
TGACGGCTGCACCTTGTCCTTGTTCCGCGAAGACAAGCCTTTCGGCCCCGGCAAGTTT
CTCGGTGACTGATATGAAAGACCAAAAGGACAAGCAGACCGGCGACCTGCTGGCCAGC
CCTGACGCTGTACGCCAAGCGCGATATGCCGAGCGCATGAAGGCCAAAGGGATGCGT
CAGCGCAAGTTCTGGCTGACCGACGACGAATACGAGGCGCTGCGCGAGTGCCTGGAA
GAACTCAGAGCGGCGCAGGGCGGGGGTAGTGACCCCGCCAGCGCCTAACCACCAACT
GCCTGCAAAGGAGGCAATCAATGGCTACCCATAAGCCTATCAATATTCTGGAGGCGTTC
GCAGCAGCGCCGCCACCGCTGGACTACGTTTTGCCCAACATGGTGGCCGGTACGGTC
GGGGCGCTGGTGTCGCCCGGTGGTGCCGGTAAATCCATGCTGGCCCTGCAACTGGCC
GCACAGATTGCAGGCGGGCCGGATCTGCTGGAGGTGGGCGAACTGCCCACCGGCCC
GGTGATCTACCTGCCCGCCGAAGACCCGCCCACCGCCATTCATCACCGCCTGCACGCC
CTTGGGGCGCACCTCAGCGCCGAGGAACGGCAAGCCGTGGCTGACGGCCTGCTGATC
CAGCCGCTGATCGGCAGCCTGCCCAACATCATGGCCCCGGAGTGGTTCGACGGCCTC
AAGCGCGCCGCCGAGGGCCGCCGCCTGATGGTGCTGGACACGCTGCGCCGGTTCCA
CATCGAGGAAGAAAACGCCAGCGGCCCCATGGCCCAGGTCATCGGTCGCATGGAGGC
CATCGCCGCCGATACCGGGTGCTCTATCGTGTTCCTGCACCATGCCAGCAAGGGCGCG
GCCATGATGGGCGCAGGCGACCAGCAGCAGGCCAGCCGGGGCAGCTCGGTACTGGT
CGATAACATCCGCTGGCAGTCCTACCTGTCGAGCATGACCAGCGCCGAGGCCGAGGA
ATGGGGTGTGGACGACGACCAGCGCCGGTTCTTCGTCCGCTTCGGTGTGAGCAAGGC
CAACTATGGCGCACCGTTCGCTGATCGGTGGTTCAGGCGGCATGACGGCGGGGTGCT
CAAGCCCGCCGTGCTGGAGAGGCAGCGCAAGAGCAAGGGGGTGCCCCGTGGTGAAG
CCTAAGAACAAGCACAGCCTCAGCCACGTCCGGCACGACCCGGCGCACTGTCTGGCC
CCCGGCCTGTTCCGTGCCCTCAAGCGGGGCGAGCGCAAGCGCAGCAAGCTGGACGTG
ACGTATGACTACGGCGACGGCAAGCGGATCGAGTTCAGCGGCCCGGAGCCGCTGGGC
GCTGATGATCTGCGCATCCTGCAAGGGCTGGTGGCCATGGCTGGGCCTAATGGCCTAG
TGCTTGGCCCGGAACCCAAGACCGAAGGCGGACGGCAGCTCCGGCTGTTCCTGGAAC
CCAAGTGGGAGGCCGTCACCGCTGATGCCATGGTGGTCAAAGGTAGCTATCGGGCGC
TGGCAAAGGAAATCGGGGCAGAGGTCGATAGTGGTGGGCGCTCAAGCACATACAGG
ACTGCATCGAGCGCCTTTGGAAGGTATCCATCATCGCCCAGAATGGCCGCAAGCGGCA
GGGGTTTCGGCTGCTGTCGGAGTACGCCAGCGACGAGGCGGACGGCGCCTGTACGT
GGCCCTGAACCCCTTGATCGCGCAGGCCGTCATGGGTGGCGGCCAGCATGTGCGCAT
CAGCATGGACGAGGTGCGGGCGCTGGACAGCGAAACCGCCCGCCTGCTGCACCAGC
GGCTGTGTGGCTGGATCGACCCCGGCAAAACCGGCAAGGCTTCCATAGATACCTTGTG
CGGCTATGTCTGGCCGTCAGAGGCCAGTGGTTCGACCATGCGCAAGCGCCGCCAGCG
GGTGCGCGAGGCGTTGCCGGAGCTGGTCGCGCTGGGCTGGACGGTAACCGAGTTCG
CGGCGGGCAAGTACGACATCACCCGGCCCAAGGCGGCAGGCTGACCCCCCCACTCT
ATTGTAAACAAGACATTTTTTATCTTTTATATTCAATGGCTTATTTTCCTGCTAATTGGTAA
TACCATGAAAAATACCATGCTCAGAAAAGGCTTAACAATATTTTGAAAAATTGCCTACTG
AGCGCTGCCGCACAGCTCCATAGGCCGCTTTCCTGGCTTTGCTTCCAGATGTATGCTCT
CCTCCGGAGAGTACCGTGACTTTATTTTCGGCACAAATACAGGGGTCGATGGATAAATA
CGGCGATAGTTTCCTGACGGATGATCCGTATGTACCGGCGGAAGACAAGCTGCAAACC
TGTCAGATGGAGATTGATTTAATGGCGGATGTGCTGAGAGCACCGCCCCGTGAATCCG
```

FIG. 11 (Continued)

```
CAGAACTGATCCGCTATGTGTTTGCGGATGATTGGCCGGAATAAATAAAGCCGGGCTTA
ATACAGATTAAGCCCGTATAGGGTATTATTACTGAATACCAAACAGCTTACGGAGGACG
GAATGTTACCCATTGAGACAACCAGACTGCCTTCTGATTATTAATATTTTTCACTATTAAT
CAGAAGGAATAACCATGAATTTTACCCGGATTGACCTGAATACCTGGAATCGCAGGGAA
CACTTTGCCCTTTATCGTCAGCAGATTAAATGCGGATTCAGCCTGACCACCAAACTCGA
TATTACCGCTTTGCGTACCGCACTGGCGGAGACAGGTTATAAGTTTTATCCGCTGATGA
TTTACCTGATCTCCCGGGCTGTTAATCAGTTTCCGGAGTTCCGGATGGCACTGAAAGAC
AATGAACTTATTTACTGGGACCAGTCAGACCCGGTCTTTACTGTCTTTCATAAAGAAACC
GAAACATTCTCTGCACTGTCCTGCCGTTATTTTCCGGATCTCAGTGAGTTTATGGCAGG
TTATAATGCGGTAACGGCAGAATATCAGCATGATACCAGATTGTTTCCGCAGGGAAATT
TACCGGAGAATCACCTGAATATATCATCACCGTGGGTGAGTTTTGACGGGATTTAA
CCTGAACATCACCGGAAATGATGATTATTTTGCCCCGGTTTTTACGATGGCAAAGTTTCA
GCAGGAAGGTGACCGCGTATTATTACCTGTTTCTGTACAGGTTCATCATGCAGTCTGTG
ATGGCTTTCATGCAGCACGGTTTATTAATACACTTCAGCTGATGTGTGATAACATACTGA
AATAAATTAATTAATTCTGTATTTAAGCCACCGTATCCGGCAGGAATGGTGGCTTTTTTTT
TATATTTTAACCGTAATCTGTAATTTCGTTTCAGACTGGTTCAGGATCACTGTACGATAAT
GCCCCCGCAGTTTGGTAATACCCTTAATAAAAAGAAACAGCAAAGACTGACAGCAATA
ATAATAAAGTAAGCAGTAACAATAATATTAACAACACCAGATGCAGTTATAATAATAGTAT
TTAAGACACCAGAAAGACTGCTGCGACAGTCATTTTGAACAACACCAAAATGCCGTAAA
GGCAGTAGTAACAACACCAGTGAAAACATCACGATAGCATAGTGATATGCCTGAGTGTG
TGTAATTAAACAATAAATAAACCGCCATATATAACAGAAGATAGTATTCTGAATGGCATG
CTTTTCTGTTCAGTATAAACATATCATCCCGGTTGGTATAAGGATGATATATAATAAGTTA
AGCTGAACACATATTTATTTTGGTTTTATTTTACAAATAAAGTAAGACGATCCGTTAAGTC
AAAGCGGGGTATATTTATTATACCCTGCTTTTTTATTTGTCCGCCGGGCGCGGATAATG
GATCAGATTATGCAGTGTCACAATGGCCTTACCGGGATTGGCGTAAGCGTGCGGGATA
TCCGCATGGAAGCGCAGGGATTCCCCGGCAGAAACGGTGTGCCACTCATCCCCCAGC
CGCAGTTGTAATGCGCCTTCCAGTACAATGACATGTTCTCTGGTTCTGAAATCCATCCCT
GTCGGTGTTGCTTATGCAGTCTGGTCGGGACTCGGCGTCGTCATAATTACAGCCATTGC
CTGGTTGCTTCATGGGCAAAGCTTTATGCTTGTAAACCGTTTTGTGAAAAAATTTTTAA
AATAAAAAAGGGGACCTCTAGGGTCCCCAATTAATTAGTAATATAATCTATTAAAGGTCA
TTCAAAAGGTCATCCACCGGATCCCACCGCGGTGGCGGCCGTCTAACGAAGAAGAGAG
CTAGATTGATTTGGAGCGTGAAGAGTCACCCCTCTTTTCCTCTTGCAAGCCCTCAAGTC
CACTCGACCAGAATGGGTGTAGATATTCATCTTCTCCCCTCTAGCAAAGCCCACTAGAG
TCACCCCTAGCTCTTGGGCTGTCTTGATTCCAAGAAAGGTTGCTGCTGCCCTAGAGACA
ATCATGGGAATGTTGTGCATGACAGCTTTAACCACCATCTCCATGGAGAGTCTTCCGCT
CACCACTAGCACAGCCTTCTCTGTATCTATTCTCCCTAGCCTGGCTTTACCCATCACCTT
ATCAATTGCATTATGACGACCAATATCCTCAGCCGTGATCTTGCTTCCATCTTCTAAGAG
AAGGGAGGCTTTATGAACGCAGCCTGTCTCATGAAAGAGATGGCTGCTCATCTCAAACT
CTTCCATCCCTTCCCAGATTCTCTCCAAAGAAATCTGCATGGGAGTAGCGATGAACTTT
CTTAGGACATTGCCTTCAAGATTCCCCGTCACTCCGACACAACAACCTGAAGTGAGTGT
CTTCTCTTTGAAGAGATTGGTGATGTTCTCATGGTTGATGAGAGCCTCTACATAGACAGA
GCTCCCATCAGAAGAGATTTGAACACTCTTTAAGTCTTCGATCTTCTCAATCACCCCCTC
ACTCATCAAGAAGCCCACCGCATGAGCATCTTGATCGGAAGGAAGAGACATCATGGAC
ATAAGCTTGGTGCCATTAAGATAGAGAGAGATTCTCTCCTCTTTGATCACCACATCTTCC
TCCTCGGCGAGCACTCTCTGATCGCCGATTCGTTCAATCACCACCTTTTTAACAAATCTA
TCGGTGTGTCTCATACTTTCCCCTCCGCCTGCAACTCTTTATAGTAGAAACTATGAAGAA
TCGCTACCTCCTCTTCACCCATATGACCATCTAGGATGGAGTGCAATGCACCCTCAATC
GCAAAGGCTGCCATATAGATGTGAGTCATAAGGAGAGCCACCACAGCAAACCCCACTA
CATTGTGCAAGATCGCCATGAGTCTTAGGGTCTCAATATTGCCCTCTTGGAAGAACATC
ACATAGCCACTATAGACCATGAAGAATCCTCCCATCGTGCAGACCCAGAACCACATCTT
CTGACCCGCATTGAATTTGCCTGCAGGAATAGGTCTCTTCACCTTGCTTAGATACCCTC
CAAGAATGAGCATCCAGTCGATGTCATACATCTTAAAGAGAGCGTGCTTCACCCACATG
ATGAACATGAGGGGACCAAAGATCGCAAAGATGATCGTGGCTAATCCATGCACATCTCT
AGCGAATCGAATAAAAGCTCCACCCCCTAGGGCATCTCCAAAGACCATCAGAAGTCCTG
TGATGCAAAGAAGCACAAAGGGAATCCCTGCAATCCAGTGCACCATGATGTTGAAGGT
GTTAAAGACCTTGATCTTCTTCCCCTCATGAGAGAATCGCTTGGGTCCAATCACCATATA
GTGACCTAGGAAGACCAAAGGGATAGCGATGATGATCGCTAGGAAGATAAGAGCAAAG
TAACCACTTTGCAAGAAGGTGAAGAGCTCTCCTAATCCTCCTATTCCTCCAATCTCTCCA
AGACCTAGAATCCCTCCACTTCCCCAAGTGGGGATTGCCTCAATCATGGGCTTTCCATA
GATTTGGGTGTTGTAGCTGAAATCCAAGGGCTCCTTGAGATTCTCAGAAGCTTGTGCCC
CCAAGGCTCCCAGAAGGGAGAGGAGGGGCAATAGAGGCTTTTTCATTCTTAATCCTTGT
AGGCTTGTGACCAGGTGTAAGGAACACTGGCTTGTCCACTGCCTCGCTTGAGCACTCT
CTCACGAATGATGAGCGAGATGCTATCAGAATCTCCTGCTAGGAGTGCCTTGGTGGAG
CACATCGCTGCACATACAGGGACTTTGCCCTCAGCGATACGATTCTGTCCATAGAGCTT
ATACTCCTTCTCGCTGTGAGTCTCTTCAGGACCTCCAGCACAGAAGGTGCACTTATCCA
TAGGTCCTCTTGAACCAAAGATTCCACTCTTGGGGAATTGAGGAGGCACCAAAGGGCA
GGCATAGAGGCAGTAACCGCATCCAATGCACTTCTCTTTGTCATGCAATACAATCCCAT
CGGCTCGAACATAGAAGCAGTCCACTGGGCAGACCTGAGCACAAGGGGCATCAGAGC
AGTGCATGCAGGCAATAGAGAGGGATTTCTCTTTGCCTACAAGACCTTCATTGAGGGTC
ACCACTCTTCTTCGGTTGACTCCCACAGGAAGGTGATGGGCCTCTTTACAAGCCACATC
ACATCCATGACAATCAATACATCTAGCCTCATCACAATAGAACTTGACTCTAGCTTGACT
TTCCATGCTTCACCCCCTACGCTTTTTCGATCGGCAGAGGCCGCACTTGGTTTCAGGA
GTACTGGTGTTGATGTCGTATGCATCACTTGTGATGGTATTGCATGATTCACCAATAACA
TAAGGCTCTGTGCCTGCAATATGATACGGAACCAGTGACTCTCCTTGATACATTCCTCC
```

FIG. 11 (Continued)

| | | | |
|---|---|---|---|
| | | | GAAATTCTGGGGGAGGAAAACACTTGTTTTGTTGACCTTGTAGCTATGTCTCGCTTTCAC<br>GAGAATCTTTGCCCCATTGGTGCCGTGCACCCAAACCATGTCACCATGCTTCACGCCTA<br>AATCCGTGGCTGTTTCGGGATGAATCTCCACAAACATCTCAGGCTGAACCTCGGCGAG<br>GTAATGAGCTGATCTTGTCTCTGTGCCTGTGCCAAACTGTGCTACTAGTCGTCCAGAAA<br>GCATATTAAGCGGGAACTCTTTGGTCCAATCTTTCTCTTTTTGGCGGCTCTCATAGCGAA<br>TATTTGCCCTAAAGTGGTTGGGCTTGTCTTTGAAGGTTGGATATTGGCTAATGAGATCGT<br>GTCGAATTGTGTAGATGGGTTCACGGTGTTTAGGAATCTGATCCGTCCACTCCCAACA<br>ATCGCTCTAGCTCTACCATTACCCATAGGGGAGAGACCTGCGGCGAGTGCTTTTTCAAC<br>CAAGATATTGGTGGTGTCAGTCGCCCATGTCTTGCCTGCCACTTTGGCTTTTTCCTCTTC<br>GGTGAGGGCGATTCCAGTGATAGCTTCGACATTTTTATCGGTGATCATGCTATGACCGC<br>CCTTGAATTTTGAGCCGGCAAAGAGCTGTCCTGGCTGGCCAACAAACTTTCTCCTGTG<br>GGTGACACATCACCCCATCGAACCCTAAAGCCAAGACCTCCATCCATTACAGGGATGCT<br>GTCATCCCATAGATTTGGTGTTCCAGGATGCTTTTCGCTCCAGCAAGGCCAAGGAAGAC<br>CATAGTATTCGCCTTTGACGGGGCCGCCCTTTCCTCTGAGGGTGAACTTATCAAACATA<br>TGCCAGTTTTCTGCATGAGCCTTGAGTCGTTCTGGAGTTCTGCCTTGGAAGCCGACAGT<br>TCGTATAGCCTTGGCCACCTCTCTAGTCGCATCATCGGGCCATACAAAGTTTCCTTTGC<br>CATCCCCCAAAGAGCGAGTGTACTCCTCATAGAATCCAAGTCGCTTAGCTAAATCAAAG<br>AGAATCTCTTCGTCAGGTCGACACTCAAAGAGTGGCTTCATAACCATGGATCGCCACTG<br>ATAGCTTCGATTCGTCGCTGCGACTCTTCCGCTGGTCTCCATCTGTGTGGCGGCAGGA<br>AGGATATAGAGATTATCTTTTCGGTTGGTGAGGGCGGCCTGCATCATTGAAATAGGGATC<br>AAAAAAGACGACTAAATCCATCTTGTCTAGAGCGTCTTTGGTGGTATCCACGCGTGCGA<br>TCGTAGAGATTCCGCTTCCCACGACAATCAAGGATCGAAGTTTAGTGCCTGCATTGTGG<br>GGGATGTTCTCCTCTTCAGTCACCCCATATCTCCATGTGGATACACTGAAACCTTTTTA<br>TGCATCATATCAGGGGTCTTAAAGCGTTTTTGCATTGCTTCGAAATCCACTTTCCAGATT<br>CCACAGAAGTGATTCCATGCATTTTTGTCTAACCCATAATAGCCAGGAAGACTGTCGGC<br>TAGGTTGCCCATGTCCGTCGCGCCTTGGACATTGTCATGACCTCGTAAACGTTAGTGC<br>CTCCACCTCGTTTGCCAATGTTTCCAAGAATCATCTGTAAAATAGGGGCCAAACGAGTG<br>TTGCTTGTACCTGTGGTGTGCTGGGTGAGACCCATCCCCCAGATCAGTGAAGCAGGCT<br>TGGCTTTAGCGAAGATCTCCGTGATCTCAATAAGTTGTTGGGCGGGCACGCCTGTGAC<br>CTCTTCGACCACTTCAGGGGTGTACTGTTCGCACTCTTTAAGAATCTCTTCGTAGCCAAA<br>TAGGCGTTGTCGAATAAATTCTTTATCTTCTAGTCCATTTTTACAATATGGCGAATCATC<br>CCATACATGAAGGCGACATCCGTGCCATTGCGCAATCTCACATAGTGATCGGCTTTAGT<br>TGCTGTTCGACTGAAGTGGGGATCCACAACGATGATTTTGCTCCTGCCTCTTTAGCGC<br>GCAAGATATGCACCATGCCTACAGGGTGATTCACTGCGGGATTTCCACCAATGATAAAA<br>ATCGCCTTGGAGTGCATCATGTCTGCCAAGTGATTGGTCATACCGCCATATCCAAGGGT<br>ATTGGAGACTCCAGCAACTGTTGGGGCATGGCAGATTCGTCGATGGTATCGAGATTG<br>TTGGTGCCAAAAAAGGCGGCAAACTTTCTAAAATAATAGGATTGTTCAATCGAACACTTG<br>GAGCCGCCAATGAACATGACGCTATCAGGGCCATATTTTTGGGTGAGATCCTGAAGCT<br>GCTTGGCAATCTTATCCATGGCGCTATCCCATGAAGTTTTACGCCCATTTTCCGCCAACTT<br>TCTCAATGGGGTATCGAAGTCTTGTTTCGCTTCGAGCCTTATCAATCATATCGGCGCCC<br>TTGCAGCAGTGACCCCCTTGACTAATGGGGTGATCTTGAGCGACCTCTTGGCGTACCC<br>ATACACCATCGACCACTTCCGCTATAATTCCACATCCGACCGAGCAATAGGTGCAAATC<br>GTTTTTACCTTTTTGGACACTGGGTATTTTTCGATTAACTCTTGTTTTGTTGCAGGTCTAA<br>GCACTTTGCTTTGGTCGGAGCCAACCGCTTGACTCACGCCTGCGACTCCTGCTAAAGC<br>CGACATCTTTAGGAACTTTCTTCGATCGTTCCCGCGTCCGCTTAACGCTTCACTCATACA<br>TCACCTCATAAATAAATTAAAAAATAATAAAAACTAATGTTTCGCATTATAGGACAAAAG<br>ATACCTAAAAAATGTTATCTAGATCAAATTATTGGAAAATATATGAAAATAATTTTTGTTTA<br>AAAAGCGAACGACATTAGTATTTTTCATAAAAATACGTACATTGTTATCCGTCGCTATTTA<br>GGTACCGGGCCCGACGTCAGGCCTC |
| 21 | 20 | Lactate Dehydrogenase DNA (ldh) from DD1 | TTGACAAAATCAGTATGTTTAAATAAGGAGCTAACTATGAAAGTTGCCGTTTACAGTACT<br>AAAAATTATGATCGCAAACATCTGGATTTGGCGAATAAAAAATTTAATTTTGAGCTTCATT<br>TCTTTGATTTTTTACTTGATGAACAAACCGCGAAAATGGCGGAGGGCGCCGATGCCGTC<br>TGTATTTTCGTCAATGATGATGCGAGCCGCCCGGTGTTAACAAAGTTGGCGCAAATCGG<br>AGTGAAAATTATCGCTTTACGTTGTGCCGGTTTTAATAATGTGGATTTGGAGGCGGCAA<br>AAGAGCTGGGATTAAAAGTCGTACGGGTGCCTGCGTATTCGCCGGAAGCCGTTGCCGA<br>GCATGCGATCGGATTAATGCTGACTTTAAACCGCCGTATCCATAAGGCTTATCAGCGTA<br>CCCGCGATGCGAATTTTCTCTGGAAGGATTGGTCGGTTTTAATATGTTCGGCAAAACC<br>GCCGGAGTGATTGGTACGGGAAAAATCGGCTTGGCGGCTATTCGCATTTTAAAAGGCTT<br>CGGTATGGACGTTCTGGCGTTTGATCCTTTTAAAAATCCGGCGGCGGAAGCGTTGGGC<br>GCAAAATATGTCGGTTTAGACGAGCTTTATGCAAAATCCCATGTTATCACTTTGCATTGC<br>CCGGCTACGGCGGATAATTATCATTTATTAAATGAAGCGGCTTTTAATAAAATGCGCGAC<br>GGTGTAATGATTATTAATACCAGCCGCGGCGTTTTAATTGACAGCCGGGCGGCAATCGA<br>AGCGTTAAAACGGCAGAAAATCGGCGCTCTCGGTATGGATGTTTATGAAAATGAACGGG<br>ATTTGTTTTTCGAGGATAAATCTAACGATGTTATTACGGATGATGTATTCCGTCGCCTTT<br>CTTCCTGTCATAATGTGCTTTTTACCGGTCATCAGGCGTTTTTAACGGAAGAAGCGCTG<br>AATAATATCGCCGATGTGACTTTATCGAATATTCAGGCGGTTTCCAAAAATGCAACGTGC<br>GAAAATAGCGTTGAAGGC |
| 22 | 21 | Lactate Dehydrogenase Prot. (Ldh) from DD1 | MTKSVCLNKELTMKVAVYSTKNYDRKHLDLANKKFNFELHFFDFLLDEQTAKMAEGADAVC<br>IFVNDDASRPVLTKLAQIGVKIIALRCAGFNNVDLEAAKELGLKVVRVPAYSPEAVAEHAIGLM<br>LTLNRRIHKAYQRTRDANFSLEGLVGFNMFGKTAGVIGTGKIGLAAIRILKGFGMDVLAFDPF<br>KNPAAEALGAKYVGLDELYAKSHVITLHCPATADNYHLLNEAAFNKMRDGVMIINTSRGVLID<br>SRAAIEALKRQKIGALGMDVYENERDLFFEDKSNDVITDDVFRRLSSCHNVLFTGHQAFLTE<br>EALNNIADVTLSNIQAVSKNATCENSVEG* |

FIG. 11 (Continued)

| 23 | 22 | Pyruvate formate lyase DNA (pflD) from DD1 | ATGGCTGAATTAACAGAAGCTCAAAAAAAAGCATGGGAAGGATTCGTTCCCGGTGAATG GCAAAACGGCGTAAATTTACGTGACTTTATCCAAAAAAACTATACTCCGTATGAAGGTGA CGAATCATTCTTAGCTGATGCGACTCCTGCAACCAGCGAGTTGTGGAACAGCGTGATG GAAGGCATCAAAATCGAAAACAAAACTCACGCACCTTTAGATTTCGACGAACATACTCC GTCAACTATCACTTCTCACAAGCCTGGTTATATCAATAAAGATTTAGAAAAAATCGTTGG TCTTCAAACAGACGCTCCGTTAAAACGTGCAATTATGCCGTACGGCGGTATCAAAATGA TCAAAGGTTCTTGCGAAGTTTACGGTCGTAAATTAGATCCGCAAGTAGAATTTATTTTCA CCGAATATCGTAAAACCCATAACCAAGGCGTATTCGACGTTTATACGCCGGATATTTAC GCTGCCGTAAATCAGGCGTGTTAACCGGTTTACCGGATGCTTACGGTCGTGGTCGTATT ATCGGTGACTACCGTCGTTAGCGGTATACGGTATTGATTACCTGATGAAAGATAAAAAA GCCCAATTCGATTCATTACAACCGCGTTTGGAAGCGGGCGAAGACATTCAGGCAACTAT CCAATTACGTGAAGAAATTGCCGAACAACACCGCGCTTTAGGCAAAATCAAAGAAATGG CGGCATCTTACGGTTACGACATTTCCGGCCCTGCGACAAACGCACAGGAAGCAATCCA ATGGACATATTTTGCTTATCTGGCAGCGGTTAAATCACAAAACGGTGCGGCAATGTCAT TCGGTCGTACGTCTACATTCTTAGATATCTATATCGAACGTGACTTAAAACGCGGTTTAA TCACTGAACAACAGGCGCAGGAATTAATGGACCACTTAGTAATGAAATTACGTATGGTT CGTTTCTTACGTACGCCGGAATACGATCAATTATTCTCAGGCGACCCGATGTGGGCAAC CGAAACTATCGCCGGTATGGGCTTAGACGGTCGTCCGTTGGTAACTAAAAACAGCTTCC GCGTATTACATACTTTATACACTATGGGTACTTCTCCGGAACCAAACTTAACTATTCTTTG GTCCGAACAATTACCTGAAGCGTTCAAACGTTTCTGTGCGAAAGTATCTATTGATACTTC CTCCGTACAATACGAAAATGATGACTTAATGCGTCCTGACTTCAACAACGATGACTATGC AATCGCATGCTGCGTATCACCGATGGTCGTAGGTAAACAAATGCAATTCTTCGGTCGCG GCGCAAACTTAGCTAAAACTATGTTATACGCAATTAACGGCGGTATCGATGAGAAAAAT GGTATGCAAGTCGGTCCTAAAACTGCGCCGATTACAGACGAAGTATTGAATTTCGATAC CGTAATCGAACGTATGGACAGTTTCATGGACTGGTTGGCGACTCAATATGTAACCGCAT TGAACATCATCCACTTCATGCACGATAAAATATGCATATGAAGCGGCCATTGATGGCGTTC CACGATCGCGACGTATTCCGTACAATGGCTTGCGGTATCGCGGGTCTTTCCGTGGCTG CGGACTCATTATCCGCAATCAAATATGCGAAAGTTAAACCGATTCGCGGCGACATCAAA GATAAAGACGGTAATGTCGTGGCCTCGAATGTTGCTATCGACTTCGAAATTGAAGGCGA ATATCCGCAATTCGGTAACAATGATCCGCGTGTTGATGATTTAGCGGTAGACTTAGTTG AACGTTTCATGAAAAAAGTTCAAAAACACAAAACTTACCGCAACGCAACTCCGACACAAT CTATCCTGACTATCACTTCTAACGTGGTATACGGTAAGAAAACCGGTAATACTCCGGAC GGTCGTCGAGCAGGCGCGCCATTCGGACCGGGTGCAAACCCAATGCACGGTCGTGAC CAAAAAGGTGCGGTTCTTCACTTACTTCTGTGGCTAAACTTCCGTTCGCTTACGCGAA AGACGGTATTTCATATACCTTCTCTATCGTACCGAACGCATTAGGTAAAGATGACGAAG CGCAAAAACGCAACCTTGCCGGTTTAATGGACGGTTATTTCCATCATGAAGCGACAGTG GAAGGCGGTCAACACTTGAATGTTAACGTTCTTAACCGTGAAATGTTGTTAGACGCGAT GGAAAATCCGGAAAAATACCCGCAATTAACCATTCGTGTTTCAGGTTACGCGGTTCGTT TCAACTCATTAACTAAAGAGCAACAACAAGACGTCATCACTCGTACGTTTACACAAT-CAATG |
| 24 | 23 | Pyruvate formate lyase Prot. (PflD) from DD1 | MAELTEAQKKAWEGFVPGEWQNGVNLRDFIQKNYTPYEGDESFLADATPATSELWNSVM EGIKIENKTHAPLDFDEHTPSTITSHKPGYINKDLEKIVGLQTDAPLKRAIMPYGGIKMIKGSC EVYGRKLDPQVEFIFTEYRKTHNQGVFDVYTPDILRCRKSGVLTGLPDAYGRGRIIGDYRRL AVYGIDYLMKDKKAQFDSLQPRLEAGEDIQATIQLREEIAEQHRALGKIKEMAASYGYDISGP ATNAQEAIQWTYFAYLAAVKSQNGAAMSFGRTSTFLDIYIERDLKRGLITEQQAQELMDHLV MKLRMVRFLRTPEYDQLFSGDPMWATETIAGMGLDGRPLVTKNSFRVLHTLYTMGTSPEP NLTILWSEQLPEAFKRFCAKVSIDTSSVQYENDDLMRPDFNNDDYAIACCVSPMVVGKQMQ FFGARANLAKTMLYAINGGIDEKNGMQVGPKTAPITDEVLNFDTVIERMDSFMDWLATQYVT ALNIIHFMHDKYAYEAALMAFHDRDVFRTMACGIAGLSVAADSLSAIKYAKVKPIRGDIKDKD GNVVASNVAIDFEIEGEYPQFGNNDPRVDDLAVDLVERFMKKVQKHKTYRNATPTQSILTIT SNVVYGKKTGNTPDGRRAGAPFGPGANPMHGRDQKGAVASLTSVAKLPFAYAKDGISYTF SIVPNALGKDDEAQKRNLAGLMDGYFHHEATVEGGQHLNVNVLNREMLLDAMENPEKYPQ LTIRVSGYAVRFNSLTKEQQQDVITRTFTQSM |

SEQUENCE LISTING

```
<160> NUMBER OF SEQ ID NOS: 24

<210> SEQ ID NO 1
<211> LENGTH: 1308
<212> TYPE: DNA
<213> ORGANISM: Yersinia mollaretii

<400> SEQUENCE: 1
atgacaacct ctcgtactca acaaattcag cagttggaac aggaatggaa atcaccgcgc      60
tggaagggca tcacccgccc ctatagcgcc gaagaagtga tcaaactgcg cggttccgtt     120
aacccagaat gtacgctggc acagcacggc gcgaaaagat tgtgggagtt gctgcacggc     180
gaatcgcgta aaggctacat caactgtctg ggggcgctaa caggcggtca ggcattgcaa     240
caggcaaagg ccggtgttga agcgatttat ctgtcgggtt ggcaggtcgc cgccgatgcc     300
aataccgcct ccagcatgta tcccgatcaa tctctttacc cggtcgactc tgttccggcc     360
gtggttaagc gtattaataa cagcttccgc cgtgcagatc agattcagtg gtcgaataat     420
attgagccgg gcagcaaagg ctataccgac tatttcctgc cgattgtggc ggatgccgaa     480
gcgggttttg gcggcgtatt gaatgcgttt gaattgatga aagccatgat tgaagccggt     540
gctgcgggcg ttcactttga agatcaattg gcggcggtga agaaatgcgg ccatatgggc     600
ggcaaagttt tggtgccaac acaagaagcg attcagaagc tggttgctgc ccgcttagcc     660
gctgacgttc ttggcgtgcc aacactgctg attgcgcgca ctgatgctga tgctgcggat     720
ttgctgacct ctgattgcga cccttatgac agcgaattta ttgctggtga tcgtactgct     780
gagggcttct tccgcactca cgcgggcatt gagcaagcca tcagccgtgg tctggcctat     840
gccccttacg ccgacttggt gtggtgtgaa acctcgacgc cagatctggc gctggctaaa     900
cgctttgcag atgcggttca cgctaaattc cccggtaaat tattggctta taactgttcg     960
ccatcattta actggaaaaa gaacctgact gaccagcaga tcgccagctt ccaagatgac    1020
ctctccgcga tgggctacaa atatcaattt attaccttgg cgggcatcca cagtatgtgg    1080
ttcaacatgt tcgacttggc ccatgcttac gcgcaaggcg agggcatgaa gcactatgtt    1140
gagaaagtgc agcagccaga atttgcctcc gttgaacgcg gctacacctt tgcttcccat    1200
caacaagaag tgggcacggg ctattttgat aaagtcacca atatcattca gggcggcgag    1260
tcatcagtca ctgcactgac tggctcgacg gaagagcagc agttctaa                 1308

<210> SEQ ID NO 2
<211> LENGTH: 435
<212> TYPE: PRT
<213> ORG

<400> SEQUENCE: 2

```
Met Thr Thr Ser Arg Thr Gln Gln Ile Gln Gln Leu Glu Gln Glu Trp
1               5                   10                  15

Lys Ser Pro Arg Trp Lys Gly Ile Thr Arg Pro Tyr Ser Ala Glu Glu
            20                  25                  30

Val Ile Lys Leu Arg Gly Ser Val Asn Pro Glu Cys Thr Leu Ala Gln
        35                  40                  45

His Gly Ala Lys Arg Leu Trp Glu Leu Leu His Gly Glu Ser Arg Lys
    50                  55                  60

Gly Tyr Ile Asn Cys Leu Gly Ala Leu Thr Gly Gly Gln Ala Leu Gln
65                  70                  75                  80

Gln Ala Lys Ala Gly Val Glu Ala Ile Tyr Leu Ser Gly Trp Gln Val
                85                  90                  95

Ala Ala Asp Ala Asn Thr Ala Ser Ser Met Tyr Pro Asp Gln Ser Leu
            100                 105                 110

Tyr Pro Val Asp Ser Val Pro Ala Val Val Lys Arg Ile Asn Asn Ser
        115                 120                 125

Phe Arg Arg Ala Asp Gln Ile Gln Trp Ser Asn Asn Ile Glu Pro Gly
130                 135                 140

Ser Lys Gly Tyr Thr Asp Tyr Phe Leu Pro Ile Val Ala Asp Ala Glu
145                 150                 155                 160

Ala Gly Phe Gly Gly Val Leu Asn Ala Phe Glu Leu Met Lys Ala Met
                165                 170                 175

Ile Glu Ala Gly Ala Ala Gly Val His Phe Glu Asp Gln Leu Ala Ala
            180                 185                 190

Val Lys Lys Cys Gly His Met Gly Gly Lys Val Leu Val Pro Thr Gln
        195                 200                 205

Glu Ala Ile Gln Lys Leu Val Ala Ala Arg Leu Ala Ala Asp Val Leu
210                 215                 220

Gly Val Pro Thr Leu Leu Ile Ala Arg Thr Asp Ala Asp Ala Ala Asp
225                 230                 235                 240

Leu Leu Thr Ser Asp Cys Asp Pro Tyr Asp Ser Glu Phe Ile Ala Gly
                245                 250                 255

Asp Arg Thr Ala Glu Gly Phe Phe Arg Thr His Ala Gly Ile Glu Gln
            260                 265                 270

Ala Ile Ser Arg Gly Leu Ala Tyr Ala Pro Tyr Ala Asp Leu Val Trp
        275                 280                 285

Cys Glu Thr Ser Thr Pro Asp Leu Ala Leu Ala Lys Arg Phe Ala Asp
290                 295                 300

Ala Val His Ala Lys Phe Pro Gly Lys Leu Leu Ala Tyr Asn Cys Ser
305                 310                 315                 320

Pro Ser Phe Asn Trp Lys Lys Asn Leu Thr Asp Gln Gln Ile Ala Ser
                325                 330                 335

Phe Gln Asp Asp Leu Ser Ala Met Gly Tyr Lys Tyr Gln Phe Ile Thr
            340                 345                 350

Leu Ala Gly Ile His Ser Met Trp Phe Asn Met Phe Asp Leu Ala His
        355                 360                 365

Ala Tyr Ala Gln Gly Glu Gly Met Lys His Tyr Val Glu Lys Val Gln
370                 375                 380

Gln Pro Glu Phe Ala Ser Val Glu Arg Gly Tyr Thr Phe Ala Ser His
385                 390                 395                 400

Gln Gln Glu Val Gly Thr Gly Tyr Phe Asp Lys Val Thr Asn Ile Ile
                405                 410                 415
```

Gln Gly Gly Glu Ser Ser Val Thr Ala Leu Thr Gly Ser Thr Glu Glu
          420                 425                 430

Gln Gln Phe
      435

<210> SEQ ID NO 3
<211> LENGTH: 1632
<212> TYPE: DNA
<213> ORGANISM: Yersinia mollaretii

<400> SEQUENCE: 3

```
atgatcgtcg agagatgggg aaggggaagg ggaatgacac aacagatagt cggcacggag      60
ttagttttca cccagcattt taatgctgct gagcggcagg ttttgcccga tgaggccatc     120
gaattttggg cagaattggt ggcgaaattt gcagagccgc gtagcaaact ccttgctgca     180
cgggccgctt ggcaacaggc cattgaccaa ggcgcattgc ctgatttcat ttcggaaacc     240
aattccattc gtaatggtga ctggaaaatt caaagtattc ctgcggattt acgtgatcgt     300
cgcgtcgaga tcaccgggcc ggttgagcgc aaaatggtga ttaatgccct caatgcgaat     360
gtgaaagtct ttatggctga cttttgaggat cgctggcac ccagttggga taaggttatc     420
gaaggtcaga ttaatttgca cgatgcggtc aaaggcacaa tctcttacgc gaatgaatcc     480
ggtaagattt atcagctaaa acccaatcca gcggtgttga ttgctcgggt gcgtggtctg     540
cacttgccag aaaaacacgt gaagtggcag ggggaggata tccccggtgg cttattcgat     600
ttcgcgttgt atttctacca taactataag ttactgcttg ccaatggcag cggcccctat     660
ttctatctac caagatgca gtcttatcag gaagcggctt ggtggagtga tgttttcagc     720
tttaccgagc agcgtttcga tctgccgcaa ggcaccatta aggccacagt attaatcgag     780
acattgcctg cggtattcca gatggatgag atcctctacc atctgcgcca tcacattgtt     840
gccctgaatt gtggccgttg ggactacatt ttcagctata tcaaaacgct gaaaaatcac     900
agcgatcgcg tgctgcccga tcgccagtcg gtcacgatga cgaaacccct tcctgagtgc     960
tactctcgtt tactgatcaa aacctgccat aagcgcggtg ccttggcgat gggcggcatg    1020
gcggccttta tcccgaacaa agatccagaa aaaaatgcgc tggtcttaga taaagttcgc    1080
gctgacaaag agctggaagc cagcaacggc acgatggta catgggtcgc acacccggt     1140
ctggccgata ccgtgatgga cgttttcaac aaagtactgg gcgatcgtcc aaaccaatta    1200
gaggtgagtc gcgcgcaaga taaaccaatc actgccgctg agttgctaga gccttgcacg    1260
ggtgagcgca ccgaagaggg gatgcgggcc aatatccggg tcgcagtgca atacatcgaa    1320
gcatggatat cgggcaatgg ctgtgtaccg atttatggcc tgatggaaga tgccgcgacg    1380
gctgagattt cccgtacttc tatctggcaa tggatacatc accagaaaag cctgagcaat    1440
ggtcagacgg tgaccaaaga gctgttccgt aacatgttga gtgaagaaat gcaggtcgtg    1500
aaacttgaac ttggcgcaga gcgttttgat ggcggcggt ttgaagaagc cgcacgtctg    1560
atggagcgga ttacaacaca agacgagctt atcgactttc tgacgttgcc gggctacgca    1620
ttactcgcct ag                                                        1632
```

<210> SEQ ID NO 4
<211> LENGTH: 543
<212> TYPE: PRT
<213> ORGANISM: Yersinia mollaretii -continued

```
<400> SEQUENCE: 4

Met Ile Val Glu Arg Trp Gly Arg Gly Arg Gly Met Thr Gln Gln Ile
1               5                   10                  15

Val Gly Thr Glu Leu Val Phe Thr Gln His Phe Asn Ala Ala Glu Arg
            20                  25                  30

Gln Val Leu Pro Asp Glu Ala Ile Glu Phe Leu Ala Glu Leu Val Ala
        35                  40                  45

Lys Phe Ala Glu Pro Arg Ser Lys Leu Leu Ala Ala Arg Ala Ala Trp
    50                  55                  60

Gln Gln Ala Ile Asp Gln Gly Ala Leu Pro Asp Phe Ile Ser Glu Thr
65                  70                  75                  80

Asn Ser Ile Arg Asn Gly Asp Trp Lys Ile Gln Ser Ile Pro Ala Asp
                85                  90                  95

Leu Arg Asp Arg Arg Val Glu Ile Thr Gly Pro Val Glu Arg Lys Met
            100                 105                 110

Val Ile Asn Ala Leu Asn Ala Asn Val Lys Val Phe Met Ala Asp Phe
        115                 120                 125

Glu Asp Ser Leu Ala Pro Ser Trp Asp Lys Val Ile Glu Gly Gln Ile
    130                 135                 140

Asn Leu His Asp Ala Val Lys Gly Thr Ile Ser Tyr Ala Asn Glu Ser
145                 150                 155                 160

Gly Lys Ile Tyr Gln Leu Lys Pro Asn Pro Ala Val Leu Ile Ala Arg
                165                 170                 175

Val Arg Gly Leu His Leu Pro Glu Lys His Val Lys Trp Gln Gly Glu
            180                 185                 190

Asp Ile Pro Gly Gly Leu Phe Asp Phe Ala Leu Tyr Phe Tyr His Asn
        195                 200                 205

Tyr Lys Leu Leu Leu Ala Asn Gly Ser Gly Pro Tyr Phe Tyr Leu Pro
    210                 215                 220

Lys Met Gln Ser Tyr Gln Glu Ala Ala Trp Trp Ser Asp Val Phe Ser
225                 230                 235                 240

Phe Thr Glu Gln Arg Phe Asp Leu Pro Gln Gly Thr Ile Lys Ala Thr
                245                 250                 255

Val Leu Ile Glu Thr Leu Pro Ala Val Phe Gln Met Asp Glu Ile Leu
            260                 265                 270

Tyr His Leu Arg His His Ile Val Ala Leu Asn Cys Gly Arg Trp Asp
        275                 280                 285

Tyr Ile Phe Ser Tyr Ile Lys Thr Leu Lys Asn His Ser Asp Arg Val
    290                 295                 300

Leu Pro Asp Arg Gln Ser Val Thr Met Thr Lys Pro Phe Leu Ser Ala
305                 310                 315                 320

Tyr Ser Arg Leu Leu Ile Lys Thr Cys His Lys Arg Gly Ala Leu Ala
                325                 330                 335

Met Gly Gly Met Ala Ala Phe Ile Pro Asn Lys Asp Pro Glu Lys Asn
            340                 345                 350

Ala Leu Val Leu Asp Lys Val Arg Ala Asp Lys Glu Leu Glu Ala Ser
        355                 360                 365

Asn Gly His Asp Gly Thr Trp Val Ala His Pro Gly Leu Ala Asp Thr
    370                 375                 380

Val Met Asp Val Phe Asn Lys Val Leu Gly Asp Arg Pro Asn Gln Leu
385                 390                 395                 400

Glu Val Ser Arg Ala Gln Asp Lys Pro Ile Thr Ala Ala Glu Leu Leu
                405                 410                 415
```

Glu Pro Cys Thr Gly Glu Arg Thr Glu Glu Gly Met Arg Ala Asn Ile
            420                 425                 430

Arg Val Ala Val Gln Tyr Ile Glu Ala Trp Ile Ser Gly Asn Gly Cys
            435                 440                 445

Val Pro Ile Tyr Gly Leu Met Glu Asp Ala Ala Thr Ala Glu Ile Ser
            450                 455                 460

Arg Thr Ser Ile Trp Gln Trp Ile His His Gln Lys Ser Leu Ser Asn
465                 470                 475                 480

Gly Gln Thr Val Thr Lys Glu Leu Phe Arg Asn Met Leu Ser Glu Glu
                485                 490                 495

Met Gln Val Val Lys Leu Glu Leu Gly Ala Glu Arg Phe Asp Gly Gly
            500                 505                 510

Arg Phe Glu Glu Ala Ala Arg Leu Met Glu Arg Ile Thr Thr Gln Asp
            515                 520                 525

Glu Leu Ile Asp Phe Leu Thr Leu Pro Gly Tyr Ala Leu Leu Ala
            530                 535                 540

<210> SEQ ID NO 5
<211> LENGTH: 1092
<212> TYPE: DNA
<213> ORGANISM: Candida boidinii

<400> SEQUENCE: 5
atgaagatcg ttttagtctt atatgatgct ggtaagcacg ctgctgatga agaaaaatta      60
tatggttgta ctgaaaataa attaggtatt gctaattggt taaaagatca aggtcatgaa     120
ctaattacta cttctgataa agaaggtgaa acaagtgaat tggataaaca tatcccagat     180
gctgatatta tcatcaccac tccttttcat cctgcttata tcactaagga aagacttgac     240
aaggctaaga acttaaaatt agtcgttgtc gctggtgttg ttctgatca cattgattta     300 gattatatta tcaaacagg taagaaaatc tcagtcttgg aagttacagg ttctaatgtt     360
gtctctgttg ctgaacacgt tgtcatgacc atgcttgtct tggttagaaa tttcgttcca     420
gcacatgaac aaattattaa ccacgattgg gaggttgctg ctatcgctaa ggatgcttac     480
gatatcgaag gtaaaactat tgctaccatt ggtgctggta gaattggtta cagagtcttg     540
gaaagattac tccctttaa tccaaaagaa ttattatact acgattatca agctttacca     600
aaagaagctg aagaaaaagt tggtgctaga gagttgaaa atattgaaga attagttgct     660
caagctgata tcgttacagt taatgctcca ttacacgcag gtacaaaagg tttaattaat     720
aaggaattat tatctaaatt taaaaaaggt gcttggttag tcaataccgc aagaggtgct     780
atttgtgttg ctgaagatgt tgcagcagct ttagaatctg gtcaattaag aggttacggt     840
ggtgatgttg gttcccaca accagctcca aaggatcacc catggagaga tatgagaaat     900
aaatatggtg ctggtaatgc catgactcct cactactctg gtactacttt agatgctcaa     960
acaagatacg ctgaaggtac taaaaatatc ttggaatcat tctttactgg taaatttgat    1020
tacagaccac aagatattat cttattaaat ggtgaatacg ttactaaagc ttacggtaaa    1080
cacgataaga aa                                                       1092

<210> SEQ ID NO 6
<211> LENGTH: 364
<212> TYPE: PRT
<213> ORGANISM: Candida boidinii

<400> SEQUENCE: 6

```
Met Lys Ile Val Leu Val Leu Tyr Asp Ala Gly Lys His Ala Ala Asp
1               5                   10                  15

Glu Glu Lys Leu Tyr Gly Cys Thr Glu Asn Lys Leu Gly Ile Ala Asn
            20                  25                  30

Trp Leu Lys Asp Gln Gly His Glu Leu Ile Thr Thr Ser Asp Lys Glu
            35                  40                  45

Gly Glu Thr Ser Glu Leu Asp Lys His Ile Pro Asp Ala Asp Ile Ile
    50                  55                  60

Ile Thr Thr Pro Phe His Pro Ala Tyr Ile Thr Lys Glu Arg Leu Asp
65                  70                  75                  80

Lys Ala Lys Asn Leu Lys Leu Val Val Ala Gly Val Gly Ser Asp
                85                  90                  95

His Ile Asp Leu Asp Tyr Ile Asn Gln Thr Gly Lys Lys Ile Ser Val
                100                 105                 110

Leu Glu Val Thr Gly Ser Asn Val Val Ser Val Ala Glu His Val Val
            115                 120                 125

Met Thr Met Leu Val Leu Val Arg Asn Phe Val Pro Ala His Glu Gln
130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Lys Val Gly
            195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Ala Leu Glu
            260                 265                 270

Ser Gly Gln Leu Arg Gly Tyr Gly Gly Asp Val Trp Phe Pro Gln Pro
    275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
            325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
            355                 360
```

<210> SEQ ID NO 7
<211> LENGTH: 1541
<212> TYPE: DNA
<213> ORGANISM: Pasteurella DSM 18541

<400> SEQUENCE: 7
attgaagagt tgatcatgg ctcagattga acgctggcgg caggcttaac acatgcaagt    60

| | |
|---|---|
| cgaacggtag cgggaggaaa gcttgctttc tttgccgacg agtggcggac gggtgagtaa | 120 |
| tgcttgggga tctggcttat ggagggggat aacgacggga aactgtcgct aataccgcgt | 180 |
| aatatcttcg gattaaaggg tgggactttc gggccacccg ccataagatg agcccaagtg | 240 |
| ggattaggta gttggtgggg taaaggccta ccaagccgac gatctctagc tggtctgaga | 300 |
| ggatgaccag ccacactgga actgagacac ggtccagact cctacgggag gcagcagtgg | 360 |
| ggaatattgc acaatggggg gaaccctgat gcagccatgc cgcgtgaatg aagaaggcct | 420 |
| tcgggttgta aagttctttc ggtgacgagg aaggtgtttg ttttaatagg acaagcaatt | 480 |
| gacgttaatc acagaagaag caccggctaa ctccgtgcca gcagccgcgg taatacggag | 540 |
| ggtgcgagcg ttaatcggaa taactgggcg taaagggcat gcaggcggac ttttaagtga | 600 |
| gatgtgaaag ccccgggctt aacctgggaa ttgcatttca gactgggagt ctagagtact | 660 |
| ttagggaggg gtagaattcc acgtgtagcg gtgaaatgcg tagagatgtg gaggaatacc | 720 |
| gaaggcgaag gcagcccctt ggaagatac tgacgctcat atgcgaaagc gtgggagca | 780 |
| aacaggatta gataccctgg tagtccacgc ggtaaacgct gtcgatttgg ggattgggct | 840 |
| ttaggcctgg tgctcgtagc taacgtgata aatcgaccgc ctgggagta cggccgcaag | 900 |
| gttaaaactc aaatgaattg acgggggccc gcacaagcgg tggagcatgt ggtttaattc | 960 |
| gatgcaacgc gaagaacctt acctactctt gacatccaga gaatcctgta gagatacggg | 1020 |
| agtgccttcg ggagctctga acaggtgct gcatggctgt cgtcagctcg tgttgtgaaa | 1080 |
| tgttgggtta agtcccgcaa cgagcgcaac ccttatcctt tgttgccagc atgtaaagat | 1140 |
| gggaactcaa aggagactgc cggtgacaaa ccggaggaag gtgggatga cgtcaagtca | 1200 |
| tcatggccct tacgagtagg gctacacacg tgctacaatg gtgcatacag agggcggcga | 1260 |
| taccgcgagg tagagcgaat ctcagaaagt gcatcgtagt ccggattgga gtctgcaact | 1320 |
| cgactccatg aagtcggaat cgctagtaat cgcaaatcag aatgttgcgg tgaatacgtt | 1380 |
| cccgggcctt gtacacaccg cccgtcacac catgggagtg ggttgtacca gaagtagata | 1440 |
| gcttaacctt cgggggggcgt ttaccacggt atgattcatg actggggtga agtcgtaaca | 1500 |
| aggtaaccgt agggggaacct gcggttggat cacctcctta c | 1541 |

<210> SEQ ID NO 8
<211> LENGTH: 2891
<212> TYPE: DNA
<213> ORGANISM: Pasteurella DSM 18541
<220> FEATURE:
<221> NAME/KEY: misc_feature
<222> LOCATION: (456)..(456)
<223> OTHER INFORMATION: n is a, c, g, or t

<400> SEQUENCE: 8

| | |
|---|---|
| gttaagtgac taagcgtaca aggtggatgc cttggcaatc agaggcgaag aaggacgtgc | 60 |
| taatctgcga aaagcttggg tgagttgata agaagcgtct aacccaagat atccgaatgg | 120 |
| ggcaacccag tagatgaaga atctactatc aataaccgaa tccataggtt attgaggcaa | 180 |
| accgggagaa ctgaaacatc taagtacccc gaggaaaaga aatcaaccga gattacgtca | 240 |
| gtagcggcga gcgaaagcgt aagagccggc aagtgatagc atgaggatta gaggaatcgg | 300 |
| ctgggaagcc gggcggcaca gggtgatagc cccgtacttg aaaatcattg tgtggtactg | 360 |
| agcttgcgag aagtagggcg ggacacgaga atcctgtttt gaagaagggg ggaccatcct | 420 |
| ccaaggctaa atactcctga ttgaccgata gtgaanagta ctgtgaagga aaggcgaaaa | 480 |
| gaaccccggt gaggggagtg aaatagaacc tgaaaccttg tacgtacaag cagtgggagc | 540 |

```
ccgcgagggt gactgcgtac cttttgtata atgggtcagc gacttatatt atgtagcgag    600
gttaaccgaa taggggagcc gaagggaaac cgagtcttaa ctgggcgtcg agttgcatga    660
tatagacccg aaacccggtg atctagccat gggcaggttg aaggttgggt aacactaact    720
ggaggaccga accgactaat gttgaaaaat tagcggatga cctgtggctg ggggtgaaag    780
gccaatcaaa ccgggagata gctggttctc cccgaaatct atttaggtag agccttatgt    840
gaataccttc gggggtagag cactgtttcg gctaggggc catcccggct taccaacccg       900
atgcaaactg cgaataccga agagtaatgc ataggagaca cacggcgggt gctaacgttc    960
gtcgtggaga gggaaacaac ccagaccgcc agctaaggtc ccaaagttta tattaagtgg    1020
gaaacgaagt gggaaggctt agacagctag gatgttggct tagaagcagc catcatttaa    1080
agaaagcgta atagctcact agtcgagtcg gcctgcgcgg aagatgtaac ggggctcaaa    1140
tatagcaccg aagctgcggc atcaggcgta agcctgttgg gtaggggagc gtcgtgtaag    1200
cggaagaagg tggttcgaga gggctgctgg acgtatcacg agtgcgaatg ctgacataag    1260
taacgataaa acgggtgaaa aacccgttcg ccggaagacc aagggttcct gtccaacgtt    1320
aatcggggca gggtgagtcg gcccctaagg cgaggctgaa gagcgtagtc gatgggaaac    1380
gggttaatat tcccgtactt gttataattg cgatgtgggg acggagtagg ttaggttatc    1440
gacctgttgg aaaaggtcgt ttaagttggt aggtggagcg tttaggcaaa tccgacgct     1500
tatcaacacc gagagatgat gacgaggcgc taaggtgccg aagtaaccga taccacactt    1560
ccaggaaaag ccactaagcg tcagattata ataaaccgta ctataaaccg acacaggtgg    1620
tcaggtagag aatactcagg cgcttgagag aactcgggtg aaggaactag gcaaaatagc    1680
accgtaactt cgggagaagg tgcgccggcg tagattgtag aggtataccc ttgaaggttg    1740
aaccggtcga agtgacccgc tggctgcaac tgtttattaa aaacacagca ctctgcaaac    1800
acgaaagtgg acgtataggg tgtgatgcct gcccggtgct ggaaggttaa ttgatggcgt    1860
tatcgcaaga gaagcgcctg atcgaagccc cagtaaacgg cggccgtaac tataacggtc    1920
ctaaggtagc gaaattcctt gtcgggtaag ttccgacctg cacgaatggc ataatgatgg    1980
ccaggctgtc tccacccgag actcagtgaa attgaaatcg ccgtgaagat gcggtgtacc    2040
cgcggctaga cggaaagacc ccgtgaacct ttactatagc ttgacactga accttgaatt    2100
ttgatgtgta ggataggtgg gaggctttga agcggtaacg ccagttatcg tggagccatc    2160
cttgaaatac cacccttaa cgtttgatgt tctaacgaag tgcccggaac gggtactcgg     2220
acagtgtctg gtgggtagtt tgactggggc ggtctcctcc caaagagtaa cggaggagca    2280
cgaaggtttg ctaatgacgg tcggacatcg tcaggttagt gcaatggtat aagcaagctt    2340
aactgcgaga cggacaagtc gagcaggtgc gaaagcaggt catagtgatc cggtggttct    2400
gaatggaagg gccatcgctc aacggataaa aggtactccg gggataacag gctgataccg    2460
cccaagagtt catatcgacg gcggtgtttg gcacctcgat gtcggctcat cacatcctgg    2520
ggctgaagta ggtcccaagg gtatggctgt tcgccattta aagtggtacg cgagctgggt    2580
ttaaaacgtc gtgagacagt ttggtcccta tctgccgtgg gcgttggaga attgagaggg    2640
gctgctccta gtacgagagg accggagtgg acgcatcact ggtgttccgg ttgtgtcgcc    2700
agacgcattg ccgggtagct acatgcggaa gagataagtg ctgaaagcat ctaagcacga    2760
aacttgcctc gagatgagtt ctcccagtat ttaatactgt aagggttgtt ggagacgacg    2820
acgtagatag gccgggtgtg taagcgttgc gagacgttga gctaaccggt actaattgcc    2880
```
cgagaggctt a                                                      2891

<210> SEQ ID NO 9
<211> LENGTH: 4285
<212> TYPE: DNA
<213> ORGANISM: Artificial Sequence
<220> FEATURE:
<223> OTHER INFORMATION: vector

<400> SEQUENCE: 9
tcgagaggcc tgacgtcggg cccggtacca cgcgtcatat gactagttcg gacctaggga      60
tatcgtcgac atcgatgctc ttctgcgtta attaacaatt gggatcctct agactccata     120
ggccgctttc ctggctttgc ttccagatgt atgctctcct ccggagagta ccgtgacttt     180
attttcggca caaatacagg ggtcgatgga taaatacggc gatagtttcc tgacggatga     240
tccgtatgta ccggcggaag acaagctgca aacctgtcag atggagattg atttaatggc     300
ggatgtgctg agagcaccgc cccgtgaatc cgcagaactg atccgctatg tgtttgcgga     360
tgattggccg gaataaataa agcccggctt aatacagatt aagcccgtat agggtattat     420
tactgaatac caaacagctt acggaggacg gaatgttacc cattgagaca accagactgc     480
cttctgatta ttaatatttt tcactattaa tcagaaggaa taaccatgaa ttttacccgg     540
attgacctga atacctggaa tcgcaggaa cactttgccc tttatcgtca gcagattaaa     600
tgcggattca gcctgaccac caaactcgat attaccgctt tgcgtaccgc actggcggag     660
acaggttata agttttatcc gctgatgatt tacctgatct cccgggctgt taatcagttt     720
ccggagttcc ggatggcact gaaagacaat gaacttattt actgggacca gtcagacccg     780
gtctttactg tctttcataa agaaaccgaa acattctctg cactgtcctg ccgttatttt     840
ccggatctca gtgagtttat ggcaggttat aatgcggtaa cggcagaata tcagcatgat     900
accagattgt tccgcaggg aaatttaccg gagaatcacc tgaatatatc atcattaccg     960
tgggtgagtt ttgacgggat ttaacctgaa catcaccgga atgatgatt attttgcccc    1020
ggttttacg atggcaaagt ttcagcagga aggtgaccgc gtattattac ctgtttctgt    1080
acaggttcat catgcagtct gtgatggctt tcatgcagca cggtttatta atacacttca    1140
gctgatgtgt gataacatac tgaaataaat taattaattc tgtatttaag ccaccgtatc    1200
cggcaggaat ggtggctttt ttttttatatt ttaaccgtaa tctgtaattt cgtttcagac    1260
tggttcagga tgagctcgct tggactcctg ttgatagatc cagtaatgac ctcagaactc    1320
catctggatt tgttcagaac gctcggttgc cgccgggcgt ttttttattgg tgagaatcca    1380
agcactagcg gcgcgccggc cggcccggtg tgaaataccg cacagatgcg taaggagaaa    1440
ataccgcatc aggcgctctt ccgcttcctc gctcactgac tcgctgcgct cggtcgttcg    1500
gctgcggcga gcggtatcag ctcactcaaa ggcggtaata cggttatcca cagaatcagg    1560
ggataacgca ggaaagaaca tgtgagcaaa aggccagcaa aaggccagga accgtaaaaa    1620
ggccgcgttg ctggcgtttt tccataggct ccgcccccct gacgagcatc acaaaaatcg    1680
acgctcaagt cagaggtggc gaaacccgac aggactataa agataccagg cgtttccccc    1740
tggaagctcc ctcgtgcgct ctcctgttcc gaccctgccg cttaccggat acctgtccgc    1800
ctttctccct tcgggaagcg tggcgctttc tcatagctca cgctgtaggt atctcagttc    1860
ggtgtaggtc gttcgctcca agctgggctg tgtgcacgaa ccccccgttc agcccgaccg    1920
ctgcgcctta tccggtaact atcgtcttga gtccaacccg gtaagacacg acttatcgcc    1980
actggcagca gccactggta acaggattag cagagcgagg tatgtaggcg gtgctacaga    2040

```
gttcttgaag tggtggccta actacggcta cactagaagg acagtatttg gtatctgcgc    2100
tctgctgaag ccagttacct tcggaaaaag agttggtagc tcttgatccg gcaaacaaac    2160
caccgctggt agcggtggtt ttttttgtttg caagcagcag attacgcgca gaaaaaaagg   2220
atctcaagaa gatcctttga tcttttctac ggggtctgac gctcagtgga acgaaaactc    2280
acgttaaggg attttggtca tgagattatc aaaaaggatc ttcacctaga tccttttaaa    2340
ggccggccgc ggccgccatc ggcatttttct tttgcgtttt tatttgttaa ctgttaattg    2400
tccttgttca aggatgctgt ctttgacaac agatgttttc ttgcctttga tgttcagcag    2460
gaagctcggc gcaaacgttg attgtttgtc tgcgtagaat cctctgtttg tcatatagct    2520
tgtaatcacg acattgtttc ctttcgcttg aggtacagcg aagtgtgagt aagtaaaggt    2580
tacatcgtta ggatcaagat ccatttttaa cacaaggcca gttttgttca gcggcttgta    2640
tgggccagtt aaagaattag aaacataacc aagcatgtaa atatcgttag acgtaatgcc    2700
gtcaatcgtc attttttgatc cgcgggagtc agtgaacagg taccatttgc cgttcatttt    2760
aaagacgttc gcgcgttcaa tttcatctgt tactgtgtta gatgcaatca gcggtttcat    2820 cactttttttc agtgtgtaat catcgtttag ctcaatcata ccgagagcgc cgtttgctaa    2880
ctcagccgtg cgttttttat cgctttgcag aagttttttga cttcttgac ggaagaatga    2940 tgtgcttttg ccatagtatg ctttgttaaa taaagattct tcgccttggt agccatcttc    3000
agttccagtg tttgcttcaa atactaagta tttgtggcct ttatcttcta cgtagtgagg    3060
atctctcagc gtatggttgt cgcctgagct gtagttgcct tcatcgatga actgctgtac    3120
attttgatac gttttttccgt caccgtcaaa gattgattta taatcctcta caccgttgat    3180
gttcaaagag ctgtctgatg ctgatacgtt aacttgtgca gttgtcagtg tttgtttgcc    3240
gtaatgttta ccggagaaat cagtgtagaa taaacggatt ttttccgtcag atgtaaatgt    3300 ggctgaacct gaccattctt gtgtttggtc ttttaggata gaatcatttg catcgaattt    3360
gtcgctgtct ttaaagacgc ggccagcgtt tttccagctg tcaatagaag tttcgccgac    3420 ttttttgatag aacatgtaaa tcgatgtgtc atccgcattt ttaggatctc cggctaatgc    3480
aaagacgatg tggtagccgt gatagtttgc gacagtgccg tcagcgtttt gtaatggcca    3540
gctgtcccaa acgtccaggc cttttgcaga agagatattt ttaattgtgg acgaatcaaa    3600 ttcagaaaact tgatattttt catttttttg ctgttcaggg atttgcagca tatcatggcg    3660
tgtaatatgg gaaatgccgt atgtttcctt atatggcttt tggttcgttt ctttcgcaaa    3720
cgcttgagtt gcgcctcctg ccagcagtgc ggtagtaaag gttaatactg ttgcttgttt    3780
tgcaaacttt ttgatgttca tcgttcatgt ctcctttttt atgtactgtg ttagcggtct    3840
gcttcttcca gccctcctgt ttgaagatgg caagttagtt acgcacaata aaaaagacc     3900 taaaatatgt aaggggtgac gccaaagtat acactttgcc ctttacacat tttaggtctt    3960
gcctgcttta tcagtaacaa acccgcgcga tttacttttc gacctcattc tattagactc    4020
tcgtttggat tgcaactggt ctattttcct cttttgtttg atagaaaatc ataaaaggat    4080
ttgcagacta cgggcctaaa gaactaaaaa atctatctgt ttcttttcat tctctgtatt    4140 tttttatagtt tctgttgcat gggcataaag ttgcctttt aatcacaatt cagaaaatat    4200
cataatatct catttcacta aataatagtg aacggcaggt atatgtgatg ggttaaaaag    4260
gatcggcggc cgctcgattt aaatc                                          4285
```

<210> SEQ ID NO 10

<211> LENGTH: 7112
<212> TYPE: DNA
<213> ORGANISM: artificial
<220> FEATURE:
<223> OTHER INFORMATION: vector

<400> SEQUENCE: 10

```
tcgagaggcc tgacgtcggg cccggtacca cgcgtcatat gactagttcg gacctaggga      60
tatcgtcgac atcgatgctc ttctgcgtta attaacaatt gggatcctct agacccgggg     120
attccaacct gaagactggc tcggtatgac cgaacccgtc aatattccgg gaaccagcac     180
tcaatatgct aactggcggc gccgtttaac cgcaaatata gaggatattt ttgccgatac     240
ggatattcaa catctgttaa agaggtgaaa tgctattcgt aaggaataat tttgttgcga     300
acgcaatgtg attttaacgg gtgccggata tggcaccctt atcaaaacga cgaatattat     360
agacctctta cgatgacgca tctttcccca gatacgcagg attagacgga tgatgttacg     420
gaatatcccg tccctgtgcg gcaacataaa ccttaatcca ttcttcctca gtgaaggaaa     480
ttcgtaacgc atccgccgcg cttttttaccc gttcaatttt accggacccc ataaccggca     540
taatttttgc cggatgcgcc aataaccagg cataagccaa tgtatctaaa cgggtttctc     600
ctttcgtttc accgatttcg agtaatgttt tttgcaccgc ccgactgttc tcatcctgat     660
tgaataaacg accgccggca agtggcgacc atgccatcgg ttgaatacgt ttttccagta     720
aaaaatccag ggtaccgtca tcaaaagcct gacgatgaag aggcgaaatc tcaatttgat     780
tagtgattaa cggctgattc acataagatt gcaacatggc gaacttagcc ggcgtatagt     840
tagatacccc gaaataacgt actttyccgg tttgataaag ttcatcaaaa gcccgcgcga     900
tttgttcggg atccgcacag ggagaaagwc ggtgaatcag caatacatct aaatagtcgc     960
attgcagttt ttcaatggaa cgttgcgccg accacataat atggcggtag ctgttgtcat    1020
agtgatggga ttttatatcg ggtaattctt cattaggata caaaatcccg catttggtca    1080
ccaaagtaag ctgtgcgcgc aaggatttat ccagcgccag cgcccgtccg aattccgcct    1140
cggaagtaaa agccccgtaa caagcggcat gatccagcgt atcaacgcct aattctaatc    1200
cttgcttaac gaatgtaagc aattcctgcg gcgatttccg ccagcttttt aaccgccaga    1260
atccttgaat taagcgactg aatgttaaat cgggagccag ttgaatgtgt tgcataaaac    1320
ctccaaataa attgaatcaa acagacttaa gtataaatct ttaaagaaaa agtgcggtag    1380
aaaaatatgg attttccgca taaaaaaagc gtacccgatt aggtacgcta ttaaaaatat    1440
aagcggcgct attctactct cttatggatc tcagtcaaga aaggatccgg caaccrccga    1500
acaaatggag rcgaaraaat tgaaaagacg aggaaatcag cgcgttaaaa attcccgaaa    1560
acccaccgca cttttttattg gaatttgcta accttaaaag tgcggtcaaa agttaaaaaa    1620
ttttaagatt gcaattccaa cggattctta cccgctttac gcaaagcctg atgttcttta    1680
ataatcgcca taaaggctg tccgaagcgc tgccatttga tggcgccgac accgttgatt    1740
tgcagcattt ccactttgct ggtcggctga tacaacgaca tttcctgcaa ggtcgcgtca    1800
ctgaacacaa tataaggcgg aatgttttct ttgtcggcaa tctgtttgcg caggaaacgc    1860
aggcgggcaa ataaatcttt gtcgtagttg gttaccgcat tgcgttgcgg agcctgtacc    1920
atggtaatgg aagataatct cggcatggcc agttccaaag acacttcgcc gcgcagcacg    1980
ggacgcgcgc tttcggtgag ctgtaatctg gtcccatgc cgaaatcgct gatgatttgt    2040
tgcacaaagc ccaaatgaat cagctgacga attaccgatt gccagtattc tttgcttta    2100
tctttgccaa ttccgtagac tttcaactca tcatgttgat tttcttttat tttctgattc    2160
```

```
tgcaaaccgc gcattacgcc gattacgtat tgcgtgccga aacgttgccc ggtgcgataa    2220
atggtcgaaa ggattttctg cgcgtctaat aatccgtcat attttttcgg cggatcgagg    2280
cagatatcac agttattaca tggcgtttgg cggttttcgc cgaaataatt taacagcact    2340
aaacgacggg aggtctggct ttcggcaaat tcgccgatgg cttccagctt atgccgttta    2400
atatcccgtt gcgggctttc cggctcttcc aataaaattt tatgcaacca ggcataatcc    2460
gccggctcgt aaaacagtac cgcttccgcc ggcaggtcgt cccgcccgc gcgcccggtt     2520 tcctgataat acgcctcaat gctgcgagat aaatcaaaat gcgccacaaa acgcacatta    2580
gatttgttga tccccatacc aaaagcaatg gtcgccacca ccacttgaat attatcccgt    2640
tgaaacgcct gttgcaccgc ttcccgctgc gacggctcca tgcccgcatg ataagcggct    2700
gcggaaatgc ctcttttctt cagggcttcc gcaatgcgct ccactttgct acggctgttg    2760
caatagacga taccgctttt acctttttgc gccgccacaa aattgtataa ttgctccatc    2820
ggtttgaatt tttccaccaa ggtataacga atattcgggc ggtcaaaact acctacatac    2880
aagtgcggtt cgttcaggct gacccgggat ttaaatcgct agcgggctgc taaaggaagc    2940
ggaacacgta gaaagccagt ccgcagaaac ggtgctgacc ccggatgaat gtcagctact    3000
gggctatctg gacaagggaa aacgcaagcg caaagagaaa gcaggtagct tgcagtgggc    3060
ttacatggcg atagctagac tgggcggttt tatggacagc aagcgaaccg gaattgccag    3120
ctggggcgcc ctctggtaag gttgggaagc cctgcaaagt aaactggatg ctttcttgc     3180 cgccaaggat ctgatggcgc aggggatcaa gatctgatca agagacagga tgaggatcgt    3240
ttcgcatgat tgaacaagat ggattgcacg caggttctcc ggccgcttgg gtggagaggc    3300
tattcggcta tgactgggca caacagacaa tcggctgctc tgatgccgcc gtgttccggc    3360
tgtcagcgca ggggcgcccg gttctttttg tcaagaccga cctgtccggt gccctgaatg    3420
aactgcagga cgaggcagcg cggctatcgt ggctggccac gacgggcgtt ccttgcgcag    3480
ctgtgctcga cgttgtcact gaagcgggaa gggactggct gctattgggc gaagtgccgg    3540
ggcaggatct cctgtcatct caccttgctc ctgccgagaa agtatccatc atggctgatg    3600
caatgcggcg gctgcatacg cttgatccgg ctacctgccc attcgaccac caagcgaaac    3660
atcgcatcga gcgagcacgt actcggatgg aagccggtct tgtcgatcag gatgatctgg    3720
acgaagagca tcaggggctc gcgccagccg aactgttcgc caggctcaag gcgcgcatgc    3780
ccgacggcga ggatctcgtc gtgacccatg gcgatgcctg cttgccgaat atcatggtgg    3840
aaaatggccg cttttctgga ttcatcgact gtggccggct gggtgtggcg gaccgctatc    3900
aggacatagc gttggctacc cgtgatattg ctgaagagct tggcggcgaa tgggctgacc    3960
gcttcctcgt gctttacggt atcgccgctc ccgattcgca gcgcatcgcc ttctatcgcc    4020
ttcttgacga gttcttctga gcgggactct ggggttcgaa atgaccgacc aagcgacgcc    4080
caacctgcca tcacgagatt tcgattccac cgccgccttc tatgaaaggt tgggcttcgg    4140
aatcgttttc cgggacgccg gctggatgat cctccagcgc ggggatctca tgctggagtt    4200
cttcgcccac gctagcggcg cgccggccgg cccggtgtga ataccgcac agatgcgtaa     4260 ggagaaaata ccgcatcagg cgctcttccg cttcctcgct cactgactcg ctgcgctcgg    4320
tcgttcggct gcggcgagcg gtatcagctc actcaaaggc ggtaatacgg ttatccacag    4380
aatcagggga taacgcagga aagaacatgt gagcaaaagg ccagcaaaag gccaggaacc    4440
gtaaaaaggc cgcgttgctg gcgttttttcc ataggctccg ccccccctgac gagcatcaca    4500
```

```
aaaatcgacg ctcaagtcag aggtggcgaa acccgacagg actataaaga taccaggcgt    4560 ttcccctgg aagctccctc gtgcgctctc ctgttccgac cctgccgctt accggatacc    4620
tgtccgcctt tctcccttcg ggaagcgtgg cgctttctca tagctcacgc tgtaggtatc    4680
tcagttcggt gtaggtcgtt cgctccaagc tgggctgtgt gcacgaaccc cccgttcagc    4740
ccgaccgctg cgccttatcc ggtaactatc gtcttgagtc caacccggta agacacgact    4800
tatcgccact ggcagcagcc actggtaaca ggattagcag agcgaggtat gtaggcggtg    4860
ctacagagtt cttgaagtgg tggcctaact acggctacac tagaaggaca gtatttggta    4920
tctgcgctct gctgaagcca gttaccttcg aaaaagagt tggtagctct tgatccggca    4980
aacaaaccac cgctggtagc ggtggttttt ttgtttgcaa gcagcagatt acgcgcagaa    5040
aaaaaggatc tcaagaagat cctttgatct tttctacggg gtctgacgct cagtggaacg    5100
aaaactcacg ttaagggatt ttggtcatga gattatcaaa aaggatcttc acctagatcc    5160
ttttaaaggc cggccgcggc cgccatcggc atttttctttt gcgttttat ttgttaactg    5220 ttaattgtcc ttgttcaagg atgctgtctt tgacaacaga tgttttcttg cctttgatgt    5280
tcagcaggaa gctcggcgca aacgttgatt gtttgtctgc gtagaatcct ctgtttgtca    5340
tatagcttgt aatcacgaca ttgttttcctt tcgcttgagg tacagcgaag tgtgagtaag    5400
taaaggttac atcgttagga tcaagatcca tttttaacac aaggccagtt ttgttcagcg    5460
gcttgtatgg gccagttaaa gaattagaaa cataaccaag catgtaaata tcgttagacg    5520
taatgccgtc aatcgtcatt tttgatccgc gggagtcagt gaacaggtac catttgccgt    5580
tcattttaaa gacgttgcg cgttcaattt catctgttac tgtgttagat gcaatcagcg    5640
gtttcatcac tttttttcagt gtgtaatcat cgtttagctc aatcataccg agagcgccgt    5700
ttgctaactc agccgtgcgt tttttatcgc tttgcagaag ttttttgactt tcttgacgga    5760 agaatgatgt gcttttgcca tagtatgctt tgttaaataa agattcttcg ccttggtagc    5820
catcttcagt tccagtgttt gcttcaaata ctaagtattt gtggcctta tcttctacgt    5880 agtgaggatc tctcagcgta tggttgtcgc ctgagctgta gttgccttca tcgatgaact    5940
gctgtacatt ttgatacgtt tttccgtcac cgtcaaagat tgatttataa tcctctacac    6000
cgttgatgtt caaagagctg tctgatgctg atacgttaac ttgtgcagtt gtcagtgttt    6060
gtttgccgta atgtttaccg gagaaatcag tgtagaataa acggattttt ccgtcagatg    6120
taaatgtggc tgaacctgac cattcttgtg tttggtcttt taggatagaa tcatttgcat    6180
cgaatttgtc gctgtcttta aagacgcggc cagcgttttt ccagctgtca atagaagttt    6240
cgccgacttt ttgatagaac atgtaaatcg atgtgtcatc cgcatttttta ggatctccgg    6300 ctaatgcaaa gacgatgtgg tagccgtgat agttttgcgac agtgccgtca gcgttttgta    6360
atggccagct gtcccaaacg tccaggcctt tgcagaaga gatatttta attgtggacg    6420 aatcaaattc agaaacttga tattttttcat ttttttgctg ttcagggatt tgcagcatat    6480
catggcgtgt aatatgggaa atgccgtatg tttccttata tggcttttgg ttcgtttctt    6540
tcgcaaacgc ttgagttgcg cctcctgcca gcagtgcggt agtaaaggtt aatactgttg    6600
cttgttttgc aaacttttttg atgttcatcg ttcatgtctc ctttttatg tactgtgtta    6660 gcggtctgct tcttccagcc ctcctgtttg aagatggcaa gttagttacg cacaataaaa    6720
aaagacctaa aatatgtaag gggtgacgcc aaagtataca ctttgcccctt tacacatttt    6780 aggtcttgcc tgctttatca gtaacaaacc cgcgcgattt acttttcgac ctcattctat    6840
tagactctcg tttggattgc aactggtcta ttttcctctt ttgtttgata gaaaatcata    6900
```

```
aaaggatttg cagactacgg gcctaaagaa ctaaaaaatc tatctgtttc ttttcattct    6960
ctgtattttt tatagtttct gttgcatggg cataaagttg ccttttttaat cacaattcag   7020 aaaatatcat aatatctcat ttcactaaat aatagtgaac ggcaggtata tgtgatgggt    7080
taaaaaggat cggcggccgc tcgatttaaa tc                                   7112

<210> SEQ ID NO 11
<211> LENGTH: 7161
<212> TYPE: DNA
<213> ORGANISM: artificial
<220> FEATURE:
<223> OTHER INFORMATION: vector

<400> SEQUENCE: 11
tcgagaggcc tgacgtcggg cccggtacca cgcgtcatat gactagttcg gacctaggga      60
tgggatcgag ctcttttcct tgccgacaag gcggaagctt taggggaaat tcccgtaggt    120
gccgtattgg tggatgaacg gggcaatatc attggtgaag gctggaacct ctctattgtg    180
aactcggatc ccaccgccca tgccgaaatt attgcgttgc gtaacgccgc gcagaaaatc    240
caaaattacc gcctgctcaa taccacttta tacgtgactt tagaaccctg caccatgtgc    300
gccggcgcga ttttacacag ccgaatcaaa cgcttggtat tcgggcgtc cgattacaaa     360 accggtgcgg tgggttccag atttcatttt tttgaggatt ataaaatgaa tcatggggtt    420
gagatcacaa gcggtgtctt ataggatcaa tgcagtcaga agttaagccg cttttttccaa   480 aagcgcaggg aacagaaaaa acaacaaaaa gctaccgcac ttttacaaca cccccggctt    540
aactcctctg aaaaatagtg acaaaaaaac cgtcataatg tttacgacgg ttttttttatt   600 tcttctaata tgtcacatta gcccgtagc ctgcaagcaa cccctttaaca tgctccatta   660 attcttttgt cggcggtttt acatcttcaa gctcgtattt atcgccgagt acttcccatt    720
tatgggcgcc tagacggtga taaggtaata attccacttt ttcgatattc ttcatatctt   780
taatgaaatt ccccagcatg tgcaaatctt cgtcactatc tgtataaccc ggcactacaa    840
catggcggat ccaggtacgc tgatttcgat ccgctaaata ttttgcgaat tcgagcactc    900
ttttattcgg cacgccaatc aggctttcgt gaacccgttc attcatttct ttcaggtcaa    960
gcaacacaag atccgtgtca tcaatcaatt catcaataat atgatcatga tgacggacga    1020
aaccgttggt atccaagcaa gtattaattc cttcttatg gcaggctctg aaccagtccc     1080
gtacaaattc cgcctgtaaa atagcttcac cgccggaagc ggtaactccg ccgcccgagg    1140
cgttcataaa atggcgatag gtcaccactt cttttcatta ttcttcaacg gaaatttctt    1200
taccgccgtg caaatcccag gtgtctctgt tatggcaata tttacaacgc attaagcagc    1260
cttgtaaaaa taaaataaag cggattcccg gcccgtcaac tgtcccgcag gtttcaaatg    1320
aatgaattcg tcctaaaacc gacataatat gcccttaaat aatcaacaaa atatagcaag    1380
aagattatag caaagaattt cgttttttc agagaatagt caaatcttcg caaaaaacta    1440
ccgcactttt atccgcttta atcaggggaa ttaaaacaaa aaaattccgc ctattgaggc    1500
ggaatttatt aagcaataag acaaactctc aattttaata cttccttctt ttctagtatt    1560
gataagattg aaaccttgca aggatgacgg cggatttgcc gtcactctca cccaactaat    1620
gtggacgact ggtaaaccat tgcattagac caatgcaaac accaccaccg acgatgttac    1680
ctaaagtaac aggaattaaa ttttaatta ctaaatggta catatctaaa tttgcaaact    1740
gctcggcatt taaacccgtt gcctgccaga attccggcga tgcgaaattt gcaattacca    1800
```

-continued

```
tgcccatagg gatcataaac atatttgcta cgcagtgttc aaagcctgaa gcgacaaaya    1860
acccgatcgg caggatcata ataaaagctt tatccgttag agtyttgccg gcataggcca    1920
tccaaacggc aatacatacc ataatgttgc aaagaatacc taaacagaag gcttcaaycc    1980
aggtatgttc tattttatgt tgtgccgtat ttaaaatggt taatccccac tgaccgtttg    2040
ccgccatgat ctgaccggaa accaaatta atgcaacaat aaataaaccg ccgacaaaat     2100
taccgaarta aaccacaatc cagttacgta acatctgaat tgttgtaatt ttactctcaa    2160
agcgggcaat agtcgataaa gttgatgaag taaatagttc acagccgcaa accgccacca   2220
taattacccc gagagagaac accaaaccgc cgaccagttt agttaatccc caaggcgctc    2280
ccgcagaggc tgtttgagtt gttgtataaa aaacgaatgc aagagcaata aacataccgg    2340
cagagatcgc cgataaaaat gaataggctt gttttttcgt agctttataa acgccgacgt    2400
ctaacccggt ttgagccatc tcggttggcg aagccatcca agccaattta aaatcttccg    2460
atttcattga gctttcctta gtaataaaac tactcggaaa tgagtagaac tgccttaaag    2520
cataaatgat agattaaaaa atccaaaatt gttgaatatt atttaacggg gggattataa    2580
aagattcata aattagataa tagctaattt gagtgatcca tatcacettt tacagatttt    2640 ttgacctaaa tcaaaattac ccaaatagag taataatacc attataaagg gtgtggattt    2700
attcctttgg tttacgagat aaattgctat ttaagctgat ttctgataaa aagtgcggta    2760
gatttttccc aaaaataagg aaacacaaaa tggcagaaga acaatttttc agtaaaatta    2820
ttcgtaaaga aattcccgcc gacattatat atcaagacga tcttgtcacc gcatttcgcg    2880
atattgcgcc gcaggcaaaa actcatattt taattattcc gaataaattg attccgacag    2940
taaacgacgt aaccgcccat cgtcgacatc gatgctcttc tgcgttaatt aacaattggg    3000
atcctctaga ctttgcttcc agatgtatgc tctcctccgg agagtaccgt gactttattt    3060
tcggcacaaa tacaggggtc gatggataaa tacggcgata gtttcctgac ggatgatccg    3120
tatgtaccgg cggaagacaa gctgcaaacc tgtcagatgg agattgattt aatggcggat    3180
gtgctgagag caccgccccg tgaatccgca gaactgatcc gctatgtgtt tgcggatgat    3240
tggccggaat aaataaagcc gggcttaata cagattaagc ccgtataggg tattattact    3300
gaataccaaa cagcttacgg aggacggaat gttacccatt gagacaacca gactgccttc    3360
tgattattaa tattttteac tattaatcag aaggaataac catgaatttt acccggattg    3420
acctgaatac ctggaatcgc agggaacact ttgcccttta tcgtcagcag attaaatgcg    3480
gattcagcct gaccaccaaa ctcgatatta ccgcttttgcg taccgcactg gcggagacag    3540
gttataagtt ttatccgctg atgatttacc tgatctcccg ggctgttaat cagtttccgg    3600
agttccggat ggcactgaaa gacaatgaac ttatttactg ggaccagtca gacccggtct    3660
ttactgtctt tcataaagaa accgaaacat tctctgcact gtcctgccgt tatttttccgg   3720 atctcagtga gtttatggca ggttataatg cggtaacggc agaatatcag catgatacca    3780
gattgtttcc gcaggggaat ttaccggaga atcacctgaa tatatcatca ttaccgtggg    3840
tgagttttga cgggatttaa cctgaacatc accggaaatg atgattattt tgccccggtt    3900
tttacgatgg caaagtttca gcaggaaggt gaccgcgtat tattacctgt ttctgtacag    3960
gttcatcatg cagtctgtga tggctttcat gcagcacggt ttattaatac acttcagctg    4020
atgtgtgata acatactgaa ataaattaat taattctgta tttaagccac cgtatccggc    4080
aggaatggtg gctttttttt tatattttaa ccgtaatctg taatttcgtt tcagactggt    4140
tcaggatgag ctcgcttgga ctcctgttga tagatccagt aatgacctca gaactccatc    4200
```

```
tggatttgtt cagaacgctc ggttgccgcc gggcgttttt tattggtgag aatccaagca    4260
ctagcggcgc gccggccggc ccggtgtgaa ataccgcaca gatgcgtaag gagaaaatac    4320
cgcatcaggc gctcttccgc ttcctcgctc actgactcgc tgcgctcggt cgttcggctg    4380
cggcgagcgg tatcagctca ctcaaaggcg gtaatacggt tatccacaga atcaggggat    4440
aacgcaggaa agaacatgtg agcaaaaggc cagcaaaagg ccaggaaccg taaaaaggcc    4500
gcgttgctgg cgtttttcca taggctccgc cccctgacg agcatcacaa aaatcgacgc    4560
tcaagtcaga ggtggcgaaa cccgacagga ctataaagat accaggcgtt ccccctgga    4620 agctccctcg tgcgctctcc tgttccgacc ctgccgctta ccggatacct gtccgccttt    4680
ctcccttcgg gaagcgtggc gctttctcat agctcacgct gtaggtatct cagttcggtg    4740
taggtcgttc gctccaagct gggctgtgtg cacgaaccc ccgttcagcc cgaccgctgc    4800
gccttatccg gtaactatcg tcttgagtcc aacccggtaa gacacgactt atcgccactg    4860
gcagcagcca ctggtaacag gattagcaga gcgaggtatg taggcggtgc tacagagttc    4920
ttgaagtggt ggcctaacta cggctacact agaaggacag tatttggtat ctgcgctctg    4980
ctgaagccag ttaccttcgg aaaaagagtt ggtagctctt gatccggcaa acaaaccacc    5040
gctggtagcg gtggtttttt tgtttgcaag cagcagatta cgcgcagaaa aaaggatct    5100 caagaagatc ctttgatctt ttctacgggg tctgacgctc agtggaacga aaactcacgt    5160
taagggattt tggtcatgag attatcaaaa aggatcttca cctagatcct tttaaaggcc    5220
ggccgcggcc gccatcggca ttttcttttg cgttttatt tgttaactgt taattgtcct    5280
tgttcaagga tgctgtcttt gacaacagat gttttcttgc ctttgatgtt cagcaggaag    5340
ctcggcgcaa acgttgattg tttgtctgcg tagaatcctc tgtttgtcat atagcttgta    5400
atcacgacat tgtttccttt cgcttgaggt acagcgaagt gtgagtaagt aaaggttaca    5460
tcgttaggat caagatccat ttttaacaca aggccagttt tgttcagcgg cttgtatggg    5520
ccagttaaag aattagaaac ataaccaagc atgtaaatat cgttagacgt aatgccgtca    5580
atcgtcattt ttgatccgcg ggagtcagtg aacaggtacc atttgccgtt catttttaaag    5640 acgttcgcgc gttcaatttc atctgttact gtgttagatg caatcagcgg tttcatcact    5700 ttttcagtg tgtaatcatc gtttagctca atcataccga gagcgccgtt tgctaactca    5760
gccgtgcgtt tttttcgct ttgcagaagt ttttgacttt cttgacgaa gaatgatgtg    5820 cttttgccat agtatgcttt gttaaataaa gattcttcgc cttggtagcc atcttcagtt    5880
ccagtgtttg cttcaaatac taagtatttg tggcctttat cttctacgta gtgaggatct    5940
ctcagcgtat ggttgtcgcc tgagctgtag ttgccttcat cgatgaactg ctgtacattt    6000
tgatacgttt ttccgtcacc gtcaaagatt gatttataat cctctacacc gttgatgttc    6060
aaagagctgt ctgatgctga tacgttaact tgtgcagttg tcagtgtttg tttgccgtaa    6120
tgtttaccgg agaaatcagt gtagaataaa cggattttc cgtcagatgt aaatgtggct    6180
gaacctgacc attcttgtgt ttggtctttt aggatagaat catttgcatc gaatttgtcg    6240
ctgtctttaa agacgcggcc agcgtttttc cagctgtcaa tagaagtttc gccgactttt    6300
tgatagaaca tgtaaatcga tgtgtcatcc gcatttttag gatctccggc taatgcaaag    6360
acgatgtggt agccgtgata gtttgcgaca gtgccgtcag cgttttgtaa tggccagctg    6420
tcccaaacgt ccaggccttt tgcagaagag atatttttaa ttgtggacga atcaaattca    6480
gaaacttgat atttttcatt ttttgctgt tcagggattt gcagcatatc atggcgtgta    6540
```

-continued

```
atatgggaaa tgccgtatgt ttccttatat ggcttttggt tcgtttcttt cgcaaacgct   6600
tgagttgcgc ctcctgccag cagtgcggta gtaaaggtta atactgttgc ttgttttgca   6660 aacttttga tgttcatcgt tcatgtctcc ttttttatgt actgtgttag cggtctgctt    6720
cttccagccc tcctgtttga agatggcaag ttagttacgc acaataaaaa aagacctaaa   6780
atatgtaagg ggtgacgcca agtatacac tttgcccttt acacatttta ggtcttgcct    6840
gctttatcag taacaaaccc gcgcgattta cttttcgacc tcattctatt agactctcgt   6900
ttggattgca actggtctat tttcctcttt tgtttgatag aaaatcataa aaggatttgc   6960
agactacggg cctaaagaac taaaaaatct atctgtttct tttcattctc tgtattttt    7020 atagtttctg ttgcatgggc ataaagttgc cttttaatc acaattcaga aaatatcata   7080
atatctcatt tcactaaata atagtgaacg gcaggtatat gtgatgggtt aaaaaggatc   7140
ggcggccgct cgatttaaat c                                             7161

<210> SEQ ID NO 12
<211> LENGTH: 11309
<212> TYPE: DNA
<213> ORGANISM: Yersinia mollaretii

<400> SEQUENCE: 12
gatccccagt agatttacgt ttaaacattt ttatttcctt ttaatttaa tttaattaac    60 agttggtgct atgacacttt acctcatagc tggcataatt cgcaatactc tgggtcttcg   120
agaggtatcc aacctgagtt gaaatacttt accatcgatt tagcagttgt atcagttata   180
tttatattac ctttaactct tcgccatcca ggagttttac cgtacagatt agaggataat   240
aataacacat aattctcgta agcaatatga gataatttcc aagactctat attagctcgt   300
gatgttttcc aaggtctaaa atcgtcacgg ttcatataat tagccaatct catatgctct   360
ctaacttccg atgataagct gtcaaacatg agaattaacg atctgataga aagggtttg    420 ctcgggtcgg tggctctggt aacgaccagt atcccgatcc cggctggccg tcctggccgc   480
cacatgaggc atgttccgcg tccttgcaat actgtgttta catacagtct atcgcttagc   540
ggaaagttct tttaccctca gccgaaatgc ctgccgttgc tagacattgc cagccagtgc   600
ccgtcactcc cgtactaact gtcacgaacc cctgcaataa ctgtcacgcc ccctgcaat    660 aactgtcacg aacccctgca ataactgtca cgccccaaa cctgcaaacc cagcaggggc   720 ggggctggc ggggtgttgg aaaatccat ccatgattat ctaagaataa tccactaggc    780
gcggttatca gcgccttgt ggggcgctgc tgcccttgcc caatatgccc ggccagaggc    840
cggatagctg gtctattcgc tgcgctaggc tacacaccgc cccaccgctg cgcggcaggg   900
ggaaaggcgg gcaaagcccg ctaaacccca caccaaaccc gcagaaaata cgctgggagc   960
gcttttagcc gctttagcgg cctttccccc tacccgaagg gtgggggcgc gtgtgcagcc   1020 ccgcagggc tgtctcggtc gatcattcag cccggctcat ccttctggcg tggcggcaga   1080
ccgaacaagg cgcggtcgtg gtcgcgttca aggtacgcat ccattgccgc catgagccga   1140
tcctccggcc actcgctgct gttcaccttg gccaaaatca tggcccccac cagcaccttg   1200
cgccttgttt cgttcttgcg ctattgctgc tgttcccttg cccgcacccg ctgaatttcg   1260
gcattgattc gcgctcgttg ttcttcgagc ttggccagcc gatccgccgc cttgttgctc   1320
cccttaacca tcttgacacc ccattgttaa tgtgctgtct cgtaggctat catggaggca   1380
cagcggcggc aatcccgacc ctactttgta ggggagggc attgcatgga gccgaaaagc   1440
aaaagcaaca gcgaggcagc atggcgattt atcaccttac ggcgaaaacc ggcagcaggt   1500
```

```
cgggcggcca atcggccagg gccaaggccg actacatcca gcgcgaaggc aagtatgccc    1560
gcgacatgga tgaagtcttg cacgccgaat ccgggcacat gccggagttc gtcgagcggc    1620
ccgccgacta ctgggatgct gccgacctgt atgaacgcgc caatgggcgg ctgttcaagg    1680
aggtcgaatt tgccctgccg gtcgagctga ccctcgacca gcagaaggcg ctggcgtccg    1740
agttcgccca gcacctgacc ggtgccgagc gcctgccgta tacgctggcc atccatgccg    1800
gtggcggcga gaacccgcac tgccacctga tgatctccga gcggatcaat gacggcatcg    1860
agcggcccgc cgctcagtgg ttcaagcggt acaacggcaa gaccccggag aagggcgggg    1920
cacagaagac cgaagcgctc aagcccaagg catggcttga gcagacccgc gaggcatggg    1980
ccgaccatgc caaccgggca ttagagcggg ctggccacga cgcccgcatt gaccacagaa    2040
cacttgaggc gcaggcatc gagcgcctgc ccggtgttca cctggggccg aacgtggtgg    2100
agatggaagg ccggggcatc cgcaccgacc gggcagacgt ggccctgaac atcgacaccg    2160
ccaacgccca gatcatcgac ttacaggaat accgggaggc aatagaccat gaacgcaatc    2220
gacagagtga agaaatccag aggcatcaac gagttagcgg agcagatcga accgctggcc    2280
cagagcatgg cgacactggc cgacgaagcc cggcaggtca tgagccagac ccagcaggcc    2340
agcgaggcgc aggcggcgga gtggctgaaa gcccagcgcc agacaggggc ggcatgggtg    2400
gagctggcca aagagttgcg ggaggtagcc gccgaggtga gcagcgccgc gcagagcgcc    2460
cggagcgcgt cgcggggggtg gcactggaag ctatggctaa ccgtgatgct ggcttccatg    2520
atgcctacgg tggtgctgct gatcgcatcg ttgctcttgc tcgacctgac gccactgaca    2580
accgaggacg gctcgatctg gctgcgcttg gtggcccgat gaagaacgac aggactttgc    2640
aggccatagg ccgacagctc aaggccatgg gctgtgagcg cttcgatatc ggcgtcaggg    2700
acgccaccac cggccagatg atgaaccggg aatggtcagc cgccgaagtg ctccagaaca    2760
cgccatggct caagcggatg aatgcccagg gcaatgacgt gtatatcagg cccgccgagc    2820
aggagcggca tggtctggtg ctggtggacg acctcagcga gtttgacctg gatgacatga    2880
aagccgaggg ccgggagcct gccctggtag tggaaaccag cccgaagaac tatcaggcat    2940
gggtcaaggt ggccgacgcc gcaggcggtg aacttcgggg gcagattgcc cggacgctgg    3000
ccagcgagta cgacgccgac ccggccagcg ccgacagccg ccactatggc cgcttggcgg    3060
gcttcaccaa ccgcaaggac aagcacacca cccgcgccgg ttatcagccg tgggtgctgc    3120
tgcgtgaatc caagggcaag accgccaccg ctggcccggc gctggtgcag caggctggcc    3180
agcagatcga gcaggcccag cggcagcagg agaaggcccg caggctggcc agcctcgaac    3240
tgcccgagcg gcagcttagc cgccaccggc gcacggcgct ggacgagtac cgcagcgaga    3300 tggcgggct ggtcaagcgc ttcggtgatg acctcagcaa gtgcgacttt atcgccgcgc    3360
agaagctggc cagccggggc cgcagtgccg aggaaatcgg caaggccatg gccgaggcca    3420
gcccagcgct ggcagagcgc aagcccggcc acgaagcgga ttacatcgag cgcaccgtca    3480
gcaaggtcat gggtctgccc agcgtccagc ttgcgcgggc cgagctggca cgggcaccgg    3540
caccccgcca gcgaggcatg gacaggggcg ggccagattt cagcatgtag tgcttgcgtt    3600
ggtactcacg cctgttatac tatgagtact cacgcacaga agggggtttt atggaatacg    3660
aaaaaagcgc ttcagggtcg gtctacctga tcaaaagtga caagggctat tggttgcccg    3720
gtggctttgg ttatacgtca aacaaggccg aggctggccg cttttcagtc gctgatatgg    3780
ccagccttaa ccttgacggc tgcaccttgt ccttgttccg cgaagacaag cctttcggcc    3840
```

```
ccggcaagtt tctcggtgac tgatatgaaa gaccaaaagg acaagcagac cggcgacctg    3900
ctggccagcc ctgacgctgt acgccaagcg cgatatgccg agcgcatgaa ggccaaaggg    3960
atgcgtcagc gcaagttctg gctgaccgac gacgaatacg aggcgctgcg cgagtgcctg    4020
gaagaactca gagcggcgca gggcgggggt agtgaccccg ccagcgccta accaccaact    4080
gcctgcaaag gaggcaatca atggctaccc ataagcctat caatattctg gaggcgttcg    4140
cagcagcgcc gccaccgctg gactacgttt tgcccaacat ggtggccggt acggtcgggg    4200
cgctggtgtc gcccggtggt gccggtaaat ccatgctggc cctgcaactg gccgcacaga    4260
ttgcaggcgg gccggatctg ctggaggtgg gcgaactgcc caccggcccg gtgatctacc    4320 tgccccgccga agacccgccc accgccattc atcaccgcct gcacgccctt ggggcgcacc    4380
tcagcgccga ggaacggcaa gccgtggctg acggcctgct gatccagccg ctgatcggca    4440
gcctgcccaa catcatggcc ccggagtggt tcgacggcct caagcgcgcc gccgagggcc    4500
gccgcctgat ggtgctggac acgctgcgcc ggttccacat cgaggaagaa aacgccagcg    4560
gccccatggc ccaggtcatc ggtcgcatgg aggccatcgc cgccgatacc gggtgctcta    4620
tcgtgttcct gcaccatgcc agcaagggcg cggccatgat gggcgcaggc gaccagcagc    4680
aggccagccg gggcagctcg gtactggtcg ataacatccg ctggcagtcc tacctgtcga    4740
gcatgaccag cgccgaggcc gaggaatggg gtgtggacga cgaccagcgc cggttcttcg    4800
tccgcttcgg tgtgagcaag gccaactatg gcgcaccgtt cgctgatcgg tggttcaggc    4860
ggcatgacgg cggggtgctc aagcccgccg tgctggagag gcagcgcaag agcaagggg    4920 tgccccgtgg tgaagcctaa gaacaagcac agcctcagcc acgtccggca cgacccggcg    4980
cactgtctgg ccccccggcct gttccgtgcc ctcaagcggg gcgagcgcaa gcgcagcaag    5040
ctggacgtga cgtatgacta cggcgacggc aagcggatcg agttcagcgg cccggagccg    5100
ctgggcgctg atgatctgcg catcctgcaa gggctggtgg ccatggctgg gcctaatggc    5160
ctagtgcttg gccccggaacc caagaccgaa ggcggacggc agctccggct gttcctggaa    5220
cccaagtggg aggccgtcac cgctgatgcc atggtggtca aaggtagcta tcgggcgctg    5280
gcaaaggaaa tcggggcaga ggtcgatagt ggtggggcgc tcaagcacat acaggactgc    5340
atcgagcgcc tttggaaggt atccatcatc gcccagaatg gccgcaagcg gcagggggttt    5400 cggctgctgt cggagtacgc cagcgacgag gcggacgggc gcctgtacgt ggccctgaac    5460 ccccttgatcg cgcaggccgt catgggtggc ggccagcatg tgcgcatcag catggacgag    5520
gtgcgggcgc tggacagcga aaccgcccgc ctgctgcacc agcggctgtg tggctggatc    5580
gaccccggca aaaccggcaa ggcttccata gataccttgt gcggctatgt ctggccgtca    5640
gaggccagtg gttcgaccat cgcaagcgc gccagcggg tgcgcgaggc gttgccggag    5700
ctggtcgcgc tgggctggac ggtaaccgag ttcgcggcgg gcaagtacga catcacccgg    5760
cccaaggcgg caggctgacc ccccccactc tattgtaaac aagacatttt ttatcttta    5820 tattcaatgg cttatttcc tgctaattgg taataccatg aaaatacca tgctcagaaa    5880 aggcttaaca atattttgaa aaattgccta ctgagcgctg ccgcacagct ccataggccg    5940
cttttcctgg tttgcttcca gatgtatgct ctcctccgga gagtaccgtg actttatttt    6000
cggcacaaat acagggggtcg atggataaat acggcgatag tttcctgacg gatgatccgt    6060
atgtaccggc ggaagacaag ctgcaaacct gtcagatgga gattgatta atggcggatg    6120 tgctgagagc accgccccgt gaatccgcag aactgatccg ctatgtgttt gcggatgatt    6180
ggccggaata aataaagccg ggcttaatac agattaagcc cgtatagggt attattactg    6240
```

```
aataccaaac agcttacgga ggacggaatg ttacccattg agacaaccag actgccttct    6300
gattattaat attttcact attaatcaga aggaataacc atgaatttta cccggattga    6360
cctgaatacc tggaatcgca gggaacactt tgccctttat cgtcagcaga ttaaatgcgg    6420
attcagcctg accaccaaac tcgatattac cgctttgcgt accgcactgg cggagacagg    6480
ttataagttt tatccgctga tgatttacct gatctcccgg gctgttaatc agtttccgga    6540
gttccggatg gcactgaaag acaatgaact tatttactgg gaccagtcag acccggtctt    6600
tactgtcttt cataaagaaa ccgaaacatt ctctgcactg tcctgccgtt attttccgga    6660
tctcagtgag tttatggcag gttataatgc ggtaacggca gaatatcagc atgataccag    6720
attgtttccg cagggaaatt taccggagaa tcacctgaat atatcatcat taccgtgggt    6780
gagttttgac gggatttaac ctgaacatca ccggaaatga tgattatttt gccccggttt    6840
ttacgatggc aaagtttcag caggaaggtg accgcgtatt attacctgtt tctgtacagg    6900
ttcatcatgc agtctgtgat ggctttcatg cagcacggtt tattaataca cttcagctga    6960
tgtgtgataa catactgaaa taaattaatt aattctgtat ttaagccacc gtatccggca    7020
ggaatggtgg cttttttttt atattttaac cgtaatctgt aatttcgttt cagactggtt    7080
caggatcact gtacgataat gcccccgcag tttggtaata cccttaataa aaaagaaaca    7140
gcaaagactg acagcaataa taataaagta agcagtaaca ataatattaa caacaccaga    7200
tgcagttata ataatagtat ttaagacacc agaaagactg ctgcgacagt cattttgaac    7260
aacaccaaaa tgccgtaaag gcagtagtaa caacaccagt gaaaacatca cgatagcata    7320
gtgatatgcc tgagtgtgtg taattaaaca ataaataaac cgccatatat aacagaagat    7380
agtattctga atggcatgct tttctgttca gtataaacat atcatcccgg ttggtataag    7440
gatgatatat aataagttaa gctgaacaca tatttatttt ggttttattt tacaaataaa    7500
gtaagacgat ccgttaagtc aaagcggggt atatttatta taccctgctt ttttatttgt    7560
ccgccgggcg cggataatgg atcagattat gcagtgtcac aatggcctta ccgggattgg    7620
cgtaagcgtg cgggatatcc gcatggaagc gcaggattc cccggcagaa acggtgtgcc    7680
actcatcccc cagccgcagt tgtaatgcgc cttccagtac aatgacatgt tctctggttc    7740
tgaaatccat ccctgtcggt gttgcttatg cagtctggtc gggactcggc gtcgtcataa    7800
ttacagccat tgcctggttg cttcatgggc aaaagcttta tgcttgtaaa ccgttttgtg    7860
aaaaaatttt taaaataaaa aaggggacct ctagggtccc caattaatta gtaatataat    7920
ctattaaagg tcattcaaaa ggtcatccac cggatccggg ccccccctcg aggtcgacgg    7980
tatcgataag cttgatatcg aattcccata ttgtgcatcg aatccctgca aaattgtctg    8040
agcgattaat tgttctaatt ttaccgccat gctcaccccc cgccatacgg aacagagcct    8100
gcatcagcag gctccagata aaacataaac tcattaatca gtggcttaga actgctgctc    8160
ttccgtcgag ccagtcagtg cagtgactga tgactcgccg ccctgaatga tattggtgac    8220
tttatcaaaa tagcccgtgc ccacttcttg ttgatgggaa gcaaggtgt agccgcgttc    8280 aacggaggca aattctggct gctgcacttt ctcaacatag tgcttcatgc cctcgccttg    8340
cgcgtaagca tgggccaagt cgaacatgtt gaaccacata ctgtggatgc cgccaaggt    8400 aataaattga tatttgtagc ccatcgcgga gaggtcatct tggaagctgg cgatctgctg    8460
gtcagtcagg ttcttttttcc agttaaatga tggcgaacag ttataagcca ataatttacc    8520
ggggaattta gcgtgaaccg catctgcaaa gcgtttagcc agcgccagat ctggcgtcga    8580
```

```
ggtttcacac cacaccaagt cggcgtaagg ggcataggcc agaccacggc tgatggcttg    8640
ctcaatgccc gcgtgagtgc ggaagaagcc ctcagcagta cgatcaccag caataaattc    8700
gctgtcataa gggtcgcaat cagaggtcag caaatccgca gcatcagcat cagtgcgcgc    8760
aatcagcagt gttggcacgc caagaacgtc agcggctaag cgggcagcaa ccagcttctg    8820
aatcgcttct tgtgttggca ccaaaacttt gccgcccata tggccgcatt tcttcaccgc    8880
cgccaattga tcttcaaagt gaacgcccgc agcaccggct tcaatcatgg ctttcatcaa    8940
ttcaaacgca ttcaatacgc cgccaaaacc cgcttcggca tccgccacaa tcggcaggaa    9000
atagtcggta tagcctttgc tgcccggctc aatattattc gaccactgaa tctgatctgc    9060
acggcggaag ctgttattaa tacgcttaac cacgccggaa acagagtcga ccgggtaaag    9120
agattgatcg ggatacatgc tggaggcggt attggcatcg cgcgcgacct gccaacccga    9180
cagataaatc gcttcaacac cggcctttgc ctgttgcaat gcctgaccgc tgttagcgc    9240 ccccagacag ttgatgtagc ctttacgcga ttcgccgtgc agcaactccc acaatctttt    9300
cgcgccgtgc tgtgccagcg tacattctgg gttaacggaa ccgcgcagtt tgatcacttc    9360
ttcggcgcta taggggcggg tgatgcccct ccagcgcggt gatttccatt cctgttccaa    9420
ctgctgaatt tgttgagtac gagaggttgt catggcgata ttccttatta cttattttg    9480 tagggttaaa taactggcct aggcgagtaa tgcgtagccc ggcaacgtca gaaagtcgat    9540 aagtcgtct tgtgttgtaa tccgctccat cagacgtgcg gcttcttcaa accgcccgcc    9600
atcaaaacgc tctgcgccaa gttcaagttt cacgacctgc atttcttcac tcaacatgtt    9660
acggaacagc tctttggtca ccgtctgacc attgctcagg cttttctggt gatgtatcca    9720
ttgccagata gaagtacggg aaatctcagc cgtcgcggca tcttccatca ggccataaat    9780
cggtacacag ccattgcccg atatccatgc ttcgatgtat tgcactgcga cccggatatt    9840
ggcccgcatc ccctcttcgg tgcgctcacc cgtgcaaggc tctagcaact cagcggcagt    9900
gattggttta tcttgcgcgc gactcacctc taattggttt ggacgatcgc ccagtacttt    9960
gttgaaaacg tccatcacgg tatcggccag accggggtgt gcgacccatg taccatcgtg   10020
gccgttgctg gcttccagct cttttgtcagc gcgaacttta tctaagacca gcgcattttt   10080
ttctggatct ttgttcggga taaaggccgc catgccgccc atcgccaagg caccgcgctt   10140
atggcaggtt ttgatcagta acgagagta ggcactcagg aagggtttcg tcatcgtgac   10200
cgactggcga tcgggcagca cgcgatcgct gtgattttc agcgttttga tatagctgaa   10260
aatgtagtcc caacgccac aattcagggc aacaatgtga tggcgcagat ggtagaggat   10320
ctcatccatc tggaataccg caggcaatgt ctcgattaat actgtggcct taatggtgcc   10380
ttgcggcaga tcgaaacgct gctcggtaaa gctgaaaaca tcactccacc aagccgcttc   10440
ctgataagac tgcatcttgg gtagatagaa ataggggccg ctgccattgg caagcagtaa   10500
cttatagtta tggtagaaat acaacgcgaa atcgaataag ccaccgggga tatcctcccc   10560
ctgccacttc acgtgttttt ctggcaagtg cagaccacgc acccgagcaa tcaacaccgc   10620
tggattgggt tttagctgat aaatcttacc ggattcattc gcgtaagaga ttgtgccttt   10680
gaccgcatcg tgcaaattaa tctgaccttc gataaccta tcccaactgg gtgccagcga   10740
atcctcaaag tcagccataa agactttcac attcgcattg agggcattaa tcaccatttt   10800
gcgctcaacc ggcccggtga tctcgacgcg acgatcacgt aaatccgcag gaatactttg   10860
aattttccag tcaccattac gaatggaatt ggtttccgaa atgaaatcag gcaatgcgcc   10920
ttggtcaatg gcctgttgcc aagcggcccg tgcagcaagg agtttgctac gcggctctgc   10980
```

-continued

| | |
|---|---|
| aaatttcgcc accaattctg ccaaaaattc gatggcctca tcgggcaaaa cctgccgctc | 11040 |
| agcagcatta aaatgctggg tgaaaactaa ctccgtgccg actatctgtt gtgtcattcc | 11100 |
| ccttcccctt ccccatctct cgacgatcat ttttcagttt cctttttgtta ttccccaaaa | 11160 |
| gtgcggtgca aatttgggga gttttagtta attaaaaaaa ttattttta cgagcttcga | 11220 |
| ttactgcagc agcaacactt gttggcgctt cagcatattt taacggttcc attgagtatg | 11280 |
| atgctctaga gcggccgcca ccgcggtgg | 11309 |

<210> SEQ ID NO 13
<211> LENGTH: 11247
<212> TYPE: DNA
<213> ORGANISM: Salmonella typhimurium

<400> SEQUENCE: 13

| | |
|---|---|
| gatcccaccg cggtggcggc cgctctagag ggttccctca tccggcacca cgtcatgccg | 60 |
| gatggcgcgt tcgcttatcc ggcctacgct atctgtaggc ccgtaagcg cagcgccacc | 120 |
| gggcatcaat caaaactgcg cttcttcggt ggaacccgtt aacgcggtaa cggatgacgc | 180 |
| gccgccctga ataatggtgg tgactttgtc gaagtaacca gtaccacctt cctgctggtg | 240 |
| ggaaacaaag gtgtagccat ctttcgccgc ggcgaactcg ggttgttgaa ccttctcaac | 300 |
| atagtgcttc atgccctcgc cctgcgcgta tgcatgcgcc aggtcgaaca tgttgaacca | 360 |
| catgctgtgg atgcccgcca gggtaataaa ctggtatttg taacccatgt ccgacaactg | 420 |
| ctgctggaag ctggcaatgg tcttgtcgtc cagattcttc tgccagttga aggatggtga | 480 |
| acagttatag gccagcagtt tgcccggata cttcgcgtgg atagcatcgg caaaacgacg | 540 |
| cgccagttcg agatccggcg tagaggtttc gcaccatacc agatcggcat acggggcata | 600 |
| cgccagaccg cggctgatcg cctgctcaat gcccgcatgg gtgcggtaga aaccttcgct | 660 |
| ggtgcgttcg ccggtaataa aaccgctgtc atagggatcg cagtcggagg tgatcagatc | 720 |
| tgccgcatcc gcatcggtac gcgcaatcac cagcgtcggg acgcccatca catcagcggc | 780 |
| cagacgcgca gcaaccagtt tctgaatcgc ctcctgcgtg gggaccagca ccttgccgcc | 840 |
| catatggccg catttcttca ccgacgccag ctgatcttcg aagtgaacgg ccgctgcacc | 900 |
| ggcttcaatc atcgatttca tcagttcgaa ggcattcaga acgccgccaa accggcttc | 960 |
| cgcatcagca acgatcggca ggaagtaatc cacatagcgc ggatcgttgg gttcaatacc | 1020 |
| ggatgcccac tggatctgat ctgcacgacg aaaagtgttg ttgatccgat ccactaccgc | 1080 |
| cggaacagag tttgccgggt acaacgattg atccggatac atgctggatg ccaggttggc | 1140 |
| atctgccgcc acctgccagc ctgaaagata aatcgcctca ataccggctt cgcctgctg | 1200 |
| caacgcctga ccgccggtca gcgcgccaag gctgttgata tagcctttttt tcgcttcacc | 1260 |
| gtgcaacagc cgccacattt tcgcggcgcc gagctgcgcc agcgtgcatt ccgggttaac | 1320 |
| cgagccgcgt aatttcacca cctcctccgc gctgtacggg cggtgatgc cttcccagcg | 1380 |
| cggttgtgtc cactctttct gtaattcttc gatttgttga gtacgggttt tcatgtgcag | 1440 |
| atgctccata ttgttatgtg gtgaattaag ccagtaagcg atagcccggc agggtgagga | 1500 |
| agtcgattaa gtcatctgag gtggtgattt gctccatcag acgtgcggca tcgtcgaagc | 1560 |
| gcccgctgct gtagcggtgc tcgcccagtt cgtcctggat tacccgcatc tcttccgcca | 1620 |
| acatttcgcg gaaaagcgtt ttcgttacgg gttttccatt gctcagtgtt ttctcatggt | 1680 |
| gaatccactg ccagatagag gttcgtgaga tttccgccgt cgcggcatcc tccatcagac | 1740 |

```
cgtaaatcgg tacacagcca ttgccggaga tccacgcttc aatgtactgc actgccacgc    1800
gaatattggc gcgcattccc gcttctgtgc gttcgcctc acatggctcc agtaactgtt    1860
cagcggtaat cggcgcatct tcatcacggg taatgaacag ctgattttg tgctcgccca    1920 gtacctcgtt aaagacggcc attgcggtat ccgccaaccc aggatgcgca atccacgtgc    1980
cgtcgtggcc gttgttcgct tccagcgctt tatccgcttt cactttggca aggacctgat    2040
tgttgcgttc aacgtctttg ctcgggataa acgccgccat accgcccatc gcgaacgcgc    2100
cgcgcttgtg gcaggttttg atcagcaggc gcgagtaggc gctcagaaac ggtttgtcca    2160
tcgttaccac ctgcctgtcc ggcaaaacgc gatccgggtg attttcaac gttttgatat    2220 agctgaaaat ataatcccag cgaccacagt tgagaccgac gatatgatca cgcagcgcat    2280
gaagaatctc atccatctgg aaaacagccg gcagcgtttc aatcaacagg gtcgctttga    2340
tcgtaccgcg cggcaggtta aagcggtctt cggcgtagct gaacacttcg ctccaccagg    2400
ctgcctcctg ccaggcttgc gttttcggca ggtaaaaata cgggccgcta cctttagcga    2460
gcagcgcttt atagttgtgg aaaaagtaca gagcaaaatc aaacaggctg ccgggaatgg    2520 cttcccccg ccaggtaaca tgttttctg gcagatgtag accacgtaca cgacaaatca    2580
atacggccgg atcgggcttg agctgataga ttttccggc ttcgttggta tagctaatgg    2640
tgccgttcac cgcatcacgc aggttgattt gaccatcaat aactttattc cagtccggcg    2700
ccagcgagtc ttcaaaatcc gccataaaca ctttcacatt tgcgttcagg cattaatca    2760 ccattttacg ttcaaccggc ccggtaattt ctactcggcg atcctgtaaa tccgccggaa    2820
taccacgaat ctgccaatta ctttctctaa tggaagtggt ttccgaaata aaatcaggca    2880
acttaccgtt atcaatatcc tgctgttgct ggatacgggc agccaggagt ttattgcgtt    2940
ttggcgtaaa acgggtgact aactccgtca aaaactcgac tgcttcagcg gtcaggactt    3000
gcttttccag ctcgccttgc ggcctggtaa aggttaattc atcagttgtg gttgcctgtg    3060
gattcatcat gcagctcctc gttgttgatc cagatacatc cccaatgcga acgaaggatc    3120
actgtgcact tttcgttcaa cacaactaag actactcaat taaatttcaa aatcaaaaac    3180
aatttccatt tttaatttaa ttatgcatta acctattgat aacaatataa attaaattta    3240
attacatgat gaggtgcgtt tcggaaagac gtcaggcctc tcgagggggg gcccggatcc    3300
ccagtagatt tacgtttaaa cattttttatt tccttttttaa tttaatttaa ttaacagttg    3360
gtgctatgac actttacctc atagctggca taattcgcaa tactctgggt cttcgagagg    3420
tatccaacct gagttgaaat actttaccat cgatttagca gttgtatcag ttatatttat    3480
attaccttta actcttcgcc atccaggagt tttaccgtac agattagagg ataataataa    3540
cacataattc tcgtaagcaa tatgagataa ttttccaagac tctatattag ctcgtgatgt    3600
tttccaaggt ctaaaatcgt cacggttcat ataattagcc aatctcatat gctctctaac    3660
ttccgatgat aagctgtcaa acatgagaat taacgatctg atagagaagg gtttgctcgg    3720
gtcggtggct ctggtaacga ccagtatccc gatcccggct ggccgtcctg ccgccacat    3780 gaggcatgtt ccgcgtcctt gcaatactgt gtttacatac agtctatcgc ttagcggaaa    3840
gttcttttac cctcagccga aatgcctgcc gttgctagac attgccagcc agtgcccgtc    3900
actcccgtac taactgtcac gaacccctgc aataactgtc acgcccccct gcaataactg    3960
tcacgaaccc ctgcaataac tgtcacgccc caaacctgc aaaccagca ggggcggggg    4020 ctggcggggt gttggaaaaa tccatccatg attatctaag aataatccac taggcgcggt    4080
tatcagcgcc cttgtggggc gctgctgccc ttgcccaata tgcccggcca gaggccggat    4140
```

```
agctggtcta ttcgctgcgc taggctacac accgccccac cgctgcgcgg caggggaaa    4200
ggcgggcaaa gcccgctaaa ccccacacca aaccccgcag aaatacgctg ggagcgcttt    4260
tagccgcttt agcggccttt cccctaccc gaagggtggg ggcgcgtgtg cagccccgca     4320
gggcctgtct cggtcgatca ttcagcccgg ctcatccttc tggcgtggcg gcagaccgaa    4380
caaggcgcgg tcgtggtcgc gttcaaggta cgcatccatt gccgccatga gccgatcctc    4440
cggccactcg ctgctgttca ccttggccaa aatcatggcc cccaccagca ccttgcgcct    4500
tgtttcgttc ttgcgctatt gctgctgttc ccttgcccgc acccgctgaa tttcggcatt    4560
gattcgcgct cgttgttctt cgagcttggc cagccgatcc gccgccttgt tgctcccctt    4620
aaccatcttg acaccccatt gttaatgtgc tgtctcgtag gctatcatgg aggcacagcg    4680
gcggcaatcc cgaccctact ttgtagggga gggccattgc atggagccga aaagcaaaag    4740
caacagcgag gcagcatggc gatttatcac cttacggcga aaaccggcag caggtcgggc    4800
ggccaatcgg ccaggccaa ggccgactac atccagcgcg aaggcaagta tgcccgcgac     4860
atggatgaag tcttgcacgc cgaatccggg cacatgccgg agttcgtcga gcggcccgcc    4920
gactactggg atgctgccga cctgtatgaa cgcgccaatg gcggctgtt caaggaggtc     4980
gaatttgccc tgccggtcga gctgaccctc gaccagcaga aggcgctggc gtccgagttc    5040
gcccagcacc tgaccggtgc cgagcgcctg ccgtatacgc tggccatcca tgccggtggc    5100
ggcgagaacc cgcactgcca cctgatgatc tccgagcgga tcaatgacgg catcgagcgg    5160
cccgccgctc agtggttcaa gcggtacaac ggcaagaccc cggagaaggg cggggcacag    5220
aagaccgaag cgctcaagcc caaggcatgg cttgagcaga cccgcgaggc atgggccgac    5280
catgccaacc gggcattaga gcgggctggc cacgacgccc gcattgacca cagaacactt    5340
gaggcgcagg gcatcgagcg cctgcccggt gttcacctgg ggcgaacgt ggtggagatg     5400
gaaggccggg gcatccgcac cgaccgggca gacgtggccc tgaacatcga caccgccaac    5460
gcccagatca tcgacttaca ggaataccgg gaggcaatag accatgaacg caatcgacag    5520
agtgaagaaa tccagaggca tcaacgagtt agcggagcag atcgaaccgc tggcccagag    5580
catggcgaca ctggccgacg aagcccggca ggtcatgagc cagacccagc aggccagcga    5640
ggcgcaggcg gcggagtggc tgaaagccca gcgccagaca ggggcggcat gggtggagct    5700
ggccaaagag ttgcgggagg tagccgccga ggtgagcagc gccgcgcaga gcgcccggag    5760
cgcgtcgcgg gggtggcact ggaagctatg gctaaccgtg atgctggctt ccatgatgcc    5820
tacggtggtc ctgctgatcg catcgttgct cttgctcgac ctgacgccac tgacaaccga    5880
ggacggctcg atctggctgc gcttggtggc ccgatgaaga acgacaggac tttgcaggcc    5940
ataggccgac agctcaaggc catgggctgt gagcgcttcg atatcggcgt cagggacgcc    6000
accaccggcc agatgatgaa ccgggaatgg tcagccgccg aagtgctcca gaacacgcca    6060
tggctcaagc ggatgaatgc ccagggcaat gacgtgtata tcaggcccgc cgagcaggag    6120
cggcatggtc tggtgctggt ggacgacctc agcgagtttg acctggatga catgaaagcc    6180
gagggccggg agcctgccct ggtagtggaa accagcccga agaactatca ggcatgggtc    6240
aaggtggcca acgccgcagg cggtgaactt cgggggcaga ttgcccggac gctgccagc     6300
gagtacgacg ccgacccggc cagcgccgac agccgccact atggccgctt ggcgggcttc    6360
accaaccgca aggacaagca caccaccgc gccggttatc agccgtgggt gctgctgcgt     6420
gaatccaagg gcaagaccgc caccgctggc ccggcgctgg tgcagcaggc tggccagcag    6480
```

```
atcgagcagg cccagcggca gcaggagaag gcccgcaggc tggccagcct cgaactgccc    6540
gagcggcagc ttagccgcca ccggcgcacg gcgctggacg agtaccgcag cgagatggcc    6600
gggctggtca agcgcttcgg tgatgacctc agcaagtgcg actttatcgc cgcgcagaag    6660
ctggccagcc ggggccgcag tgccgaggaa atcggcaagg ccatggccga ggccagccca    6720
gcgctggcag agcgcaagcc cggccacgaa gcggattaca tcgagcgcac cgtcagcaag    6780
gtcatgggtc tgcccagcgt ccagcttgcg cgggccgagc tggcacgggc accggcaccc    6840
cgccagcgag gcatggacag gggcgggcca gatttcagca tgtagtgctt gcgttggtac    6900
tcacgcctgt tatactatga gtactcacgc acagaagggg gttttatgga atacgaaaaa    6960
agcgcttcag ggtcggtcta cctgatcaaa agtgacaagg ctattggtt gcccggtggc     7020
tttggttata cgtcaaacaa ggccgaggct ggccgctttt cagtcgctga tatgccagc     7080
cttaaccttg acggctgcac cttgtccttg ttccgcgaag acaagccttt cggccccggc    7140
aagtttctcg gtgactgata tgaaagacca aaggacaag cagaccggcg acctgctggc     7200
cagccctgac gctgtacgcc aagcgcgata tgccgagcg atgaaggcca aagggatgcg     7260
tcagcgcaag ttctggctga ccgacgacga atacgaggcg ctgcgcgagt gcctggaaga    7320
actcagagcg gcgcagggcg ggggtagtga ccccgccagc gcctaaccac caactgcctg    7380
caaaggaggc aatcaatggc tacccataag cctatcaata ttctggaggc gttcgcagca    7440
gcgccgccac cgctggacta cgttttgccc aacatggtgg ccggtacggt cggggcgctg    7500
gtgtcgcccg gtggtgccgg taaatccatg ctggccctgc aactggccgc acagattgca    7560
ggcgggccgg atctgctgga ggtgggcgaa ctgcccaccg gccggtgat ctacctgccc     7620
gccgaagacc cgcccaccgc cattcatcac cgcctgcacg cccttggggc gcacctcagc    7680
gccgaggaac ggcaagccgt ggctgacggc ctgctgatcc agccgctgat cggcagcctg    7740
cccaacatca tggccccgga gtggttcgac ggcctcaagc gcgccgccga gggccgccgc    7800
ctgatggtgc tggacacgct gcgccggttc cacatcgagg aagaaaacgc cagcggcccc    7860
atggcccagg tcatcggtcg catggaggcc atcgccgccg ataccgggtg ctctatcgtg    7920
ttcctgcacc atgccagcaa gggcgcggcc atgatgggcg caggcgacca gcagcaggcc    7980
agccggggca gctcggtact ggtcgataac atccgctggc agtcctacct gtcgagcatg    8040
accagcgccg aggccgagga tgggggtgtg gacgacgacc agcgccggtt cttcgtccgc    8100
ttcggtgtga gcaaggccaa ctatggcgca ccgttcgctg atcggtggtt caggcggcat    8160
gacggcgggg tgctcaagcc cgccgtgctg gagaggcagc gcaagagcaa ggggtgccc    8220
cgtggtgaag cctaagaaca agcacagcct cagccacgtc cggcacgacc cggcgcactg    8280
tctggccccc ggcctgttcc gtgccctcaa gcggggcgag cgcaagcgca gcaagctgga    8340
cgtgacgtat gactacggcg acggcaagcg gatcgagttc agcggcccgg agccgctggg    8400
cgctgatgat ctgcgcatcc tgcaagggct ggtggccatg gctgggccta atggcctagt    8460
gcttggcccg gaacccaaga ccgaaggcgg acggcagctc cggctgttcc tggaacccaa    8520
gtgggaggcc gtcaccgctg atgccatggt ggtcaaaggt agctatcggg cgctggcaaa    8580
ggaaatcggg gcagaggtcg atagtggtgg ggcgctcaag cacatacagg actgcatcga    8640
gcgcctttgg aaggtatcca tcatcgccca gaatggccgc aagcggcagg gtttcggct    8700
gctgtcggag tacgcagcg acgaggcgga cgggcgcctg tacgtggccc tgaacccctt    8760
gatcgcgcag gccgtcatgg gtggcggcca gcatgtgcgc atcagcatgg acgaggtgcg    8820
ggcgctggac agcgaaaccg cccgcctgct gcaccagcgg ctgtgtggct ggatcgaccc    8880
```

```
cggcaaaacc ggcaaggctt ccatagatac cttgtgcggc tatgtctggc cgtcagaggc    8940
cagtggttcg accatgcgca agcgccgcca gcgggtgcgc gaggcgttgc cggagctggt    9000
cgcgctgggc tggacggtaa ccgagttcgc ggcgggcaag tacgacatca cccggcccaa    9060
ggcggcaggc tgacccccc cactctattg taaacaagac atttttatc ttttatattc      9120 aatggcttat tttcctgcta attggtaata ccatgaaaaa taccatgctc agaaaaggct    9180
taacaatatt ttgaaaaatt gcctactgag cgctgccgca cagctccata ggccgctttc    9240
ctggctttgc ttccagatgt atgctctcct ccggagagta ccgtgacttt attttcggca    9300
caaatacagg ggtcgatgga taaatacggc gatagtttcc tgacggatga tccgtatgta    9360
ccggcggaag acaagctgca aacctgtcag atggagattg atttaatggc ggatgtgctg    9420
agagcaccgc cccgtgaatc cgcagaactg atccgctatg tgtttgcgga tgattggccg    9480
gaataaataa agccgggctt aatacagatt aagcccgtat agggtattat tactgaatac    9540
caaacagctt acgaggacg gaatgttacc cattgagaca accagactgc cttctgatta     9600
ttaatatttt tcactattaa tcagaaggaa taaccatgaa ttttacccgg attgacctga    9660
atacctggaa tcgcagggaa cactttgccc tttatcgtca gcagattaaa tgcggattca    9720
gcctgaccac caaactcgat attaccgctt tgcgtaccgc actggcggag acaggttata    9780
agttttatcc gctgatgatt tacctgatct cccgggctgt taatcagttt ccggagttcc    9840
ggatggcact gaaagacaat gaacttattt actgggacca gtcagacccg gtctttactg    9900
tctttcataa agaaaccgaa acattctctg cactgtcctg ccgttatttt ccggatctca    9960
gtgagtttat ggcaggttat aatgcggtaa cggcagaata tcagcatgat accagattgt    10020
ttccgcaggg aaatttaccg gagaatcacc tgaatatatc atcattaccg tgggtgagtt    10080
ttgacgggat ttaacctgaa catcaccgga aatgatgatt attttgcccc ggtttttacg    10140
atggcaaagt ttcagcagga aggtgaccgc gtattattac ctgtttctgt acaggttcat    10200
catgcagtct gtgatggctt tcatgcagca cggtttatta atacacttca gctgatgtgt    10260
gataacatac tgaaataaat taattaattc tgtatttaag ccaccgtatc cggcaggaat    10320
ggtggctttt tttttatatt ttaaccgtaa tctgtaattt cgtttcagac tggttcagga    10380
tcactgtacg ataatgcccc cgcagtttgg taatacccct aataaaaaag aaacagcaaa    10440
gactgacagc aataataata aagtaagcag taacaataat attaacaaca ccagatgcag    10500
ttataataat agtatttaag acaccagaaa gactgctgcg acagtcattt tgaacaacac    10560
caaaatgccg taaaggcagt agtaacaaca ccagtgaaaa catcacgata gcatagtgat    10620
atgcctgagt gtgtgtaatt aaacaataaa taaccgcca tatataacag aagatagtat     10680
tctgaatggc atgcttttct gttcagtata aacatatcat cccggttggt ataaggatga    10740
tatataataa gttaagctga acacatattt attttggttt tattttacaa ataaagtaag    10800
acgatccgtt aagtcaaagc ggggtatatt tattataccc tgcttttta tttgtccgcc     10860 gggcgcggat aatggatcag attatgcagt gtcacaatgg ccttaccggg attggcgtaa    10920
gcgtgcggga tatccgcatg gaagcgcagg gattccccgg cagaaacggt gtgccactca    10980
tcccccagcc gcagttgtaa tgcgccttcc agtacaatga catgttctct ggttctgaaa    11040
tccatccctg tcggtgttgc ttatgcagtc tggtcgggac tcggcgtcgt cataattaca    11100
gccattgcct ggttgcttca tgggcaaaag ctttatgctt gtaaccgtt ttgtgaaaaa     11160 attttaaaa taaaaagggg gacctctagg gtccccaatt aattagtaat ataatctatt    11220
```
aaaggtcatt caaaaggtca tccaccg                                        11247

<210> SEQ ID NO 14
<211> LENGTH: 9310
<212> TYPE: DNA
<213> ORGANISM: Candida boidinii

<400> SEQUENCE: 14
ctagttctag agcggccgcc accgcggtgg atccccagta gatttacgtt taaacatttt      60
tatttccttt ttaatttaat ttaattaaca gttggtgcta tgacacttta cctcatagct    120
ggcataattc gcaatactct gggtcttcga gaggtatcca acctgagttg aaatacttta    180
ccatcgattt agcagttgta tcagttatat ttatattacc tttaactctt cgccatccag    240
gagttttacc gtacagatta gaggataata ataacacata attctcgtaa gcaatatgag    300
ataatttcca agactctata ttagctcgtg atgttttcca aggtctaaaa tcgtcacggt    360
tcatataatt agccaatctc atatgctctc taacttccga tgataagctg tcaaacatga    420
gaattaacga tctgatagag aagggtttgc tcgggtcggt ggctctggta acgaccagta    480
tcccgatccc ggctggccgt cctggccgcc acatgaggca tgttccgcgt ccttgcaata    540
ctgtgtttac atacagtcta tcgcttagcg gaaagttctt ttaccctcag ccgaaatgcc    600
tgccgttgct agacattgcc agccagtgcc cgtcactccc gtactaactg tcacgaaccc    660
ctgcaataac tgtcacgccc ccctgcaata actgtcacga accctgcaa taactgtcac    720 gcccccaaac ctgcaaaccc agcaggggcg ggggctggcg gggtgttgga aaaatccatc    780
catgattatc taagaataat ccactaggcg cggttatcag cgcccttgtg gggcgctgct    840
gcccttgccc aatatgcccg gccagaggcc ggatagctgg tctattcgct gcgctaggct    900
acacaccgcc ccaccgctgc gcggcagggg gaaaggcggg caaagcccgc taaaccccac    960
accaaacccc gcagaaatac gctgggagcg ctttagccg ctttagcggc ctttcccct    1020 acccgaaggg tggggcgcg tgtgcagccc cgcagggcct gtctcggtcg atcattcagc    1080
ccggctcatc cttctggcgt ggcggcagac cgaacaaggc gcggtcgtgg tcgcgttcaa    1140
ggtacgcatc cattgccgcc atgagccgat cctccggcca ctcgctgctg ttcaccttgg    1200
ccaaaatcat ggccccacc agcaccttgc gccttgtttc gttcttgcgc tattgctgct    1260
gttcccttgc ccgcacccgc tgaatttcgg cattgattcg cgctcgttgt tcttcgagct    1320
tggccagccg atccgccgcc ttgttgctcc ccttaaccat cttgacaccc cattgttaat    1380
gtgctgtctc gtaggctatc atggaggcac agcggcggca atcccgaccc tactttgtag    1440
gggagggcca ttgcatggag ccgaaaagca aaagcaacag cgaggcagca tggcgattta    1500
tcaccttacg gcgaaaaccg gcagcaggtc gggcggccaa tcggcagggg caaggccga    1560 ctacatccag cgcgaaggca agtatgcccg cgacatggat gaagtcttgc acgccgaatc    1620
cgggcacatg ccggagttcg tcgagcggcc cgccgactac tgggatgctg ccgacctgta    1680
tgaacgcgcc aatgggcggc tgttcaagga ggtcgaattt gccctgccgg tcgagctgac    1740
cctcgaccag cagaaggcgc tggcgtccga gttcgcccag cacctgaccg gtgccgagcg    1800
cctgccgtat acgctggcca tccatgccgg tggcggcgag aacccgcact gccacctgat    1860
gatctccgag cggatcaatg acggcatcga gcggcccgcc gctcagtggt tcaagcggta    1920
caacggcaag accccggaga agggcggggc acagaagacc gaagcgctca gcccaaggcc    1980
atggcttgag cagacccgcg aggcatgggc cgaccatgcc aacgggcat tagagcgggc    2040 tggccacgac gcccgcattg accacagaac acttgaggcg cagggcatcg agcgcctgcc    2100

```
cggtgttcac ctggggccga acgtggtgga gatggaaggc cggggcatcc gcaccgaccg    2160
ggcagacgtg gccctgaaca tcgacaccgc caacgcccag atcatcgact acaggaata    2220 ccgggaggca atagaccatg aacgcaatcg acagagtgaa gaaatccaga ggcatcaacg    2280
agttagcgga gcagatcgaa ccgctggccc agagcatggc gacactggcc gacgaagccc    2340
ggcaggtcat gagccagacc cagcaggcca gcgaggcgca ggcggcggag tggctgaaag    2400
cccagcgcca gacaggggcg gcatgggtgg agctggccaa agagttgcgg gaggtagccg    2460
ccgaggtgag cagcgccgcg cagagcgccc ggagcgcgtc gcggggggtgg cactggaagc    2520 tatggctaac cgtgatgctg gcttccatga tgcctacggt ggtgctgctg atcgcatcgt    2580
tgctcttgct cgacctgacg ccactgacaa ccgaggacgg ctcgatctgg ctgcgcttgg    2640
tggcccgatg aagaacgaca ggactttgca ggccataggc cgacagctca aggccatggg    2700
ctgtgagcgc ttcgatatcg gcgtcaggga cgccaccacc ggccagatga tgaaccggga    2760
atggtcagcc gccgaagtgc tccagaacac gccatggctc aagcggatga atgcccaggg    2820
caatgacgtg tatatcaggc ccgccgagca ggagcggcat ggtctggtgc tggtggacga    2880
cctcagcgag tttgacctgg atgacatgaa agccgagggc cgggagcctg ccctggtagt    2940
ggaaaccagc ccgaagaact atcaggcatg ggtcaaggtg gccgacgccg caggcggtga    3000
acttcggggg cagattgccc ggacgctggc cagcgagtac gacgccgacc cggccagcgc    3060
cgacagccgc cactatggcc gcttggcggg cttcaccaac cgcaaggaca gcacaccac    3120 ccgcgccggt tatcagccgt gggtgctgct gcgtgaatcc aagggcaaga ccgccaccgc    3180
tggcccggcg ctggtgcagc aggctggcca gcagatcgag caggcccagc ggcagcagga    3240
gaaggcccgc aggctggcca gcctcgaact gcccgagcgg cagcttagcc gccaccggcg    3300
cacggcgctg gacgagtacc gcagcgagat ggccgggctg gtcaagcgct cggtgatga    3360 cctcagcaag tgcgactta tcgccgcgca gaagctggcc agccggggcc gcagtgccga    3420
ggaaatcggc aaggccatgg ccgaggccag cccagcgctg gcagagcgca agcccggcca    3480
cgaagcggat tacatcgagc gcaccgtcag caaggtcatg gtctgccca gcgtccagct    3540 tgcgcgggcc gagctggcac gggcaccggc accccgccag cgaggcatgg acaggggcgg    3600
gccagatttc agcatgtagt gcttgcgttg gtactcacgc ctgttatact atgagtactc    3660
acgcacagaa gggggttta tggaatacga aaaagcgct tcagggtcgg tctacctgat    3720
caaaagtgac aagggctatt ggttgcccgg tggctttggt tatacgtcaa acaaggccga    3780
ggctggccgc ttttcagtcg ctgatatggc cagccttaac cttgacggct gcaccttgtc    3840
cttgttccgc gaagacaagc ctttcggccc cggcaagttt ctcggtgact gatatgaaag    3900
accaaaagga caagcagacc ggcgacctgc tggccagccc tgacgctgta cgccaagcgc    3960
gatatgccga gcgcatgaag gccaaaggga tgcgtcagcg caagttctgg ctgaccgacg    4020
acgaatacga ggcgctgcgc gagtgcctgg aagaactcag agcggcgcag ggcggggta    4080 gtgaccccgc cagcgcctaa ccaccaactg cctgcaaagg aggcaatcaa tggctaccca    4140
taagcctatc aatattctgg aggcgttcgc agcagcgccg ccaccgctgg actacgtttt    4200
gcccaacatg gtgccggta cggtcggggc gctggtgtcg cccggtggtg ccggtaaatc    4260
catgctggcc ctgcaactgg ccgcacagat tgcaggcggg ccggatctgc tggaggtggg    4320
cgaactgccc accggcccgg tgatctacct gcccgccgaa gacccgccca ccgccattca    4380
tcaccgcctg cacgcccttg gggcgcacct cagcgccgag gaacggcaag ccgtggctga    4440
```

```
cggcctgctg atccagccgc tgatcggcag cctgcccaac atcatggccc cggagtggtt    4500
cgacggcctc aagcgcgccg ccgagggccg ccgcctgatg gtgctggaca cgctgcgccg    4560
gttccacatc gaggaagaaa acgccagcgg ccccatggcc caggtcatcg gtcgcatgga    4620
ggccatcgcc gccgataccg ggtgctctat cgtgttcctg caccatgcca gcaagggcgc    4680
ggccatgatg ggcgcaggcg accagcagca ggccagccgg ggcagctcgg tactggtcga    4740
taacatccgc tggcagtcct acctgtcgag catgaccagc gccgaggccg aggaatgggg    4800
tgtggacgac gaccagcgcc ggttcttcgt ccgcttcggt gtgagcaagg ccaactatgg    4860
cgcaccgttc gctgatcggt ggttcaggcg gcatgacggc ggggtgctca agcccgccgt    4920
gctggagagg cagcgcaaga gcaaggggt gccccgtggt gaagcctaag aacaagcaca    4980
gcctcagcca cgtccggcac gacccggcgc actgtctggc ccccggcctg ttccgtgccc    5040
tcaagcgggg cgagcgcaag cgcagcaagc tggacgtgac gtatgactac ggcgacggca    5100
agcggatcga gttcagcggc ccggagccgc tgggcgctga tgatctgcgc atcctgcaag    5160
ggctggtggc catggctggg cctaatggcc tagtgcttgg cccggaaccc aagaccgaag    5220
gcggacggca gctccggctg ttcctggaac ccaagtggga ggccgtcacc gctgatgcca    5280
tggtggtcaa aggtagctat cgggcgctgg caaaggaaat cggggcagag gtcgatagtg    5340
gtggggcgct caagcacata caggactgca tcgagcgcct ttggaaggta tccatcatcg    5400
cccagaatgg ccgcaagcgg caggggttc ggctgctgtc ggagtacgcc agcgacgagg    5460
cggacgggcg cctgtacgtg gccctgaacc ccttgatcgc gcaggccgtc atgggtggcg    5520
gccagcatgt gcgcatcagc atggacgagg tgcgggcgct ggacagcgaa accgcccgcc    5580
tgctgcacca gcggctgtgt ggctggatcg accccggcaa aaccggcaag gcttccatag    5640
ataccttgtg cggctatgtc tggccgtcag aggccagtgg ttcgaccatg cgcaagcgcc    5700
gccagcgggt gcgcgaggcg ttgccggagc tggtcgcgct gggctggacg gtaaccgagt    5760
tcgcggcggg caagtacgac atcacccggc ccaaggcggc aggctgaccc cccccactct    5820
attgtaaaca agacatttt tatcttttat attcaatggc ttattttcct gctaattggt    5880
aataccatga aaataccat gctcagaaaa ggcttaacaa tatttgaaa aattgcctac    5940 tgagcgctgc cgcacagctc cataggccgc tttcctggct ttgcttccag atgtatgctc    6000
tcctccggag agtaccgtga ctttattttc ggcacaaata caggggtcga tggataaata    6060
cggcgatagt ttcctgacgg atgatccgta tgtaccggcg gaagacaagc tgcaaacctg    6120
tcagatggag attgatttaa tggcggatgt gctgagagca ccgccccgtg aatccgcaga    6180
actgatccgc tatgtgtttg cggatgattg gccggaataa ataaagccgg gcttaataca    6240
gattaagccc gtatagggta ttattactga ataccaaaca gcttacggag gacgaatgt    6300 tacccattga gacaaccaga ctgccttctg attattaata tttttcacta ttaatcagaa    6360
ggaataacca tgaattttac ccggattgac ctgaataccct ggaatcgcag ggaacacttt    6420 gcccttatc gtcagcagat taaatgcgga ttcagcctga ccaccaaact cgatattacc    6480
gctttgcgta ccgcactggc ggagacaggt tataagtttt atccgctgat gatttacctg    6540
atctcccggg ctgttaatca gtttccggag ttccggatgg cactgaaaga caatgaactt    6600
atttactggg accagtcaga cccggtcttt actgtctttc ataaagaaac cgaaacattc    6660
tctgcactgt cctgccgtta ttttccggat ctcagtgagt ttatggcagg ttataatgcg    6720
gtaacggcag aatatcagca tgataccaga ttgtttccgc agggaaattt accggagaat    6780
cacctgaata tatcatcatt accgtgggtg agttttgacg ggatttaacc tgaacatcac    6840
```

```
cggaaatgat gattattttg ccccggtttt tacgatggca aagtttcagc aggaaggtga   6900
ccgcgtatta ttacctgttt ctgtacaggt tcatcatgca gtctgtgatg gctttcatgc   6960
agcacggttt attaatacac ttcagctgat gtgtgataac atactgaaat aaattaatta   7020
attctgtatt taagccaccg tatccggcag gaatggtggc ttttttttta tattttaacc   7080
gtaatctgta atttcgtttc agactggttc aggatcactg tacgataatg cccccgcagt   7140
ttggtaatac ccttaataaa aagaaacag caaagactga cagcaataat aataaagtaa   7200
gcagtaacaa taatattaac aacaccagat gcagttataa taatagtatt taagacacca   7260
gaaagactgc tgcgacagtc atttgaaca acaccaaaat gccgtaaagg cagtagtaac   7320
aacaccagtg aaaacatcac gatagcatag tgatatgcct gagtgtgtgt aattaaacaa   7380
taaataaacc gccatatata acagaagata gtattctgaa tggcatgctt ttctgttcag   7440
tataaacata tcatcccggt tggtataagg atgatatata ataagttaag ctgaacacat   7500
attttattttg gttttatttt acaaataaag taagacgatc cgttaagtca aagcggggta   7560
tatttattat accctgcttt tttatttgtc cgccggcgc ggataatgga tcagattatg   7620
cagtgtcaca atggccttac cgggattggc gtaagcgtgc gggatatccg catggaagcg   7680
cagggattcc ccggcagaaa cggtgtgcca ctcatccccc agccgcagtt gtaatgcgcc   7740
ttccagtaca atgacatgtt ctctggttct gaaatccatc cctgtcggtg ttgcttatgc   7800
agtctggtcg ggactcggcg tcgtcataat tacagccatt gcctggttgc ttcatgggca   7860
aaagctttat gcttgtaaac cgttttgtga aaaattttt aaataaaaa agggggacctc   7920
tagggtcccc aattaattag taatataatc tattaaaggt cattcaaaag gtcatccacc   7980
gggggccccc cctcgagagg cctgacgtcg ggcccggtac cacgcgttta tttcttatcg   8040
tgtttaccgt aagctttagt aacgtattca ccatttaata agataatatc ttgtggtctg   8100
taatcaaatt taccagtaaa gaatgattcc aagatatttt tagtaccttc agcgtatctt   8160
gtttgagcat ctaaagtagt accagagtag tgaggagtca tggcattacc agcaccatat   8220
ttatttctca tatctctcca tgggtgatcc tttggagctg ttgtgggaa ccaaacatca   8280
ccaccgtaac ctcttaattg accagattct aaagctgctg caacatcttc agcaacacaa   8340
atagcacctc ttgcggtatt gactaaccaa gccaccttttt taaatttaga taataattcc   8400
ttattaatta aaccttttgt acctgcgtgt aatggagcat taactgtaac gatatcagct   8460
tgagcaacta attcttcaat attttcaact cttctagcac caactttttc ttcagcttct   8520
tttggtaaag cttgataatc gtagtataat aattcttttg gattaaaagg gagtaatctt   8580
tccaagactc tgtaaccaat tctaccagca ccaatggtag caatagtttt accttcgata   8640
tcgtaagcat cctagcgat agcagcaacc tcccaatcgt ggttaataat tgttcatgt   8700
gctggaacga aatttctaac caagacaagc atggtcatga caacgtgttc agcaacagag   8760
acaacattag aacctgtaac ttccaagact gagattttct tacctgtttg attaatataa   8820
tctaaatcaa tgtgatcaga accaacacca gcgacaacga ctaattttaa gttcttagcc   8880
ttgtcaagtc tttccttagt gatataagca ggatggaaag gagtggtgat gataatatca   8940
gcatctggga tatgttttatc caattcactt gtttcacctt ctttatcaga agtagtaatt   9000
agttcatgac cttgatcttt taaccaatta gcaatactca atttattttc agtacaacca   9060
tataattttt cttcatcagc agcgtgctta ccagcatcat ataagactaa aacgatcttc   9120
atacatcacc tcataaaata aattaaaaaa taataaaaac taatgttttcg cattatagga   9180
```

```
caaaagatac ctaaaaaatg ttatctagat caaattattg gaaaatatat gaaaataatt      9240
tttgtttaaa aagcgaacga cattagtatt tttcataaaa atacgtacat tgttatccgt      9300
cgctatttaa                                                             9310

<210> SEQ ID NO 15
<211> LENGTH: 11309
<212> TYPE: DNA
<213> ORGANISM: Yersinia mollaretii

<400> SEQUENCE: 15 gatcccagt agatttacgt ttaaacattt ttatttcctt tttaatttaa tttaattaac        60
agttggtgct atgacacttt acctcatagc tggcataatt cgcaatactc tgggtcttcg       120
agaggtatcc aacctgagtt gaaatacttt accatcgatt tagcagttgt atcagttata       180
tttatattac ctttaactct tcgccatcca ggagttttac cgtacagatt agaggataat       240
aataacacat aattctcgta agcaatatga gataatttcc aagactctat attagctcgt       300
gatgttttcc aaggtctaaa atcgtcacgg ttcatataat tagccaatct catatgctct       360
ctaacttccg atgataagct gtcaaacatg agaattaacg atctgataga aagggtttg        420 ctcgggtcgg tggctctggt aacgaccagt atcccgatcc cggctggccg tcctggccgc       480
cacatgaggc atgttccgcg tccttgcaat actgtgttta catacagtct atcgcttagc       540
ggaaagttct tttaccctca gccgaaatgc ctgccgttgc tagacattgc cagcagtgc        600 ccgtcactcc cgtactaact gtcacgaacc cctgcaataa ctgtcacgcc ccctgcaat       660 aactgtcacg aaccctgca ataactgtca cgccccaaa cctgcaaacc cagcagggc        720 ggggctggc ggggtgttgg aaaaatccat ccatgattat ctaagaataa tccactaggc        780
gcggttatca gcgcccttgt ggggcgctgc tgcccttgcc caatatgccc ggccagaggc       840
cggatagctg gtctattcgc tgcgctaggc tacacaccgc cccaccgctg cgcggcaggg      900
ggaaaggcgg gcaaagcccg ctaaaccca caccaaaccc gcagaaaata cgctgggagc      960
gcttttagcc gctttagcgg ccttttcccc tacccgaagg gtgggggcgc gtgtgcagcc      1020
ccgcagggcc tgtctcggtc gatcattcag cccggctcat ccttctggcg tggcggaga     1080 ccgaacaagg cgcggtcgtg gtcgcgttca aggtacgcat ccattgccgc catgagccga     1140
tcctccggcc actcgctgct gttcaccttg gccaaaatca tggcccccac cagcaccttg    1200
cgccttgttt cgttcttgcg ctattgctgc tgttcccttg cccgcacccg ctgaatttcg     1260
gcattgattc gcgctcgttg ttcttcgagc ttggccagcc gatccgccgc cttgttgctc     1320
cccttaacca tcttgacacc ccattgttaa tgtgctgtct cgtaggctat catggaggca     1380
cagcggcggc aatcccgacc ctactttgta ggggaaggggcc attgcatgga gccgaaaagc  1440
aaaagcaaca gcgaggcagc atggcgattt atcaccttac ggcgaaaacc ggcagcaggt    1500
cgggcggcca atcggccagg gccaaggccg actacatcca gcgcgaaggc aagtatgccc     1560
gcgacatgga tgaagtcttg cacgccgaat ccgggcacat gccggagttc gtcgagcggc    1620
ccgccgacta ctgggatgct gccgacctgt atgaacgcgc caatgggcgg ctgttcaagg   1680
aggtcgaatt tgccctgccg gtcgagctga ccctcgacca gcagaaggcg ctggcgtccg    1740
agttcgccca gcacctgacc ggtgccgagc gcctgccgta cgctggcc atccatgccg     1800 gtggcggcga gaacccgcac tgccacctga tgatctccga gcggatcaat gacggcatcg    1860
agcggcccgc cgctcagtgg ttcaagcggt acaacggcaa gaccccggag aagggcgggg    1920
cacagaagac cgaagcgctc aagcccaagg catggcttga gcagaccccgc gaggcatggg    1980
```

```
ccgaccatgc caaccgggca ttagagcggg ctggccacga cgcccgcatt gaccacagaa    2040
cacttgaggc gcagggcatc gagcgcctgc ccggtgttca cctggggccg aacgtggtgg    2100
agatggaagg ccggggcatc cgcaccgacc gggcagacgt ggccctgaac atcgacaccg    2160
ccaacgccca gatcatcgac ttacaggaat accgggaggc aatagaccat gaacgcaatc    2220
gacagagtga agaaatccag aggcatcaac gagttagcgg agcagatcga accgctggcc    2280
cagagcatgg cgacactggc cgacgaagcc cggcaggtca tgagccagac ccagcaggcc    2340
agcgaggcgc aggcggcgga gtggctgaaa gcccagcgcc agacaggggc ggcatgggtg    2400
gagctggcca aagagttgcg ggaggtagcc ccgaggtga gcagcgccgc gcagagcgcc    2460
cggagcgcgt cgcggggggtg gcactggaag ctatggctaa ccgtgatgct ggcttccatg    2520
atgcctacgg tggtgctgct gatcgcatcg ttgctcttgc tcgacctgac gccactgaca    2580
accgaggacg gctcgatctg gctgcgcttg gtggcccgat gaagaacgac aggactttgc    2640
aggccatagg ccgacagctc aaggccatgg gctgtgagcg cttcgatatc ggcgtcaggg    2700
acgccaccac cggccagatg atgaaccggg aatggtcagc cgccgaagtg ctccagaaca    2760
cgccatggct caagcggatg aatgcccagg gcaatgacgt gtatatcagg cccgccgagc    2820
aggagcggca tggtctggtg ctggtggacg acctcagcga gtttgacctg gatgacatga    2880
aagccgaggg ccgggagcct gccctggtag tggaaaccag cccgaagaac tatcaggcat    2940
gggtcaaggt ggccgacgcc gcaggcggtg aacttcgggg gcagattgcc cggacgctgg    3000
ccagcgagta cgacgccgac ccggccagcg ccgacagccg ccactatggc cgcttggcgg    3060
gcttcaccaa ccgcaaggac aagcacacca cccgcgccgg ttatcagccg tgggtgctgc    3120
tgcgtgaatc caagggcaag accgccaccg ctggcccggc gctggtgcag caggctggcc    3180
agcagatcga gcaggcccag cggcagcagg agaaggcccg caggctggcc agcctcgaac    3240
tgcccgagcg gcagcttagc cgccaccggc gcacggcgct ggacgagtac cgcagcgaga    3300
tggccgggct ggtcaagcgc ttcggtgatg acctcagcaa gtgcgacttt atcgccgcgc    3360
agaagctggc cagccggggc cgcagtgccg aggaaatcgg caaggccatg gccgaggcca    3420
gcccagcgct ggcagagcgc aagcccggcc acgaagcgga ttacatcgag cgcaccgtca    3480
gcaaggtcat gggtctgccc agcgtccagc ttgcgcgggc cgagctggca cgggcaccgg    3540
caccccgcca gcgaggcatg gacaggggcg ggccagattt cagcatgtag tgcttgcgtt    3600
ggtactcacg cctgttatac tatgagtact cacgcacaga agggggtttt atggaatacg    3660
aaaaaagcgc ttcagggtcg gtctacctga tcaaaagtga caagggctat tggttgcccg    3720
gtggctttgg ttatacgtca aacaaggccg aggctggccg ctttccagtc gctgatatgg    3780
ccagccttaa ccttgacggc tgcaccttgt ccttgttccg cgaagacaag cctttcggcc    3840
ccggcaagtt tctcggtgac tgatatgaaa gaccaaaagg acaagcagac cggcgacctg    3900
ctggccagcc tgacgctgt acgccaagcg cgatatgccg agcgcatgaa ggccaaaggg    3960
atgcgtcagc gcaagttctg gctgaccgac gacgaatacg aggcgctgcg cgagtgcctg    4020
gaagaactca gagcggcgca gggcggggggt agtgaccccg ccagcgccta accaccaact    4080
gcctgcaaag gaggcaatca atggctaccc ataagcctat caatattctg gaggcgttcg    4140
cagcagcgcc gccaccgctg gactacgttt tgcccaacat ggtggccggt acggtcgggg    4200
cgctggtgtc gcccggtggt gccggtaaat ccatgctggc cctgcaactg gccgcacaga    4260
ttgcaggcgg gccggatctg ctggaggtgg gcgaactgcc caccggcccg gtgatctacc    4320
```

```
tgcccgccga agacccgccc accgccattc atcaccgcct gcacgccctt ggggcgcacc      4380
tcagcgccga ggaacggcaa gccgtggctg acggcctgct gatccagccg ctgatcggca      4440
gcctgcccaa catcatggcc ccggagtggt tcgacggcct caagcgcgcc gccgagggcc      4500
gccgcctgat ggtgctggac acgctgcgcc ggttccacat cgaggaagaa aacgccagcg      4560
gccccatggc ccaggtcatc ggtcgcatgg aggccatcgc cgccgatacc gggtgctcta      4620
tcgtgttcct gcaccatgcc agcaaggcg cggccatgat gggcgcaggc gaccagcagc      4680
aggccagccg gggcagctcg gtactggtcg ataacatccg ctggcagtcc tacctgtcga      4740
gcatgaccag cgccgaggcc gaggaatggg gtgtggacga cgaccagcgc cggttcttcg      4800
tccgcttcgg tgtgagcaag gccaactatg gcgcaccgtt cgctgatcgg tggttcaggc      4860
ggcatgacgg cggggtgctc aagcccgccg tgctggagag gcagcgcaag agcaaggggg      4920
tgccccgtgg tgaagcctaa gaacaagcac agcctcagcc acgtccggca cgacccggcg      4980
cactgtctgg cccccggcct gttccgtgcc ctcaagcggg gcgagcgcaa gcgcagcaag      5040
ctggacgtga cgtatgacta cggcgacggc aagcggatcg agttcagcgg cccggagccg      5100
ctgggcgctg atgatctgcg catcctgcaa gggctggtgg ccatggctgg gcctaatggc      5160
ctagtgcttg gcccggaacc caagaccgaa ggcgacggc agctccggct gttcctggaa      5220
cccaagtggg aggccgtcac cgctgatgcc atggtggtca aggtagcta tcgggcgctg      5280 gcaaggaaa tcgggcaga ggtcgatagt ggtggggcgc tcaagcacat acaggactgc      5340
atcgagcgcc tttggaaggt atccatcatc gcccagaatg gccgcaagcg gcaggggttt      5400
cggctgctgt cggagtacgc cagcgacgag gcggacgggc gcctgtacgt ggccctgaac      5460
cccttgatcg cgcaggccgt catgggtggc ggccagcatg tgcgcatcag catggacgag      5520
gtgcgggcgc tggacagcga aaccgcccgc ctgctgcacc agcggctgtg tggctggatc      5580
gaccccggca aaaccggcaa ggcttccata gataccttgt gcggctatgt ctggccgtca      5640
gaggccagtg gttcgaccat gcgcaagcgc cgccagcggg tgcgcgaggc gttgccggag      5700
ctggtcgcgc tgggctggac ggtaaccgag ttcgcggcgg gcaagtacga catcacccgg      5760
cccaaggcgg caggctgacc cccccactc tattgtaaac aagacatttt ttatctttta      5820
tattcaatgg cttatttttcc tgctaattgg taataccatg aaaaatacca tgctcagaaa      5880
aggcttaaca atattttgaa aaattgccta ctgagcgctg ccgcacagct ccataggccg      5940
ctttcctggc tttgcttcca gatgtatgct ctcctccgga gagtaccgtg actttatttt      6000
cggcacaaat acaggggtcg atggataaat acggcgatag tttcctgacg gatgatccgt      6060
atgtaccggc ggaagacaag ctgcaaacct gtcagatgga gattgattta atggcggatg      6120
tgctgagagc accgccccgt gaatccgcag aactgatccg ctatgtgttt gcggatgatt      6180
ggccggaata aataaagccg gcttaatac agattaagcc cgtatagggt attattactg      6240
aataccaaac agcttacgga ggacggaatg ttacccattg agacaaccag actgccttct      6300
gattattaat atttttcact attaatcaga aggaataacc atgaatttta cccggattga      6360
cctgaatacc tggaatcgca gggaacactt tgcccttat cgtcagcaga ttaaatgcgg      6420
attcagcctg accaccaaac tcgatattac cgctttgcgt accgcactgg cggagacagg      6480
ttataagttt tatccgctga tgatttacct gatctcccgg gctgttaatc agtttccgga      6540
gttccggatg gcactgaaag acaatgaact tatttactgg gaccagtcag acccggtctt      6600
tactgtcttt cataaagaaa ccgaaacatt ctctgcactg tcctgccgtt attttccgga      6660
tctcagtgag tttatggcag gttataatgc ggtaacggca gaatatcagc atgataccag      6720
```

| | | | | |
|---|---|---|---|---|
| attgtttccg | cagggaaatt | taccggagaa | tcacctgaat | atatcatcat | taccgtgggt | 6780 |
| gagttttgac | gggatttaac | ctgaacatca | ccggaaatga | tgattatttt | gccccggttt | 6840 |
| ttacgatggc | aaagtttcag | caggaaggtg | accgcgtatt | attacctgtt | tctgtacagg | 6900 |
| ttcatcatgc | agtctgtgat | ggctttcatg | cagcacggtt | tattaataca | cttcagctga | 6960 |
| tgtgtgataa | catactgaaa | taaattaatt | aattctgtat | ttaagccacc | gtatccggca | 7020 |
| ggaatggtgg | cttttttttt | atattttaac | cgtaatctgt | aatttcgttt | cagactggtt | 7080 |
| caggatcact | gtacgataat | gccccgcag | tttggtaata | cccttaataa | aaagaaaca | 7140 |
| gcaaagactg | acagcaataa | taataaagta | agcagtaaca | ataatattaa | caacaccaga | 7200 |
| tgcagttata | ataatagtat | ttaagacacc | agaaagactg | ctgcgacagt | cattttgaac | 7260 |
| aacaccaaaa | tgccgtaaag | gcagtagtaa | caacaccagt | gaaaacatca | cgatagcata | 7320 |
| gtgatatgcc | tgagtgtgtg | taattaaaca | ataaataaac | cgccatatat | aacagaagat | 7380 |
| agtattctga | atggcatgct | tttctgttca | gtataaacat | atcatcccgg | ttggtataag | 7440 |
| gatgatatat | aataagttaa | gctgaacaca | tatttatttt | ggttttattt | tacaaataaa | 7500 |
| gtaagacgat | ccgttaagtc | aaagcggggt | atatttatta | taccctgctt | ttttatttgt | 7560 |
| ccgccgggcg | cggataatgg | atcagattat | gcagtgtcac | aatggcctta | ccgggattgg | 7620 |
| cgtaagcgtg | cgggatatcc | gcatggaagc | gcagggattc | cccggcagaa | acggtgtgcc | 7680 |
| actcatcccc | cagccgcagt | tgtaatgcgc | cttccagtac | aatgacatgt | tctctggttc | 7740 |
| tgaaatccat | ccctgtcggt | gttgcttatg | cagtctggtc | gggactcggc | gtcgtcataa | 7800 |
| ttacagccat | tgcctggttg | cttcatgggc | aaaagcttta | tgcttgtaaa | ccgttttgtg | 7860 |
| aaaaaatttt | taaataaaa | aagggggacct | ctagggtccc | caattaatta | gtaatataat | 7920 |
| ctattaaagg | tcattcaaaa | ggtcatccac | cggatccggg | cccccctcg | aggtcgacgg | 7980 |
| tatcgataag | cttgatatcg | aattcccata | ttgtgcatcg | aatccctgca | aaattgtctg | 8040 |
| agcgattaat | tgttctaatt | ttaccgccat | gctcaccccc | cgccatacgg | aacagagcct | 8100 |
| gcatcagcag | gctccagata | aaacataaac | tcattaatca | gtggcttaga | actgctgctc | 8160 |
| ttccgtcgag | ccagtcagtg | cagtgactga | tgactcgccg | ccctgaatga | tattggtgac | 8220 |
| tttatcaaaa | tagcccgtgc | ccacttcttg | ttgatgggaa | gcaaaggtgt | agccgcgttc | 8280 |
| aacggaggca | aattctggct | gctgcacttt | ctcaacatag | tgcttcatgc | cctcgccttg | 8340 |
| cgcgtaagca | tgggccaagt | cgaacatgtt | gaaccacata | ctgtggatgc | cgccaaggt | 8400 |
| aataaattga | tatttgtagc | ccatcgcgga | gaggtcatct | tggaagctgg | cgatctgctg | 8460 |
| gtcagtcagg | ttcttttttcc | agttaaatga | tggcgaacag | ttataagcca | ataatttacc | 8520 |
| ggggaattta | gcgtgaaccg | catctgcaaa | gcgtttagcc | agcgccagat | ctggcgtcga | 8580 |
| ggtttcacac | cacaccaagt | cggcgtaagg | ggcataggcc | agaccacggc | tgatggcttg | 8640 |
| ctcaatgccc | gcgtgagtgc | ggaagaagcc | ctcagcagta | cgatcaccag | caataaattc | 8700 |
| gctgtcataa | gggtcgcaat | cagaggtcag | caaatccgca | gcatcagcat | cagtgcgcgc | 8760 |
| aatcagcagt | gttggcacgc | caagaacgtc | agcggctaag | cgggcagcaa | ccagcttctg | 8820 |
| aatcgcttct | tgtgttggca | ccaaaacttt | gccgcccata | tggccgcatt | tcttcaccgc | 8880 |
| cgccaattga | tcttcaaagt | gaacgcccgc | agcaccggct | tcaatcatgg | ctttcatcaa | 8940 |
| ttcaaacgca | ttcaatacgc | cgccaaaacc | cgcttcggca | tccgcacaa | tcggcaggaa | 9000 |
| atagtcggta | tagcctttgc | tgcccggctc | aatattattc | gaccactgaa | tctgatctgc | 9060 |

```
acggcggaag ctgttattaa tacgcttaac cacggccgga acagagtcga ccgggtaaag      9120
agattgatcg ggatacatgc tggaggcggt attggcatcg gcggcgacct gccaacccga      9180
cagataaatc gcttcaacac cggcctttgc ctgttgcaat gcctgaccgc ctgttagcgc      9240
ccccagacag ttgatgtagc ctttacgcga ttcgccgtgc agcaactccc acaatctttt      9300
cgcgccgtgc tgtgccagcg tacattctgg gttaacgaaa ccgcgcagtt tgatcacttc      9360
ttcggcgcta taggggcggg tgatgcccct ccagcgcgt gatttccatt cctgttccaa       9420
ctgctgaatt tgttgagtac gagaggttgt catggcgata ttccttatta cttattttg      9480 tagggttaaa taactggcct aggcgagtaa tgcgtagccc ggcaacgtca gaaagtcgat      9540
aagctcgtct tgtgttgtaa tccgctccat cagacgtgcg gcttcttcaa accgcccgcc      9600
atcaaaacgc tctgcgccaa gttcaagttt cacgacctgc atttcttcac tcaacatgtt      9660
acggaacagc tctttggtca ccgtctgacc attgctcagg ctttctggt gatgtatcca       9720 ttgccagata gaagtacggg aaatctcagc cgtcgcggca tcttccatca ggccataaat      9780
cggtacacag ccattgcccg atatccatgc ttcgatgtat tgcactgcga cccggatatt      9840
ggcccgcatc ccctcttcgg tgcgctcacc cgtgcaaggc tctagcaact cagcggcagt      9900
gattggttta tcttgcgcgc gactcacctc taattggttt ggacgatcgc ccagtacttt      9960
gttgaaaacg tccatcacgg tatcggccag accggggtgt gcgacccatg taccatcgtg     10020
gccgttgctg gcttccagct cttttgtcagc gcgaacttta tctaagacca gcgcattttt     10080
ttctggatct ttgttcggga taaaggccgc catgccgccc atcgccaagg caccgcgctt     10140
atggcaggtt ttgatcagta acgagagta ggcactcagg aagggtttcg tcatcgtgac      10200
cgactggcga tcgggcagca cgcgatcgct gtgattttc agcgttttga tatagctgaa      10260
aatgtagtcc caacgccac aattcagggc aacaatgtga tggcgcagat ggtagaggat      10320
ctcatccatc tggaataccg caggcaatgt ctcgattaat actgtggcct taatggtgcc     10380
ttgcggcaga tcgaaacgct gctcggtaaa gctgaaaaca tcactccacc aagccgcttc     10440
ctgataagac tgcatcttgg gtagatagaa ataggggccg ctgccattgg caagcagtaa     10500
cttatagtta tggtagaaat acaacgcgaa atcgaataag ccaccgggga tatcctcccc      10560
ctgccacttc acgtgttttt ctggcaagtg cagaccacgc acccgagcaa tcaacaccgc     10620
tggattgggt tttagctgat aaatcttacc ggattcattc gcgtaagaga ttgtgccttt     10680
gaccgcatcg tgcaaattaa tctgaccttc gataacctta tcccaactgg gtgccagcga     10740
atcctcaaag tcagccataa agactttcac attcgcattg agggcattaa tcaccattt      10800 gcgctcaacc ggcccggtga tctcgacgcg acgatcacgt aaatccgcag gaatactttg     10860
aattttccag tcaccattac gaatggaatt ggtttccgaa atgaaatcag gcaatgcgcc      10920
ttggtcaatg gcctgttgcc aagcggcccg tgcagcaagg agtttgctac gcggctctgc     10980
aaatttcgcc accaattctg ccaaaaattc gatggcctca tcgggcaaaa cctgccgctc      11040
agcagcatta aaatgctggg tgaaaactaa ctccgtgccg actatctgtt gtgtcattcc     11100
ccttcccctt ccccatctct cgacgatcat ttttcagttt cctttttgtta ttccccaaaa     11160 gtgcggtgca aatttgggga gttttagtta attaaaaaaa ttatttttta cgagcttcga    11220
ttactgcagc agcaacactt gttggcgctt cagcatattt taacggttcc attgagtatg     11280
atgctctaga gcggccgcca ccgcggtgg                                        11309

<210> SEQ ID NO 16
<211> LENGTH: 2628
```

```
<212> TYPE: DNA
<213> ORGANISM: Pasteurella DSM 18541

<400> SEQUENCE: 16
atgattatga gtaacgctgt tgaaaacaca gtaagccccg ctcaagcgga ggtgaactca    60
ctggttgaga aaggtttagt ggcactggag caattccgcc aactaaatca ggaacaggtg   120
gactacattg tagcgaaagc ttctgttgcc gctttagacc aacatggagc attggcgcta   180
catgcgttag aggaaaccgg gcgcggcgtg ttcgaggaca aagccactaa aaacctgttt   240
gcctgcgaac atgtagtgaa caaaatgcga cattggaaaa ccgccgggat tatcagtgac   300
gacgatgtca caggtatcac cgaaattgcc gatccggtgg gagtggtctg cggcattaca   360
cctaccacta atcctacttc cacggctatc ttcaaatcac tgatcgcttt aaaaacccgc   420
aatcctattg ttttcgcttt ccacccttcc gcccaacagt cttccgctca tgccgcacaa   480
attgtgcgcg atgccgcggt agccgccggt gcgccggaaa actgtattca atggattgca   540
caaccctcta tggaaggaac taatgcgtta atgaaccatc cgggtattgc caccattctg   600
gctaccggcg gtaacgctat ggtgcaggcc gcttattcat gcggcaagcc ggcgttggga   660
gtcggtgccg gaaatgtacc cgcttatgtg gaaaaatccg ccgatattaa acaggcaact   720
cacgatatcg tgatgtcgaa atcctttgat aacggtatgg tatgcgcttc agagcaagcc   780
gctattgccg atgcggaaat ttatgacgaa ttcgtcaacg aattaaaatc ctacggtgtg   840
tatttcgtca ataaaaaaga aaaaacttta ttggaagaat ttatgttcgg tgtaaaagct   900
aacggtgcaa attgcgccgg tgcgaaacta acgccgacg tggtaggtaa atccgcatac   960
tggattgctc aacaagcggg ctttgaagtg ccgaaaaaaa ccaatattct tgccgcagaa  1020
tgtaaagaag tcagcccgaa agaaccttta acccgggaaa aattatcacc ggtgcttgcc  1080
gttttaaaat cccgttctac cgaagaggga ttaacgcttg ccgaagccat ggtggaattt  1140
aacggtttag acactccgc ggcaattcac accaaagatg cggcgcttgc caaacgcttc  1200
ggcgagcgcg ttaaagccat tcgcgttatc tggaattcgc cttctacctt cggcggtatc  1260
ggcgacgttt ataacgcttt cctgccttca ttaaccctgg gttgcggttc ttacggcaaa  1320
aattccgtca gcaacaatgt cagcgccatg aacttagtaa atatcaaacg tgtgggaaga  1380
cggagaaata atatgcaatg gtttaaagta ccttcaaaaa tctatttga acgggattca  1440
attcaatatt tacaatccgt accggatatg cgacgagtag ttatcgtaac cgaccgcact  1500
atggtggatc ttgggtttgt acaaaaaatc gcccatcagt tggaatcccg tcgcgatccg  1560
gtttcttacc agttatttgc cgatgtagaa ccggatccga gtattcaaac cgtgcgccgc  1620
ggtgtggatt taatccgtaa tttcaaaccg gacactatta tcgcgcttgg cggcggttcc  1680
gccatggatg cggcaaaagt gatgtggtta ttctatgaac aaccggaaat tgacttccgt  1740
gatttggttc aaaaattcat ggatattcgt aaacgtgcct ttaaatttcc atcattggga  1800
aaaaagcccc gctatatcgg cattccgacc acatccggta cggttcgga agtgaccccg  1860
tttgcggtga ttaccgaagg taacaaaaaa tatccgattg cggactattc gctaacgccg  1920
actatcgctt tagtggatcc ggcattagtt atgacggtac ccgcccatgt agcggcggat  1980
acgggattag acgtattaac tcatgccacc gaagcttatg tttccgtact ggccaacgat  2040
tataccgacg gtcttgcttt acaggcgatt aaactggtat ccggtatttt ggaaaaatcc  2100
gtaaagaaa atgatccgga ggcaagagaa aagatgcata atgcgtccac cattgcgggt  2160
atggcgtttg ccaatgcatt cttaggtatg aatcattccc ttgcgcataa acttggcggc  2220
```

```
catttccata cgcctcacgg gcgcactaat gcgatcttaa tgccgcacgt gatccgttat    2280
aacggtacta aaccgacgaa aaccgccaca tggccgaaat acaactatta caaagcggac    2340
gaaaaatatc aggatatcgc ccgtttatta ggcttacctg cggcgacccc ggaagagggc    2400
gtgaaatctt atgccaaagc ggtttacgat ttagcggtac gttgcggtat taaaatgtcc    2460
ttcaaagaac agggactgga agaacaggcc tggatggacg cccgccatga aattgcattg    2520
cttgcctatg aagaccaatg ttcgccggca atccgcgat taccgattgt ggcggacatg    2580
gaagaaattc tcactaacgc ctactatggt tatgacgaaa gcaaatac                2628
```

```
<210> SEQ ID NO 17
<211> LENGTH: 876
<212> TYPE: PRT
<213> ORGANISM: Pasteurella DSM 18541

<400> SEQUENCE: 17

Met Ile Met Ser Asn Ala Val Glu Asn Thr Val Ser Pro Ala Gln Ala
1               5                   10                  15

Glu Val Asn Ser Leu Val Glu Lys Gly Leu Val Ala Leu Glu Gln Phe
            20                  25                  30

Arg Gln Leu Asn Gln Glu Gln Val Asp Tyr Ile Val Ala Lys Ala Ser
        35                  40                  45

Val Ala Ala Leu Asp Gln His Gly Ala Leu Ala Leu His Ala Leu Glu
    50                  55                  60

Glu Thr Gly Arg Gly Val Phe Glu Asp Lys Ala Thr Lys Asn Leu Phe
65                  70                  75                  80

Ala Cys Glu His Val Val Asn Lys Met Arg His Trp Lys Thr Ala Gly
                85                  90                  95

Ile Ile Ser Asp Asp Val Thr Gly Ile Thr Glu Ile Ala Asp Pro
            100                 105                 110

Val Gly Val Val Cys Gly Ile Thr Pro Thr Thr Asn Pro Thr Ser Thr
        115                 120                 125

Ala Ile Phe Lys Ser Leu Ile Ala Leu Lys Thr Arg Asn Pro Ile Val
    130                 135                 140

Phe Ala Phe His Pro Ser Ala Gln Gln Ser Ser Ala His Ala Ala Gln
145                 150                 155                 160

Ile Val Arg Asp Ala Ala Val Ala Ala Gly Ala Pro Glu Asn Cys Ile
                165                 170                 175

Gln Trp Ile Ala Gln Pro Ser Met Glu Gly Thr Asn Ala Leu Met Asn
            180                 185                 190

His Pro Gly Ile Ala Thr Ile Leu Ala Thr Gly Gly Asn Ala Met Val
        195                 200                 205

Gln Ala Ala Tyr Ser Cys Gly Lys Pro Ala Leu Gly Val Gly Ala Gly
    210                 215                 220

Asn Val Pro Ala Tyr Val Glu Lys Ser Ala Asp Ile Lys Gln Ala Thr
225                 230                 235                 240

His Asp Ile Val Met Ser Lys Ser Phe Asp Asn Gly Met Val Cys Ala
                245                 250                 255

Ser Glu Gln Ala Ala Ile Ala Asp Ala Glu Ile Tyr Asp Glu Phe Val
            260                 265                 270

Asn Glu Leu Lys Ser Tyr Gly Val Tyr Phe Val Asn Lys Lys Glu Lys
        275                 280                 285

Thr Leu Leu Glu Glu Phe Met Phe Gly Val Lys Ala Asn Gly Ala Asn
    290                 295                 300
```

```
Cys Ala Gly Ala Lys Leu Asn Ala Asp Val Val Gly Lys Ser Ala Tyr
305                 310                 315                 320

Trp Ile Ala Gln Gln Ala Gly Phe Glu Val Pro Lys Lys Thr Asn Ile
            325                 330                 335

Leu Ala Ala Glu Cys Lys Glu Val Ser Pro Lys Glu Pro Leu Thr Arg
            340                 345                 350

Glu Lys Leu Ser Pro Val Leu Ala Val Leu Lys Ser Arg Ser Thr Glu
            355                 360                 365

Glu Gly Leu Thr Leu Ala Glu Ala Met Val Glu Phe Asn Gly Leu Gly
            370                 375                 380

His Ser Ala Ala Ile His Thr Lys Asp Ala Ala Leu Ala Lys Arg Phe
385                 390                 395                 400

Gly Glu Arg Val Lys Ala Ile Arg Val Ile Trp Asn Ser Pro Ser Thr
            405                 410                 415

Phe Gly Gly Ile Gly Asp Val Tyr Asn Ala Phe Leu Pro Ser Leu Thr
            420                 425                 430

Leu Gly Cys Gly Ser Tyr Gly Lys Asn Ser Val Ser Asn Asn Val Ser
            435                 440                 445

Ala Met Asn Leu Val Asn Ile Lys Arg Val Gly Arg Arg Asn Asn
450                 455                 460

Met Gln Trp Phe Lys Val Pro Ser Lys Ile Tyr Phe Glu Arg Asp Ser
465                 470                 475                 480

Ile Gln Tyr Leu Gln Ser Val Pro Asp Met Arg Val Val Ile Val
            485                 490                 495

Thr Asp Arg Thr Met Val Asp Leu Gly Phe Val Gln Lys Ile Ala His
            500                 505                 510

Gln Leu Glu Ser Arg Arg Asp Pro Val Ser Tyr Gln Leu Phe Ala Asp
            515                 520                 525

Val Glu Pro Asp Pro Ser Ile Gln Thr Val Arg Arg Gly Val Asp Leu
            530                 535                 540

Ile Arg Asn Phe Lys Pro Asp Thr Ile Ile Ala Leu Gly Gly Gly Ser
545                 550                 555                 560

Ala Met Asp Ala Ala Lys Val Met Trp Leu Phe Tyr Glu Gln Pro Glu
            565                 570                 575

Ile Asp Phe Arg Asp Leu Val Gln Lys Phe Met Asp Ile Arg Lys Arg
            580                 585                 590

Ala Phe Lys Phe Pro Ser Leu Gly Lys Lys Ala Arg Tyr Ile Gly Ile
            595                 600                 605

Pro Thr Thr Ser Gly Thr Gly Ser Glu Val Thr Pro Phe Ala Val Ile
610                 615                 620

Thr Glu Gly Asn Lys Lys Tyr Pro Ile Ala Asp Tyr Ser Leu Thr Pro
625                 630                 635                 640

Thr Ile Ala Leu Val Asp Pro Ala Leu Val Met Thr Val Pro Ala His
            645                 650                 655

Val Ala Ala Asp Thr Gly Leu Asp Val Leu Thr His Ala Thr Glu Ala
            660                 665                 670

Tyr Val Ser Val Leu Ala Asn Asp Tyr Thr Asp Gly Leu Ala Leu Gln
            675                 680                 685

Ala Ile Lys Leu Val Phe Arg Tyr Leu Glu Lys Ser Val Lys Glu Asn
            690                 695                 700

Asp Pro Glu Ala Arg Glu Lys Met His Asn Ala Ser Thr Ile Ala Gly
705                 710                 715                 720

Met Ala Phe Ala Asn Ala Phe Leu Gly Met Asn His Ser Leu Ala His
```

```
                    725                 730                 735
Lys Leu Gly Gly His Phe His Thr Pro His Gly Arg Thr Asn Ala Ile
                740                 745                 750

Leu Met Pro His Val Ile Arg Tyr Asn Gly Thr Lys Pro Thr Lys Thr
            755                 760                 765

Ala Thr Trp Pro Lys Tyr Asn Tyr Tyr Lys Ala Asp Glu Lys Tyr Gln
        770                 775                 780

Asp Ile Ala Arg Leu Leu Gly Leu Pro Ala Ala Thr Pro Glu Glu Gly
785                 790                 795                 800

Val Lys Ser Tyr Ala Lys Ala Val Tyr Asp Leu Ala Val Arg Cys Gly
                805                 810                 815

Ile Lys Met Ser Phe Lys Glu Gln Gly Leu Glu Gln Ala Trp Met
            820                 825                 830

Asp Ala Arg His Glu Ile Ala Leu Leu Ala Tyr Glu Asp Gln Cys Ser
        835                 840                 845

Pro Ala Asn Pro Arg Leu Pro Ile Val Ala Asp Met Glu Glu Ile Leu
    850                 855                 860

Thr Asn Ala Tyr Tyr Gly Tyr Asp Glu Ser Lys Tyr
865                 870                 875

<210> SEQ ID NO 18
<211> LENGTH: 7284
<212> TYPE: DNA
<213> ORGANISM: artificial
<220> FEATURE:
<223> OTHER INFORMATION: integrational plasmid

<400> SEQUENCE: 18
tcgagataaa ttcgcggaac cggcgcaggc tcacctggct gttgcgatcg ataggtacgt      60
tgattatggt gttgattaca tctcttgtac ctggcacatt tgccgtttta tcaatttcac     120
tgctcacctc gttttgtgcg ttcacgttga ttacaatgat gttttttaat tgattcttta     180
ccgcttcctg atacatacct tcctgacccg caacatcata aatatcaatt aagccggaca     240
gtcctaaatt atccgttaaa ccgccgtcca ccaaatgaat aaaagggcgt tctttgctgt     300
tttgatataa agacaaggta ttttttaatt cttccagatt ttttgatttt tgcgcatcat     360
tgctgatatt ttggctgatt tgaattaatt ccggtatatc gaaatggcag ttgccgccgt     420
tgttgtttaa agtcaacggg ctgaacagca acggtaccga acttgatgcg gcgacggcac     480
gggaaatttc cattttactt aagtcaatac aaagaccgtc gaaaaattct tgcgtaaagg     540 ttatttttg tcctaaattc atatccgtcg cactcactac gacaaacggt cctttacgtt     600
ttcgctcaag atcaccgaag gtagcgcctt tgtataatgt ttgatccagc tgttcctgta     660
ataagtcgcc gcgaccgaat tgaggggagg ttattcgcgg taaattggaa agggataaaa     720
cctgactgat aatttcccgc tggaaatttt tttttaggaa gttttcttca aatttaggca     780
ccgcatcccg cccgtatagg aataataag tggctaaaac ggatccgccg gatacgccgt     840
ataccaaatc cacattatca attagggttg tacctttgc cgtcgggcgc acggcggcgt     900
ttttaaattc ctctaacacg ccgtagccca aacttgccgc cggctgccg ccgcccgaaa     960 acattaaaat aatcaaattg ccgtcgggtt gctgaatggc atttctcatt cgataccctt    1020
gcttagcgtt cacatggctg atggtatcaa cgggctgata agtcactaag gtacaagctg    1080
acaacaacaa aacagtcaaa ccggcgaaaa tattttttag catcatagtt gtaacggata    1140
aatctaaatt tttatttata gaaaagaaa ataatatgct acatcgtact atattaattt    1200
```

```
tatcctgcgt tcatatctta tcagaaggca aaccgctttt tctatgcaag gaaaatttta    1260
taaatgacta atgtactcaa ataatgaaga aagataaaca aacatttttt catgagaaaa    1320
ttcttatgaa ttctaagcct cggtaattcc tattggtatt ttatttttgaa accgattacc   1380 ttttaaatta aaatttttta tttgatttaa atcaatttaa tcgcattatt aatcccattt    1440
cataactcca aagtagtaaa attcgcacca gtaaccaaat ttaaatatta aacaacttta    1500
ggagaataat ttgtaaaatt cttaaaaatc gtaccgcact ttttctaaaa gtgcggtatt    1560
tttttgattg tttttatccg tctaaagggt aaaatcaacg ggatttattg atattaaagg    1620
aaacaattat ggcaacaact attcatacag aaaacgcgcc cgcagcaatc ggtccttatg    1680
ttcaagcggt agatttaggc aatttagtgc tgacttcggg gcaaattccg gtgaatccgg    1740
caaccggcga agtgccggcg atattagcg cacaagcccg ccaatcttta gaaaacgtta     1800
aagcgattat cgaacaggca gggttaaccg tggcggatat tgtaaaaact acggtttttg    1860
ttaaggattt aaacgatttt gccaccgtaa atgcggaata cgaacgtttt ttcaaagaga    1920
atgaccatcc gaatttccct gctcgctcat gcgttgaagt ggcgcgttta ccgaaagacg    1980
tcggcttgga aattgaagct attgcggtgc gcaaataagg ctgggttaag cgcttattta    2040
tacaaaagtg cggtcaaaaa atccgttttt tgtaaaagaa aaggcatagt tttattgacc    2100
gtgccttttt gctatttgat gatttatttg cgcaacttca cttcttgtac cgcatggtcg    2160
gcacctttgc gtaaaattaa atttgcccgt tcacgggtcg gcaaaatatt ttgccgtaaa    2220
tttaagccgt aatagtatt ccaaatatta gcggcggttt caaccgcttc ttctttagag     2280
agttttgcat aatcttaaa ataggaattc ggatcggtaa acgcgctttc acggaatttc     2340
aaaaagcggc gaatatacca ttcctttaat aaggcttcat cggcgtccac ataaacggaa    2400
aaatcaacaa atcggagac aaaagtctgt tccgctttgc gcgaaccggt ttgtaatacg     2460
tttaaacctt ccaatataag aatatccggg cgatctacct tgttaaattt atcggggata    2520
atatcatagg tcaaatgcga ataaatcggc gccgacacgt tcggtttgcc ggattttacg    2580
tccgccagaa atttgattaa tttgggcgta tcgtaagaga cggggaagcc ttttttatgc    2640
aataaatttt ctttttttaa tttttctaaa ggatagagaa aaccgtcggt ggtaatcaaa    2700
tccactttgc gattttcagg ccagttagac agtaaagact gcaaaatacg cgcggaagtg    2760
cttttcccga ccgaaacgct gccggcaata ctgataatat aaggtacatt ggcgttggta    2820
ttgccgagaa aacggttcat tacggtctgg cgacgtaaat tttcttcaat ataataatta    2880
attaaacgcg caagaggcag gtaaatggtg ctgacttctt ccaacgataa ttcttcgtta    2940
aaaccgagta aaggctttaa atcttgttct gtcagtttta aaggcacgga tttccgcaat    3000
tccgcccatt gtttacgggt aaatgtcaaa aacgggctga atttctctga aactgacgat    3060
tggctttcta tgttcacggc tcattctaat gttaagaaag taaaaatcta gactccatag    3120 gccgcttttcc tggctttgct tccagatgta tgctctcctc cggagagtac cgtgacttta    3180
ttttcggcac aaatacaggg gtcgatggat aaatacggcg atagtttcct gacggatgat    3240
ccgtatgtac cggcggaaga caagctgcaa acctgtcaga tggagattga tttaatggcg    3300
gatgtgctga gagcaccgcc ccgtgaatcc gcagaactga tccgctatgt gtttgcggat    3360
gattggccgg aataaataaa gccgggctta atacagatta agcccgtata gggtattatt    3420
actgaatacc aaacagctta cggaggacgg aatgttaccc attgagacaa ccagactgcc    3480
ttctgattat taatatttt cactattaat cagaaggaat aaccatgaat tttacccgga    3540
ttgacctgaa tacctggaat cgcagggaac actttgccct ttatcgtcag cagattaaat    3600
```

-continued

```
gcggattcag cctgaccacc aaactcgata ttaccgcttt gcgtaccgca ctggcggaga   3660
caggttataa gttttatccg ctgatgattt acctgatctc ccgggctgtt aatcagtttc   3720
cggagttccg gatggcactg aaagacaatg aacttattta ctgggaccag tcagacccgg   3780
tctttactgt ctttcataaa gaaaccgaaa cattctctgc actgtcctgc cgttattttc   3840
cggatctcag tgagtttatg gcaggttata atgcggtaac ggcagaatat cagcatgata   3900
ccagattgtt tccgcaggga aatttaccgg agaatcacct gaatatatca tcattaccgt   3960
gggtgagttt tgacgggatt taacctgaac atcaccggaa atgatgatta ttttgccccg   4020
gttttttacga tggcaaagtt tcagcaggaa ggtgaccgcg tattattacc tgtttctgta   4080
caggttcatc atgcagtctg tgatggcttt catgcagcac ggtttattaa tacacttcag   4140
ctgatgtgtg ataacatact gaaataaatt aattaattct gtatttaagc caccgtatcc   4200
ggcaggaatg gtggcttttt ttttatattt taaccgtaat ctgtaatttc gtttcagact   4260
ggttcaggat gagctcgctt ggactcctgt tgatagatcc agtaatgacc tcagaactcc   4320
atctggattt gttcagaacg ctcggttgcc gccgggcgtt ttttattggt gagaatccaa   4380
gcactagcgg cgcgccggcc ggcccggtgt gaaataccgc acagatgcgt aaggagaaaa   4440
taccgcatca ggcgctcttc cgcttcctcg ctcactgact cgctgcgctc ggtcgttcgg   4500
ctgcggcgag cggtatcagc tcactcaaag gcggtaatac ggttatccac agaatcaggg   4560
gataacgcag gaaagaacat gtgagcaaaa ggccagcaaa aggccaggaa ccgtaaaaag   4620
gccgcgttgc tggcgttttt ccataggctc cgcccccctg acgagcatca caaaaatcga   4680
cgctcaagtc agaggtggcg aaacccgaca ggactataaa gataccaggc gtttccccct   4740
ggaagctccc tcgtgcgctc tcctgttccg accctgccgc ttaccggata cctgtccgcc   4800
tttctccctt cgggaagcgt ggcgctttct catagctcac gctgtaggta tctcagttcg   4860
gtgtaggtcg ttcgctccaa gctgggctgt gtgcacgaac cccccgttca gcccgaccgc   4920
tgcgccttat ccggtaacta tcgtcttgag tccaacccgg taagacacga cttatcgcca   4980
ctggcagcag ccactggtaa caggattagc agagcgaggt atgtaggcgg tgctacagag   5040
ttcttgaagt ggtggcctaa ctacggctac actagaagga cagtatttgg tatctgcgct   5100
ctgctgaagc cagttacctt cggaaaaaga gttggtagct cttgatccgg caaacaaacc   5160
accgctggta gcggtggttt ttttgtttgc aagcagcaga ttacgcgcag aaaaaaagga   5220
tctcaagaag atcctttgat cttttctacg gggtctgacg ctcagtggaa cgaaaactca   5280
cgttaaggga ttttggtcat gagattatca aaaaggatct tcacctagat ccttttaaag   5340
gccggccgcg gccgccatcg gcattttctt ttgcgttttt atttgttaac tgttaattgt   5400
ccttgttcaa ggatgctgtc tttgacaaca gatgttttct tgcctttgat gttcagcagg   5460
aagctcggcg caaacgttga ttgtttgtct gcgtagaatc ctctgtttgt catatagctt   5520
gtaatcacga cattgtttcc tttcgcttga ggtacagcga agtgtgagta agtaaaggtt   5580
acatcgttag gatcaagatc cattttaac acaaggccag ttttgttcag cggcttgtat   5640
gggccagtta aagaattaga aacataacca agcatgtaaa tatcgttaga cgtaatgccg   5700
tcaatcgtca tttttgatcc gcgggagtca gtgaacaggt accatttgcc gttcatttta   5760
aagacgttcg cgcgttcaat ttcatctgtt actgtgttag atgcaatcag cggtttcatc   5820
acttttttca gtgtgtaatc atcgtttagc tcaatcatac cgagagcgcc gtttgctaac   5880
tcagccgtgc gttttttatc gctttgcaga agttttttgac tttcttgacg gaagaatgat   5940
```

```
gtgcttttgc catagtatgc tttgttaaat aaagattctt cgccttggta gccatcttca      6000
gttccagtgt ttgcttcaaa tactaagtat ttgtggcctt tatcttctac gtagtgagga      6060
tctctcagcg tatggttgtc gcctgagctg tagttgcctt catcgatgaa ctgctgtaca      6120
ttttgatacg ttttttccgtc accgtcaaag attgatttat aatcctctac accgttgatg     6180
ttcaaagagc tgtctgatgc tgatacgtta acttgtgcag ttgtcagtgt ttgtttgccg      6240
taatgtttac cggagaaatc agtgtagaat aaacggattt ttccgtcaga tgtaaatgtg      6300
gctgaacctg accattcttg tgtttggtct tttaggatag aatcatttgc atcgaatttg      6360
tcgctgtctt taaagacgcg gccagcgttt ttccagctgt caatagaagt ttcgccgact      6420
ttttgataga acatgtaaat cgatgtgtca tccgcatttt taggatctcc ggctaatgca      6480
aagacgatgt ggtagccgtg atagtttgcg acagtgccgt cagcgttttg taatggccag      6540
ctgtcccaaa cgtccaggcc ttttgcagaa gagatatttt taattgtgga cgaatcaaat      6600
tcagaaactt gatattttc attttttgc tgttcaggga tttgcagcat atcatggcgt        6660
gtaatatggg aaatgccgta tgtttcctta tatggctttt ggttcgtttc tttcgcaaac     6720
gcttgagttg cgcctcctgc cagcagtgcg gtagtaaagg ttaatactgt tgcttgtttt      6780 gcaaacttt tgatgttcat cgttcatgtc tccttttta tgtactgtgt tagcggtctg       6840
cttcttccag ccctcctgtt tgaagatggc aagttagtta cgcacaataa aaaaagacct    6900
aaaatatgta aggggtgacg ccaaagtata cactttgccc tttacacatt ttaggtcttg     6960
cctgctttat cagtaacaaa cccgcgcgat ttacttttcg acctcattct attagactct     7020
cgtttggatt gcaactggtc tattttcctc ttttgtttga tagaaaatca taaaggatt     7080 tgcagactac gggcctaaag aactaaaaaa tctatctgtt tcttttcatt ctctgtattt     7140
tttatagttt ctgttgcatg ggcataaagt tgccttttta atcacaattc agaaaatatc     7200
ataatatctc atttcactaa ataatagtga acggcaggta tatgtgatgg gttaaaaagg     7260
atcggcggcc gctcgattta aatc                                             7284
```

<210> SEQ ID NO 19
<211> LENGTH: 5210
<212> TYPE: DNA
<213> ORGANISM: Wolinella succinogenes

<400> SEQUENCE: 19

```
atgagtgaag cgttaagcgg acgcgggaac gatcgaagaa agttcctaaa gatgtcggct       60
ttagcaggag tcgcaggcgt gagtcaagcg gttggctccg accaaagcaa agtgcttaga     120
cctgcaacaa aacaagagtt aatcgaaaaa tacccagtgt ccaaaaaggt aaaaacgatt     180
tgcacctatt gctcggtcgg atgtggaatt atagcggaag tggtcgatgg tgtatgggta     240
cgccaagagg tcgctcaaga tcaccccatt agtcaagggg gtcactgctg caagggcgcc     300
gatatgattg ataaggctcg aagcgaaaca agacttcgat accccattga aaagttggc      360 ggaaaatggc gtaaaacttc atgggatagc gccatggata agattgccaa gcagcttcag     420
gatctcaccc aaaaatatgg ccctgatagc gtcatgttca ttggcggctc caagtgttcg     480
attgaacaat cctattattt tagaaagttt gccgcctttt ttggcaccaa caatctcgat     540
accatcgcac gaatctgcca tgccccaaca gttgctggag tctccaatac ccttggatat    600
ggcggtatga ccaatcactt ggcagacatg atgcactcca aggcgatttt tatcattggt     660
ggaaatcccg cagtgaatca ccctgtaggc atggtgcata tcttgcgcgc taaagaggca    720
ggagcaaaaa tcatcgttgt ggatccccac ttcagtcgaa cagcaactaa agccgatcac   780
```

```
tatgtgagat tgcgcaatgg cacggatgtc gccttcatgt atgggatgat tcgccatatt      840
gtaaaaaatg gactagaaga taagaatttt attcgacaac gcctatttgg ctacgaagag      900
attcttaaag agtgcgaaca gtacacccct gaagtggtcg aagaggtcac aggcgtgccc      960
gcccaacaac ttattgagat cacggagatc ttcgctaaag ccaagcctgc ttcactgatc     1020
tgggggatgg gtctcaccca gcacaccaca ggtacaagca acactcgttt ggcccctatt     1080
ttacagatga ttcttggaaa cattggcaaa cgaggtggag cactaacgt tttacgaggt      1140 catgacaatg tccaaggcgc gacggacatg ggcaacctag ccgacagtct tcctggctat     1200
tatgggttag acaaaaatgc atggaatcac ttctgtggaa tctggaaagt ggatttcgaa     1260
gcaatgcaaa aacgctttaa gacccctgat atgatgcata aaaaaggttt cagtgtatcc     1320
acatggagat atggggtgac tgaagaggag aacatccccc acaatgcagg cactaaactt     1380
cgatccttga ttgtcgtggg aagcggaatc tctacgatcg cacgcgtgga taccaccaaa     1440
gacgctctag acaagatgga tttagtcgtc tttttgatc cctatttcaa tgatgcagcc      1500
gccctcacca accgaaaaga taatctctat atccttcctg ccgccacaca gatggagacc     1560 agcggaaagag tcgcagcgac gaatcgaagc tatcagtggc gatccatggt tatgaagcca     1620
ctctttgagt gtcgacctga cgaagagatt ctctttgatt tagctaagcg acttggattc     1680
tatgaggagt acactcgctc tttgggggat ggcaaaggaa actttgtatg cccgatgat      1740 gcgactagag aggtggccaa ggctatacga actgtcggct tccaaggcag aactccagaa     1800
cgactcaagg ctcatgcaga aaactggcat atgtttgata agttcaccct cagaggaaag     1860
ggcggccccg tcaaggcga atactatggt cttccttggc cttgctggag cgaaaagcat       1920
cctggaacac caaatctatg ggatgacagc atccctgtaa tggatggagg tcttggcttt     1980
agggttcgat ggggtgatgt gtcacccaca ggagaaagtt tgttggccag ccaggacagc     2040
tctttgcccg gctcaaaatt caagggcggt catagcatga tcaccgataa aaatgtcgaa     2100
gctatcactg gaatcgccct caccgaagag gaaaaagcca agtggcagg caagacatgg       2160 gcgactgaca ccaccaatat cttggttgaa aaagcactcg ccgcaggtct ctcccctatg     2220
ggtaatggta gagctagagc gattgtttgg gagtggacgg atcagattcc taaacaccgt     2280
gaacccatct acacaattcg acacgatctc attagccaat atccaacctt caaagacaag     2340
cccaaccact ttagggcaaa tattcgctat gagagccgcc aaaaagagaa agattggacc     2400
aaagagttcc cgcttaatat gctttctgga cgactagtag cacagtttgg cacaggcaca     2460
gagacaagat cagctcatta cctcgccgag gttcagcctg atgtttgt ggagattcat        2520 cccgaaacag ccacggattt aggcgtgaag catggtgaca tggtttgggt gcacggcacc     2580 aatgggcaa agattctcgt gaaagcgaga catagctaca aggtcaacaa acaagtgtt       2640 ttcctccccc agaatttcgg aggaatgtat caaggagagt cactggttcc gtatcatatt     2700
gcaggcacag agcctatgt tattggtgaa tcatgcaata ccatcacaag tgatgcatac      2760
gacatcaaca ccagtactcc tgaaaccaag tgcggcctct gccgcatcga aaaagcgtag     2820
ggggtgaagc atggaaagtc aagctagagt caagttctat tgtgatgagg ctagatgtat     2880
tgattgtcat ggatgtgatg tggcttgtaa agaggcccat caccttcctg tgggagtcaa     2940
ccgaagaaga gtggtgaccc tcaatgaagg tcttgtaggc aaagagaaat ccctctctat     3000
tgcctgcatg cactgctctg atgccccttg tgctcaggtc tgcccagtgg actgcttcta     3060
tgttcgagcc gatgggattg tattgcatga caaagagaag tgcattggat gcggttactg     3120
```

```
cctctatgcc tgcccctttg gtgctcctca attccccaag agtggaatct ttggttcaag    3180
aggacctatg gataagtgca ccttctgtgc tggaggtcct gaagagactc acagcgagaa    3240
ggagtataag ctctatggac agaatcgtat cgctgagggc aaagtccctg tatgtgcagc    3300
gatgtgctcc accaaggcac tcctagcagg agattctgat agcatctcgc tcatcattcg    3360
tgagagagtg ctcaagcgag gcagtggaac agccagtgtt ccttacacct ggtcacaagc    3420
ctacaaggat taagaatgaa aaagcctcta ttgcccctcc tctcccttct gggagccttg    3480
ggggcacaag cttctgagaa tctcaaggag cccttggatt tcagctacaa cacccaaatc    3540
tatgaaaagc ccatgattga ggcaatcccc acttggggaa gtggagggat tctaggtctt    3600
ggagagattg gaggaatagg aggattagga gagctcttca ccttcttgca aagtggttac    3660
tttgctctta tcttcctagc gatcatcatc gctatccctt tggtcttcct aggtcactat    3720
atggtgattg gacccaagcg attctctcat gaggggaaga agatcaaggt ctttaacacc    3780
ttcaacatca tggtgcactg gattgcaggg attcccttg tgcttctttg catcacagga    3840
cttctgatgg tctttggaga tgccctaggg ggtggagctt ttattcgatt cgctagagat    3900
gtgcatggat tagccacgat catctttgcg atctttggtc ccctcatgtt catcatgtgg    3960
gtgaagcacg ctctctcttaa gatgtatgac atcgactgga tgctcattct ggagggtat    4020 ctaagcaagg tgaagagacc tattcctgca ggcaaattca atgcgggtca gaagatgtgg    4080
ttctgggtct gcacgatggg aggattcttc atggtctata gtggctatgt gatgttcttc    4140
caagagggca atattgagac cctaagactc atggcgatct tgcacaatgt agtggggttt    4200
gctgtggtgg ctctccttat gactcacatc tatatggcag cctttgcgat tgagggtgca    4260
ttgcactcca tcctagatgg tcatatgggt gaagaggagg tagcgattct tcatagtttc    4320
tactataaag agttgcaggc ggaggggaaa gtatgagaca caccgataga tttgttaaaa    4380
aggtggtgat tgaacgaatc ggcgatcaga gagtgctcgc cgaggaggaa gatgtggtga    4440
tcaaagagga gagaatctct ctctatctta atggcaccaa gcttatgtcc atgatgtctc    4500
ttccttccga tcaagatgct catgcggtgg gcttcttgat gagtgagggg gtgattgaga    4560
agatcgaaga cttaaagagt gttcaaatct cttctgatgg gagctctgtc tatgtagagg    4620
ctctcatcaa ccatgagaac atcaccaatc tcttcaaaga gaagacactc acttcaggtt    4680
gttgtgtcgg agtgacgggg aatcttgaag gcaatgtcct aagaaagttc atcgctactc    4740
ccatgcagat ttctttggag agaatctggg aagggatgga agagtttgag atgagcagcc    4800
atctctttca tgagacaggc tgcgttcata aagcctccct tctcttagaa gatgaaagca    4860
agatcacggc tgaggatatt ggtcgtcata atgcaattga aaggtgatg ggtaaagcca    4920 ggctagggag aatagataca gagaaggctg tgctagtggt gagcggaaga ctctccatgg    4980
agatggtggt taaagctgtc atgcacaaca ttcccatgat tgtctctagg gcagcagcaa    5040
cctttcttgg aatcaagaca gcccaagagc taggggtgac tctagtgggc tttgctagag    5100
gggagaagat gaatatctac acccattctg gtcgagtgga cttgagggct tgcaagagga    5160 aaagagggt gactcttcac gctccaaatc aatctagctc tcttcttcgt              5210

<210> SEQ ID NO 20
<211> LENGTH: 13415
<212> TYPE: DNA
<213> ORGANISM: Wolinella succinogenes

<400> SEQUENCE: 20 tcgaggggg gcccggatcc ccagtagatt tacgtttaaa catttttatt tccttttaa      60
```

-continued

```
tttaatttaa ttaacagttg gtgctatgac actttacctc atagctggca taattcgcaa    120
tactctgggt cttcgagagg tatccaacct gagttgaaat actttaccat cgatttagca    180
gttgtatcag ttatatttat attacccttta actcttcgcc atccaggagt tttaccgtac   240
agattagagg ataataataa cacataattc tcgtaagcaa tatgagataa tttccaagac    300
tctatattag ctcgtgatgt tttccaaggt ctaaaatcgt cacggttcat ataattagcc    360
aatctcatat gctctctaac ttccgatgat aagctgtcaa acatgagaat taacgatctg    420
atagagaagg gtttgctcgg gtcggtggct ctggtaacga ccagtatccc gatcccggct    480
ggccgtcctg gccgccacat gaggcatgtt ccgcgtcctt gcaatactgt gtttacatac    540
agtctatcgc ttagcggaaa gttcttttac cctcagccga aatgcctgcc gttgctagac    600
attgccagcc agtgccgtc actcccgtac taactgtcac gaaccctgc aataactgtc       660 acgcccccct gcaataactg tcacgaaccc ctgcaataac tgtcacgccc caaacctgc      720 aaacccagca ggggcggggg ctggcggggt gttggaaaaa tccatccatg attatctaag    780
aataatccac taggcgcggt tatcagcgcc cttgtggggc gctgctgccc ttgcccaata    840
tgcccggcca gaggccggat agctggtcta ttcgctgcgc taggctacac accgccccac    900
cgctgcgcgg cagggggaaa ggcgggcaaa gcccgctaaa ccccacacca aaccccgcag    960
aaatacgctg ggagcgcttt tagccgcttt agcggccttt cccctacccc gaagggtggg   1020
ggcgcgtgtg cagccccgca gggcctgtct cggtcgatca ttcagcccgg ctcatccttc   1080
tggcgtggcg gcagaccgaa caaggcgcgg tcgtggtcgc gttcaaggta cgcatccatt   1140
gccgccatga gccgatcctc cggccactcg ctgctgttca ccttggccaa aatcatggcc   1200
cccaccagca ccttgcgcct tgtttcgttc ttgcgctatt gctgctgttc ccttgcccgc   1260
acccgctgaa tttcggcatt gattcgcgct cgttgttctt cgagcttggc cagccgatcc   1320
gccgccttgt tgctcccctt aaccatcttg acaccccatt gttaatgtgc tgtctcgtag   1380
gctatcatgg aggcacagcg gcggcaatcc cgaccctact ttgtagggga gggccattgc   1440
atggagccga aaagcaaaag caacagcgag gcagcatggc gatttatcac cttacggcga   1500
aaaccggcag caggtcgggc ggccaatcgg ccagggccaa ggccgactac atccagcgcg   1560
aaggcaagta tgcccgcgac atggatgaag tcttgcacgc cgaatccggg cacatgccgg   1620
agttcgtcga gcggcccgcc gactactggg atgctgccga cctgtatgaa cgcgccaatg   1680
ggcggctgtt caaggaggtc gaatttgccc tgccggtcga gctgaccctc gaccagcaga   1740
aggcgctggc gtccgagttc gcccagcacc tgaccggtgc cgagcgcctg ccgtatacgc   1800
tggccatcca tgccggtggc ggcgagaacc cgcactgcca cctgatgatc tccgagcgga   1860
tcaatgacgg catcgagcgg cccgccgctc agtggttcaa gcggtacaac ggcaagaccc   1920
cggagaaggg cgggcacag aagaccgaag cgctcaagcc caaggcatgg cttgagcaga   1980
cccgcgaggc atgggccgac catgccaacc gggcattaga gcgggctggc cacgacgccc   2040
gcattgacca cagaacactt gaggcgcagg gcatcgagcg cctgcccggt gttcacctgg   2100
ggccgaacgt ggtggagatg aaggccggg gcatccgcac cgaccgggca gacgtggccc    2160
tgaacatcga caccgccaac gcccagatca tcgacttaca ggaataccgg gaggcaatag   2220
accatgaacg caatcgacag agtgaagaaa tccagaggca tcaacgagtt agcggagcag   2280
atcgaaccgc tggcccagag catggcgaca ctggccgacg aagccggca ggtcatgagc      2340 cagacccagc aggccagcga ggcgcaggcg gcggagtggc tgaaagccca gcgccagaca   2400
```

```
ggggcggcat gggtggagct ggccaaagag ttgcgggagg tagccgccga ggtgagcagc    2460
gccgcgcaga gcgcccggag cgcgtcgcgg gggtggcact ggaagctatg gctaaccgtg    2520
atgctggctt ccatgatgcc tacggtggtg ctgctgatcg catcgttgct cttgctcgac    2580
ctgacgccac tgacaaccga ggacggctcg atctggctgc gcttggtggc ccgatgaaga    2640
acgacaggac tttgcaggcc ataggccgac agctcaaggc catgggctgt gagcgcttcg    2700
atatcggcgt cagggacgcc accaccggcc agatgatgaa ccgggaatgg tcagccgccg    2760
aagtgctcca gaacacgcca tggctcaagc ggatgaatgc ccagggcaat gacgtgtata    2820
tcaggcccgc cgagcaggag cggcatggtc tggtgctggt ggacgacctc agcgagtttg    2880
acctggatga catgaaagcc gagggccggg agcctgccct ggtagtggaa accagcccga    2940
agaactatca ggcatgggtc aaggtggccg acgccgcagg cggtgaactt cgggggcaga    3000
ttgcccggac gctggccagc gagtacgacg ccgacccggc cagcgccgac agccgccact    3060
atggccgctt ggcgggcttc accaaccgca aggacaagca caccaccgc gccggttatc     3120
agccgtgggt gctgctgcgt gaatccaagg gcaagaccgc caccgctggc ccggcgctgg    3180
tgcagcaggc tggccagcag atcgagcagg cccagcggca gcaggagaag gcccgcaggc    3240
tggccagcct cgaactgccc gagcggcagc ttagccgcca ccggcgcacg cgctggacg     3300
agtaccgcag cgagatggcc gggctggtca agcgcttcgg tgatgacctc agcaagtgcg    3360
actttatcgc cgcgcagaag ctggccagcc ggggccgcag tgccgaggaa atcggcaagg    3420
ccatggccga ggccagccca gcgctggcag agcgcaagcc cggccacgaa gcggattaca    3480
tcgagcgcac cgtcagcaag gtcatgggtc tgcccagcgt ccagcttgcg cgggccgagc    3540
tggcacgggc accggcaccc cgccagcgag gcatggacag gggcgggcca gatttcagca    3600
tgtagtgctt gcgttggtac tcacgcctgt tatactatga gtactcacgc acagaagggg    3660
gttttatgga atacgaaaaa agcgcttcag ggtcggtcta cctgatcaaa agtgacaagg    3720
gctattggtt gccggtggc tttggttata cgtcaaacaa ggccgaggct ggccgctttt     3780
cagtcgctga tatggccagc cttaaccttg acggctgcac cttgtccttg ttccgcgaag    3840
acaagccttt cggccccggc aagtttctcg gtgactgata tgaaagacca aaaggacaag    3900
cagaccggcg acctgctggc cagccctgac gctgtacgcc aagcgcgata tgccgagcgc    3960
atgaaggcca aagggatgcg tcagcgcaag ttctggctga ccgacgacga atacgaggcg    4020
ctgcgcgagt gcctggaaga actcagagcg cgcagggcg ggggtagtga ccccgccagc     4080
gcctaaccac caactgcctg caaaggaggc aatcaatggc tacccataag cctatcaata    4140
ttctggaggc gttcgcagca gcgccgccac cgctggacta cgttttgccc aacatggtgg    4200
ccggtacggt cggggcgctg gtgtcgcccg gtggtgccgg taaatccatg ctggccctgc    4260
aactggccgc acagattgca ggcgggccgg atctgctgga ggtgggcgaa ctgcccaccg    4320
gcccggtgat ctacctgccc gccgaagacc cgcccaccgc cattcatcac cgcctgcacg    4380
cccttggggc gcacctcagc gccgaggaac ggcaagccgt ggctgacggc ctgctgatcc    4440
agccgctgat cggcagcctg cccaacatca tggccccgga gtggttcgac ggcctcaagc    4500
gcgccgccga gggccgccgc ctgatggtgc tggacacgct cgccggttc cacatcgagg     4560
aagaaaacgc cagcggcccc atggcccagg tcatcggtcg catggaggcc atcgccgccg    4620
ataccgggtg ctctatcgtg ttcctgcacc atgccagcaa gggcgcggcc atgatgggcg    4680
caggcgacca gcagcaggcc agccggggca gctcggtact ggtcgataac atccgctggc    4740
agtcctacct gtcgagcatg accagcgccg aggccgagga atgggtgtg gacgacgacc     4800
```

```
agcgccggtt cttcgtccgc ttcggtgtga gcaaggccaa ctatggcgca ccgttcgctg   4860
atcggtggtt caggcggcat gacggcgggg tgctcaagcc cgccgtgctg gagaggcagc   4920
gcaagagcaa gggggtgccc cgtggtgaag cctaagaaca agcacagcct cagccacgtc   4980
cggcacgacc cggcgcactg tctggccccc ggcctgttcc gtgccctcaa gcggggcgag   5040
cgcaagcgca gcaagctgga cgtgacgtat gactacggcg acggcaagcg gatcgagttc   5100 agcgcccgg agccgctggg cgctgatgat ctgcgcatcc tgcaagggct ggtggccatg   5160
gctgggccta atggcctagt gcttggcccg gaacccaaga ccgaaggcgg acggcagctc   5220
cggctgttcc tggaacccaa gtgggaggcc gtcaccgctg atgccatggt ggtcaaaggt   5280
agctatcggg cgctggcaaa ggaaatcggg gcagaggtcg atagtggtgg ggcgctcaag   5340
cacatacagg actgcatcga gcgcctttgg aaggtatcca tcatcgccca gaatggccgc   5400
aagcggcagg ggtttcggct gctgtcggag tacgccagcg acgaggcgga cgggcgcctg   5460
tacgtggccc tgaaccccct tgatcgcgca gccgtcatgg gtggcggcca gcatgtgcgc   5520
atcagcatgg acgaggtgcg ggcgctggac agcgaaaccg cccgcctgct gcaccagcgg   5580
ctgtgtggct ggatcgaccc cggcaaaacc ggcaaggctt ccatagatac cttgtgcggc   5640
tatgtctggc cgtcagaggc cagtggttcg accatgcgca agcgccgcca gcgggtgcgc   5700
gaggcgttgc cggagctggt cgcgctgggc tggacggtaa ccgagttcgc ggcgggcaag   5760
tacgacatca cccggcccaa ggcggcaggc tgaccccccc cactctattg taaacaagac   5820 atttttttatc ttttatattc aatggcttat tttcctgcta attggtaata ccatgaaaaa   5880
taccatgctc agaaaaggct taacaatatt ttgaaaaatt gcctactgag cgctgccgca   5940
cagctccata ggccgctttc ctggctttgc ttccagatgt atgctctcct ccggagagta   6000
ccgtgacttt attttcggca caaatacagg ggtcgatgga taaatacggc gatagtttcc   6060
tgacggatga tccgtatgta ccggcggaag acaagctgca aacctgtcag atggagattg   6120
atttaatggc ggatgtgctg agagcaccgc cccgtgaatc cgcagaactg atccgctatg   6180
tgtttgcgga tgattggccg gaataaataa agccgggctt aatacagatt aagcccgtat   6240
agggtattat tactgaatac caaacagctt acggaggacg gaatgttacc cattgagaca   6300
accagactgc cttctgatta ttaatatttt tcactattaa tcagaaggaa taaccatgaa   6360
ttttacccgg attgacctga atacctggaa tcgcaggaa cactttgccc tttatcgtca   6420
gcagattaaa tgcggattca gcctgaccac caaactcgat attaccgctt gcgtaccgc   6480 actggcggag acaggttata agttttatcc gctgatgatt tacctgatct cccgggctgt   6540
taatcagttt ccggagttcc ggatggcact gaaagacaat gaacttattt actgggacca   6600
gtcagacccg gtctttactg tctttcataa agaaaccgaa acattctctg cactgtcctg   6660
ccgttatttt ccggatctca gtgagtttat ggcaggttat aatgcggtaa cggcagaata   6720
tcagcatgat accagattgt ttccgcaggg aaatttaccg gagaatcacc tgaatatatc   6780
atcattaccg tgggtgagtt ttgacgggat ttaacctgaa catcaccgga aatgatgatt   6840
attttgcccc ggttttttacg atggcaaagt ttcagcagga aggtgaccgc gtattattac   6900
ctgtttctgt acaggttcat catgcagtct gtgatggctt tcatgcagca cggtttatta   6960
atacacttca gctgatgtgt gataacatac tgaaataaat taattaattc tgtatttaag   7020
ccaccgtatc cggcaggaat ggtggctttt tttttatatt ttaaccgtaa tctgtaattt   7080
cgtttcagac tggttcagga tcactgtacg ataatgcccc cgcagtttgg taatacccct   7140
```

```
aataaaaaag aaacagcaaa gactgacagc aataataata aagtaagcag taacaataat    7200
attaacaaca ccagatgcag ttataataat agtatttaag acaccagaaa gactgctgcg    7260
acagtcattt tgaacaacac caaaatgccg taaaggcagt agtaacaaca ccagtgaaaa    7320
catcacgata gcatagtgat atgcctgagt gtgtgtaatt aaacaataaa taaaccgcca    7380
tatataacag aagatagtat tctgaatggc atgcttttct gttcagtata aacatatcat    7440
cccggttggt ataaggatga tatataataa gttaagctga acacatattt attttggttt    7500
tattttacaa ataaagtaag acgatccgtt aagtcaaagc ggggtatatt tattataccc    7560 tgcttttta tttgtccgcc gggcgcggat aatggatcag attatgcagt gtcacaatgg     7620
ccttaccggg attggcgtaa gcgtgcggga tatccgcatg gaagcgcagg gattccccgg    7680
cagaaacggt gtgccactca tcccccagcc gcagttgtaa tgcgccttcc agtacaatga    7740
catgttctct ggttctgaaa tccatccctg tcggtgttgc ttatgcagtc tggtcgggac    7800
tcggcgtcgt cataattaca gccattgcct ggttgcttca tgggcaaaag ctttatgctt    7860
gtaaaccgtt ttgtgaaaaa attttaaaa taaaaagggg gacctctagg gtccccaatt    7920
aattagtaat ataatctatt aaggtcatt caaaggtca tccaccggat cccaccgcgg      7980
tggcggccgt ctaacgaaga agagagctag attgatttgg agcgtgaaga gtcacccctc    8040
ttttcctctt gcaagccctc aagtccactc gaccagaatg ggtgtagata ttcatcttct    8100
cccctctagc aaagcccact agagtcaccc ctagctcttg ggctgtcttg attccaagaa    8160
aggttgctgc tgccctagag acaatcatgg gaatgttgtg catgacagct ttaaccacca    8220
tctccatgga gagtcttccg ctcaccacta gcacagcctt ctctgtatct attctcccta    8280
gcctggcttt acccatcacc ttatcaattg cattatgacg accaatatcc tcagccgtga    8340
tcttgcttcc atcttctaag agaagggagg ctttatgaac gcagcctgtc tcatgaaaga    8400
gatggctgct catctcaaac tcttccatcc cttcccagat tctctccaaa gaaatctgca    8460
tgggagtagc gatgaacttt cttaggacat tgccttcaag attccccgtc actccgacac    8520
aacaacctga agtgagtgtc ttctctttga agagattggt gatgttctca tggttgatga    8580
gagcctctac atagacagag ctcccatcag aagagatttg aacactcttt aagtcttcga    8640
tcttctcaat caccccctca ctcatcaaga agcccaccgc atgagcatct tgatcggaag    8700
gaagagacat catggacata agcttggtgc cattaagata gagagagatt ctctcctctt    8760
tgatcaccac atcttcctcc tcggcgagca ctctctgatc gccgattcgt tcaatcacca    8820
cctttttaac aaatctatcg gtgtgtctca tactttcccc tccgcctgca actctttata    8880
gtagaaacta tgaagaatcg ctacctcctc ttcacccata tgaccatcta ggatggagtg    8940
caatgcaccc tcaatcgcaa aggctgccat atagatgtga gtcataagga gagccaccac    9000
agcaaacccc actacattgt gcaagatcgc catgagtctt agggtctcaa tattgccctc    9060
ttggaagaac atcacatagc cactatagac catgaagaat cctcccatcg tgcagaccca    9120
gaaccacatc ttctgacccg cattgaattt gcctgcagga ataggtctct tcaccttgct    9180
tagataccct ccaagaatga gcatccagtc gatgtcatac atcttaaaga gagcgtgctt    9240
cacccacatg atgaacatga ggggaccaaa gatcgcaaag atgatcgtgg ctaatccatg    9300
cacatctcta gcgaatcgaa taaaagctcc accccctagg gcatctccaa agaccatcag    9360
aagtcctgtg atgcaaagaa gcacaaaggg aatccctgca atccagtgca ccatgatgtt    9420
gaaggtgtta aagaccttga tcttcttccc ctcatgagag aatcgcttgg gtccaatcac    9480
catatagtga cctaggaaga ccaaagggat agcgatgatg atcgctagga agataagagc    9540
```

```
aaagtaacca ctttgcaaga aggtgaagag ctctcctaat cctcctattc ctccaatctc   9600
tccaagacct agaatccctc cacttcccca agtggggatt gcctcaatca tgggctttcc   9660
atagatttgg gtgttgtagc tgaaatccaa gggctccttg agattctcag aagcttgtgc   9720
ccccaaggct cccagaaggg agaggagggg caatagaggc ttttcattc ttaatccttg    9780 taggcttgtg accaggtgta aggaacactg gctgttccac tgcctcgctt gagcactctc   9840
tcacgaatga tgagcgagat gctatcagaa tctcctgcta ggagtgcctt ggtggagcac   9900
atcgctgcac atacagggac tttgccctca gcgatacgat tctgtccata gagcttatac   9960
tccttctcgc tgtgagtctc ttcaggacct ccagcacaga aggtgcactt atccataggt  10020
cctcttgaac caaagattcc actcttgggg aattgaggag caccaagggg gcaggcatag  10080
aggcagtaac cgcatccaat gcacttctct tgtcatgca atacaatccc atcggctcga   10140
acatagaagc agtccactgg gcagacctga gcacaagggg catcagagca gtgcatgcag  10200
gcaatagaga gggatttctc tttgcctaca agaccttcat tgagggtcac cactcttctt  10260
cggttgactc ccacaggaag gtgatgggcc tctttacaag ccacatcaca tccatgacaa  10320
tcaatacatc tagcctcatc acaatagaac ttgactctag cttgactttc catgcttcac  10380 ccctacgct ttttcgatgc ggcagaggcc gcacttggtt tcaggagtac tggtgttgat   10440
gtcgtatgca tcacttgtga tggtattgca tgattcacca ataacataag gctctgtgcc  10500
tgcaatatga tacggaacca gtgactctcc ttgatacatt cctccgaaat tctggggag   10560 gaaaacactt gttttgttga ccttgtagct atgtctcgct ttcacgagaa tctttgcccc  10620
attggtgccg tgcacccaaa ccatgtcacc atgcttcacg cctaaatccg tggctgtttc  10680
gggatgaatc tccacaaaca tctcaggctg aacctcggcg aggtaatgag ctgatcttgt  10740
ctctgtgcct gtgccaaact gtgctactag tcgtccagaa agcatattaa gcgggaactc  10800
tttggtccaa tctttctctt tttggcggct ctcatagcga atatttgccc taaagtggtt  10860
gggcttgtct ttgaaggttg gatattggct aatgagatcg tgtcgaattg tgtagatggg  10920
ttcacggtgt ttaggaatct gatccgtcca ctcccaaaca atcgctctag ctctaccatt  10980
acccataggg gagagacctg cggcgagtgc tttttcaacc aagatattgg tggtgtcagt  11040
cgcccatgtc ttgcctgcca cttcggcttt ttcctcttcg gtgagggcga ttccagtgat  11100
agcttcgaca ttttttatcgg tgatcatgct atgaccgccc ttgaattttg agccgggcaa  11160
agagctgtcc tggctggcca acaaactttc tcctgtgggt gacacatcac cccatcgaac  11220
cctaaagcca agacctccat ccattacagg gatgctgtca tcccatagat ttggtgttcc  11280
aggatgcttt tcgctccagc aaggccaagg aagaccatag tattcgcctt tgacggggcc  11340 gcccttcct ctgagggtga acttatcaaa catatgccag ttttctgcat gagccttgag   11400
tcgttctgga gttctgcctt ggaagccgac agttcgtata gccttggcca cctctctagt  11460
cgcatcatcg ggccatacaa agtttccttt gccatccccc aaagagcgag tgtactcctc  11520
atagaatcca agtcgcttag ctaaatcaaa gagaatctct tcgtcaggtc gacactcaaa  11580
gagtggcttc ataaccatgg atcgccactg atagcttcga ttcgtcgctg cgactcttcc  11640
gctggtctcc atctgtgtgg cggcaggaag gatatagaga ttatcttttc ggttggtgag  11700
ggcggctgca tcattgaaat agggatcaaa aaagacgact aaatccatct tgtctagagc  11760
gtctttggtg gtatccacgc gtgcgatcgt agagattccg cttcccacga caatcaagga  11820
tcgaagttta gtgcctgcat tgtgggggat gttctcctct tcagtcaccc catatctcca  11880
```

```
tgtggataca ctgaaacctt ttttatgcat catatcaggg gtcttaaagc gttttttgcat    11940 tgcttcgaaa tccactttcc agattccaca gaagtgattc catgcatttt tgtctaaccc    12000
ataatagcca ggaagactgt cggctaggtt gcccatgtcc gtcgcgcctt ggacattgtc    12060
atgacctcgt aaaacgttag tgcctccacc tcgtttgcca atgtttccaa gaatcatctg    12120 taaaatagggg gccaaacgag tgttgcttgt acctgtggtg tgctgggtga gacccatccc    12180
ccagatcagt gaagcaggct tggctttagc gaagatctcc gtgatctcaa taagttgttg    12240
ggcgggcacg cctgtgacct cttcgaccac ttcaggggtg tactgttcgc actctttaag    12300
aatctcttcg tagccaaata ggcgttgtcg aataaattct ttatcttcta gtccattttt    12360
tacaatatgg cgaatcatcc catacatgaa ggcgacatcc gtgccattgc gcaatctcac    12420
atagtgatcg gctttagttg ctgttcgact gaagtgggga tccacaacga tgattttgc     12480 tcctgcctct ttagcgcgca agatatgcac catgcctaca gggtgattca ctgcgggatt    12540
tccaccaatg ataaaaatcg ccttggagtg catcatgtct gccaagtgat tggtcatacc    12600
gccatatcca agggtattgg agactccagc aactgttggg gcatggcaga ttcgtgcgat    12660
ggtatcgaga ttgttggtgc caaaaaaggc ggcaaacttt ctaaaataat aggattgttc    12720
aatcgaacac ttggagccgc caatgaacat gacgctatca gggccatatt ttgggtgag    12780 atcctgaagc tgcttggcaa tcttatccat ggcgctatcc catgaagttt tacgccattt    12840
tccgccaact ttctcaatgg ggtatcgaag tcttgtttcg cttcgagcct tatcaatcat    12900
atcggcgccc ttgcagcagt gaccccttg actaatgggg tgatcttgag cgacctcttg    12960
gcgtacccat acaccatcga ccacttccgc tataattcca catccgaccg agcaataggt    13020
gcaaatcgtt tttacctttt tggacactgg gtatttttcg attaactctt gttttgttgc    13080
aggtctaagc actttgcttt ggtcggagcc aaccgcttga ctcacgcctg cgactcctgc    13140
taaagccgac atctttagga actttcttcg atcgttcccg cgtccgctta acgcttcact    13200
catacatcac ctcataaaat aaattaaaaa ataataaaaa ctaatgtttc gcattatagg    13260
acaaaagata cctaaaaaat gttatctaga tcaaattatt ggaaaatata tgaaaataat    13320
ttttgtttaa aaagcgaacg acattagtat ttttcataaa aatacgtaca ttgttatccg    13380
tcgctattta ggtaccgggc ccgacgtcag gcctc                               13415
```

<210> SEQ ID NO 21
<211> LENGTH: 1026
<212> TYPE: DNA
<213> ORGANISM: Pasteurella DSM 18541

<400> SEQUENCE: 21

```
ttgacaaaat cagtatgttt aaataaggag ctaactatga agttgccgt ttacagtact       60 aaaaattatg atcgcaaaca tctggatttg gcgaataaaa aatttaattt tgagcttcat     120
ttctttgatt ttttacttga tgaacaaacc gcgaaatgg cggagggcgc cgatgccgtc      180 tgtatttttcg tcaatgatga tgcgagccgc ccggtgttaa caaagttggc gcaaatcgga    240
gtgaaaatta tcgctttacg ttgtgccggt tttaataatg tggatttgga ggcggcaaaa    300
gagctgggat taaagtcgt acgggtgcct gcgtattcgc cggaagccgt tgccgagcat    360
gcgatcggat taatgctgac tttaaaccgc cgtatccata aggcttatca gcgtacccgc    420
gatgcgaatt tttctctgga aggattggtc ggttttaata tgttcggcaa aaccgccgga    480
gtgattggta cgggaaaaat cggcttggcg gctattcgca ttttaaaagg cttcggtatg    540
gacgttctgg cgtttgatcc ttttaaaaat ccggcggcgg aagcgttggg cgcaaaatat    600
```

| | | |
|---|---|---|
| gtcggtttag acgagcttta tgcaaaatcc catgttatca ctttgcattg cccggctacg | 660 | |
| gcggataatt atcatttatt aaatgaagcg gcttttaata aaatgcgcga cggtgtaatg | 720 | |
| attattaata ccagccgcgg cgttttaatt gacagccggg cggcaatcga agcgttaaaa | 780 | |
| cggcagaaaa tcgcgctctc cggtatggat gtttatgaaa atgaacggga tttgttttc | 840 | |
| gaggataaat ctaacgatgt tattacggat gatgtattcc gtcgcctttc ttcctgtcat | 900 | |
| aatgtgcttt ttaccggtca tcaggcgttt taacgaaag aagcgctgaa taatatcgcc | 960 | |
| gatgtgactt tatcgaatat tcaggcggtt tccaaaaatg caacgtgcga aatagcgtt | 1020 | |
| gaaggc | 1026 | |

<210> SEQ ID NO 22
<211> LENGTH: 342
<212> TYPE: PRT
<213> ORGANISM: Pasteurella DSM 18541

<400> SEQUENCE: 22

```
Met Thr Lys Ser Val Cys Leu Asn Lys Glu Leu Thr Met Lys Val Ala
1               5                   10                  15

Val Tyr Ser Thr Lys Asn Tyr Asp Arg Lys His Leu Asp Leu Ala Asn
            20                  25                  30

Lys Lys Phe Asn Phe Glu Leu His Phe Phe Asp Phe Leu Leu Asp Glu
        35                  40                  45

Gln Thr Ala Lys Met Ala Glu Gly Ala Asp Ala Val Cys Ile Phe Val
    50                  55                  60

Asn Asp Asp Ala Ser Arg Pro Val Leu Thr Lys Leu Ala Gln Ile Gly
65                  70                  75                  80

Val Lys Ile Ile Ala Leu Arg Cys Ala Gly Phe Asn Asn Val Asp Leu
                85                  90                  95

Glu Ala Ala Lys Glu Leu Gly Leu Lys Val Val Arg Val Pro Ala Tyr
            100                 105                 110

Ser Pro Glu Ala Val Ala Glu His Ala Ile Gly Leu Met Leu Thr Leu
        115                 120                 125

Asn Arg Arg Ile His Lys Ala Tyr Gln Arg Thr Arg Asp Ala Asn Phe
    130                 135                 140

Ser Leu Glu Gly Leu Val Gly Phe Asn Met Phe Gly Lys Thr Ala Gly
145                 150                 155                 160

Val Ile Gly Thr Gly Lys Ile Gly Leu Ala Ala Ile Arg Ile Leu Lys
                165                 170                 175

Gly Phe Gly Met Asp Val Leu Ala Phe Asp Pro Phe Lys Asn Pro Ala
            180                 185                 190

Ala Glu Ala Leu Gly Ala Lys Tyr Val Gly Leu Asp Glu Leu Tyr Ala
        195                 200                 205

Lys Ser His Val Ile Thr Leu His Cys Pro Ala Thr Ala Asp Asn Tyr
    210                 215                 220

His Leu Leu Asn Glu Ala Ala Phe Asn Lys Met Arg Asp Gly Val Met
225                 230                 235                 240

Ile Ile Asn Thr Ser Arg Gly Val Leu Ile Asp Ser Arg Ala Ala Ile
                245                 250                 255

Glu Ala Leu Lys Arg Gln Lys Ile Gly Ala Leu Gly Met Asp Val Tyr
            260                 265                 270

Glu Asn Glu Arg Asp Leu Phe Phe Glu Asp Lys Ser Asn Asp Val Ile
        275                 280                 285
```

```
Thr Asp Asp Val Phe Arg Arg Leu Ser Ser Cys His Asn Val Leu Phe
    290                 295                 300

Thr Gly His Gln Ala Phe Leu Thr Glu Glu Ala Leu Asn Asn Ile Ala
305                 310                 315                 320

Asp Val Thr Leu Ser Asn Ile Gln Ala Val Ser Lys Asn Ala Thr Cys
                325                 330                 335

Glu Asn Ser Val Glu Gly
            340

<210> SEQ ID NO 23
<211> LENGTH: 2310
<212> TYPE: DNA
<213> ORGANISM: Pasteurella DSM 18541

<400> SEQUENCE: 23
atggctgaat taacagaagc tcaaaaaaaa gcatgggaag gattcgttcc cggtgaatgg      60
caaaacggcg taaatttacg tgactttatc caaaaaaact atactccgta tgaaggtgac     120
gaatcattct tagctgatgc gactcctgca accagcgagt tgtggaacag cgtgatggaa     180
ggcatcaaaa tcgaaaacaa aactcacgca cctttagatt cgacgaaca tactccgtca     240 actatcactt ctcacaagcc tggttatatc aataaagatt tagaaaaaat cgttggtctt     300
caaacagacg ctccgttaaa acgtgcaatt atgccgtacg gcggtatcaa aatgatcaaa     360
ggttcttgcg aagtttacgg tcgtaaatta gatccgcaag tagaatttat tttcaccgaa     420
tatcgtaaaa cccataacca aggcgtattc gacgtttata cgccggatat tttacgctgc     480
cgtaaatcag gcgtgttaac cggtttaccg gatgcttacg tcgtggtcg tattatcggt      540 gactaccgtc gtttagcggt atacggtatt gattacctga tgaaagataa aaaagcccaa     600
ttcgattcat tacaaccgcg tttggaagcg gcgaagaca ttcaggcaac tatccaatta      660
cgtgaagaaa ttgccgaaca acaccgcgct ttaggcaaaa tcaaagaaat ggcggcatct     720
tacggttacg acatttccgg ccctgcgaca acgcacagg aagcaatcca atggacatat      780
tttgcttatc tggcagcggt taaatcacaa acggtgcgg caatgtcatt cggtcgtacg      840
tctacattct tagatatcta tatcgaacgt gacttaaaac gcggtttaat cactgaacaa     900
caggcgcagg aattaatgga ccacttagta atgaaattac gtatggttcg tttcttacgt     960
acgccggaat acgatcaatt attctcaggc gacccgatgt gggcaaccga actatcgcc     1020 ggtatgggct tagacggtcg tccgttggta actaaaaaca gcttccgcgt attacatact    1080
ttatacacta tgggtacttc tccggaacca aacttaacta ttctttggtc cgaacaatta    1140
cctgaagcgt tcaaacgttt ctgtgcgaaa gtatctattg atacttcctc cgtacaatac    1200
gaaaatgatg acttaatgcg tcctgacttc aacaacgatg actatgcaat cgcatgctgc    1260
gtatcaccga tggtcgtagg taaacaaatg caattcttcg gtgcgcgcgc aaacttagct    1320
aaaactatgt tatacgcaat taacggcggt atcgatgaga aaaatggtat gcaagtcggt    1380
cctaaaactg cgccgattac agacgaagta ttgaatttcg ataccgtaat cgaacgtatg    1440
gacagtttca tggactggtt ggcgactcaa tatgtaaccg cattgaacat catccacttc    1500
atgcacgata aatatgcata tgaagcggca ttgatggcgt tccacgatcg cgacgtattc    1560
cgtacaatgg cttgcggtat cgcgggtctt tccgtggctg cggactcatt atccgcaatc    1620
aaatatgcga agttaaaacc gattcgcggc gacatcaaag ataaagacgg taatgtcgtg    1680
gcctcgaatt tgctatcga cttcgaaatt gaaggcgaat atccgcaatt cggtaacaat    1740
gatccgcgtg ttgatgattt agcggtagac ttagttgaac gtttcatgaa aaaagttcaa    1800
```

-continued

```
aaacacaaaa cttaccgcaa cgcaactccg acacaatcta tcctgactat cacttctaac  1860
gtggtatacg gtaagaaaac cggtaatact ccggacggtc gtcgagcagg cgcgccattc  1920
ggaccgggtg caaacccaat gcacggtcgt gaccaaaaag gtgcggttgc ttcacttact  1980
tctgtggcta aacttccgtt cgcttacgcg aaagacggta tttcatatac cttctctatc  2040
gtaccgaacg cattaggtaa agatgacgaa gcgcaaaaac gcaaccttgc cggtttaatg  2100
gacggttatt tccatcatga agcgacagtg gaaggcggtc aacacttgaa tgttaacgtt  2160
cttaaccgtg aaatgttgtt agacgcgatg gaaaatccgg aaaaatacccc gcaattaacc  2220 attcgtgttt caggttacgc ggttcgtttc aactcattaa ctaaagagca acaacaagac  2280
gtcatcactc gtacgtttac acaatcaatg                                   2310
```

```
<210> SEQ ID NO 24
<211> LENGTH: 770
<212> TYPE: PRT
<213> ORGANISM: Pasteurella DSM 18541

<400> SEQUENCE: 24
```

Met Ala Glu Leu Thr Glu Ala Gln Lys Lys Ala Trp Glu Gly Phe Val
1               5                   10                  15

Pro Gly Glu Trp Gln Asn Gly Val Asn Leu Arg Asp Phe Ile Gln Lys
            20                  25                  30

Asn Tyr Thr Pro Tyr Glu Gly Asp Glu Ser Phe Leu Ala Asp Ala Thr
        35                  40                  45

Pro Ala Thr Ser Glu Leu Trp Asn Ser Val Met Glu Gly Ile Lys Ile
    50                  55                  60

Glu Asn Lys Thr His Ala Pro Leu Asp Phe Asp Glu His Thr Pro Ser
65                  70                  75                  80

Thr Ile Thr Ser His Lys Pro Gly Tyr Ile Asn Lys Asp Leu Glu Lys
                85                  90                  95

Ile Val Gly Leu Gln Thr Asp Ala Pro Leu Lys Arg Ala Ile Met Pro
            100                 105                 110

Tyr Gly Gly Ile Lys Met Ile Lys Gly Ser Cys Glu Val Tyr Gly Arg
        115                 120                 125

Lys Leu Asp Pro Gln Val Glu Phe Ile Phe Thr Glu Tyr Arg Lys Thr
    130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Leu Ala Val Tyr Gly Ile Asp Tyr
            180                 185                 190

Leu Met Lys Asp Lys Lys Ala Gln Phe Asp Ser Leu Gln Pro Arg Leu
        195                 200                 205

Glu Ala Gly Glu Asp Ile Gln Ala Thr Ile Leu Arg Glu Glu Ile
    210                 215                 220

Ala Glu Gln His Arg Ala Leu Gly Lys Ile Lys Glu Met Ala Ala Ser
225                 230                 235                 240

Tyr Gly Tyr Asp Ile Ser Gly Pro Ala Thr Asn Ala Gln Glu Ala Ile
                245                 250                 255

Gln Trp Thr Tyr Phe Ala Tyr Leu Ala Ala Val Lys Ser Gln Asn Gly
            260                 265                 270

Ala Ala Met Ser Phe Gly Arg Thr Ser Thr Phe Leu Asp Ile Tyr Ile

```
              275                 280                 285
Glu Arg Asp Leu Lys Arg Gly Leu Ile Thr Glu Gln Gln Ala Gln Glu
290                 295                 300
Leu Met Asp His Leu Val Met Lys Leu Arg Met Val Arg Phe Leu Arg
305                 310                 315                 320
Thr Pro Glu Tyr Asp Gln Leu Phe Ser Gly Asp Pro Met Trp Ala Thr
                325                 330                 335
Glu Thr Ile Ala Gly Met Gly Leu Asp Gly Arg Pro Leu Val Thr Lys
                340                 345                 350
Asn Ser Phe Arg Val Leu His Thr Leu Tyr Thr Met Gly Thr Ser Pro
                355                 360                 365
Glu Pro Asn Leu Thr Ile Leu Trp Ser Glu Gln Leu Pro Glu Ala Phe
370                 375                 380
Lys Arg Phe Cys Ala Lys Val Ser Ile Asp Thr Ser Ser Val Gln Tyr
385                 390                 395                 400
Glu Asn Asp Asp Leu Met Arg Pro Asp Phe Asn Asn Asp Asp Tyr Ala
                405                 410                 415
Ile Ala Cys Cys Val Ser Pro Met Val Val Gly Lys Gln Met Gln Phe
                420                 425                 430
Phe Gly Ala Arg Ala Asn Leu Ala Lys Thr Met Leu Tyr Ala Ile Asn
                435                 440                 445
Gly Gly Ile Asp Glu Lys Asn Gly Met Gln Val Gly Pro Lys Thr Ala
450                 455                 460
Pro Ile Thr Asp Glu Val Leu Asn Phe Asp Thr Val Ile Glu Arg Met
465                 470                 475                 480
Asp Ser Phe Met Asp Trp Leu Ala Thr Gln Tyr Val Thr Ala Leu Asn
                485                 490                 495
Ile Ile His Phe Met His Asp Lys Tyr Ala Tyr Glu Ala Ala Leu Met
                500                 505                 510
Ala Phe His Asp Arg Asp Val Phe Arg Thr Met Ala Cys Gly Ile Ala
                515                 520                 525
Gly Leu Ser Val Ala Ala Asp Ser Leu Ser Ala Ile Lys Tyr Ala Lys
530                 535                 540
Val Lys Pro Ile Arg Gly Asp Ile Lys Asp Lys Asp Gly Asn Val Val
545                 550                 555                 560
Ala Ser Asn Val Ala Ile Asp Phe Glu Ile Glu Gly Glu Tyr Pro Gln
                565                 570                 575
Phe Gly Asn Asn Asp Pro Arg Val Asp Asp Leu Ala Val Asp Leu Val
                580                 585                 590
Glu Arg Phe Met Lys Lys Val Gln Lys His Lys Thr Tyr Arg Asn Ala
                595                 600                 605
Thr Pro Thr Gln Ser Ile Leu Thr Ile Thr Ser Asn Val Val Tyr Gly
610                 615                 620
Lys Lys Thr Gly Asn Thr Pro Asp Gly Arg Arg Ala Gly Ala Pro Phe
625                 630                 635                 640
Gly Pro Gly Ala Asn Pro Met His Gly Arg Asp Gln Lys Gly Ala Val
                645                 650                 655
Ala Ser Leu Thr Ser Val Ala Lys Leu Pro Phe Ala Tyr Ala Lys Asp
                660                 665                 670
Gly Ile Ser Tyr Thr Phe Ser Ile Val Pro Asn Ala Leu Gly Lys Asp
                675                 680                 685
Asp Glu Ala Gln Lys Arg Asn Leu Ala Gly Leu Met Asp Gly Tyr Phe
690                 695                 700
```

```
His His Glu Ala Thr Val Glu Gly Gly Gln His Leu Asn Val Asn Val
705             710                 715                 720

Leu Asn Arg Glu Met Leu Leu Asp Ala Met Glu Asn Pro Glu Lys Tyr
            725                 730                 735

Pro Gln Leu Thr Ile Arg Val Ser Gly Tyr Ala Val Arg Phe Asn Ser
            740                 745                 750

Leu Thr Lys Glu Gln Gln Gln Asp Val Ile Thr Arg Thr Phe Thr Gln
        755                 760                 765

Ser Met
    770
```

BACTERIAL CELLS EXHIBITING FORMATE DEHYDROGENASE ACTIVITY FOR THE MANUFACTURE OF SUCCINIC ACID

RELATED APPLICATIONS

This application claims benefit under 35 U.S.C. §119(a) of European application 08172795.0, filed Dec. 23, 2008.

SUBMISSION OF SEQUENCE LISTING

The Sequence Listing associated with this application is filed in electronic format via EFS-Web and hereby incorporated by reference into the specification in its entirety. The name of the text file containing the Sequence Listing is SEQUENCE_LISTING_13156_00311_ST25.txt. The size of the text file is 160 kb, and the text file was created on Dec. 21, 2009.

BACKGROUND OF THE INVENTION

Description of Related Art

The fermentative production of succinic acid (SA) from biomass has already drawn much attention because said acid represents an important constituent of synthetic resins or is a source of further valuable low-molecular chemical compounds, in particular tetrahydrofuran (THF), 1,4-butanediol (BDO), gamma-butyrolactone (GBL) and pyrrolidones (WO-A-2006/066839).

A SA-producing bacterium isolated from bovine rumen was described by Lee et al., Appl Microbiol Biotechnol 58, 663-668. The bacterium is a non-motile, non-spore-forming, mesophilic and capnophilic gram-negative rod or *coccobacillus*. Phylogenetic analysis based on the 16S rRNA sequence and physiological analysis indicated that the strain belongs to genus *Mannheimia* as a novel species, and has been named *Mannheimia succiniciproducens* MBEL55E. Under 100% $CO_2$ conditions, it grows well in the pH range of 6.0-7.5 and produces succinic acid, acetic acid and formic acid at a constant ratio of 2:1:1. When *M. succiniciproducens* MBEL55E was cultured anaerobically under $CO_2$-saturation with glucose as carbon source, 19.8 g/L of glucose were consumed and 13.3 g/L of SA were produced in 7.5 h of incubation.

A significant drawback of said organism is, however, its inability to metabolize glycerol, which, as a constituent of triacyl glycerols (TAGs), becomes readily available e. g. as byproduct in the transesterification reaction of Biodiesel production (Dharmadi et al., 2006, Biotech Bioeng 94, 821-829).

The fermentative production of succinic acid from glycerol has been described in the scientific literature (Lee et al., 2001, Biotech Bioeng 72, 41-48; Dharmadi et al., 2006, Biotech Bioeng 94, 821-829) and with glycerol higher yields [mass of SA produced/mass of raw material consumed] than with common sugars like glucose were achieved (Lee et al., 2001, Biotech Bioeng 72, 41-48). However, the space time yield obtained with glycerol was substantially lower than with glucose (0.14 vs. 1.0 g SA/[L h]) and no crude glycerol was used.

There is, therefore, a need for further bacterial strains, which have the ability to produce organic acids, in particular SA, from glycerol. In particular, such strains should produce said acids with high productivity from glycerol, especially if crude glycerol e. g. from bio diesel production can be used without prior purification.

BRIEF SUMMARY OF THE INVENTION

The present invention is concerned with bacteria for succinic acid manufacture. It relates to a bacterial cell of the genus *Pasteurella* comprising a heterologous polypeptide having formate dehydrogenase activity. Moreover, the present invention also relates to a method of manufacturing succinic acid and the use of the bacterial cell for the manufacture of succinic acid.

The technical problem underlying this invention could be seen as the provision of means and methods for complying with the aforementioned needs. The technical problem is solved by the embodiments described in the claims and herein below.

BRIEF DESCRIPTION OF THE DRAWINGS

FIG. 6: A schematic map of the plasmid pJFF224 (icl ms Y.m.).

FIG. 11: The sequences of SEQ ID No: 1 to 21.

DETAILED DESCRIPTION OF THE INVENTION

Figure 1:
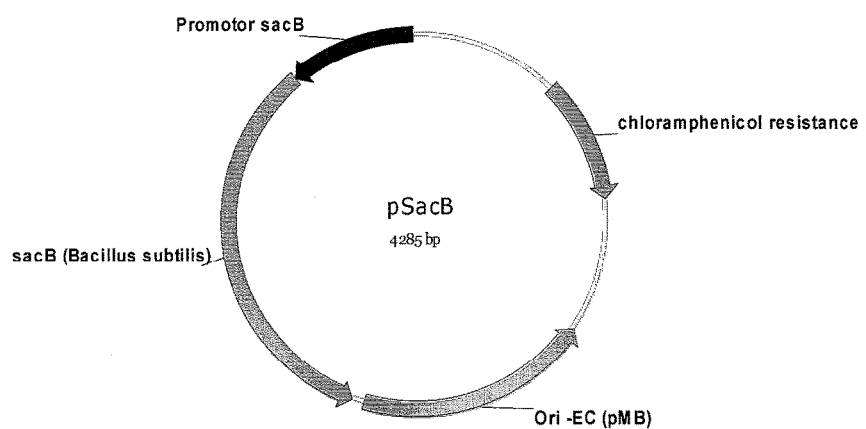
FIG. 1: A schematic map of plasmid pSacB.

The present invention relates to a bacterial cell of the genus *Pasteurella* comprising a heterologous polypeptide having formate dehydrogenase activity.

The term "bacterial cell" as used herein refers to a prokaryotic organism, i.e. a bacterium. Bacteria can be classified based on their biochemical and microbiological properties as well as their morphology. These classification criteria are well known in the art. The bacterial cell referred to in accordance with the present invention is from the genus of *Pasteurella*. The bacteria of the genus *Pasteurella* are gram-negative and facultative anaerobic. *Pasteurella* species are non-motile, pleimorphic and most often catalase- and oxidase-positive (Kuhnert and Christensen, 2008, ISBN 978-1-904455-34-9).

Preferably, the bacterial cell is a *Pasteurella* bacterial cell and, more preferably, a *Pasteurella* strain DD1 cell. Most preferably, the *Pasteurella* DD1 strain is the bacterial strain deposited under the Budapest Treaty with DSMZ (Deutsche Sammlung von Mikroorganismen and Zellkulturen, GmbH), Germany, having the deposit number DSM 18541.

*Pasteurella* bacteria can be isolated from the gastro-intestinal tract of animals and, preferably, mammals. The bacterial strain *Pasteurella* DD1, in particular, can be isolated from bovine rumen and is capable of utilizing glycerol (including crude glycerol) as a carbon source. Preferably, the said strain has the ability to produce succinic acid from glycerol (including crude glycerol), in particular, under anaerobic conditions.

Moreover, the *Pasteurella* DD1 strain exhibits at least one of the following additional metabolic characteristics:
a) production of succinic acid from sucrose; in particular, under anaerobic conditions;
b) production of succinic acid from D-fructose; in particular, under anaerobic conditions;
c) production of succinic acid from D-galactose; in particular, under anaerobic conditions;
d) production of succinic acid from D-mannose; in particular, under anaerobic conditions;
e) production of succinic acid from D-glucose; in particular, under anaerobic conditions;
f) production of succinic acid from D-xylose; in particular, under anaerobic conditions;
g) production of succinic acid from L-arabinose; in particular, under anaerobic conditions;
h) no utilization of of xylitol, inositol and sorbitol;
i) growth both under aerobic and anaerobic conditions;
j) growth at initial glucose concentrations of 75 g/L or more;
k) ammonia tolerance.

In particular, said strain shows at least 2, 3, 4, 5, 6, 7, 8, 9, 10 or all of said metabolic characteristics.

Also preferably, the *Pasteurella* DD1 strain has a 16S rDNA having a nucleic acid sequence as shown in SEQ ID NO: 7 or a sequence which is at least 96, 97, 98, 99 or 99.9% identical thereto and/or a 23S rDNA having a nucleic acid sequence as shown in SEQ ID NO: 8or a sequence which shows a sequence homology of at least 95, 96, 97, 98, 99 or 99.9% thereto.

The identity in percentage values referred to in connection with the various polypeptides or polynucleotides to be used for the bacterial cell of the present invention is, preferably, calculated as identity of the residues over the complete length of the aligned sequences, such as, for example, the identity calculated (for rather similar sequences) with the aid of the program needle from the bioinformatics software package EMBOSS (Version 5.0.0) with the default parameters which are, i.e. gap open (penalty to open a gap): 10.0, gap extend (penalty to extend a gap): 0.5, and data file (scoring matrix file included in package): EDNAFUL.

The term "heterologous" as used herein refers to a polypeptide which does not naturally occur in the bacterial cell, i.e. which is not encoded by the endogenous bacterial genes or derived by posttranslational processing from a polypeptide precursor being encoded by the said bacterial genes. A heterologous polypeptide as referred to in accordance with the present invention, thus, can be exogenously introduced into the bacterial cell. Alternatively, the heterologous polypeptide is encoded by a heterologous polynucleotide which has been exogenously introduced into the bacterial cell. In this case, the heterologous polypeptide will be expressed from the heterologous polynucleotide. It will be understood that the heterologous polynucleotide, preferably, comprises in addition to an open reading frame nucleic acid sequence encoding the heterologous polypeptide further sequences which are required for gene expression in bacteria. Such sequences, preferably, include an expression control sequence, e.g., a promoter being active in *Pasteurella*, and a termination sequence. The heterologous polynucleotide encoding the heterologous polypeptide can be introduced episomally by transformation of an episomal plasmid comprising the heterologous polynucleotide or can be integrated into the bacterial genome by homologous recombination techniques. How to introduce and to achieve expression of heterologous polynucleotides in bacteria and, in particular, *Pasteurella* is well known to the person skilled in the art and described elsewhere in this specification in detail.

The bacterial cell of the present invention shall comprise a heterologous polypeptide having formate dehydrogenase activity. Formate dehydrogenase activity as meant herein refers to the capability of a polypeptide to convert formate into $CO_2$. This enzymatic reaction yields redox-equivalents, i.e. NADH. Polypeptides having formate dehydrogenase activity are well known in the art (Ferry 1990, FEMS Microbiol Rev 7: 377-382). The enzymatic activity can be determined, preferably, as described in Müller et al. (Müller 1978, Eur J Biochem 83: 485-498) or in the accompanying Examples.

Preferably, said heterologous polypeptide having formate dehydrogenase activity is encoded by a polynucleotide comprising a nucleic acid selected from the group consisting of:
a) a nucleic acid having a nucleotide sequence as shown in SEQ ID NO: 5 or 18;
b) a nucleic acid encoding an amino acid sequence as shown in SEQ ID NO: 6;
c) a nucleic acid which is at least 70% identical to the nucleic acid of a) or b); and
d) a nucleic acid encoding an amino acid sequence which is at least 70% identical to the amino acid sequence encoded by the nucleic acid of a) or b).

The term "polynucleotide" as used in accordance with the present invention relates to a nucleic acid molecule which encodes a polypeptide having the aforementioned biological activity. A polynucleotide encoding a polypeptide having the aforementioned biological activity has been obtained in accordance with the present invention from *Candida boidinii* or *Wolinella succinogenis*. Thus, the polynucleotide, preferably, comprises the nucleic acid sequence shown in SEQ ID NO: 5 encoding the polypeptide having an amino acid sequence as shown in SEQ ID NO: 6 or a nucleic acid sequence as shown in SEQ ID NO: 18. It is to be understood that a polypeptide having an amino acid sequence as shown in SEQ ID NO: 6 may be also encoded due to the degenerated genetic code by other polynucleotides as well. Moreover, the term "polynucleotide" as used in accordance with the present invention further encompasses variants of the aforementioned specific polynucleotides. Said variants may represent orthologs, paralogs or other homologs of the polynucleotide of the present invention. The polynucleotide variants, preferably, comprise a nucleic acid sequence characterized in that the sequence can be derived from the aforementioned specific nucleic acid sequences shown in SEQ ID NO: 5 or 18 by at least one nucleotide substitution, addition and/or deletion whereby the variant nucleic acid sequence shall still encode a polypeptide having the activity as specified above. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N. Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA: DNA hybrids are preferably for example 0.1×SSC and 20° C. to 45° C., preferably between 30° C. and 45° C. The hybridization conditions for DNA: RNA hybrids are preferably, for example, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., 1989, "Molecular Cloning", Cold Spring Harbor Laboratory; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptide of the present invention may be identified by a sequence comparison of the nucleic acid sequence of the polynucleotide or the amino acid sequence of the polypeptide of the present invention with sequences of other formate dehydrogenase. Oligonucleotides suitable as PCR primers as well as suitable PCR conditions are described in the accompanying Examples. As a template, DNA or cDNA from bacteria, fungi, plants or animals may be used. Further, variants include polynucleotides comprising nucleic acid sequences which are at least 70%, at least 75%, at least 80%, at least 85%, at least 90%, at least 95%, at least 98% or at least 99% identical to the nucleic acid sequences shown in SEQ ID NO: 5 or 18. Moreover, also encompassed are polynucleotides which comprise nucleic acid sequences encoding amino acid sequences which are at least 70%, at least 75%, at least 80%, at least 85%, at least 90%, at least 95%, at least 98% or at least 99% identical to the amino acid sequences shown in SEQ ID NO: 6. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Feng & Doolittle, 1987, J Mol Evol 25, 351-360; Higgins & Sharp, 1989, Comput Appl Biosci 5, 151-153) or the programs Gap and BestFit (Needleman & Wunsch, 1970, J Mol Biol 48, 443-453; Smith & Waterman, 1981, J Mol Biol 147, 195-197), which are part of the GCG software packet [Genetics Computer Group, 575 Science Drive, Madison, Wis., USA 53711 (1991)], are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. It is to be understood that the aforementioned variant polynucleotides shall encode polypeptides having formate dehydrogenase activity. A polynucleotide comprising a fragment of any of the aforementioned nucleic acid sequences is also encompassed as a polynucleotide of the present invention. The fragment shall encode a polypeptide which still has the activity as specified above. Accordingly, the polypeptide may comprise or consist of the domains of the polypeptide of the present invention conferring the said biological activity. A fragment as meant herein, preferably, comprises at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences. The polynucleotides of the present invention either essentially consist of the aforementioned nucleic acid sequences or comprise the aforementioned nucleic acid sequences. Thus, they may contain further nucleic acid sequences as well. Specifically, the polynucleotides of the present invention may encode fusion proteins wherein one partner of the fusion protein is a polypeptide being encoded by a nucleic acid sequence recited above. Such fusion proteins may comprise as additional part so called "tags" which may serve as a detectable marker or as an auxiliary measure for purification purposes. Tags for the different purposes are well known in the art and comprise FLAG-tags, 6-histidine-tags, MYC-tags and the like. The polynucleotide, preferably, is DNA or RNA. The term encompasses single as well as double stranded polynucleotides. Moreover, comprised are also chemically modified polynucleotides including naturally occurring modified polynucleotides or artificial modified ones.

The aforementioned heterologous polynucleotide may be introduced into the bacterial cell by transformation using a suitable vector. Suitable vectors, preferably, encompass phage or plasmid vectors as well artificial chromosomes, such as bacterial artificial chromosomes. Moreover, the term also relates to targeting constructs which allow for random or site-directed integration of the targeting construct into genomic DNA. Such target constructs, preferably, comprise DNA of sufficient length for either homologous or heterologous recombination with the bacterial genome. The vector, preferably, comprises at least one of the heterologous polynucleotides referred to herein. It is to be understood that the vector may also comprise two or even three heterologous polynucleotides referred to herein above and below. Preferably, the vector further comprises selectable markers for propagation and/or selection in the bacterial cell. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerenes. Alternatively, a vector may be introduced by heat shock or electroporation techniques. The vector, preferably, further comprises an expression control sequences allowing expression in the *Pasteurella* bacterial cells. Moreover, the vector, preferably, further comprise regulatory sequences ensuring initiation of transcription and, optionally, poly-A signals ensuring termination of transcription and stabilization of the transcript. Possible regulatory elements permitting expression in bacterial cells comprise, e.g., the lac, trp or tac promoters. Preferred vectors to be used for *Pasteurella* species are selected from the group consisting of: pSacB, pJFF224.

Advantageously, it has been found in the studies underlying the present invention that by introducing a formate dehydrogenase into the bacterial cells referred to above, the production of succinic acid can be significantly increased. Due to the presence of the formate dehydrogenase, redox-equivalents are produced in a sufficient amount for increasing the NADH-dependent succinic acid production. In accordance with the present invention, it has been found that a bacterial cell as defined herein can be advantageously used for the manufacture of succinic acid, preferably in an industrial scale.

In a further preferred embodiment of the bacterial cell of the present invention, said bacterial cell has reduced lactate dehydrogenase activity.

In yet a further preferred embodiment of the bacterial cell of the present invention, said bacterial cell has reduced lactate dehydrogenase and reduced pyruvate formate lyase activity.

The term "reduced lactate dehydrogenase activity" and "reduced lactate dehydrogenase and reduced pyruvate formate lyase activity" encompasses a modified bacterial cell which has no detectable lactate dehydrogenase activity or no detectable lactate dehydrogenase and no detectable pyruvate formate lyase activity. Moreover, the term encompasses a bacterial cell which has a significantly reduced lactate dehydrogenase activity or significantly reduced lactate dehydrogenase and reduced pyruvate lyase activity when compared to a bacterial cell exhibiting physiological lactate dehydrogenase activity levels or significantly reduced lactate dehydrogenase and pyruvate formate lyase activity levels when compared to a bacterial cell exhibiting physiological activity levels of said enzymes. Whether a reduction is significant can be determined by statistical methods well known to those skilled in the art. Bacterial cells being deficient in lactate dehydrogenase or being deficient in lactate dehydrogenase and pyruvate formate lyase activity may occur naturally, i.e. due to spontaneous mutations. A bacterial cell can be modified to lack or to have significantly reduced lactate dehydrogenase activity or significantly reduced lactate dehydrogenase and pyruvate formate lyase activity by various techniques. Preferably, such bacterial cells are obtainable by chemical treatment or radiation. To this end, bacterial cells will be treated by, e.g., a mutagenizing chemical agent, X-rays, or UV light. In a subsequent step, those bacterial cells which lack lactate dehydrogenase or lactate dehydrogenase and pyruvate formate lyase activity or which at least have a reduced lactate dehydrogenase or a reduced lactate dehydrogenase and pyruvate formate lyase activity activity will be selected. Bacterial cells are also obtainable by homologous recombination techniques which aim to mutate, disrupt or excise the lactate dehydrogenase gene or the lactate dehydrogenase and pyruvate formate lyase activity genes in the genome of the bacterial cell. In the following, a preferred technique for recombination, in particular for introducing mutations or for deleting sequences, is described.

This technique is also sometimes referred to as the "Campbell recombination" herein (Leenhouts et al., 1989, Appl Env Microbiol 55, 394-400). "Campbell in," as used herein, refers to a transformant of an original host cell in which an entire circular double stranded DNA molecule (for example a plasmid) has integrated into a chromosome by a single homologous recombination event (a cross in event), and that effectively results in the insertion of a linearized version of said circular DNA molecule into a first DNA sequence of the chromosome that is homologous to a first DNA sequence of the said circular DNA molecule. "Campbelled in" refers to the linearized DNA sequence that has been integrated into the chromosome of a "Campbell in" transformant. A "Campbell in" contains a duplication of the first homologous DNA sequence, each copy of which includes and surrounds a copy of the homologous recombination crossover point.

"Campbell out," as used herein, refers to a cell descending from a "Campbell in" transformant, in which a second homologous recombination event (a cross out event) has occurred between a second DNA sequence that is contained on the linearized inserted DNA of the "Campbelled in" DNA, and a second DNA sequence of chromosomal origin, which is homologous to the second DNA sequence of said linearized insert, the second recombination event resulting in the deletion (jettisoning) of a portion of the integrated DNA sequence, but, importantly, also resulting in a portion (this can be as little as a single base) of the integrated Campbelled in DNA remaining in the chromosome, such that compared to the original host cell, the "Campbell out" cell contains one or more intentional changes in the chromosome (for example, a single base substitution, multiple base substitutions, insertion of a heterologous gene or DNA sequence, insertion of an additional copy or copies of a homologous gene or a modified homologous gene, or insertion of a DNA sequence comprising more than one of these aforementioned examples listed above). A "Campbell out" cell is, preferably, obtained by a counter-selection against a gene that is contained in a portion (the portion that is desired to be jettisoned) of the "Campbelled in" DNA sequence, for example the *Bacillus subtilis* sacB gene, which is lethal when expressed in a cell that is grown in the presence of about 5% to 10% sucrose. Either with or without a counter-selection, a desired "Campbell out" cell can be obtained or identified by screening for the desired cell, using any screenable phenotype, such as, but not limited to, colony morphology, colony color, presence or absence of antibiotic resistance, presence or absence of a given DNA sequence by polymerase chain reaction, presence or absence of an auxotrophy, presence or absence of an enzyme, colony nucleic acid hybridization, antibody screening, etc. The term "Campbell in" and "Campbell out" can also be used as verbs in various tenses to refer to the method or process described above.

It is understood that the homologous recombination events that leads to a "Campbell in" or "Campbell out" can occur over a range of DNA bases within the homologous DNA sequence, and since the homologous sequences will be identical to each other for at least part of this range, it is not usually possible to specify exactly where the cross-over event occurred. In other words, it is not possible to specify precisely which sequence was originally from the inserted DNA, and which was originally from the chromosomal DNA. Moreover, the first homologous DNA sequence and the second homologous DNA sequence are usually separated by a region of partial non-homology, and it is this region of non-homology that remains deposited in a chromosome of the "Campbell out" cell.

Preferably, first and second homologous DNA sequence are at least about 200 base pairs in length, and can be up to several thousand base pairs in length. However, the procedure can be made to work with shorter or longer sequences. For example, a length for the first and second homologous sequences can range from about 500 to 2000 bases, and the obtaining of a "Campbell out" from a "Campbell in" is facilitated by arranging the first and second homologous sequences to be approximately the same length, preferably with a difference of less than 200 base pairs and most preferably with the shorter of the two being at least 70% of the length of the longer in base pairs.

It has been found in the studies underlying the present invention that the production of SA is even more increased in bacterial cells lacking lactate dehydrogenase activity or lacking lactate dehydrogenase and pyruvate formate lyase activity.

A preferred lactate dehydrogenase as referred to in accordance with the present invention is encoded by a polynucleotide comprising a nucleic acid selected from the group consisting of:

a) a nucleic acid having a nucleotide sequence as shown in SEQ ID NO: 20;
b) a nucleic acid encoding an amino acid sequence as shown in SEQ ID NO: 21;
c) a nucleic acid which is at least 70% identical to the nucleic acid of a) or b); and
d) a nucleic acid encoding an amino acid sequence which is at least 70% identical to the amino acid sequence encoded by the nucleic acid of a) or b).

A preferred pyruvate formate lyase as referred to in accordance with the present invention is encoded by a polynucleotide comprising a nucleic acid selected from the group consisting of:
a) a nucleic acid having a nucleotide sequence as shown in SEQ ID NO: 22;
b) a nucleic acid encoding an amino acid sequence as shown in SEQ ID NO: 23;
c) a nucleic acid which is at least 70% identical to the nucleic acid of a) or b); and
d) a nucleic acid encoding an amino acid sequence which is at least 70% identical to the amino acid sequence encoded by the nucleic acid of a) or b).

In a further preferred embodiment, the bacterial cell of the present invention shall comprise a heterologous polypeptide having isocitrate lyase activity. Isocitrate lyase activity as meant herein refers to the capability of a polypeptide to convert isocitrate into succinate and glyoxylate. Polypeptides having isocitrate lyase activity are well known in the art (Robertson 1987, Curr Microbiol 14: 347-350). The enzymatic activity can be determined, preferably, as described in Watanabe et al. (Watanabe 2001, Biosci Biotechnol Biochem 65: 1095-1103) or in the accompanying Examples.

Preferably, said heterologous polypeptide having isocitrate lyase activity is encoded by a polynucleotide comprising a nucleic acid selected from the group consisting of:
a) a nucleic acid having a nucleotide sequence as shown in SEQ ID NO: 1;
b) a nucleic acid encoding an amino acid sequence as shown in SEQ ID NO: 2;
c) a nucleic acid which is at least 70% identical to the nucleic acid of a) or b); and
d) a nucleic acid encoding an amino acid sequence which is at least 70% identical to the amino acid sequence encoded by the nucleic acid of a) or b).

The definitions of the term "polynucleotide" made above apply accordingly. Specifically, the polynucleotide shall comprise a nucleic acid sequence which encodes a polypeptide having the aforementioned biological activity. A polynucleotide encoding a polypeptide having the aforementioned biological activity has been obtained in accordance with the present invention from *Salmonella typhimurium* or *Yersinia molaretii*. Thus, the polynucleotide, preferably, comprises the nucleic acid sequence shown in SEQ ID NO: 1 encoding the polypeptide having an amino acid sequence as shown in SEQ ID NO: 2. It is to be understood that a polypeptide having an amino acid sequence as shown in SEQ ID NO: 2 may be also encoded due to the degenerated genetic code by other polynucleotides as well. The definitions of variant polynucleotides or polynucleotides comprising a fragment of the aforementioned polynucleotides made before apply accordingly to variant polynucleotides encoding a polypeptide having isocitrate lyase activity.

The bacterial cell of the present invention, in another preferred embodiment, shall comprise a heterologous polypeptide having malate synthase activity. Malate synthase activity as meant herein refers to the capability of a polypeptide to convert glyoxylate into malate. This enymatic reaction is dependent on acetyl-CoA. Polypeptides having malate synthase activity are well known in the art (Sundaram 1980, Arch Biochem Biophys 199: 515-525). The enzymatic activity can be determined, preferably, as described in Eggerer & Klette (Eggerer 1967, Eur J Biochem 1: 447-475) or Drchschlag et al. (Durchschlag 1981, Eur J Biochem 114: 255-262) or in the accompanying Examples.

Preferably, said heterologous polypeptide having malate synthase activity is encoded by a polynucleotide comprising a nucleic acid selected from the group consisting of:
a) a nucleic acid having a nucleotide sequence as shown in SEQ ID NO: 3;
b) a nucleic acid encoding an amino acid sequence as shown in SEQ ID NO: 4;
c) a nucleic acid which is at least 70% identical to the nucleic acid of a) or b); and
d) a nucleic acid encoding an amino acid sequence which is at least 70% identical to the amino acid sequence encoded by the nucleic acid of a) or b).

The definitions of the term "polynucleotide" made above apply accordingly. Specifically, the polynucleotide shall comprise a nucleic acid sequence which encodes a polypeptide having the aforementioned biological activity. A polynucleotide encoding a polypeptide having the aforementioned biological activity has been obtained in accordance with the present invention from *Salmonella typhimurium* or *Yersinia molaretii*. Thus, the polynucleotide, preferably, comprises the nucleic acid sequence shown in SEQ ID NO: 3 encoding the polypeptide having an amino acid sequence as shown in SEQ ID NO: 4. It is to be understood that a polypeptide having an amino acid sequence as shown in SEQ ID NO: 4 may be also encoded due to the degenerated genetic code by other polynucleotides as well. The definitions of variant polynucleotides or polynucleotides comprising a fragment of the aforementioned polynucleotides made before apply accordingly to variant polynucleotides encoding a polypeptide having malate synthase activity.

The production of succinic acid could be increased further by expressing either or both of the above mentioned enzyme (isocitrate lyase and/or malate synthase). Due to the expression of these enzymes, a glyoxylate shunt will be established in the *Pasteurella* bacterial cells which normally lack these enzymes. The said glyoxylate shunt will enhance the production of succinic acid and will avoid losses due to $CO_2$ as a result of the citric acid cycle.

Further, in another preferred embodiments of the bacterial cell of the present invention, said bacterial cell is deficient in alcohol dehydrogenase.

The term "deficient in alcohol dehydrogenase" refers to a bacterial cell which has either no detectable alcohol dehydrogenase activity or at least a significantly reduced alcohol dehydrogenase activity when compared to a bacterial cell exhibiting physiological alcohol dehydrogenase activity levels. Whether a reduction is significant can be determined by statistical methods well known to those skilled in the art. Bacterial cells being deficient in alcohol dehydrogenase may occur naturally, i.e. due to spontaneous mutations. A bacterial cell can be modified to lack or to have significantly reduced alcohol dehydrogenase activity by various techniques which are described in detail above for bacterial cells being deficient in lactate dehydrogenase.

A preferred alcohol dehydrogenase according to the invention is encoded by a nucleic acid sequence selected from the group consisting of:
a) a nucleic acid having a nucleotide sequence as shown in SEQ ID NO: 15;

b) a nucleic acid encoding an amino acid sequence as shown in SEQ ID NO: 16;
c) a nucleic acid which is at least 70% identical to the nucleic acid of a) or b); and
d) a nucleic acid encoding an amino acid sequence which is at least 70% identical to the amino acid sequence encoded by the nucleic acid of a) or b).

It has been found in the studies underlying this invention that a bacterial cell expressing formate dehydrogenase lacking alcohol dehydrogenase also allows for increased succinic acid production. Moreover, the amount of undesired ethanol in such cells is significantly reduced.

Finally, the present invention relates to a method for manufacturing SA comprising
i) cultivating a bacterial cell of the present invention under suitable culture conditions; and
ii) obtaining SA from the cultured bacterial cells.

The term "succinic acid" (SA) has to be understood in its broadest sense and also encompasses salts thereof, as for example alkali metal salts, like Na and K salts, or earth alkali salts, like Mg and Ca salts, or ammonium salts; or anhydrides of said acids.

Suitable culture conditions and techniques for obtaining the SA to be applied in the method of the invention, i.e. the fermentative process for the production of SA, are as follows:

The bacterial cell of the present invention is, preferably, incubated in a medium containing an carbon source which can be assimilated and cultivated at a temperature in the range of about 10 to 60 or 20 to 50 or 30 to 45° C. at a pH of 5.0 to 9.0 or 5.5 to 8.0 or 6.0 to 7.0 in the presence of carbon dioxide.

Preferably, SA is produced under anaerobic conditions. Anaerobic conditions may be established by means of conventional techniques, as for example by degassing the constituents of the reaction medium and maintaining anaerobic conditions by introducing carbon dioxide or nitrogen or mixtures thereof and optionally hydrogen at a flow rate of, for example, 0.1 to 1 or 0.2 to 0.5 vvm. Aerobic conditions may be established by means of conventional techniques, as for example by introducing air or oxygen at a flow rate of, for example, 0.1 to 1 or 0.2 to 0.5 vvm. If appropriate, a slight over pressure of 0.1 to 1.5 bar may be applied in the process.

The assimilable carbon source is preferably selected from glycerol, D-glucose, D-xylose, L-arabinose, D-galactose, D-mannose and mixtures thereof or compositions containing at least one of said compounds, or is selected from decomposition products of starch, cellulose, hemicellulose and/or lignocellulose.

The initial concentration of the assimilable carbon source is, preferably, adjusted to a value in a range of 5 to 100 g/l and may be maintained in said range during cultivation.

The pH of the reaction medium may be controlled by addition of suitable bases as for example, ammonium hydroxide in the form of an at least 5% (w/v) or more concentrated (up to saturation) aqueous solution or gaseous ammonia or other bases.

Particularly preferred conditions for producing SA are:
Carbon source: Glucose or glycerol (including crude glycerol)
Temperature: 30 to 45° C.
pH: 5.5 to 7.0
supplied gas: $CO_2$ The term "crude glycerol" has to be understood as untreated glycerol-containing stream as it accrues in processes in which glycerol is a by product, as for example the production of bio diesel or bio ethanol. Unless otherwise stated the term "glycerol" as used herein also encompasses "crude glycerol".

Further preferred conditions will be derivable from the attached examples and figures.

Succinic acid and/or SA salts produced are, preferably, obtained by methods known in the art, as for example crystallization, filtration, electrodialysis, and chromatography. For example, they may be isolated by precipitating as a calcium succinate product in the fermenter during the fermentation by using calcium hydroxide,—oxide,—carbonate or hydrogen carbonate for neutralization and filtration of the precipitate.

The desired SA product is recovered from the precipitated calcium or succinate by acidification of the succinate with sulfuric acid followed by filtration to remove the calcium sulfate (gypsum) or which precipitates. The resulting solution may be further purified by means of ion exchange chromatography in order to remove undesired residual ions.

Another embodiment of the invention relates to a process for the production of SA and/or SA salts, in particular ammonium salts, which method comprises the fermentative production of SA as defined above and controlling the pH with a suitable base, in particular inorganic base, like ammonia, or an aqueous solution thereof.

Another embodiment of the invention relates to a process for the production of tetrahydrofuran (THF) and/or 1,4-butanediol (BDO) and/or gamma-butyrolactone (GBL) which comprises
a) the fermentative production of SA and/or SA salts, e. g. ammonium salts as defined above, and
b1) either the direct catalytic hydrogenation of the obtained free acid to THF and/or BDO and/or GBL or
b2) the chemical esterification of obtained free SA and/or SA ammonium salts to its corresponding di-loweralkyl ester and subsequent catalytic hydrogenation of said ester to THF and/or BDO and/or GBL.

Lower alkyl preferably represent a straight chain or branched $C_1$-$C_6$-, preferably $C_1$-$C_4$-alkyl residue, in particular methyl, ethyl, n-propyl, isopropyl, n-butyl, sec-butyl, isobutyl, tert-butyl, as well as n-pentyl and n-nexyl and branched analogues thereof.

Another embodiment of the invention relates to a process for the production of pyrrolidones which comprises
a) the fermentative production of SA ammonium salts as defined above, and
b) the chemical conversion of SA ammonium salts to pyrrolidones in a manner known per se, for example as described in WO-A-2006/066839 (which document is herewith incorporated by reference).

In a preferred embodiment, said glycerol, which is used as assimilable carbon source, is crude glycerol.

More Details on Direct Hydrogenation of SA:

Suitable experimental conditions for performing direct catalytic hydrogenation are well known, and for example, described in U.S. Pat. No. 4,550,185, incorporated herewith by reference.

The SA is hydrogenated in a manner known per se using processes, apparatus and assistants, such as solvents, familiar to the person skilled in the art. In particular, a continuous or batch wise liquid phase hydrogenation is carried out in the presence of a heterogeneous catalyst suitable for the acid hydrogenation. The optimal process parameters can be established by the person skilled in the art without unacceptable effort. For example, the reaction temperature is in the range from about 100 to about 300° C., preferably in the range from about 130 to 285° C., and the pressure is from about 20 to 350 bar, for example from 100 to 250 bar. Catalysts usable for the hydrogenation reaction are known to the person skilled in the art. For example, various palladium/rhenium/carbon catalysts may be used. Solvents usable for the hydrogenation reaction are known to the person skilled in the art. For example, an aqueous solvent medium may be used.

More Details on Esterification of SA Followed by Hydrogenation:

Suitable experimental conditions for performing the chemical esterification, followed by direct catalytic hydrogenation are well known, and for example, described in European Patent application 06007118.0 incorporated herewith by reference.

a) Esterification Process:

The esterification process which may comprise a reactive distillation can be performed using an apparatus known per se in various designs.

For example an esterification plant which is operated in continuous mode can be used which comprises a rectification column with an appropriate number of theoretical stages achieved by installation of trays or packings. The aqueous charge comprising the ammonium salt of SA is fed into the top of the column from a reservoir vessel as soon as a steady-state temperature profile has formed in the column as a result of feeding-in alkanol that is evaporated in the evaporator loop adherent to the sump of the column. The reaction forms a countercurrent flow of descending, ammonium salt-containing liquid and condensate, and ascending, alkanol-containing vapor phase. To catalyze the esterification reaction, a homogeneous catalyst may be added to the ammonium salt initial charge. Alternatively, heterogeneous catalysts may be provided in the column internals. The carboxylic ester formed is liquid under the process conditions and passes via the lower end of the column into the sump of the distillation column and is continuously withdrawn from the sump. Gaseous components, for example azeotropic mixtures comprising alkanol-water and/or ammonia, are removed from the reaction column and hence from the reaction equilibrium at the top of the column.

Further modifications of the above-described specific embodiments can be implemented by the person skilled in the art without unacceptable effort.

Suitable process parameter ranges for the esterification process according to the invention can be determined easily by the person skilled in the art depending on the configuration of the apparatus used, for example type of column internals used, type and amount of the reactants, type and amount of the catalyst used if appropriate. For instance, without being restrictive thereto, individual parameters may be set within the following parameter ranges:

Column temperature: 0-300° C., in particular 40-250° C., or 70-200° C.

Pressure: from 0.1 to 6 bar, in particular standard pressure

Residence time: a few seconds (for example from 1 to 60) up to days (for example from 1 to 5), in particular from a few minutes (for example from 1 to 60) to a few hours (for example from 1 to 15), more preferably from a few minutes (for example from 5 to 20) to 2 h.

b) Hydrogenation Process

The SA esters prepared in accordance with the invention are hydrogenated in a manner known per se using processes, apparatus and assistants, such as catalysts, familiar to the person skilled in the art.

In particular, a continuous or batch wise gas phase hydrogenation is carried out in the presence of a heterogeneous catalyst suitable for the ester hydrogenation. The optimal process parameters can be established by the person skilled in the art for the particular ester without unacceptable effort. For example, the reaction temperature is in the range from about 100 to about 300° C., preferably in the range from about 200 to 280° C., and the pressure is from about 5 to 100 bar, for example from 10 to 50 bar. The molar ratio of reactant to hydrogen is set within the range from about 1:100 to about 1:2000, for example from 1:800 to 1:1500.

Catalysts usable for the inventive hydrogenation reaction are known to the person skilled in the art. For example, various copper catalysts may be used. The prior art describes, for example, the use of reduced copper chromite catalysts which are obtainable under the name 85/1 from Davy Process Technology Ltd., England. However, catalysts particularly suitable in accordance with the invention are supported copper oxide catalysts, the copper oxide being applied to alumina or silica support materials. The examples of the hydrogenation of succinic esters to BDO (1,4-Butanediol)/GBL (gamma-butyrlactone)/THF with copper catalysts are also well known in the art.

Fermentation as used according to the present invention can be performed in stirred fermenters, bubble columns and loop reactors. The possible method types including stirrer types and geometric designs are well known in the art and can be found in standard text books. In the process, typical variants available are the following variants known to those skilled in the art or explained, for example, in a standard textbook (Chmiel H, Hammes W P, Bailey J E, 1987, "Biochemical engineering. A challenge for interdisciplinary cooperation.", ISBN: 3-437-30574-3.), such as batch, fed batch, repeated fed batch or else continuous fermentation with and without recycling of the biomass. Depending on the production strain, sparging with air, oxygen, carbon dioxide, hydrogen, nitrogen or appropriate gas mixtures can/must be effected in order to achieve good yields.

Before the chemical conversion in the fermentation broth in the process according to the invention, the fermentation broth can be pretreated; for example, the biomass of the broth can be removed. Processes for removing the biomass are known to those skilled in the art, for example filtration, sedimentation and flotation. Consequently, the biomass can be removed, for example, with centrifuges, separators, decanters, filters or in flotation apparatus. For maximum recovery of the product of value, washing of the biomass is often advisable, for example in the form of a diafiltration. The selection of the method is dependent upon the biomass content in the fermenter broth and the properties of the biomass, and also the interaction of the biomass with the product of value. In one embodiment, the fermentation broth can be sterilized or pasteurized.

In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The term "fermentation broth" is understood to mean an aqueous solution which is based on a fermentative process and has not been worked up or has been worked up, for example, as described herein.

In apparatus terms, stirred tanks, falling-film evaporators, thin-film evaporators, forced-flash circulation evaporators and other evaporator types can be utilized in natural or forced circulation mode.

All references cited in this specification are herewith incorporated by reference with respect to their entire disclosure content and the disclosure content specifically mentioned in this specification.

The invention will be now described by the following examples which shall not be construed, whatsoever, as a limitation of its scope.

EXAMPLES

Example 1

Transformation of DD1

TABLE 1

Nomenclature of the DD1 wildtype and mutants referred to in the Examples.

| Strain | Description |
| --- | --- |
| LU13843 | Wildtype DD1 (deposit DSM18541) |
| LU15050 | DD1 delta ldh |
| LU15224 | DD1 delta ldh pflD |
| LU15224 pJFF224 (icl ms Y.m.) | DD1 delta ldh pflD pJFF224 (icl ms Y.m.) |
| LU15224 pJFF224 | DD1 delta ldh pflD pJFF224 |
| LU13843 pJFF224 | DD1 pJFF224 |
| LU13843 pJFF224 (icl ms S.t.) | DD1 pJFF224 (icl ms S.t.) |
| LU 15050 pJFF224 | DD1 delta ldh pJFF224 |
| LU15050 pJFF224 (icl ms S.t.) | DD1 delta ldh pJFF224 (icl ms S.t.) |
| LU 15050 pJFF224 (icl ms Y.m.) | DD1 delta ldh pJFF224 (icl ms Y.m.) |
| LU 13843 pJFF224 (PpckA fdh C.b.) | DD1 pJFF224 (PpckA fdh C.b.) |
| LU 15050 pJFF224 (PpckA fdh C.b.) | DD1 delta ldh pJFF224 (PpckA fdh C.b.) |
| LU 13843 pJFF224 (PpckA fdh C.b., PEFTU icl ms Y.m.) | DD1 pJFF224 (PpckA fdh C.b., PEFTU icl ms Y.m.) |
| LU15050 delta adhE. | DD1 delta ldh delta adhE |
| LU15050 delta adhE. pJFF224 (PpckA fdh C.b.) | DD1 delta ldh delta adhE pJFF224 (PpckA fdh C.b.) |
| LU 13843 pJFF224 (fdh W.s.) | DD1 pJFF224 (fdh W.s.) |
| LU 15050 pJFF224 (fdh W.s.) | DD1 delta ldh pJFF224 (fdh W.s.) |
| LU 15050 delta adhE pJFF224 (fdh W.s.) | DD1 delta ldh delta adhE pJFF224 (fdh W.s.) |

*Pasteurella* strain LU13843 was transformed with DNA by electroporation using the following protocol:

Pre-Culture:
LU 13843 was inoculated from a freshly grown BHI-Agar plate into 40 ml BHI (brain heart infusion, Difco) in 100 ml shake flask. Incubation was performed over night at 30° C.; 200 rpm.

Main-Culture:
50 ml BHI in 100 ml shake flask
Inoculated to a final OD(610) of 0.4
Incubation: approximately 1.5 h at 30° C., 200 rpm
The cells were harvested at an OD of approximately 1.3
Pellet washed once with 10% cold glycerol at 4° C.
Resuspended in 1.7 ml 10% glycerol (4° C.)
100 µl of competent cells were mixed with 5-10 µg DNA (10-20 µl) and kept on ice for 2 min in an electroporation cuvette with a width of 0.2 cm.

Electroporation conditions: 800 Ω; 25 µF; 2 kV (Gene Pulser, Bio-Rad)
Addition of 1 ml of BHI immediately after electroporation
Incubation for 2 h at 30° C.

Cells were plated on BHI with 5 mg/L chloramphenicol and incubated for 2-5 d at 30° C. until the colonies of the transformants were visible. Clones were isolated and re-streaked onto BHI with 5 mg/L chloramphenicol until purity of clones was obtained.

Example 2

Generation of Deletion Constructs

Figure 2:
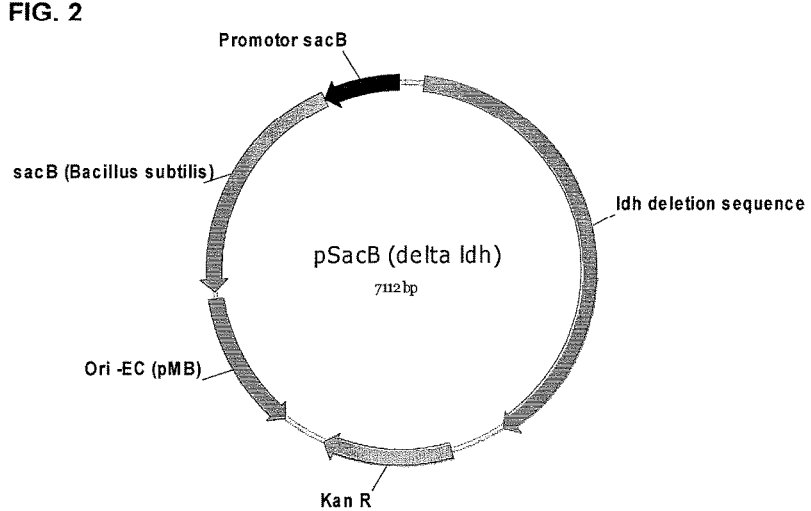
FIG. 2: A schematic map of plasmid pSacB (delta ldhA) (lactate dehydrogenase).
Figure 3:
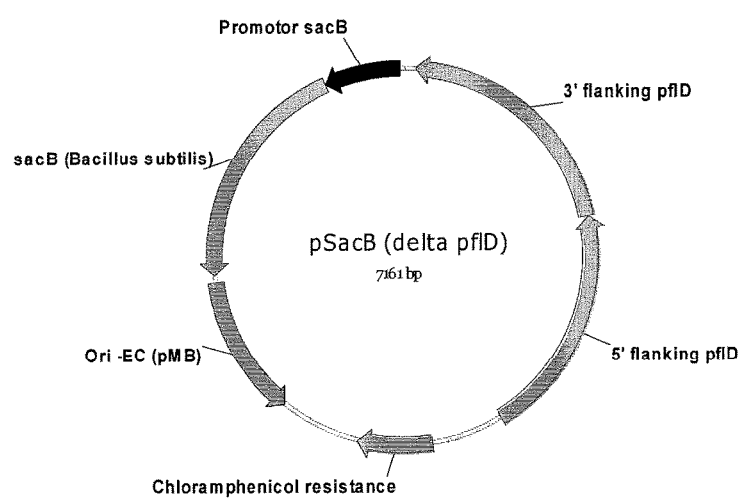
FIG. 3: A schematic map of plasmid pSacB (delta pflD) (pyruvate formate lyase).
Figure 4:
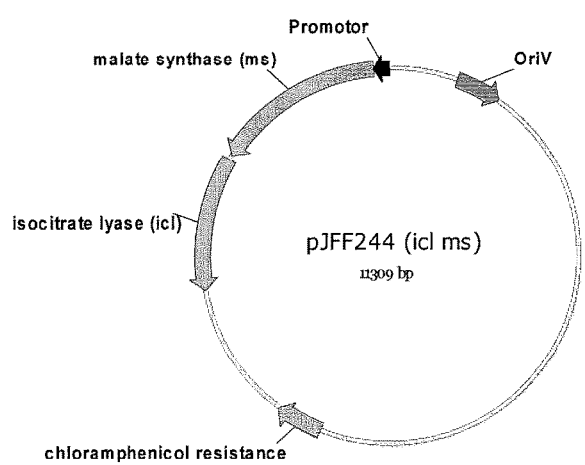
FIG. 4: A schematic map of an expression plasmid pJFF224 (icl ms Y.m.) for the expression of the glyoxylate shunt operon of *Yersinia molaretii* (isocitrate lyase (icl) and malate synthase (ms)).

Deletion plasmids were constructed based on the vector pSacB (SEQ ID NO 9). FIG. 1 shows a schematic map of plasmid pSacB. 5'- and 3'-flanking regions of the chromosomal fragment which should be deleted were amplified by PCR from chromosomal DNA of LU 13843 and introduced into the vector using standard techniques. Normally, at least 80% of the ORF were targeted for a deletion. In such a way, the deletion plasmids for lactate dehydrogenase ldhA, pSacB (delta ldhA), and for the pyruvate formate lyase pflD, pSacB (delta pflD) were constructed. FIGS. 2 and 3 show schematic maps of plasmid pSacB (delta ldhA) and pSacB (delta pflD).

Example 3

Generation of Improved Succinate Producing Strains

LU 13843 was transformed as described above with the pSacB (delta ldh) and "Campbelled in" to yield a "Campbell in" strain. Transformation and integration into the genome of LU 13843 was confirmed by PCR yielding bands for the integrational event of the plasmid into the genome of LU 13843. The "Campbell in" strain was then "Campbelled out" using agar plates containing sucrose as a counter selection medium, selecting for the loss (of function) of the sacB gene. Therefore, the "Campbell in" strains were incubated in 25-35 ml of non selective medium (BHI containing no antibiotic) at 37° C., 220 rpm over night. The overnight culture was then streaked onto freshly prepared BHI containing sucrose plates (10%, no antibiotics) and incubated overnight at 37° C. ("first sucrose transfer"). Single colony obtained from first transfer were again streaked onto freshly prepared BHI containing sucrose plates (10%) and incubated overnight at 37° C. ("second sucrose transfer"). This procedure was repeated until a minimal completion of five transfers ("third, forth, fifth sucrose transfer") in sucrose. The term "first to fifth sucrose transfer" refers to the transfer of a strain after chromosomal integration of a vector containing a sacB levansucrase gene onto sucrose and growth medium containing agar plates for the purpose of selecting for strains with the loss of the sacB gene and the surrounding plasmid sequences. Single colony from the fifth transfer plates were inoculated onto 25-35 ml of non selective medium (BHI containing no antibiotic) and incubated at 37° C., 220 rpm over night. The overnight culture was serially diluted and plated onto BHI plates to obtain isolated single colonies. The "Campbelled out" strains containing the deletion of the ldhA gene were confirmed by chloramphenicol sensitivity. The deletion mutants among these strains were identified and confirmed by PCR analysis. This led to the ldhA deletion mutant LU15050.

LU15050 was transformed with pSacB (delta pflD) as described above and "Campbelled in" to yield a "Campbell in" strain. Transformation and integration was confirmed by PCR. The "Campbell in" strain was then "Campbelled out" as described previously. The deletion mutants among these strains were identified and confirmed by PCR analysis. This led to the ldhA pflD double deletion mutant LU15224.

LU15224 was transformed with pJFF224 (icl ms Y.m.) expressing the gyloxylate shunt operon from *Yersinia molaretii* and pJFF224 as a vector control. Resulting transformants were used for further experiments. LU15050 was transformed with pJFF224 (icl ms S.t.) expressing the gyloxylate shunt operon from *Salmonella typhimurium*. Resulting transformants were used for further experiments.

Example 4

Cell Bank Preparation

1. Media Preparation

Composition of the cultivation media is described in table 3.

TABLE 3

Composition of solid and liquid media for the preparation of cell banks.

| Compound | Concentration [g/L] | Concentration of stock solution [g/L] |
|---|---|---|
| Glucose | varying[a] | 650 |
| Bacto yeast extrakt (Becton Dickinson) | 5 | — |
| Bacto peptone (Becton Dickinson) | 5 | — |
| (NH4)$_2$SO$_4$ | 1 | 500 |
| CaCl$_2$*2H$_2$O | 0.2 | 20 |
| MgCl$_2$*6H$_2$O | 0.2 | 20 |
| NaCl | 1 | 100 |
| K$_2$HPO$_4$ | 3 | 500 |
| MgCO$_3$ | varying[b] | — |
| Bacto-Agar (for solid media only) | 12 | — |

[a]Glucose concentrations were 15 g/L (in plates) and 20 or 50 g/L (in liquid media).
[b]MgCO$_3$ (Riedel-de Haen, product number: 13117 by Sigma-Aldrich Laborchemikalien GmbH) concentrations were 5 g/L (in plates) and 0 or 30 g/L (in liquid media).

5 g yeast extract, 5 g peptone, MgCO3 and (for solid media) 12 g Bacto-Agar were mixed in 900 mL distilled water and autoclaved (20 min). After cooling down to about 65° C. the missing components were added as sterile stock solutions. Glucose, ammonium sulfate and K2HPO4 were all separately autoclaved. Ca-, Mg- and Na-chlorides were autoclaved together.

2. MCB Preparation

Two agar plates were freshly inoculated with the desired strain and incubated at 37° C. in an anaerobic jar (Anaerocult A, Merck) over night. The biomass was taken off the plates and resuspended in the MgCO3-free liquid medium with 20 g/L glucose to adjust OD600≈1.0. Inoculation was performed with 0.5 mL of this cell suspension. Cultivations were performed in 100 mL-serum bottles with gas tight butyl rubber stoppers (Ochs GmbH, Bovenden/Lenglern, Germany) containing 50 mL of the liquid medium with 20 g/L glucose and 30 g/L MgCO3 and a CO2-atmosphere with 0.8 bar overpressure. The serum bottles (in total 10) were incubated at 37° C., a rotary speed of 160 rpm and a shaking diameter of 2.5 cm.

To monitor glucose consumption the cultivation of one bottle was stopped and sampling and HPLC analysis were performed after 0, 3, 4, 5, 7, 8 and 8.5 h. After 8.5 h (the glucose concentration was 3.4 g/L) the cultivation was stopped. Aliquots of 0.5 mL cell suspension and 0.5 mL sterile glycerol were filled in cryovials, mixed and stored for 13 h at −20 and afterwards at −80° C. as MCB. The MCB was tested for purity by streaking a loop of the last cryovial on agar plates for contamination control and checking in liquid culture (media as described table 8) the product spectrum and for contamination (by microscopy).

Consumption of glucose and formation of SA and by-products were quantified via HPLC analyses of the undiluted cell free supernatants of the cultivation broth using RI-detection. Broth samples were taken with a sterile syringe through the butyl rubber plug, cell separation was performed by filtration (0.22 μm). A 300×7.8 mm I. D. Column Aminex HPX-87 H (Biorad) and 5 mm H2SO4 were used as stationary and mobile phase, respectively. The column temperature was 30° C., the flow rate was 0.5 mL min$^{-1}$.

3. WCB Preparation

One vial of the MCB was used to inoculate a 100 mL-serum bottle with gas tight butyl rubber stopper (see above) containing 50 mL of the liquid medium with 50 g/L glucose. Incubation was performed for 10 h at 37° C. in a shaking incubator (rotary speed: 180 rpm, shaking diameter: 2.5 cm). At the end of the cultivation the glucose concentration was 20 g/L and the pH around 6.5. Aliquots of 0.5 mL cell suspension and 0.5 mL sterile glycerol were filled in cryovials, mixed and stored at −80° C. as WCB. Purity checks were the same as for the MCB. HPLC conditions were the same as those described above.

Example 5

Fermentation of Mutant Strains LU15224 pJFF224 (icl ms Y.m.) and LU15224 pJFF224

The mutant strain of DD1 LU15224 pJFF224 (icl ms Y.m.), which is a double knockout for ΔIdh and ΔpflD and over-expresses the plasmid pJFF224 (icl ms Y.m.), containing the glyoxylate shunt operon genes, was analyzed by anaerobic fermentation experiments in comparison to the plasmid control strain LU15224 pJFF224, containing the same genetic background as LU15224 pJFF224 (icl ms Y.m.) but only an empty expression plasmid pJFF224. Mutant strains were generated as described in example 1 to 3.

1. Medium Preparation

The composition of the cultivation medium is described in the following table 4.

TABLE 4

Medium composition for batch cultivations of DD1-mutants with over-expression plasmids.

| Compound | Concentration [g/L] | Concentration of stock solution [g/L] |
|---|---|---|
| Glucose-Monohydrat | 50 | 722 |
| Bacto yeast extrakt (Becton Dickinson) | 5 | 100 |
| (NH$_4$)$_2$SO$_4$ | 1 | 500 |
| CaCl$_2$*2H$_2$O | 0.2 | 20 |
| MgCl$_2$*6H$_2$O | 0.2 | 20 |
| NaCl | 1 | 100 |
| K$_2$HPO$_4$ | 3 | 500 |
| Chloramphenicol | 0.005 | 5 |
| MgCO$_3$[a] | 50 | — |

[a]MgCO$_3$ was used as buffering agent in serum bottle experiments only.

MgCO$_3$ was supplemented with ddH$_2$O and autoclaved in serum bottles. Yeast extract, glucose, ammonium sulfate and potassium phosphate were all separately autoclaved. Ca-, Mg- and Na-chlorides were autoclaved together. After cooling down the ddH$_2$O autoclaved fermenters and serum bottles the missing components were added as sterile stock solutions. For the seed cultures the same medium was used.

2. Cultivations and Analytics

The seed culture was grown anaerobically in a 100 mL-serum bottle with gas tight butyl rubber stoppers containing 50 mL medium at 37° C. in a shaking incubator (rotary speed: 170 rpm, shaking diameter: 2.5 cm). Inoculation of the seed culture was performed with 1 mL of the WCB (as described in example 4) under sterile conditions. Immediately after the inoculation the aerobic gas atmosphere was substituted by pure CO2 with an overpressure of about 0.8 bar. After 11 h and 17 h of incubation for LU15224 pJFF224 (icl ms Y.m.) and LU15224 pJFF224, respectively, the fermenter was inoculated with 20 mL to start the cultivation in the 500 mL fermenter (Sixfors, Infors Switzerland) containing 380 mL of cultivation medium which had been gassed over night with CO$_2$ to ensure oxygen-free conditions. The cultivation temperature was maintained at 37° C. and the pH at 6.5 with 25% NH$_4$OH. The CO$_2$-gas stream was adjusted to 0.4 1*min$^{-1}$. The stirrer speed was adjusted to 500 rpm.

Consumption of glucose and formation of SA and by-products were quantified via HPLC as described in example 4.

3. Results

The results are summarized in table 5 showing values after glucose depletion.

Heterologous over-expression of the glyoxylate shunt genes lead to a significant increase of the succinate yield compared to the control strain LU15224 pJFF224. It is also detected that acetate is produced with a lower titer in LU15224 pJFF224 (icl ms Y.m.) compared to the control, hinting to an improved flux from pyruvate via acetyl-CoA, isocitrate, malate, fumarate to succinate introduced by the heterologous glyoxylate shunt operon.

TABLE 5

Production of succinate by the mutant LU15224 pJFF224 (icl ms Y.m.) and the plasmid control LU15224 pJFF224 after glucose depletion in a SixFors fermentation broth.

| Parameter | LU15224 pJFF224 (icl ms Y.m.) | LU15224 pJFF224 |
|---|---|---|
| Final volume of fermentation broth [ml] | 432 | 435 |
| consumed glucose [g] | 22.98 | 23.17 |
| produced succinate [g] | 20 | 19.16 |
| succinate yield [g/g] | 0.87 | 0.83 |
| produced lactate [g] | 0 | 0 |
| produced pyruvate [g] | 0 | 0 |
| produced acetate [g] | 3.12 | 3.26 |
| produced formate [g] | 0 | 0 |

Example 6

Cloning and Expression of the Glyoxylate Shunt Operon from *Salmonella typhimurium* LT2

In another embodiment the glyoxylate shunt operon from *Salmonella typhimurium* (*S. typhimurium*) LT2 ATCC 15277 is amplified by PCR cloned from chromosomal DNA of from *S. typhimurium* LT2 ATCC 15277 using the PfuTurbo™ DNA polymerase (Roche) and is inserted into the vector pJFF224.

Figure 5:
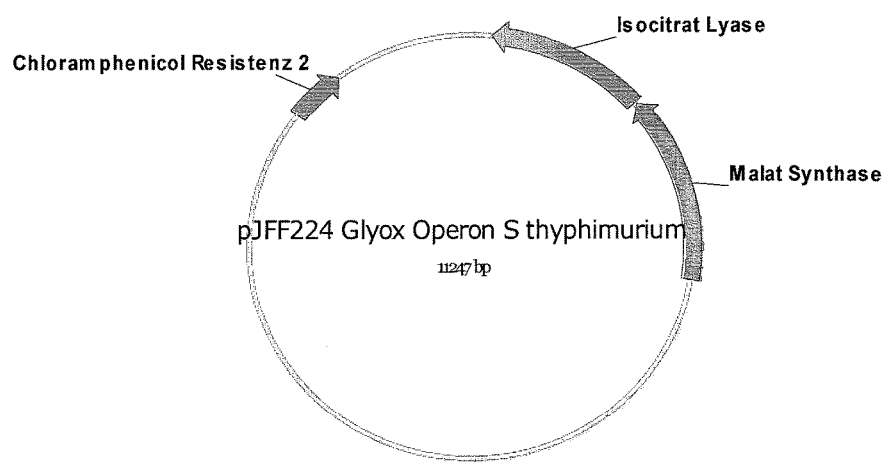
FIG. 5: A schematic map of the plasmid pJFF224 (icl ms S.t.) for the expression of the glyoxylate shunt operon of *Salmonella typhimurium*.

The expression of the genes in this construct is driven by the native promoter of the operon as well as by a T4 promoter located on the vector pJFF224. FIG. 5 shows a schematic map of the resulting plasmid termed pJFF224 (icl ms S.t.). The strain DD1 (termed LU13843) was transformed with the plasmid pJFF224 (icl ms S.t.) as described above. A serum bottle experiment was performed and analyzed as described above. It can be found that upon overexpression of the glyoxylate shunt operon from *S. typhimurium* the succinic acid production was increased over the control. The yield of glucose converted to succinic was increased from 0.42 g SA/g glucose to 0.51 g SA/g glucose.

TABLE 6

Results after expression of the glyoxylate shunt operon from *S. typhimurium* LT2 in LU13843.

| Strain | succinic acid | lactic acid | formic acid | acetic acid | yield succinic acid g SA/g substrate |
|---|---|---|---|---|---|
| LU13843 pJFF224 | 15.1 | 10.1 | 6.8 | 7.5 | 0.42 |
| LU13843 pJFF224 (icl ms *S.t.*) | 18.1 | 6.5 | 6 | 8.1 | 0.51 |

Example 7

Strain Expression of the Glyoxylate Shunt Operon from *S. typhimurium* LT2 in the Strain DD1 Delta LDH (LU15050)

The strain DD1 delta ldh (LU15050) was transformed with the plasmid pJFF224 (icl ms S.t.) as described above. A serum bottle experiment was performed and analyzed as described above. Cells were grown overnight on BHI agar plates with chloramphenicol, added to 4 μg/ml. Cells were scraped off the agar plate and inoculated with an OD 600 nm of 0.1. It can be found that upon overexpression of the glyoxylate shunt operon from *S. typhimurium* in LU15050 the succinic acid production was increased over the control. The yield of glucose converted to succinic was increased from 0.62 g SA/g glucose to 0.72 g SA/g glucose.

TABLE 7

Results after expression of the glyoxylate shunt operon from *S. typhimurium* LT2 in LU15050.

| | succinic acid | Formic acid | Acetic acid | ethanol | yield succinic acid, SA/g substrate |
|---|---|---|---|---|---|
| LU15050 | 31.10 | 6.40 | 7.11 | 0.98 | 0.62 |
| LU15050 pJFF224 (icl ms *S.t.*) | 35.90 | 5.60 | 7.50 | 1.15 | 0.72 |

Example 8

Cloning and Expression of the Glyoxylate Shunt Operon from *Yersinia molaretii* ATCC 43969

In another embodiment the glyoxylate shunt operon from *Yersinia molaretii* (*Y. molaretii*) ATCC 43969 is amplified by PCR cloned from chromosomal DNA of *Y. molaretii* ATCC 43969 using the PfuTurbo™ DNA polymerase (Roche) and is inserted into the vector pJFF224. The expression of the genes in this construct is driven by the native promoter of the operon as well as by a T4 promoter located on the vector pJFF224. FIG. 6 shows a schematic map of the resulting plasmid termed pJFF224 (icl ms Y.m.). The strain DD1 delta ldh (LU15050) was transformed with the plasmid pJFF224 (icl ms Y.m.) as described above. A serum bottle experiment using 48 g/l glucose was performed and analyzed as described above. Cells were grown overnight on BHI agar plates with chloramphenicol, added to 4 µg/ml. Cells were scraped off the agar plate and inoculated with an OD 600 nm of 0.1. It can be found that upon overexpression of the glyoxylate operon from *Y. molaretii* in LU15505 the succinic acid production was significantly increased over the control. The yield of glucose converted to succinic was increased from 0.60 g SA/g glucose for LU15050 to 0.69 g SA/g glucose for LU15050 pJFF224 (icl ms Y.m.).

TABLE 8

Results from expression of the glyoxylate operon from *Y. molaretii* ATCC 43969 in LU 15050.

| | succinic acid | formic acid | acetic acid | yield succinic acid, g SA/g substrate |
|---|---|---|---|---|
| LU 15050 | 28.7 | 5.2 | 7.3 | 0.60 |
| LU 15050 pJFF224 (icl ms Y.m.) | 33.0 | 5.5 | 6.7 | 0.69 |

Example 9

Cloning and Expression of the Formate Dehydrogenase Gene from *Candida boidinii*

Figure 7:
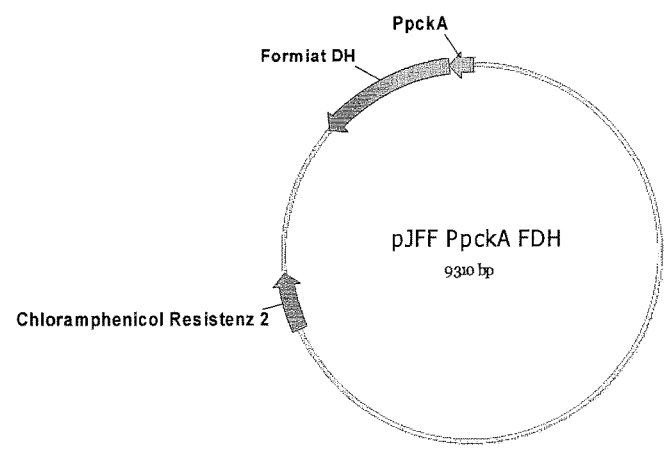
FIG. 7: A schematic map of the plasmid pJFF224 (PpckA fdh C.b.)

The formate dehydrogenase gene (fdh) from *Candida boidinii* (*C. boidinii*) ATCC 18810 was amplified by PCR from chromosomal DNA from *C. boidinii* ATCC 18810 using the PfuTurbo™ DNA polymerase (Roche). The gene was fused to the PpckA promoter from the strain DD1 and was inserted into the vector pJFF224. The expression of the genes in this construct is driven by the PpckA promoter as well as by a T4 promoter located on the vector pJFF224. FIG. 7 shows a schematic map of the resulting plasmid termed pJFF224 (PpckA fdh C.b.). The strains DD1 (LU13843) and DD1 delta ldh (LU 15050) were transformed with the plasmid pJFF224 pJFF224 (PpckA fdh C.b.) as described above.

The resulting strains were selected on agar containing 4 µg/ml chloramphenicol.

The succinic acid productivity was analyzed as described above. It was found that upon overexpression of fdh the amount of succinic acid was increased from 27.5 to 30.3 g/l, while the amount of formate as a side product was reduced to either lower than 0.1 g/l or 0.16 g/l in LU 15050. The yield of succinic acid was increased from 0.57 to 0.63 in LU 13843 or from 0.67 to 0.68 for LU 15050.

TABLE 9

Results after expression of fdh from *C. boidinii* in LU 13843 and LU 15050.

| strain | succinic acid | lactic acid | formic acid | acetic acid | yield succinic acid, g SA/g substrate |
|---|---|---|---|---|---|
| LU 13843 pJFF224 | 27.5 | 7.80 | 4.74 | 7.32 | 0.57 |
| LU 13843 pJFF224 (PpckA fdh C.b.) | 30.3 | 5.82 | — | 6.39 | 0.63 |
| LU 15050 pJFF224 | 32.40 | 0.26 | 4.51 | 7.19 | 0.67 |
| LU 15050 pJFF224 (PpckA fdh C.b.) | 32.61 | 0.25 | 0.16 | 6.59 | 0.68 |

Example 10

Simultaneous Over Expression of the Formate Dehydrogenase Gene from *C. boidinii* and the Glyoxylate Shunt Operon from *Y. molaretii*

The formate dehydrogenase gene from *C. boidinii* ATCC 18810 under the control of the PpckA promoter and the glyoxylate shunt operon from *Y. molaretii* under the control of the EFTU promoter from DD1 were inserted into the vector pJFF224 to yield pJFF224 (PpckA fdh C.b., PEFTU icl ms Y.m.). The expression of the genes in this construct is driven by the PpckA promoter, the PEFTU promoter as well as by a T4 promoter located on the vector pJFF224. FIG. 7 shows a schematic map of the resulting plasmid termed pJFF224 (PpckA fdh PEFTU icl ms Y.m.). The strains LU13843 and LU 15050 were transformed with the plasmid pJFF224 and pJFF224 (PpckA fdh C.b., PEFTU icl ms Y.m.) as described above.

The resulting strains were selected on agar containing 4 µg/ml chloramphenicol.

The succinic acid productivity was analyzed as described above except that xylose was added as the carbon source instead of glucose. It was found that upon overexpression of fdh the amount of succinic acid was increased from 35.6 g/l to 36.4 g/l, while the amount of lactic acid as a side product was reduced from 2.1 g/l to 1.7 g/l in LU 13843. The yield of succinic acid was increased from 0.75 in LU 13843 to 0.76 in LU 13843 pJFF224 (PpckA fdh C.b., PEFTU icl ms Y.m.).

TABLE 10

Results after expression of fdh from *C. boidinii* and the glyoxylate shunt operon from *Y. molaretii* in LU 13843 after growth in xylose.

| strain | succinic acid | lactic acid | formic acid | acetic acid | yield succinic acid, g SA/g substrate |
|---|---|---|---|---|---|
| LU 13843 pJFF224 | 35.6 | 2.1 | 3.4 | 10.2 | 0.75 |
| LU 13843 pJFF224 (PpckA fdh C.b., PEFTU icl ms Y.m.) | 36.4 | 1.7 | 3.9 | 10.4 | 0.76 |

Example 11

Deletion of adhE Gene from DD1 and DD1 Mutant Strains

Figure 8:
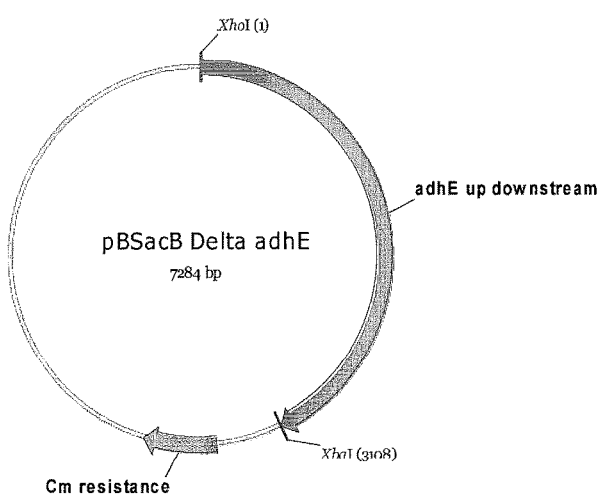
FIG. 8: A schematic map of the pSacB (delta adhE).

The adhE gene was identified on the chromosome of the DD1 genome by sequence analysis using the know adhE gene from *E. coli* and analyzing for homologues in DD1. A gene deletion fragment for the adhE gene is obtained through PCR amplification of 1500 bp covering the upstream region and the respective downstream region of the adhE gene from DD1 with forward and reverse primers carrying the restriction sequences for XhoI and XbaI. The fragment is purified and digested with XhoI and XbaI, as well as the vector which is additionally dephosphorylated. The ligated vector carrying the fragment of the DD1 genome with the adhE up- and downstream regions is propagated in *E. coli* and is used for the transformation of DD1. The strain LU15050 DD1 delta ldh is transformed as described above with the pSacB (delta adhE) and "Campbelled in" to yield a "Campbell in" strain. FIG. 8 shows a schematic map of the pSacB (delta adhE). Transformation and integration into the genome of LU15050 is confirmed by PCR yielding bands for the integrational event of the plasmid into the genome of LU15050. The "Campbell in" strain is then "Campbelled out" using agar plates containing sucrose as a counter selection medium, selecting for the loss (of function) of the sacB gene. Therefore, the "Campbell in" strains are incubated in 25-35 mL of non selective medium (BHI containing no antibiotic) at 37° C., 220 rpm over night. The overnight culture is then streaked onto freshly prepared BHI containing sucrose plates (10%, no antibiotics) and incubated overnight at 37° C. ("first sucrose transfer"). Single colony obtained from first transfer are again streaked onto freshly prepared BHI containing sucrose plates (10%) and are incubated overnight at 37° C. ("second sucrose transfer"). This procedure is repeated until a minimal completion of five transfers ("third, forth, fifth sucrose transfer") in sucrose. The term "first to fifth sucrose transfer" refers to the transfer of a strain after chromosomal integration of a vector containing a sacB levansucrase gene onto sucrose and growth medium containing agar plates for the purpose of selecting for strains with the loss of the sacB gene and the surrounding plasmid sequences. Single colony from the fifth transfer plates are inoculated onto 25-35 ml of non selective medium (BHI containing no antibiotic) and are incubated at 37° C., 220 rpm over night. The overnight culture was serially diluted and plated onto BHI plates to obtain isolated single colonies. The "Campbelled out" strains containing the deletion of the adhE gene are confirmed by chloramphenicol sensitivity. The deletion mutants among these strains are identified and confirmed by PCR analysis. This led to the adhe deletion mutant LU15050 delta adhE. LU15050 delta adhE is transformed with pJFF224 (PpckA fdh C.b.) expressing the formate dehydrogenase from *Candida boidinii* and pJFF224 as a vector control. Resulting transformants are used for further experiments. After growth in serum bottles as described above the strains are found to contain significantly increased amounts of succinic acid if compared to the plasmid control not containing a fdh gene. Also the amount of side products such as ethanol is significantly reduced in the DD1 delta adhE strain over expressing a formate dehydrogenase.

Example 12

Figure 9:
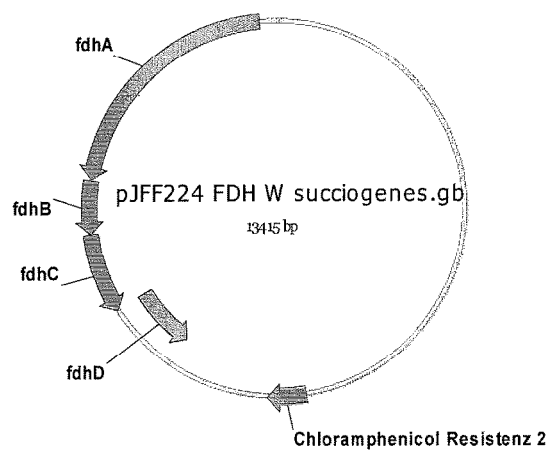
FIG. 9: A schematic map of the pJFF224 (fdh W.s.) for the expression of the *W. succiogenes* formate dehydrogenase (fdh W.s.).
Figure 10:
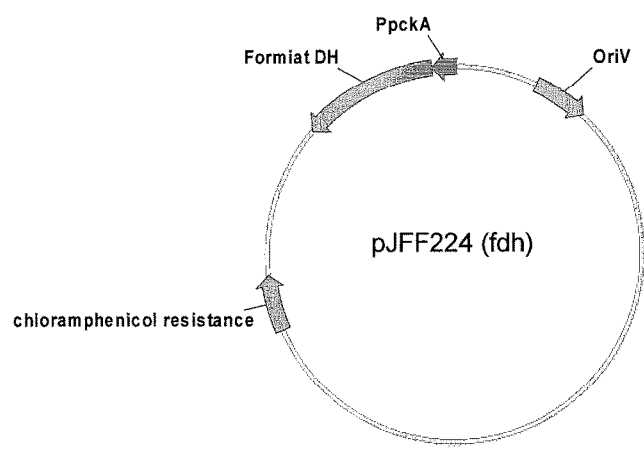
FIG. 10: A schematic map of an expression plasmid pJFF224 (fdh C.b.) for the expression of the *Candida boidinii* formate dehydrogenase (fdh C.b.).

Cloning and Expression of the *Wolinella succinogenes* fdh in DD1 and DD1 Mutant Strains In another embodiment of formate dehydrogenase operon encoding the genes: fdhA, fdhB, fdhC and fdhD from *Wolinella succinogenes* (*W. succinogenes*) DSMZ 1714 is amplified by PCR cloned from chromosomal DNA of *W. succinogenes* DSMZ 1714 using the PfuTurbo™ DNA polymerase (Roche) and is inserted into the vector pJFF224. The expression of the genes in this construct is driven by a promoter fragment amplified from the 5'-region of the phosphoenolypyruvate carboxykinase (pck) gene from DD1 and by a T4 promoter located on the vector. FIG. 9 shows a schematic map of the resulting plasmid termed pJFF224 (fdh W.s.).

The resulting plasmid is transformed into the strains LU 13843 and LU 15050 and DD1 delta (ldh adhE). The resulting strains selected for plasmid content by the addition of 4 µg/ml chloramphenicol are analyzed for succinic acid production in serum bottle experiments as described above. It is found that the expression of the formate dehydrogenase operon encoding the genes: fdhA, fdhB fdhC and fdhD from *Wolinella succinogenes* DSMZ 1714 increases the succinic acid yield as well as decreasing amount of the side product formate.

Reference List

Kim J M, Lee K H, Lee S Y, 2008, "Development of a markerless gene knock-out system for *Mannheimia succiniciproducens* using a temperature-sensitive plasmid." Fems Microbiol Lett 278, 78-85.

Lee S J, Song H, Lee S Y, 2006, "Genome-based metabolic engineering of *Mannheimia succiniciproducens* for succinic acid production.", Appl Environ Microbiol 72,1939-48.

Lee S Y, 2005, "BTEC 18 Genome-scale metabolic engineering of *Mannheimia succiniciproducens* for enhanced succinic acid production.", The 229th ACS National Meeting, in San Diego, Calif., Mar. 13-17, 2005

Frey J, 1992, "Construction of a broad host range shuttle vector for gene cloning and expression in *Actinobacillus pleuropneumoniae* and other pasteurellaceae." Res Microbiol 143, 263-269.

Lee P C, Lee S Y, Hong S H, Chang H N, 2002, "Isolation and characterization of a new succinic acid-producing bacterium, *Mannheimia succiniciproducens* MBEL55E, from bovine rumen.", Appl Microbiol Biotechnol 58, 663-668.

Dharmadi Y, Murarka A, Gonzalez R, 2006, "Anaerobic fermentation of glycerol by *Escherichia coli:* a new platform for metabolic engineering." Biotechnol Bioeng 94, 821-829.

Lee P C, Lee W G, Lee S Y, Chang H N, 2001, "Succinic acid production with reduced by-product formation in the fermentation of *Anaerobiospirillum succiniciproducens* using glycerol as a carbon source.", Biotechnol Bioeng 72, 41-48.

Robertson E F, Reeves H C, 1987, "Purification and characterization of isocitrate lyase from *Escherichia coli.*", Curr Microbiol 14, 347-350.

Hoyt J C, Robertson E F, Berlyn K A, Reeves H C, 1988, "*Escherichia coli* isocitrate lyase: properties and comparisons.", Biochim Biophys Acta 966, 30-5.

MacKintosh C, Nimmo H G, 1988, "Purification and regulatory properties of isocitrate lyase from *Escherichia coli* ML308.", Biochem J 250, 25-31.

Watanabe S, Takada Y, Fukunaga N, 2001, "Purification and characterization of a cold-adapted isocitrate lyase and a malate synthase from *Colwellia maris*, a psychrophilic bacterium.", Biosci Biotechnol Biochem 65, 1095-1103.

Sundaram T K, Chell R M, Wilkinson A E, 1980, "Monomeric malate synthase from a thermophilic *Bacillus*. Molecular and kinetic characteristics.", Arch Biochem Biophys 1980 February; 199, 515-525.

Eggerer H and Klette A, 1967, "On the catalysis principle of malate synthase.", Eur J Biochem 1, 447-75.

Durchschlag H, Biedermann G, Eggerer H, 1981, "Large-scale purification and some properties of malate synthase from baker's yeast.", Eur J Biochem 114, 255-262.

Feng D F and Doolittle R F, 1987, "Progressive sequence alignment as a prerequisite to correct phylogenetic trees." J Mol Evol 25, 351-360.

Higgins D G and Sharp P M, 1989, "Fast and sensitive multiple sequence alignments on a microcomputer.", Comput Appl Biosci 5, 151-153.

Needleman S B and Wunsch C D, 1970, J Mol Biol 48, 443-453

Smith T F and Waterman M S, 1981, "Identification of Common Molecular Subsequences.", J Mol Biol 147, 195-197

Ferry J G, 1990, "Formate dehydrogenase", FEMS Microbiol Rev 7, 377-382.

Müller U, Willnow P, Ruschig U, Höpner T, 1978, "Formate dehydrogenase from *Pseudomonas oxalaticus.*", Eur J Biochem 83, 485-498.

Leenhouts K J, Kok J, Venema G, 1989, "Campbell-Like Integration of Heterologous Plasmid DNA into the Chromosome of *Lactococcus lactis* subsp. *lactis.*", Appl Env Microbiol 55, 394-400.

The invention claimed is:

1. A *Pasteurella* bacterial cell comprising a heterologous polypeptide having formate dehydrogenase activity, wherein the bacterial cell has increased succinic acid production relative to a corresponding control bacterial cell, the bacterial cell characterized by the 16S rDNA of SEQ ID NO: 7 or a 16S rDNA at least 99.9% identical thereto, wherein the heterologous polypeptide having formate dehydrogenase activity is encoded by a polynucleotide comprising a nucleic acid selected from the group consisting of:
   a. a nucleic acid having a nucleotide sequence as shown in SEQ ID NO: 5,
   b. a nucleic acid encoding an amino acid sequence as shown in SEQ ID NO: 6;
   c. a nucleic acid which is at least 90% identical to the nucleic acid of a) or b); and
   d. a nucleic acid encoding an amino acid sequence which is at least 90% identical to the amino acid sequence encoded by the nucleic acid of a) or b).

2. The bacterial cell of claim 1, wherein the bacterial cell has reduced lactate dehydrogenase activity.

3. The bacterial cell of claim 2, wherein the bacterial cell has reduced pyruvate formate lyase activity.

4. The bacterial cell of claim 1, wherein the bacterial cell is *Pasteurella* strain DD1 as deposited under DSM 18541 with the DSMZ, Germany.

5. A method for manufacturing succinic acid comprising:
   a. cultivating the bacterial cell of claim 1 under suitable culture conditions; and
   b. obtaining succinic acid from the cultured bacterial cells.

6. The bacterial cell of claim 1, wherein the nucleic acid is selected from the group consisting of:
   a. a nucleic acid having at least 95% sequence identity to the nucleic acid sequence of SEQ ID NO: 5; and
   b. a nucleic acid encoding an amino acid sequence having at least 95% sequence identity to the amino acid sequence of SEQ ID NO: 6.

* * * * *